(12) United States Patent
Vepachedu et al.

(10) Patent No.: US 11,103,499 B2
(45) Date of Patent: *Aug. 31, 2021

(54) COMPOSITIONS AND METHODS THEREOF

(71) Applicants: EXCIVA (UG) (haftungsbeschränkt), Heidelberg (DE); Sreenivasarao Vepachedu, Vernon Hills, IL (US)

(72) Inventors: Sreenivasarao Vepachedu, Vernon Hills, IL (US); Hans J Moebius, Wollerau (CH); Anton Bespalov, Heidelberg (DE)

(*) Notice: Subject to any disclaimer, the term of this patent is extended or adjusted under 35 U.S.C. 154(b) by 48 days.

This patent is subject to a terminal disclaimer.

(21) Appl. No.: 16/328,678

(22) PCT Filed: Aug. 25, 2017

(86) PCT No.: PCT/US2017/048748
§ 371 (c)(1),
(2) Date: Feb. 26, 2019

(87) PCT Pub. No.: WO2018/039642
PCT Pub. Date: Mar. 1, 2018

(65) Prior Publication Data
US 2019/0183885 A1   Jun. 20, 2019

Related U.S. Application Data

(60) Provisional application No. 62/501,696, filed on May 4, 2017, provisional application No. 62/477,435, filed
(Continued)

(51) Int. Cl.
*A61K 31/485* (2006.01)
*A61K 47/58* (2017.01)
(Continued)

(52) U.S. Cl.
CPC .......... *A61K 31/485* (2013.01); *A61K 31/138* (2013.01); *A61K 31/225* (2013.01);
(Continued)

(58) Field of Classification Search
None
See application file for complete search history.

(56) References Cited

U.S. PATENT DOCUMENTS 2,133,894 A   10/1938 Hodgins
2,780,355 A   2/1957 Palermo et al.
(Continued)

FOREIGN PATENT DOCUMENTS

CN   103242179 B   5/2013
WO   97/036893 A1   10/1997
(Continued)

OTHER PUBLICATIONS

Weinbroum et al., The role of dextromethorphan in pain control, 2000, Canadian Journal of Anaesthesia, 47:6, pp. 585-596 (Year: 2000).*
(Continued)

*Primary Examiner* — Kortney L. Klinkel
*Assistant Examiner* — Tori Strong

(57) ABSTRACT

Compounds of Formula I:

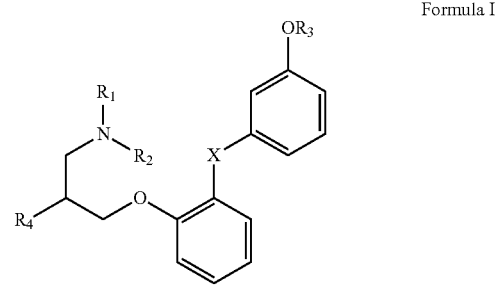

or enantiomers thereof, metabolites thereof, derivatives thereof, deuterated derivatives thereof, prodrugs thereof, pharmaceutically acceptable salts thereof, N-oxides thereof, or a combination thereof, processes and intermediates for preparation thereof, compositions thereof, and uses thereof, are provided. Pharmaceutical compositions comprising a compound of formula I and a compound of Formula II:

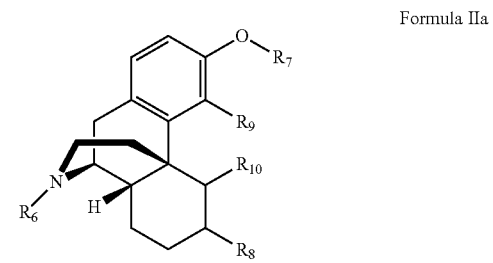

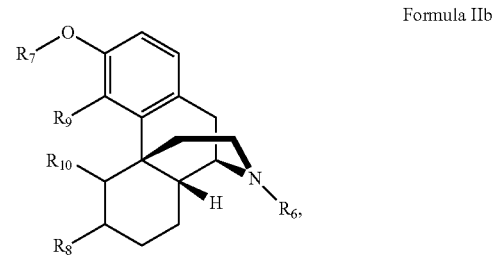

or enantiomers thereof, metabolites thereof, derivatives thereof, deuterated derivatives thereof, prodrugs thereof, pharmaceutically acceptable salts thereof, N-oxides thereof, or a combination thereof. Compositions and methods for improving the efficacy of DEX, or providing beneficial pharmacokinetic effects to DEX, comprising co-administer-
(Continued)

ing a compound of formula I or SARPO, and a compound of Formula II or DEX to a subject in need thereof, and dosage forms, drug delivery systems, methods of treatment thereof.

17 Claims, 12 Drawing Sheets

Related U.S. Application Data on Mar. 28, 2017, provisional application No. 62/380,325, filed on Aug. 26, 2016.

(51) Int. Cl.
| | |
|---|---|
| A61P 25/28 | (2006.01) |
| A61P 9/00 | (2006.01) |
| A61P 25/00 | (2006.01) |
| A61K 31/138 | (2006.01) |
| A61K 31/225 | (2006.01) |
| A61K 45/06 | (2006.01) |

(52) U.S. Cl.
CPC ............ *A61K 45/06* (2013.01); *A61K 47/585* (2017.08); *A61P 9/00* (2018.01); *A61P 25/00* (2018.01); *A61P 25/28* (2018.01)

(56) References Cited

U.S. PATENT DOCUMENTS

| | | | |
|---|---|---|---|
| 4,221,778 | A | 9/1980 | Raghunathan et al. |
| 4,762,709 | A | 8/1988 | Sheumaker et al. |
| 4,777,033 | A | 10/1988 | Ikura et al. |
| 4,788,055 | A | 11/1988 | Fischer et al. |
| 4,874,473 | A | 10/1989 | Arlt et al. |
| 4,959,219 | A | 9/1990 | Chow et al. |
| 4,996,047 | A | 2/1991 | Kelleher et al. |
| 4,999,189 | A | 3/1991 | Kogan et al. |
| 5,071,646 | A | 12/1991 | Malkowska et al. |
| 5,128,142 | A | 7/1992 | Mulligan et al. |
| 5,186,930 | A | 2/1993 | Kogan et al. |
| 5,651,985 | A | 7/1997 | Penners et al. |
| 5,891,885 | A | 4/1999 | Caruso |
| 6,261,601 | B1 | 7/2001 | Talwar et al. |
| 7,119,211 | B2 | 10/2006 | Sakai et al. |
| 7,230,135 | B2 | 6/2007 | Hoge, II et al. |
| 7,750,013 | B2 | 7/2010 | Koopman et al. |
| 7,932,294 | B2 | 4/2011 | Satyam |
| 8,288,557 | B2 | 10/2012 | Vlahov et al. |
| 8,349,901 | B2 | 1/2013 | Satyam |
| 8,354,455 | B2 | 1/2013 | Satyam |
| 8,357,723 | B2 | 1/2013 | Satyam |
| 8,785,472 | B2 | 7/2014 | Lu |
| 9,090,563 | B2 | 7/2015 | Vlahov et al. |
| 9,550,734 | B2 | 1/2017 | Vlahov et al. |
| 2006/0046967 | A1 | 3/2006 | Satyam |
| 2006/0167032 | A1 | 7/2006 | Galer et al. |
| 2007/0225505 | A1 | 9/2007 | Cid |
| 2009/0131728 | A1 | 5/2009 | Shiflett et al. |
| 2011/0274695 | A1 | 11/2011 | Satyam |
| 2013/0053301 | A1 | 2/2013 | Rau et al. |
| 2013/0158271 | A1 | 6/2013 | Vlahov et al. |
| 2014/0058063 | A1 | 2/2014 | Vlahov et al. |
| 2015/0328323 | A1 | 11/2015 | Satyam |
| 2016/0002167 | A1 | 1/2016 | Vlahov et al. |
| 2016/0220694 | A1 | 8/2016 | Vlahov et al. |

FOREIGN PATENT DOCUMENTS

| | | | |
|---|---|---|---|
| WO | 1998043961 | A1 | 10/1998 |
| WO | 00/029397 | A1 | 5/2000 |
| WO | 01/085725 | A1 | 11/2001 |
| WO | 2006136586 | A1 | 12/2006 |
| WO | 2011089216 | A1 | 7/2011 |
| WO | 2015/008973 | A1 | 1/2015 |

OTHER PUBLICATIONS

Gupta et al., Salts of Therapeutic Agents: Chemical, Physiochemical, and Biological Considerations, 2018, Molecules, 23, 1719, pp. 1-15 (Year: 2018).*
Cho et al., Effect of the potent CYP2D6 inhibitor sarpogrelate, on the pharmacokinetics and pharmacodynamics of metoprolol in healthy male Korean volunteers. Xenobiotica, 45(3):256-63 (Mar. 2015)
Cummings et al., Effect of dextromethorphan quinidine on agitation in patients with Alzheimer Disease dementia: a randomized clinical trial. JAMA 314(12):1242-1254 (2015).
Cummings et al., Pimavanserin for patients with Parkinson's disease psychosis: a randomized, placebo-controlled phase 3 trial. Lancet, 383(9916):533-40 (Feb. 8, 2014).
Jamero et al., The Emerging Role of NMDA Antagonists in Pain Management, US Pharm. 36(5): HS4-HS8 (2011).
Sang, NMDA-receptor antagonists in neuropathic pain: experimental methods to clinical trials, J Pain Symptom Manage 19 (1 Suppl) S21-5 (2000).
Moosmann et al., Neuroprotective potential of aromatic alcohols against oxidative cell death, FEBS Letters 413, 467-472 (1997).
Cerejeira et al., Behavioral and psychological symptoms of dementia, Frontiers in Neurology, vol. 3, Article 73 (May 7, 2012).
DSM-IV-TR: numerical listing of codes and diagnoses; ICD-10-CM Official Guidelines for Coding and Reporting, FY 2018 (Oct. 1, 2017-Sep. 30, 2018).
Goldwaser et al., Breakdown of the Cerebrovasculature and Blood-Brain Barrier: A Mechanistic Link between Diabetes Mellitus and Alzheimer's Disease. J Alzheimers Dis 54(2):445-56 (Aug. 1, 2016).
Grandal Leiros et al., Prevalence and concordance between the clinical and the post-mortem diagnosis of dementia in a psychogeriatric clinic, Neurologia S0213-4853(16)30070-6 (2016).
Zilliox et al., Diabetes and Cognitive Impairment. Curr Diab Rep 16 (9):87 (2016).
HHS Publication Substance Abuse and Mental Health Services Administration, Results from the 2012 National Survey on Drug Use and Health: Summary of National Findings, NSDUH Series H-46, HHS Publication No. (SMA) 13-4795. Rockville, MD: Substance Abuse and Mental Health Services Administration, 2013.
Pradip et al., Associations of Nonmedical Pain Reliever Use and Initiation of Heroin Use in the US, Center for Behavioral Health Statistics and Quality Data Review, SAMHSA (2013).
Kosten et al., The Neurobiology of Opioid Dependence: Implications for Treatment, Sci Pract Perspect 1(1): 13-20 (Jul. 2002).
Nicholson et al., Evaluation of the reinforcing and discriminative stimulus properties of the low-affinity N-methyl-D-aspartate channel blocker memantine. Behav Pharmacol 9(3):231-43 (1998).
Shin et al., Neuropsychotoxicity of abused drugs: potential of dextromethorphan and novel neuroprotective analogs of dextromethorphan with improved safety profiles in terms of abuse and neuroprotective effects. J Pharmacol Sci 106 (1):22-7 (2008).
Hirschfeld, Bipolar Disorder—Costs and Comorbidity. Am J Manag Care,11: S85-S90 (2005).
Feinberg et al., The size, burden and cost of disorders of the brain in the UK, J Psychopharmacol. 27(9): 761-770 (Sep. 2013).
Mariotto et al., Projections of the Cost of Cancer Care in the United States: 2010-2020, J Natl Cancer Inst. 103(2): 117-128 (Jan. 19, 2011).
DiLuca, The Cost of Brain Diseases: A Burden or a Challenge? Neuron 82(6):1205-8 (2014).
Global Burden of Neurological and Mental Disorders, Nov. 10, 2014.
World Health Organization: The global burden of disease: 2004 update (2004).
World Health Organization: Neurological Disorders: Public Health Challenges (2006).
The Global Economic Burden of Non-communicable Diseases (2011).
Olesen et al., The economic cost of brain disorders in Europe. European Journal of Neurology. 19: 155-162 (2012).

(56) References Cited

OTHER PUBLICATIONS

Brain Facts: A Primer on the Brain and Nervous System. Society for Neuroscience (2012).
The Numbers Count: Mental Disorders in America. National Institute of Mental Health (2010).
Pender, et al., Toxicity with dextromethorphan-containing preparations: a literature review and report of two additional cases. Pediatr Emerg Care 7(3):163-5 (1991).
Church et al., Dextromethorphan and phencyclidine receptor ligands: differential effects on K(+)- and NMDA-evoked increases in cytosolic free $Ca^{2+}$ concentration. Neurosci Lett 124(2):232-4 (1991).
Woodworth et al., The polymorphic metabolism of dextromethorphan. J Clin Pharmacol 27(2):139-43 (1987).
Avenet et al., Antagonist properties of eliprodil and other NMDA receptor antagonists at rat NR1A/NR2A and NR1A/NR2B receptors expressed in Xenopus oocytes. Neurosci Lett 223(2):133-6 (1997).
Taylor et al., Pharmacology of dextromethorphan: Relevance to dextromethorphan/quinidine (Nuedexta®) clinical use. Pharmacol Ther. 164:170-82 (Aug. 2016).
Nishio et al., Binding affinity of sarpogrelate to 5-HT2A receptor ligand recognition sites in rat renal cortical and cells in mesangial culture. Gen Pharmacol 33: 51-57 (Mar.-Apr. 1999).
Pertz et al., In-vitro pharmacology of sarpogrelate and the enantiomers of its major metabolite: 5-HT2A receptor specificity, stereoselectivity and modulation of ritanserin-induced depression of 5-HT contractions in rat tail artery. J Pharm Pharmacol. 47(4):310-6 (Apr. 1995).
Miyazaki et al., Sarpogrelate hydrochloride, a selective 5-HT2A antagonist, improves vascular function in patients with peripheral arterial disease. J Cardiovasc Pharmacol. 49(4):221-7 (Apr. 2007).
Saini et al., Therapeutic Potentials of Sarpogrelate in Cardiovascular Disease. Cardiovascular Drug Reviews 22: 27-54 (2004).
Kinugawa et al., Effectiveness of a novel serotonin blocker, sarpogrelate, for patients with angina pectoris. Am Heart J 144(2):E1 (2002).
Pietraszek et al., The effect of MCI-9042 on serotonin-induced platelet aggregation in type 2 diabetes mellitus. Thromb Res 70(2):131-8 (1993).
Ogawa et al., Reduced Albuminuria with Sarpogrelate Is Accompanied by a Decrease in Monocyte Chemoattractant Protein-1 Levels in Type 2 Diabetes. Clin J Am Soc Nephrol 3: 362-368 (2008).
Doggrell, Sarpogrelate: cardiovascular and renal clinical potential. Expert Opinion Invest Drugs 13: 865-874 (2004).
Michalets, Update: clinically significant cytochrome P-450 drug interactions. Pharmacotherapy 18(1):84-112 (1998).
Taylor, Cytochromes and psychotropic drug interactions. Br J Psychiatry 168(5):529-32 (1996).
Sproule et al., Selective serotonin reuptake inhibitors and CNS drug interactions. A critical review of the evidence. Clin Pharmacokinet 33(6): 454-71 (1997).
Ereshefsky, Pharmacokinetics and drug interactions: update for new antipsychotics. J Clin Psychiatry 57 (Suppl 11):12-25 (1996).
Shin et al., Effect of Antipsychotic Drugs on Human Liver Cytochrome P-450 (CYP) Isoforms in Vitro: Preferential Inhibition of CYP2D6, Drug Metab Dispos 27 (9): 1078-84 (1999).
Savjani et al., Drug Solubility: Importance and Enhancement Techniques, International Scholarly Research Network ISRN Pharmaceutics vol. 2012, Article ID 195727, 10 pages.
Popik et al., Inhibition of reinforcing effects of morphine and motivational aspects of naloxone-precipitated opioid withdrawal by N-methyl-D-aspartate receptor antagonist, memantine. J. Pharmacol. Exp. Ther. 280: 854-865 (1997).
Popik et al., Inhibition of reinforcing effects of morphine and naloxone-precipitated opioid withdrawal by novel glycine site and uncompetitive NMDA receptor antagonists. Neuropharmacology. 37: 1033-1042 (1998).
Cornish et al., A randomized, double-blind, placebo-controlled safety study of high-dose dextromethorphan in methadone-maintained male inpatients. Drug & Alcohol Dependence. 67(2): 177-83(2002).

Kim et al., Inhibition by MK-801 of morphine-induced conditioned place preference and postsynaptic dopamine receptor supersensitivity in mice. Pharmacol. Biochem. Behav. 55: 11-17 (1996).
Sakhaee et al., The role of NMDA receptor and nitric oxide/cyclic guanosine monophosphate pathway in the antidepressant-like effect of dextromethorphan in mice forced swimming test and tail suspension test. Biomed Pharmacother 85:627-634 (2017).
Singh et al., A Double-Blind, Randomized, Placebo-Controlled, Dose-Frequency Study of Intravenous Ketamine in Patients With Treatment-Resistant Depression. Am J Psychiatry 173(8):816-26 (2016).
Murrough et al., Dextromethorphan/quinidine pharmacotherapy in patients with treatment resistant depression: A proof of concept clinical trial. J Affect Disord 218:277-283 (2017).
Stahl, Mechanism of action of dextromethorphan/quinidine: comparison with ketamine. CNS Spectrums 18: 225-227 (2013).
Nguyen et al., Involvement of sigma-1 receptors in the antidepressant-like effects of dextromethorphan. PLoS One 9 (2):e89985 (2014).
Lam et al., 5-HT2A T102C receptor polymorphism and neuropsychiatric symptoms in Alzheimer's disease. Int J Geriatr Psychiatry 19(6):523-6 (2004).
Davidson et al., Efficacy and Safety of MIN-101: A 12-Week Randomized, Double-Blind, Placebo-Controlled Trial of a New Drug in Development for the Treatment of Negative Symptoms in Schizophrenia. Am J Psychiatry DOI: 10.1176/appi.ajp.2017.17010122 (2017).
Links et al., A case of apathy due to frontotemporal dementia responsive to memantine. Neurocase 19(3):256-61 (2013).
Paraschakis, Tackling negative symptoms of schizophrenia with memantine. Case Rep Psychiatry 2014:384783 (2014).
Adamec et al., Prophylactic and therapeutic effects of acute systemic injections of EMD 281014, a selective serotonin 2A receptor antagonist on anxiety induced by predator stress in rats. Eur J Pharmacol 504(1-2):79-96 (2004).
Millan, The neurobiology and control of anxious states. Progr Neurobiol 70: 83-244 (2003).
Hornboll et al., Acute serotonin 2A receptor blocking alters the processing of fearful faces in the orbitofrontal cortex and amygdala. J Psychopharmacol 27(10):903-14 (2013).
Chojnacka-Wójcik et al., Glutamate receptor ligands as anxiolytics. Curr Opin Investig Drugs 2(8):1112-9 (2001).
Dere et al., NMDA-receptor antagonism via dextromethorphan and ifenprodil modulates graded anxiety test performance of C57BL/6 mice. Behav Pharmacol 14(3):245-9 (2003).
Kamei et al., (+)-SKF-10,047 and dextromethorphan ameliorate conditioned fear stress through the activation of phenytoin-regulated sigma 1 sites. Eur J Pharmacol 299(1-3):21-8 (1996).
Ishikawa et al., The effect of memantine on sleep architecture and psychiatric symptoms in patients with Alzheimer's disease. Acta Neuropsychiatr 28(3):157-64 (2016).
Drevets, Amphetamine-induced dopamine release in human ventral striatum correlates with euphoria. Biol Psychiatry 49(2):81-96 (2001).
Vollenweider et al., 5-HT modulation of dopamine release in basal ganglia in psilocybin-induced psychosis in man—a PET study with [11C]raclopride. Neuropsychopharmacology 20(5):424-33 (1999).
Vazquez-Borsetti et al., Pyramidal neurons in rat prefrontal cortex projecting to ventral tegmental area and dorsal raphe nucleus express 5-HT2A receptors. Cereb Cortex 19:1678-86 (2009).
Erbdrup et al., Serotonin 2A receptor antagonists for treatment of schizophrenia. Expert Opin Investig Drugs 20 (9):1211-1223 (2011).
McCallum et al., $\alpha3\beta4$ nicotinic acetylcholine receptors in the medial habenula modulate the mesolimbic dopaminergic response to acute nicotine in vivo. Neuropharmacology 63(3):434-40 (2012).
Maisonneuve et al., Anti-addictive actions of an iboga alkaloid congener: a novel mechanism for a novel treatment. Pharmacol Biochem Behav 75(3):607-18 (2003).
Anastasio et al., Serotonin (5-hydroxytryptamine) 5-HT(2A) receptor: association with inherent and cocaine-evoked behavioral disinhibition in rats. Behav Pharmacol 22(3):248-61 (2011).
Jakubczyk A et al. The CC genotype in HTR2A T102C polymorphism is associated with behavioral impulsivity in alcohol-dependent patients. J Psychiatr Res 46(1):44-9 (2012).

(56) References Cited

OTHER PUBLICATIONS

Tomson et al., Effect of a human serotonin 5-HT2A receptor gene polymorphism on impulsivity: Dependence on cholesterol levels. J Affect Disord 206:23-30 (2016).
Santillo et al., Grey and White Matter Clinico-Anatomical Correlates of Disinhibition in Neurodegenerative Disease. PLoS One 11(10):e0164122 (2016).
Pioro, Review of Dextromethorphan 20 mg/Quinidine 10 mg (NUEDEXTA®) for Pseudobulbar Affect. Neurol Ther 3 (1):15-28 (2014).
Ahmed et al., Pseudobulbar affect: prevalence and management. Ther Clin Risk Manag 9:483-9 (2013).
Aznar et al., Regulating prefrontal cortex activation: an emerging role for the 5-HT$_2$A serotonin receptor in the modulation of emotion-based actions? Mol Neurobiol 48(3):841-53 (2013).
Pritchard et al., Role of 5HT 2A and 5HT 2C polymorphisms in behavioural and psychological symptoms of Alzheimer's disease. Neurobiol Aging 29(3):341-7 (2008).
Chase et al., Striatal glutamatergic mechanisms and extrapyramidal movement disorders. Neurotox Res 5(1-2):139-46 (2003).
Vanover et al., Role of 5-HT2A receptor antagonists in the treatment of insomnia. Nat Sci Sleep 2:139-50 (2010).
European Medicines Agency. Withdrawal Assessment Report for Sliwens (Eplivanserin), Mar. 18, 2010, London. EMA/CHMP/90435/2010.
Steiger, Eating disorders and the serotonin connection: state, trait and developmental effects. J Psychiatry Neurosci 29 (1):20-9 (2004).
Norton et al., HTR2A: association and expression studies in neuropsychiatric genetics. Ann Med 37(2):121-9 (2005).
Spies et al., The serotonin transporter in psychiatric disorders: insights from PET imaging. Lancet Psychiatry 2 (8):743-55 (2015)
Ying et al., Neuroprotective effects of dextromethorphan against transient cerebral ischemia/reperfusion injury in gerbils, Acta Pharmacol Sinica 16(2):133-6 (Mar. 1995).
Sivaneswari et al., Ion exchange resins as drug delivery carriers, Journal of Chemical and Pharmaceutical Research, 7 (4):1436-1445 (2015).
Chen et al., A practical synthesis of sarpogrelate hydrochloride and in vitro platelet aggregation inhibitory activities of its analogues, Chinese Chemical Letters, vol. 21, Issue 3, pp. 287-28 (Mar. 2010 ).
Moloney et al., Chiral carboxylic acid ligands derived from camphoric acid, Tetrahedron: Asymmetry, vol. 7, Issue 9, pp. 2551-2562 (Sep. 1996).
Hu et al., Adventure in Asymmetric Hydrogenation: Synthesis of Chiral Phosphorus Ligands and Asymmetric Hydrogenation of Heteroaromatics, Top Organomet Chem 36:313-354 (2011).
Ishihara et al., An extremely simple, convenient, and selective method for acetylating primary alcohols in the presence of secondary alcohols, J. Org. Chem., 58 (15), pp. 3791-3793 (1993).
Fulgentius et al., Facile and Efficient Acetylation of Primary Alcohols and Phenols with Acetic Anhydride Catalyzed by Dried Sodium Bicarbonate, Catalysts, 3,954-965 (2013).
Edwards et al., The stereoselective replacement of hydroxyl groups by chlorine, using the mesyl chloride-N,N-dimethylformamide reagent, Carbohydrate Research, vol. 35, Issue 1, pp. 111-129 (Jul. 1974).
Simplicio et al., Prodrugs for Amines, Molecules 13, 519-547 (2008).
Mahato et al., Prodrugs for Improving Tumor Targetability and Efficiency, Adv Drug Deliv Rev. 63(8): 659-670 (Jul. 18, 2011).
Jornada et al., The Prodrug Approach: A Successful Tool for Improving Drug Solubility, Molecules 21, 42 (2016).
Jain et al., Mutual prodrugs containing bio-cleavable and drug releasable disulfide linkers, Bioorganic Chemistry 49C:40-48 (Jul. 2013).
Fekete et al., Comparative Study Separation of Diastereomers by HPLC, Chromatographia, 57, No. ¾ (Feb. 2003).
Chilson, Five Unexpected Benefits Delivered to the Body by Malic Acid, Newsmax, p. 1 (Mar. 31, 2015).
Kim et al., Alexithymia and Stress Response Patterns among Patients with Depressive Disorders in Korea. Psychiatry Investig 6(1): 13-8 (2009).
Fitzgerald et al., Drugs of abuse and stress increase the expression of GluR1 and NMDAR1 glutamate receptor subunits in the rat ventral tegmental area: common adaptations among cross-sensitizing agents. J. Neurosci. 16: 274-282 (1996).
Inturrisi, Preclinical evidence for a role of glutamatergic systems in opioid tolerance and dependence. Semin. Neurosci. 9: 110-119 (1997).
Herman et al., Clinical medication development for opiate addiction: focus on nonopioids and opioid antagonists for the amelioration of opiate withdrawal symptoms and relapse prevention. Semin. Neurosci. 9: 158-172 (1997).
Li et al., Protective effect of dextromethorphan against endotoxic shock in mice. Biochemical Pharmacology. 69(2): 233-40 (2005).
Liu et al., Dextromethorphan protects dopaminergic neurons against inflammation-mediated degeneration through inhibition of microglial activation. Journal of Pharmacology & Experimental Therapeutics. 305(1):212-8 (2003).
Zhang et al., 3-hydroxymorphinan is neurotrophic to dopaminergic neurons and is also neuroprotective against LPS-induced neurotoxicity. FASEB Journal. 19(3): 395-7 (2005).
Madden et al., Opiate binding sites in the cellular immune system: expression and regulation. J Neuroimmunol 83(1-2): 57-62 (1998).
Fuchs et al., Morphine induces apoptosis in murine thymocytes in vivo but not in vitro: involvement of both opiate and glucocorticoid receptors. J Pharmacol Exp Ther 266(1): 417-23 (1993).
Sei et al., Morphine-induced thymic hypoplasia is glucocorticoid-dependent. J. Immunol. 146(1): 194-8 (1991).
Freier et al., A mechanism of action for morphine-induced immunosuppression: corticosterone mediates morphine-induced suppression of natural killer cell activity. J Pharmacol Exp Ther 270(3): 1127-33 (1994).
Mellon et al., Role of central opioid receptor subtypes in morphine-induced alterations in peripheral lymphocyte activity. Brain Res 789(1): 56-67 (1998).
Yeh et al., Analysis of pharmacokinetic parameters for assessment of dextromethorphan metabolic phenotypes. J. Biomed. Sci. 10: 552-564 (2003).
O'Brien et al., Cytokine profiles in bipolar affective disorder: focus on acutely ill patients. J Affect Disord. 90(2-3): 263-7 (2006).
Brietzke et al., Comparison of cytokine levels in depressed, manic and euthymic patients with bipolar disorder. J Affect Disord. 116(3): 214-7 (2009).
Rao et al., Increased excitotoxicity and neuroinflammatory markers in postmortem frontal cortex from bipolar disorder patients. Mol. Psychiatry. 15(4): 384-92 (2010).
Mendlewicz et al., Shortened onset of action of antidepressants in major depression using acetylsalicylic acid augmentation: a pilot open-label study. Int. Clin. Psychopharmacol. 21(4): 227-31 (2006).
Chen et al., Valproate protects dopaminergic neurons in midbrain neuron/glia cultures by stimulating the release of neurotrophic factors from astrocytes. Mol Psychiatry. 11(12):1116-1125 (Dec. 2006).
Robert et al., The Apathy Inventory: assessment of apathy and awareness in Alzheimer's disease, Parkinson's disease and mild cognitive impairment, the Journal of Geriatric Psychiatry, vol. 17, Issue 12, pp. 1099-1105 (Dec. 2002).
Landes et al., Apathy in Alzheimer's Disease, the Journal of American Geriatric Society, vol. 49, Issue 12, pp. 1700-1707 (Dec. 2001).
Malloy et al., Apathy and Its Treatment in Alzheimer's Disease and Other Dementias, Psychiatric Times, vol. XXII, Issue 13 (Nov. 1, 2005).
Ruthirakuhan et al., Pharmacological interventions for apathy in Alzheimer's disease (Protocol), Cochran Database of Systemic Studies, 2016, Issue 5. Art. No. CD012197, Published by John Wiley & Sons, Ltd. Theleritis et al., Pharmacological and Nonpharmacological Treatment for Apathy in Alzheimer Disease: A Systematic Review Across Modalities, Journal of Geriatric Psychiatry and Neurology 30 (1): 26-49 (2017).

(56) References Cited

OTHER PUBLICATIONS

Kazui et al., Differences of Behavioral and Psychological Symptoms of Dementia in Disease Severity in Four Major Dementias. PLoS One 11(8): e0161092 (2016).
Van der Schyf, Psychotropic Drug Development Strategies that Target Neuropsychiatric Etiologies in Alzheimer's and Parkinson's Diseases. Drug Dev Res. 77: 458-468 (2016).
Peters et al., Neuropsychiatric Symptoms as Predictors of Progression to Severe Alzheimer's Dementia and Death: The Cache County Dementia Progression Study. Am J Psychiatry 172: 460-465 (2015).
McClam et al., Interventions for neuropsychiatric symptoms in neurocognitive impairment due to Alzheimer's disease: a review of the literature Harv Rev Psychiatry 23: 377-393 (2015).
Nikolic et al., Drug design for CNS diseases: polypharmacological profiling of compounds using cheminformatic, 3D-QSAR and virtual screening methodologies. Front Neurosci 10: 265 (2016).
Aouizerate et al., Pathophysiology of obsessive-compulsive disorder: a necessary link between phenomenology, neuropsychology, imagery and physiology. Prog Neurobiol 72(3):195-221 (2004).
Aghajanian et al., Serotonin, via 5-HT2A receptors, increases EPSCs in layer V pyramidal cells of prefrontal cortex by an asynchronous mode of glutamate release. Brain Res 825:161-71 (1999).
Van Dyck et al., PET quantification of 5-HT2A receptors in the human brain: a constant infusion paradigm with [18F] altanserin. J Nucl Med 41(2):234-41 (2000).
Kharazia et al., Glutamate in thalamic fibers terminating in layer IV of primary sensory cortex. J Neurosci 14(10):6021-6032 (1994).
Sherman SM. Thalamus plays a central role in ongoing cortical functioning. Nat Neurosci 19(4):533-41 (2016).
Cummings, The Neuropsychiatric Inventory: Assessing psychopathology in dementia patients. Neurology 48:S10-S16 (1997).
Johnson et al., Neuropsychiatric profiles in dementia. Alzheimer Dis Assoc Disord 25(4): 326-332 (2011).
Geda et al., The Prevalence of Neuropsychiatric Symptoms in Mild Cognitive Impairment and Normal Cognitive Aging: A Population-Based Study. Arch Gen Psychiatry 65(10): 1193-1198 (2008).
Lyketsos et al., Prevalence of neuropsychiatric symptoms in dementia and mild cognitive impairment: results from the cardiovascular health study. JAMA 288(12):1475-83 (2002).
Zhao et al., The prevalence of neuropsychiatric symptoms in Alzheimer's disease: Systematic review and meta-analysis. J Affect Disord 190:264-71 (2016).
Weiner et al., 5-hydroxytryptamine2A receptor inverse agonists as antipsychotics. J Pharmacol Exp Ther 299 (1):268-76 (2001).
Meltzer et al., Placebo-controlled evaluation of four novel compounds for the treatment of schizophrenia and schizoaffective disorder. Am J Psychiatry 161: 975-84 (2004).
Cummings et al., Pimavanserin for patients with Parkinson's disease psychosis: a randomised, placebo-controlled phase 3 trial. Lancet 383: 533-40 (2014).
Ramanathan et al., Serotonergic system genes in psychosis of Alzheimer dementia: meta-analysis. Am J Geriatr Psychiatry 17(10):839-46 (2009).
Zawertailo et al., Effect of metabolic blockade on the psychoactive effects of dextromethorphan. Hum Psychopharmacol 25(1):71-9 (2010).
Székely et al., Induction of phencyclidine-like behavior in rats by dextrorphan but not dextromethorphan. Pharmacol Biochem Behav 40(2):381-6 (1991).
Kishi et al., The effects of memantine on behavioral disturbances in patients with Alzheimer's disease: a meta-analysis. Neuropsychiatr Dis Treatment 13: 1909-1928 (2017).
Sakaue et al., Modulation by 5-hT2A receptors of aggressive behavior in isolated mice. Jpn J Pharmacol 89(1):89-92 (2002).
Banlaki et al., Polymorphism in the serotonin receptor 2a (HTR2A) gene as possible predisposal factor for aggressive traits. PLoS One 10(2):e0117792 (2015).
Belozertseva, Effects of NMDA receptor channel blockade on aggression in isolated male mice. Aggr Behav 25:381-396 (1999).
Benaliouad et al., Blockade of 5-HT2a receptors reduces haloperidol-induced attenuation of reward. Neuropsychopharmacology 32(3):551-61 (2007).
Marek et al., The selective 5-HT2A receptor antagonist M100907 enhances antidepressant-like behavioral effects of the SSRI fluoxetine. Neuropsychopharmacology 30: 2205-2215 (2005).
Patel et al., The highly selective 5-hydroxytryptamine (5-HT)2A receptor antagonist, EMD 281014, significantly increases swimming and decreases immobility in male congenital learned helpless rats in the forced swim test. Synapse 52: 73-75 (2004).
Doggrell, sarpogrelate: cardiovascular and renal clinical potential, Expert Opinion on Investigational Drugs, 13:7, 865-874 (2004).
Ma et al., Effective treatment with combination of peripheral 5-hydroxytryptamine synthetic inhibitor and 5-hydroxytryptamine 2 receptor antagonist on glucocorticoid-induced whole-body insulin resistance with hyperglycemia. J Diabetes Investig 7(6):833-844 (2016).
Marquard et al., Characterization of pancreatic NMDA receptors as possible drug targets for diabetes treatment. Nat Med 21(4):363-72 (2015).
Yamada et al., Hyperglycemia induced by the 5-HT receptor agonist, 5-methoxytryptamine, in rats: involvement of the peripheral 5-HT2A receptor. Eur J Pharmacol.323(2-3):235-40 (1997).
Gilles et al., Antagonism of the serotonin (5-HT)-2 receptor and insulin sensitivity: implications for atypical antipsychotics. Psychosom Med. 67(5):748-51 (2005).
Takishita et al., Effect of sarpogrelate hydrochloride, a 5-HT2 blocker, on insulin resistance in Otsuka Long-Evans Tokushima fatty rats (OLETF rats), a type 2 diabetic rat model. J Cardiovasc Pharmacol 43(2):266-70 (2004).
Iizuka et al., Beneficial effects of a compound of sarpogrelate hydrochloride, a 5-HT2A receptor antagonist or inverse agonist, supplemented with pioglitazone on diabetic model mice. Endocr Res. 34(1-2):18-30 (2009).
Kokubu et al., Persistent insulin-sensitizing effects of sarpogrelate hydrochloride, a serotonin 2A receptor antagonist, in patients with peripheral arterial disease. Circ J 70(11):1451-6 (2006).
Grandal et al., Prevalence and concordance between the clinical and the post-mortem diagnosis of dementia in a psychogeriatric clinic, Neurologia S0213-4853(16)30070-6 (2016).
Obata et al. Antinociception in rat by sarpogrelate, a selective 5-HT(2A) receptor antagonist, is peripheral. Eur J Pharmacol 404(1-2):95-102 (2000).

\* cited by examiner

COMPOSITIONS AND METHODS THEREOF

TECHNICAL FIELD

This disclosure relates to novel compositions and methods useful in the symptomatic and disease-modifying treatments and therapies, and methods of making such compositions, therapeutic formulations and kits thereof.

BACKGROUND

Brain disorders, including developmental, psychiatric and neurodegenerative diseases, and cancers, represent an enormous disease burden, regarding human suffering and economic cost.

Diseases affecting the brain and central nervous system represent one of the largest global healthcare challenges and greatest medical needs due to the devastating personal and economic consequences for patients, caregivers and society. An estimated 55 million people worldwide suffer from neurodegenerative diseases with no currently approved disease-modifying therapies available. As modern therapeutic interventions increase life expectancy, the number of patients suffering from these diseases is expected to double every 20 years. Costs for treating these diseases are currently estimated at $818 billion and expected to grow to more than $1 trillion by 2030.

As many as one million Americans live with Parkinson's disease and more than 10 million people worldwide are living with Parkinson's disease. Approximately 60,000 Americans are diagnosed with Parkinson's disease each year. The combined direct and indirect cost of Parkinson's, including treatment, social security payments and lost income from inability to work, is estimated to be nearly $25 billion per year in the United States alone. Medication costs for an individual person with PD average $2,500 a year, and therapeutic surgery can cost up to $100,000 dollars per patient.

Alzheimer's disease (AD) accounts for over half of all diagnosed cases of dementia, a degenerative condition that impairs memory, thinking, and independent functioning. AD is currently estimated to afflict between 3 million and 5 million people in the United States and 35 million people worldwide. Without effective treatments to prevent or slow the course of Alzheimer's and related dementias, the number of people living with AD is projected to double by 2035 and triple by 2060 as the world population ages.

Regardless of the many potential etiologies of cerebrovascular disease, the term Vascular Dementia (VaD) is now established to describe the end stage of vascular cognitive impairment (VCI). Because of historical uncertainty around the diagnostic classification, epidemiologic data are variable. However, age-adjusted rates for Alzheimer disease and VaD are 19.2 and 14.6, respectively, per 1000 person-years, showing that VaD is the second leading cause for dementia in the affluent countries (Gorelik et al., Vascular Contributions to Cognitive Impairment and Dementia. Stroke 42: 2672-2713 (2011)). In many cases, there is overlap or co-morbidity with AD as large post-mortem series have shown repeatedly ("mixed dementia"). As the onset of VaD may be insidious as in AD, diagnostic specificity in a given subject remains a challenge, while the medical need for treatment is no less than in AD.

Dementia with Lewy Bodies (DLB) has been confirmed in the recent years as a major form of dementia. Its clinical features distinguish DLB from AD and VaD. In particular, there are cognitive, neuropsychiatric, motor, and other symptoms occurring. Therapy is non-specific, and acetylcholine esterase inhibitors (AChEIs) used in AD may worsen the condition, and in particular trigger or worsen delusions and hallucinations. The use of antipsychotics for the acute management of substantial behavioral disturbance, delusions, or visual hallucinations comes with attendant mortality risks in patients with dementia, and particularly in the case of DLB they should be avoided whenever possible, given the increased risk of a serious sensitivity reaction (McKeith et al., Diagnosis and management of dementia with Lewy bodies. Neurology 89: 88-100 (2017)).

Fronto-Temporal Lobar Degeneration (FTLD) is a clinically and pathologically heterogenous basket of dementias, which show behavioral, cognitive, motor, speech, and other impairments (Rabinovici, Miller, Frontotemporal Lobar Degeneration: Epidemiology, Pathophysiology, Diagnosis and Management. CNS Drugs 24: 375-398 (2010)). The most frequent form is behavioral variant fronto-temporal dementia (bvFTD) characterized by prominent symptoms of the BPSD spectrum. Treatment is non-specific and always off-label as no specific pharmacotherapy exists. In particular in bvFTD, there is a high medical need for a non-neuroleptic therapy addressing specifically the behavioral impairments.

Progress in specifically addressing therapeutic needs in dementia, in general, has been slow in the past two decades. In fact, virtually all development projects in Alzheimer's Disease have failed since the approval of memantine by the EMA (2002) and the FDA (2003). Rather than insisting on "treatment" indications, regulators have addressed the persisting high medical need by opening up the range of approvable medications to therapies with syndromal indication labels. Such a syndromal indication label could cover, e.g., Behavioral and Psychiatric Symptoms in Dementia (BPSD), or even sub-syndromal indications, like aggression or apathy in Alzheimer's Disease.

SUMMARY OF THE INVENTION

An embodiment of the invention is a composition comprising a compound of formula

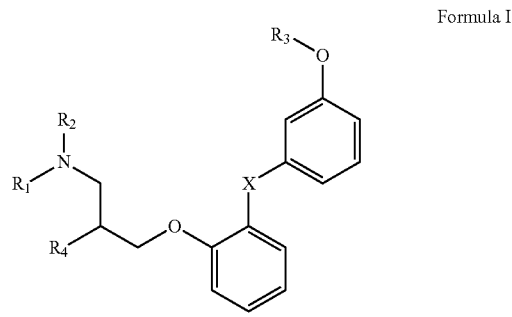

Formula I

Another embodiment is a composition comprising a compound of Formula II.

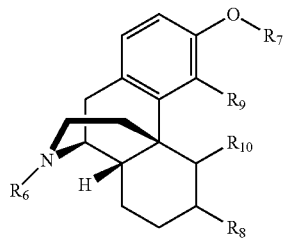

Formula IIa

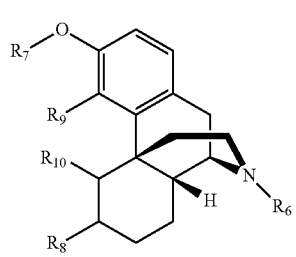

Formula IIb

Another embodiment is a composition comprising a compound of Formula I and a compound of Formula II.

Some embodiments include a method of treating a disease or disorder in a subject in need thereof comprising an effective amount of a composition comprising a compound of Formula II, enantiomers, metabolites, derivatives, or prodrugs thereof, or a combination thereof; and a compound of Formula I, enantiomers thereof, metabolites thereof, derivatives thereof, and/or prodrugs thereof, or a combination thereof; or a combination of a compound of Formula II and a compound of formula I, salts and diastereomers thereof, pharmaceutically acceptable salts thereof, N-oxides thereof, processes and intermediates for preparation thereof, compositions thereof, and uses thereof.

Some embodiments include a method of treating a disease or disorder in a subject in need thereof comprising an effective amount of a composition comprising dextromethorphan, enantiomers, metabolites, derivatives, or prodrugs thereof, or a combination thereof (DEX); sarpogrelate (SGL), enantiomers thereof, metabolites thereof, derivatives thereof, and/or prodrugs thereof, or a combination thereof (a compound of formula I or SARPO); or a combination of DEX and a compound of formula I or SARPO (SARPO-DEX™), salts and diastereomers thereof, pharmaceutically acceptable salts thereof, N-oxides thereof, processes and intermediates for preparation thereof, compositions thereof, and uses thereof.

In an embodiment, the method is a method of decreasing the number of doses and/or total daily dose of DEX that can be administered while increasing efficacy and safeguarding tolerability and safety; a method of reducing an adverse event associated with treatment by DEX, wherein the subject is at risk of experiencing the adverse event as a result being treated with DEX; a method of decreasing dextrorphan (DO) plasma levels, a method of treating a neurological disorder, a method of increasing DEX plasma levels in a subject in need of treatment with DEX, wherein the subject is an extensive metabolizer of DEX; a method of inhibiting the metabolism of DEX; a method of increasing the metabolic lifetime of DEX; a method of correcting extensive metabolism of DEX; a method of improving the antitussive properties of DEX; a method of treating cough. Another embodiment is the method, wherein the disease or disorder is a neurological disorder, wherein the composition is administered at least once a day for at least 1 day, 2 days, 3 days, 4 days, 5 days, 6 days, 7 days, or 8 days.

Some embodiments include a method of treating a neurological disorder comprising administering about 5 mg/day to about 600 mg/day, about 5 mg/day to about 300 mg/day, about 5 mg/day to about 400 mg/day, about 5 mg/day to about 500 mg/day, about 5 mg/day to about 600 mg/day, about 5 mg/day to about 1,000 mg/day, about 50 mg/day to about 1000 mg/day, about 100 mg/day to about 1000 mg/day, about 150 mg/day to about 1000 mg/day, about 150 mg/day to about 5000 mg/day, about 150 mg/day to about 300 mg/day, or about 150 mg/day to about 100 mg/day, or an amount as required of a compound of formula I or SARPO, and about 0.1 mg/day to about 1 mg/day, about 0.5 mg/day to about 15 mg/day, about 15 mg/day to about 60 mg/day, about 15 mg/day to about 120 mg/day, about 0.1 mg/day to about 200 mg/day, or an amount as required of DEX to a subject in need thereof.

Another embodiment is a pharmaceutical composition comprising DEX and one or more agents selected from the group comprising 5-HT2A receptor antagonist, inverse agonist, and CYP2D6 inhibitor. In another embodiment, the agent is an agent having properties of both 5-HT2A receptor antagonist or inverse agonist and CYP2D6 inhibitor. In another embodiment, the agent is an agent having properties of both 5-HT2A receptor inverse agonist and CYP2D6 inhibitor. In another embodiment, the agent is a compound of formula I or SARPO. In another embodiment, the pharmaceutical composition comprises SARPODEX™.

In an embodiment, the method of treating a disorder or disorder, wherein the disorder or disease is Behavioral and Psychiatric Symptoms in Dementia (BPSD).

Figure 1:
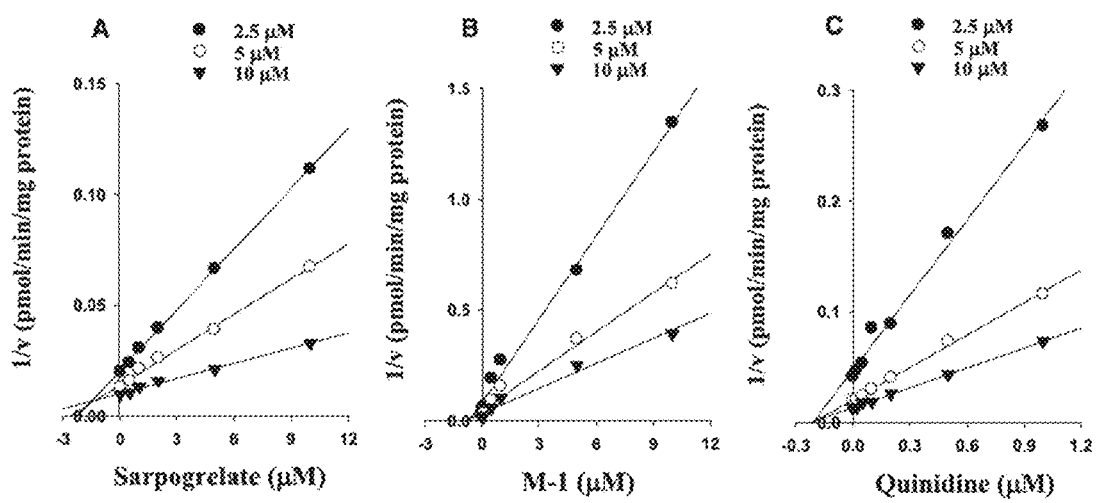
FIG. 1: Dixon plots to determine Ki values for CYP2D6 of a compound of formula I or SARPO (A), M-1 (B), and quinidine (C). The concentrations of dextromethorphan were determined 2.5 (filled circles), 5 (open circles), and 10 (triangles) mM, respectively. V represents formation rate of dextrorphan (pmol/min/mg protein). Data are the mean values of triplicate determinations. The solid lines of a compound of formula I or SARPO, M-1, and quinidine fit well to all competitive inhibition types (Cho et al., Effect of the potent CYP2D6 inhibitor sarpogrelate, on the pharmacokinetics and pharmacodynamics of metoprolol in healthy male Korean volunteers. Xenobiotica, 45(3):256-63 (2015 March), incorporated in entirety by reference).
Figure 2:
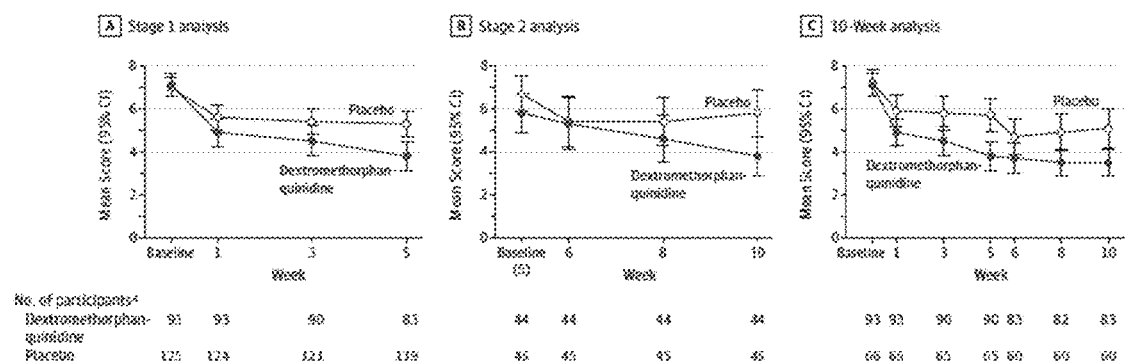
FIG. 2: Mean Neuropsychiatric Inventory Agitation/Aggression Domain Scores by Stage and Visit for Patients Included in the Sequential Parallel Comparison Design and 10-Week Analyses. A, Stage 1 (weeks 1-5); B, stage 2 (weeks 6-10) for placebo nonresponders rerandomized after stage 1; C, 10-week results (the 10-week secondary analysis includes only patients who continued the same treatment assignment throughout study participation; ie, were randomized to receive only dextromethorphan-quinidine or only placebo [excludes patients who were re-randomized from placebo to dextromethorphan-quinidine in stage 2], thus simulating a parallel-group design). Analysis-of-covariance models with treatment as fixed effect and baseline as covariate were used to compare mean change from baseline between groups at each time point. Baseline for stage 2 is the patients' scores at the start of stage 2. Least squares mean treatment differences are as follows: for stage 1, week 1, −0.8 (95% CI, −1.5 to −0.03; P=0.04), week 3, −1.0 (95% CI, −1.8 to −0.2; P=0.01), and week 5, −1.5 (95% CI, −2.3 to −0.7; P<0.001); for stage 2, week 6, 0.7 (95% CI, −0.4 to 1.9; P=0.19), week 8, −0.1 (95% CI, −1.3 to 1.2; P=0.93), and week 10, −1.6 (95% CI, −2.9 to −0.3; P=0.02); for 10-week analysis, week 1, −0.9 (95% CI, −1.8 to −0.04; P=0.047), week 3, −1.3 (95% CI, −2.2 to −0.3; P=0.01), week 5, −1.8 (95% CI, −2.7 to −0.9; P<0.001), week 6, −0.9 (95% CI, −2.0 to 0.1; P=0.06), week 8, −1.3 (95% CI, −2.4 to −0.3; P=0.01), and week 10, −1.8 (95% CI, −2.8 to −0.7; P=0.003). a Observed cases (Cummings et al., Effect of dextromethorphan quinidine on agitation in patients with Alzheimer Disease dementia: a randomized clinical trial. JAMA 314(12):1242-1254 (2015), incorporated in entirety by reference).
Figure 3:
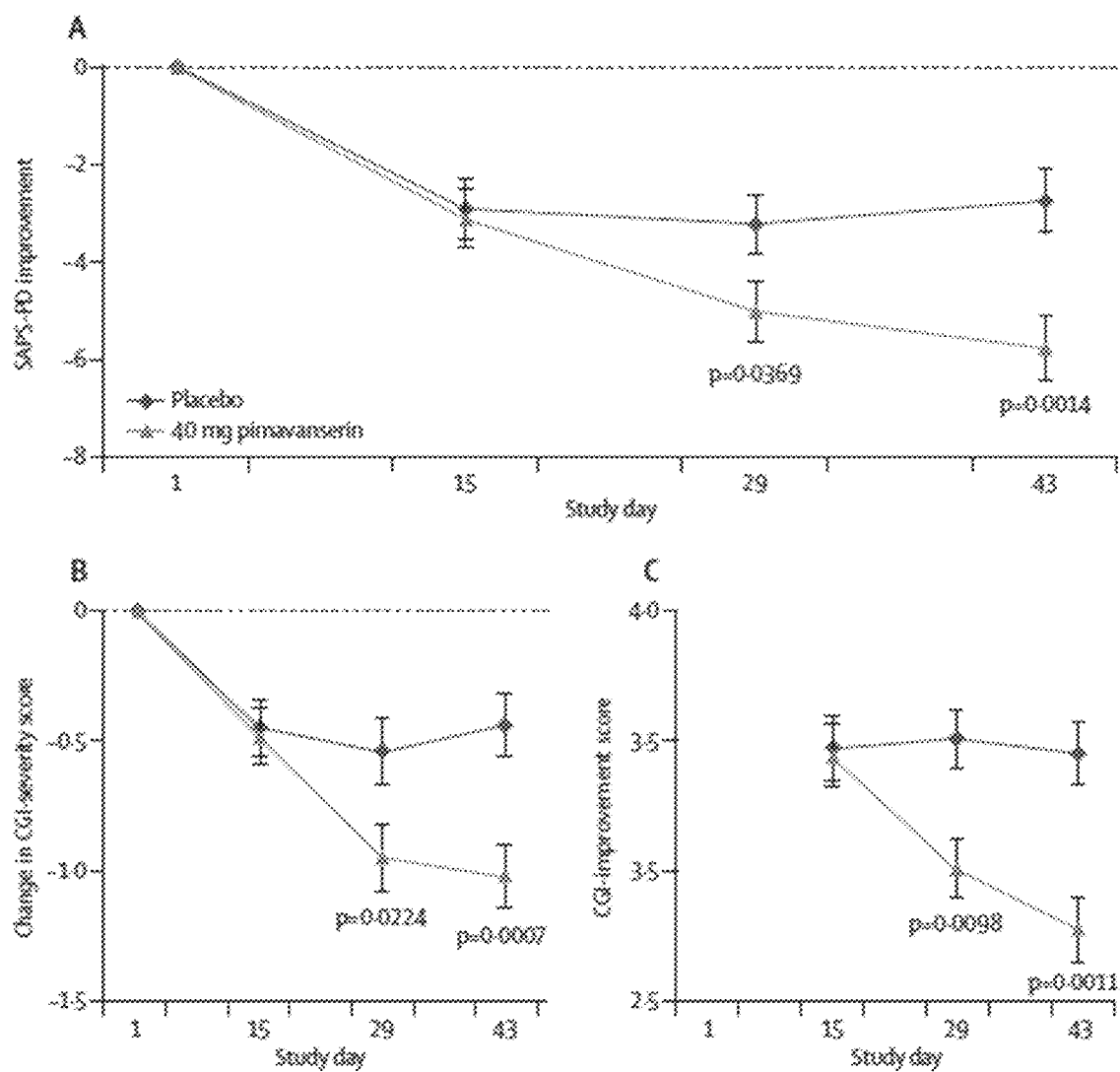

FIG. 3: Treatment effects on psychosis severity reduction in the 6-week study period in the full analysis set. The full analysis set includes all patients who received ≥1 dose and had a SAPS assessment at baseline and at least one afterward. Data points show least squares means (standard error). (A) SAPS-PD improvement. (B) Change in CGI-severity score. (C) CGI-improvement scores. SAPS=scale for assessment of positive symptoms. CGI=clinical global impression (Cummings et al., Pimavanserin for patients with Parkinson's disease psychosis: a randomized, placebo-controlled phase 3 trial. *Lancet*, 383(9916):533-40 (2014 February 8), incorporated in entirety by reference).

Figure 4:
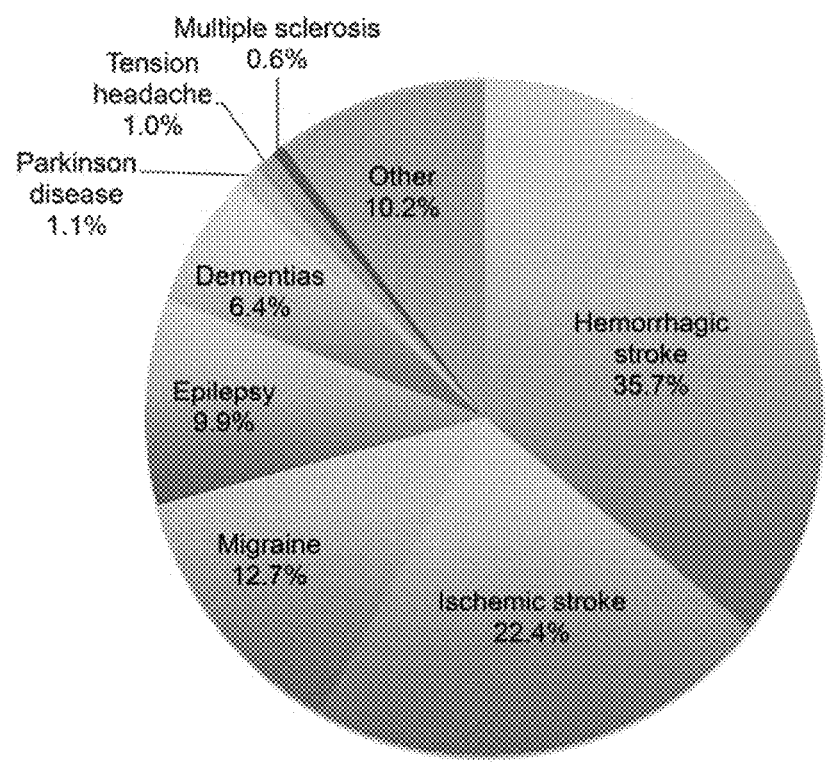

FIG. 4: Contribution of specific causes to the combined burden of neurologic disorders and cerebrovascular disease (percent of total disability-adjusted life-years) (Global Burden of Disease Study 2010 (GBD 2010) Results by Cause 1990-2010, Global Health Data Exchange (GHDx)).

Figure 5:
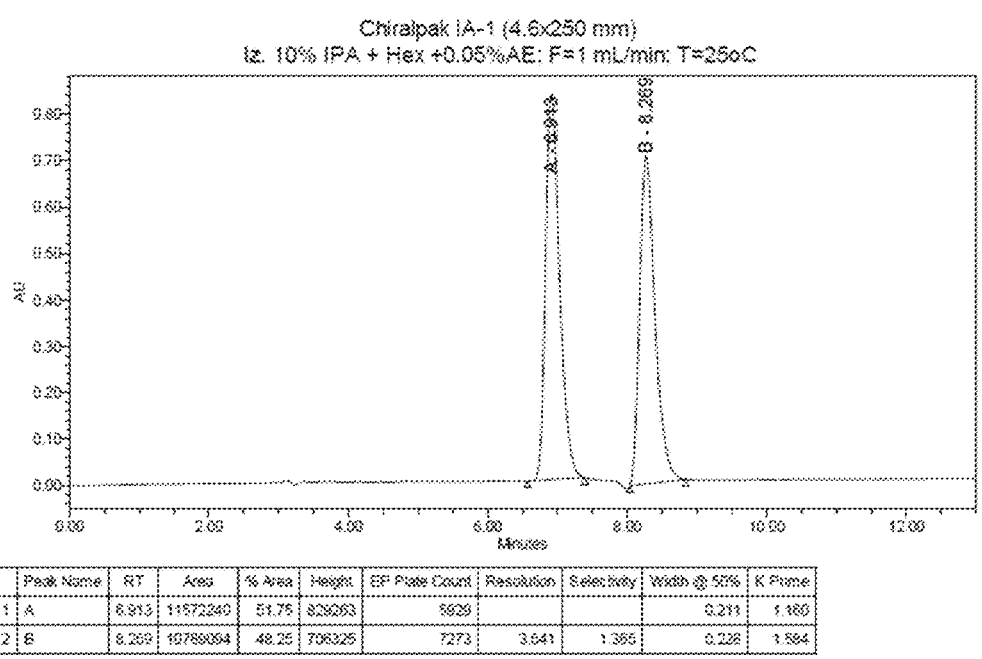

FIG. 5: Chiralpak IA-1 (4.6×250 mm) Iz. 10% IPA+Hex+ 0.05% AE; F=1 mL/min; T=25° C. FIG. 5 shows separation of M1 enantiomers using Chiralpak.

Figure 6:
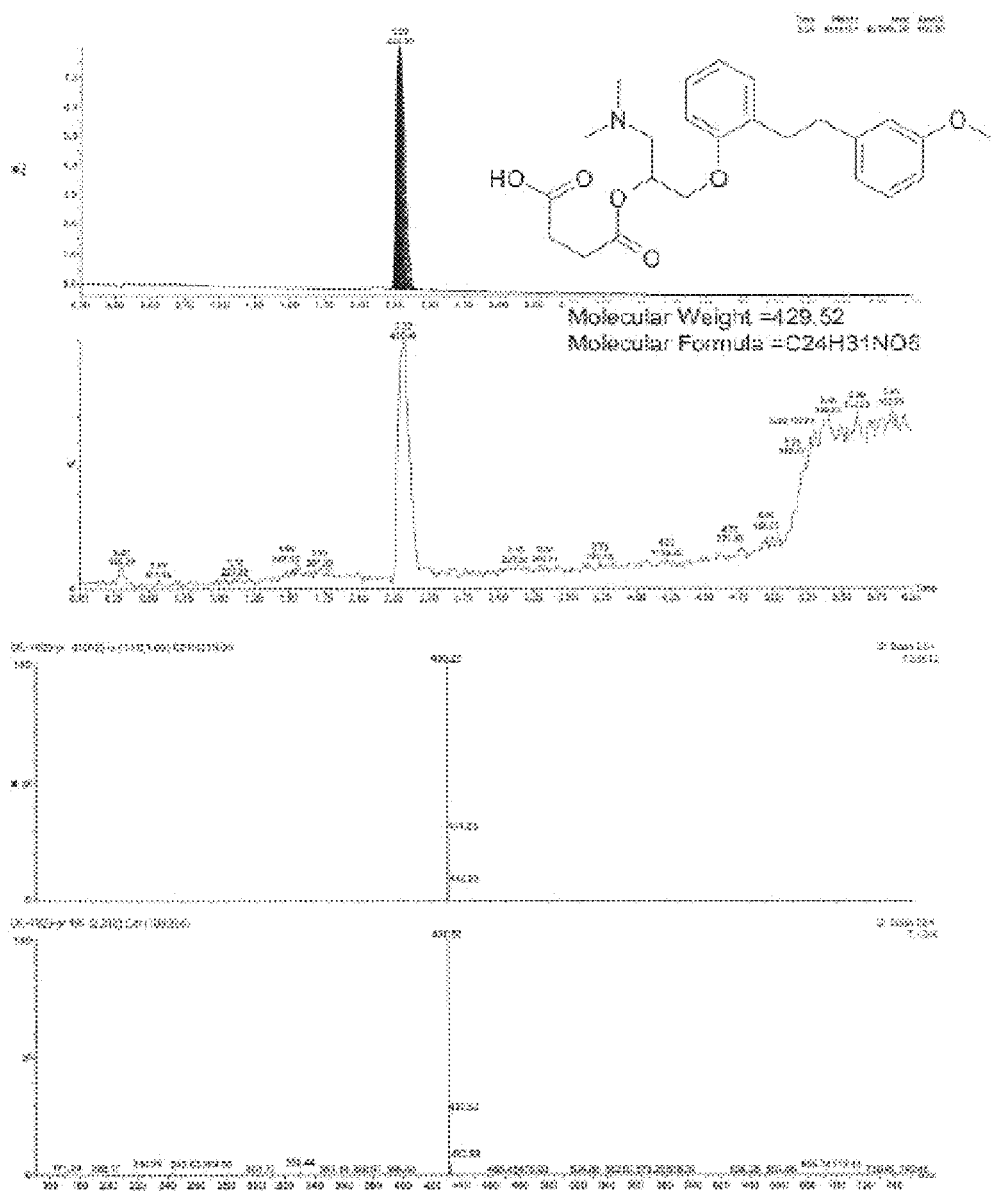

FIG. 6: Chromatogram of (−) sarpogrelate obtained by chromatography with a column of XBridge® C, 18 3.5 m, 2.1×50 mm mobile phase, gradient elution from 10% MeCN in 0.01% TFA to 95% MeCN in 0.01% TFA, rate: 0.5 ml/min. Detection: UV 254 nm.

Figure 7:
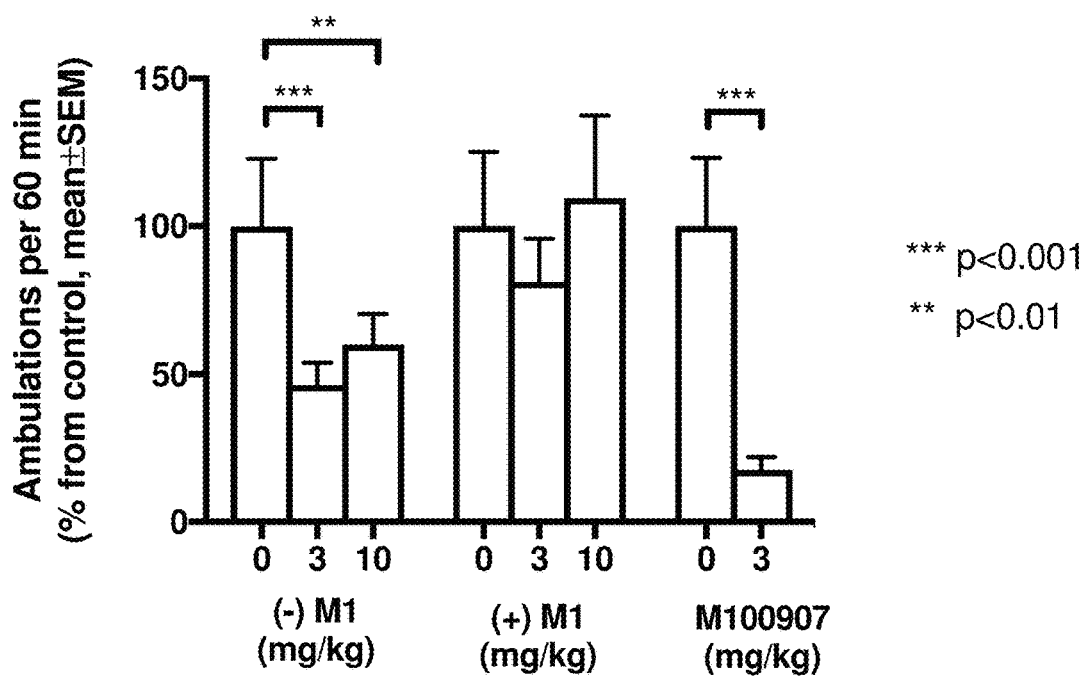

FIG. 7: Effects of (−) and (+) enantiomers of M1 as well as M-100,907 on MK-801-induced hyperactivity in rats. Data are presented as mean (±SEM) average activity over a 60-min test session. N=5-9 per group.

Figure 8:
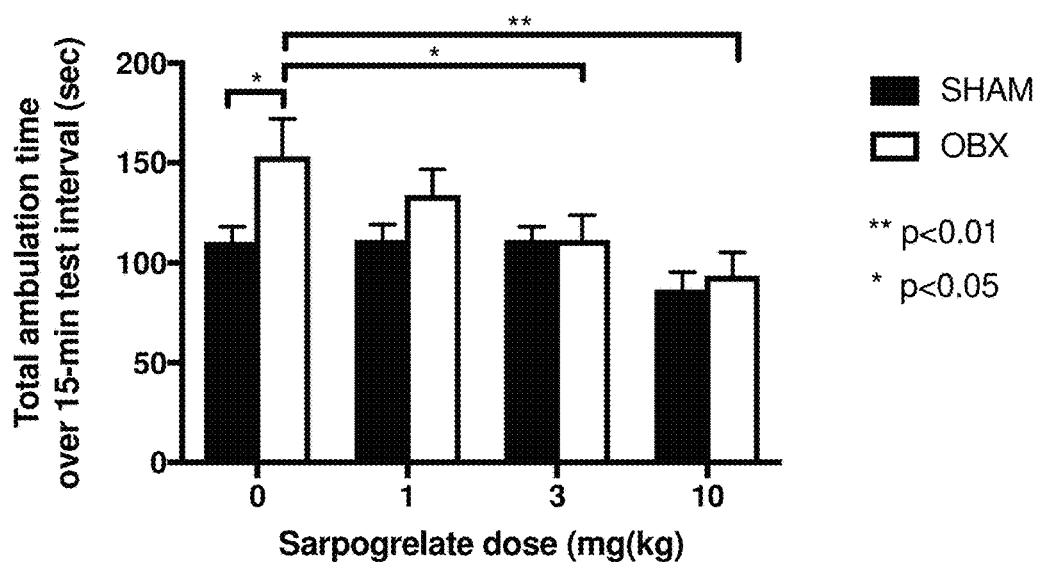

FIG. 8: Effects of sarpogrelate on motor activity in rats after olfactory bulbectomy (OBX) or sham surgery (SHAM). Data are presented as mean (±SEM) average activity over a 5-min test session. N=12 per group.

Figure 9:
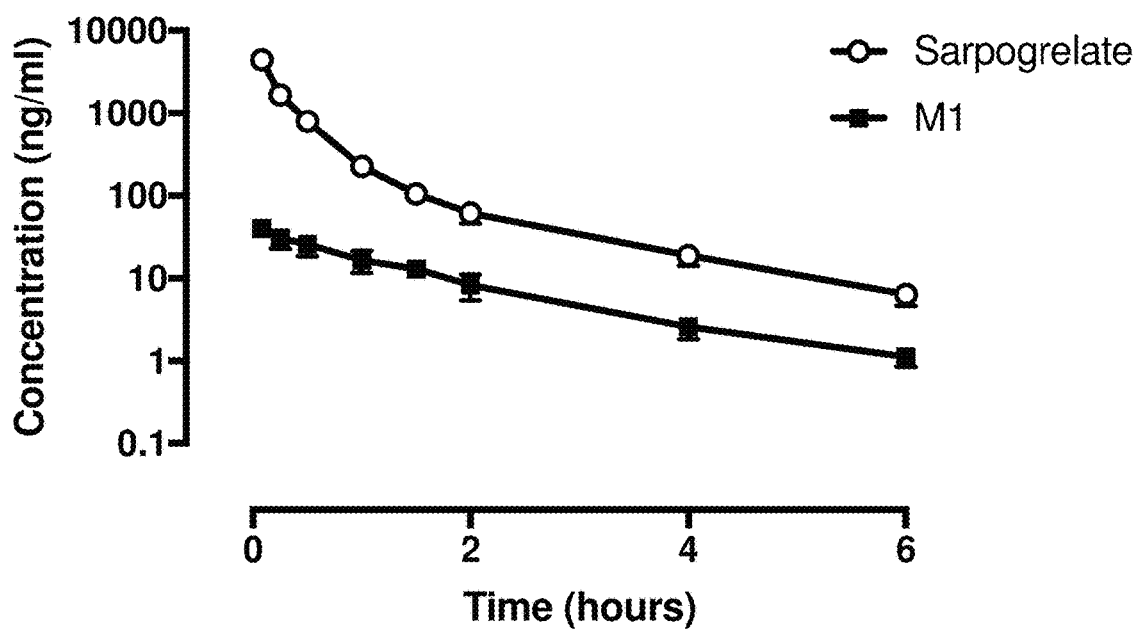

FIG. 9: Plasma level curves of sarpogrelate and M1 in male Wistar rats after single intravenous administrations of sarpogrelate hydrochloride (2 mg/kg). Data are presented as mean (±SD) concentration (ng/ml). N=4.

Figure 10:
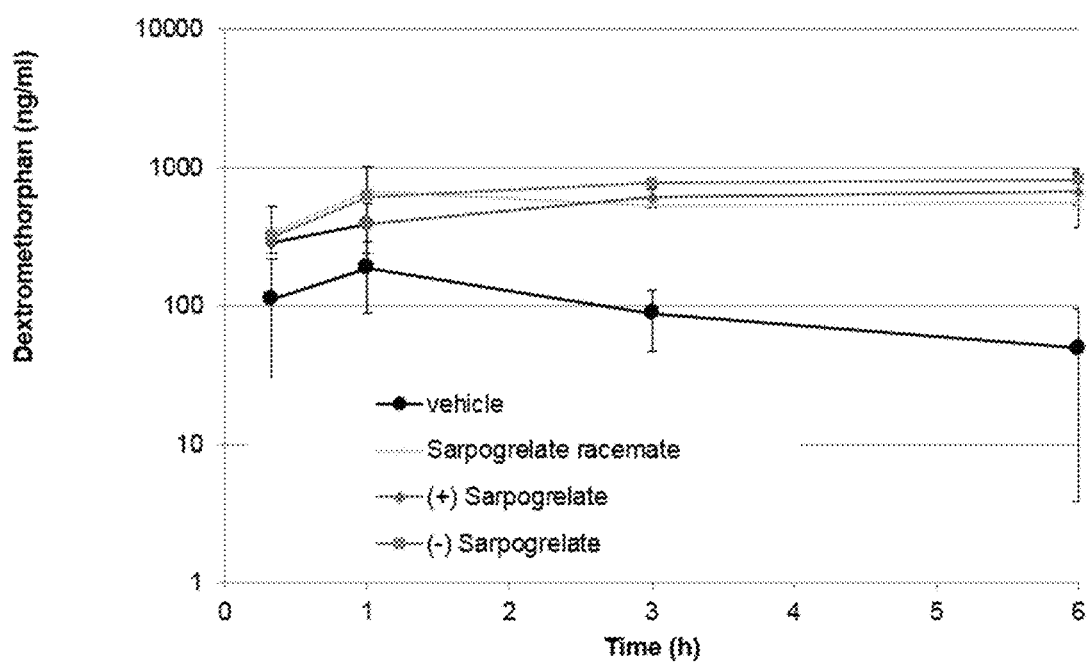

FIG. 10: Plasma level curves of dextromethorphan in male Wistar rats that received dextromethorphan (50 mg/kg, per os) immediately followed by intravenous bolus injection of sarpogrelate (1, 3 or 10 mg/kg; racemate or one of the enantiomers) or vehicle via vascular access port at t=0 h. Data are presented as mean (±SD) concentration (ng/ml). N=2-3.

Figure 11:
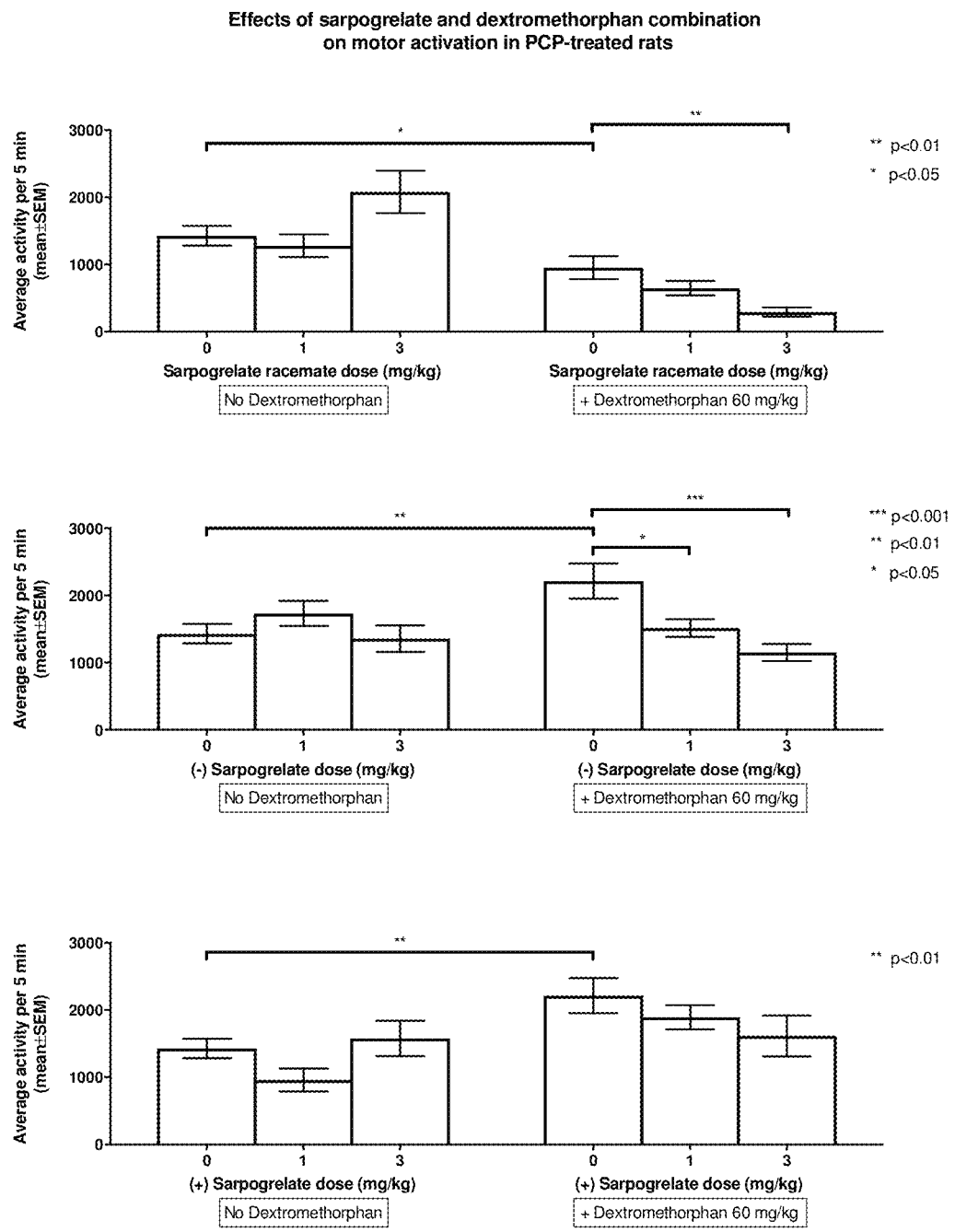

FIG. 11: Effects of a combination of dextromethorphan with sarpogrelate racemate (upper panel), (−) sarpogrelate (middle panel) or (+) sarpogrelate on PCP-induced hyperactivity in rats.

Figure 12:
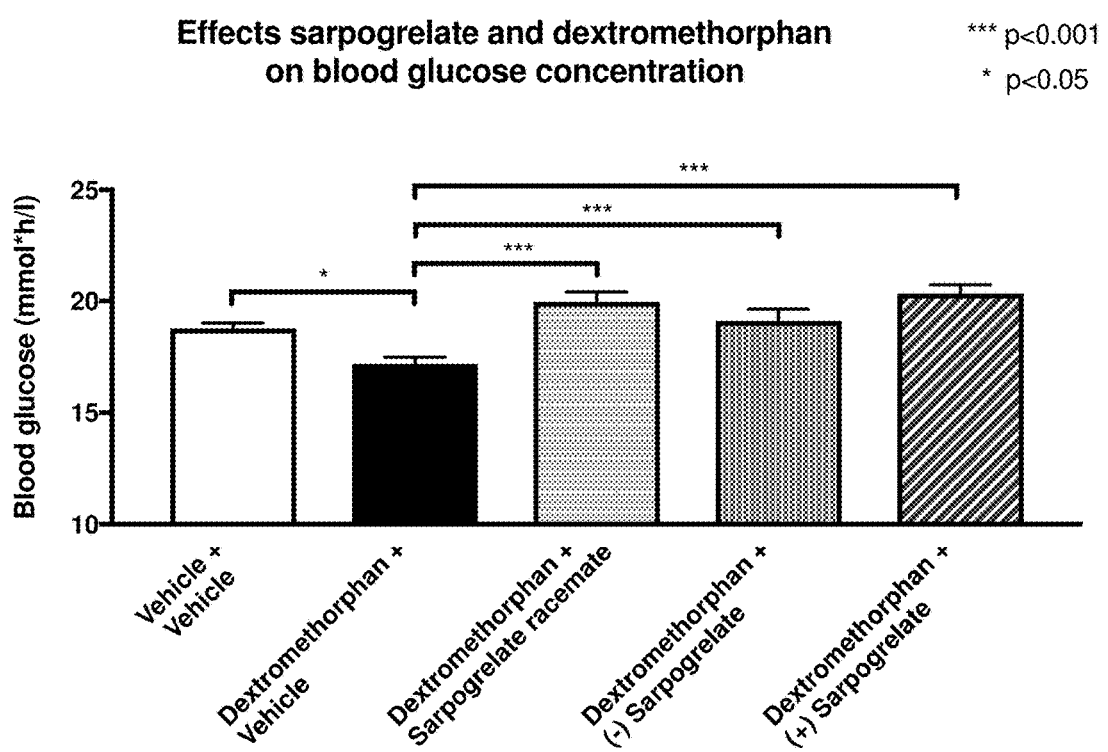

FIG. 12: Effects of dextromethorphan and sarpogrelate racemate on blood glucose level. Data are presented as area under the curve (mean±SEM) for blood glucose level over the period of time 30-180 min after oral glucose (2 g/kg) challenge. N=8 per group.

ABBREVIATIONS AND DEFINITION OF TERMS

The term "antagonist" is an agent that reduces the effect of an agonist by preventing it from binding to receptors. A neutral antagonist has no activity in the absence of an agonist or inverse agonist but can block the activity of either.

The term "inverse agonist" is an agent that binds to the same receptor as an agonist but typically have the opposite effect on the target cell and inhibit the spontaneous receptor agonist-independent activity. The main pharmacological effect of inverse agonists is receptor antagonism.

Both antagonists and inverse agonists reduce the activity of a receptor. In the present context, antagonist and inverse agonist are used interchangeably.

The term "dual agent" in the present specification is defined as an agent that acts as an inhibitor or antagonist against two different target receptors or enzymes. In the present context, compounds of Formula I and derivatives thereof are dual agents having activity against 5-HT2A receptor and CYP2D6, represented by sarpogrelate (Compound 50), its enantiomers (Compound 51 and Compound 52), and its metabolites.

The term SGL represents Sarpogrelate racemate or pharmaceutically acceptable salts thereof.

The term SGL-E1 represents (R) sarpogrelate or pharmaceutically acceptable salts thereof.

The term SGL-E2 represents (S) sarpogrelate or pharmaceutically acceptable salts thereof.

The term M1 represents Sarpogrelate racemate metabolite 1 or pharmaceutically acceptable salts thereof.

The term M1-E1 represents (R) sarpogrelate metabolite 1 or pharmaceutically acceptable salts thereof.

The term M1-E2 represents (S) sarpogrelate metabolite 1 or pharmaceutically acceptable salts thereof.

Glucuronide (Glu) of a drug is as shown below.

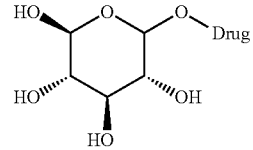

Glucuronidation is a major pathway of xenobiotic biotransformation in most mammalian species for the formation of water-soluble substrates, and requires the cofactor uridine diphosphate-glucuronic acid and is one of the most important reactions for the elimination of xenobiotics from the body and involves the reaction of uridine 5'-diphosphoglucuronic acid, The site of glucuronidation is generally an electron-rich nucleophilic heteroatom (oxygen, nitrogen, or sulfur) such as R—OH, R—NH$_2$, R—COOH, RSH, and others. The glucuronidation of many drugs in human liver is also stereo- and enantioselective.

The term SG1 represents sarpogrelate glucuronide 1 or pharmaceutically acceptable salts thereof.

The term SG2 represents sarpogrelate glucuronide 2 or pharmaceutically acceptable salts thereof.

The term SMG1 represents sarpogrelate metabolite glucuronide 1 or pharmaceutically acceptable salts thereof.

The term SMG2 represents sarpogrelate metabolite glucuronide 2 or pharmaceutically acceptable salts thereof.

The term SMG3 represents sarpogrelate metabolite glucuronide 3 or pharmaceutically acceptable salts thereof.

The term DEX represents one or more compounds selected from the group consisting of Formula II, dextromethorphan (DEX-H$_3$), enantiomers thereof, metabolites thereof, derivatives thereof, deuterated derivatives thereof, prodrugs thereof, pharmaceutically acceptable salts, N-oxides thereof, or a combination thereof. Metabolites include, but not limited to, dextrorphan (DO), 3-hydroxymorphinan (HYM), and 3-methoxymorphinan (MEM). Deuterated derivatives include, but not limited to, DEX-D$_3$, and DO-D$_3$.

include, but not limited to, salts derived from all stable forms of inorganic bases include aluminum, ammonium, calcium, copper, iron, lithium, magnesium, manganese, potassium, sodium, zinc, etc., and salts derived from pharmaceutically acceptable organic non-toxic bases include salts of primary, secondary, tertiary amines, and substituted amines including naturally occurring substituted amines, cyclic amines and basic ion-exchange resins such as arginine, betaine, caffeine, choline, N,N dibenzylethylenediamine, diethylamine, 2-di-

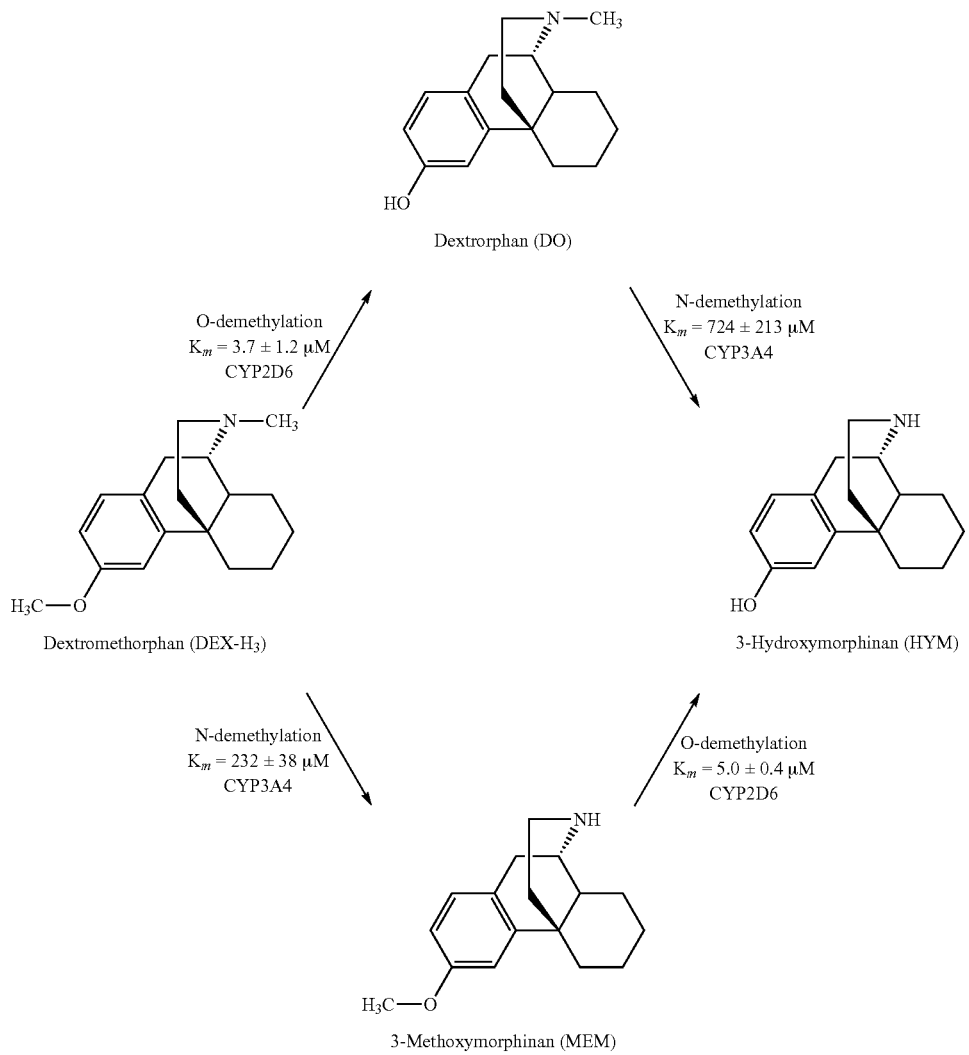

The term "pharmaceutically acceptable salts" refers to salts prepared from pharmaceutically acceptable non-toxic acids when the pharmaceutically active compound of the present invention is basic, or salts prepared from pharmaceutically acceptable non-toxic bases when the pharmaceutically active compound of the present invention is acidic. Pharmaceutically acceptable organic and inorganic acid salts include, but not limited to, salts formed with acids such as acetic, benzenesulfonic, benzoic, camphorsulfonic, citric, ethane-sulfonic, fumaric, gluconic, glutamic, hydrobromic, hydrochloric, isethionic, lactic, maleic, mandelic, methanesulfonic, mucic, nitric, pamoic, pantothenic, phosphoric, succinic, sulfuric, tartaric, p-toluenesulfonic, etc. Salts may be prepared from pharmaceutically acceptable non-toxic bases. Pharmaceutically acceptable non-toxic basic salts ethylaminoethanol, 2-dimethylaminoethanol, ethanolamine, ethylenediamine, N-ethylmorpholine, N-ethylpiperidine, glucamine, glucosamine, histidine, isopropylamine, lysine, methyl-glucosamine, morpholine, piperazine, piperidine, polyamine resins, procaine, purine, theobromine, triethylamine, trimethylamine, tripropylamine, etc.

Positron Emission Tomography (PET) is a non-invasive imaging method that provides high resolution (2-3 mm) and quantitative information on specific target areas. PET requires a radioligand labeled with a positron emitting nuclide, typically $^{11}$C ($t_{1/2}$=20 min) or $^{18}$F ($t_{1/2}$=110 min).

The term SARPO represents one or more compounds selected from the group consisting of a compound of Formula I, sarpogrelate (SGL), enantiomers thereof, a derivative thereof, a deuterated derivative thereof, a prodrug thereof, a metabolite thereof M1, SG1, SG2, SMG1, SMG2, SMG3; or a combination thereof.

The term SARPODEX™ represents a combination of DEX and SARPO, as defined above.

The term SARPODEXTER™ represents an ester of SGL and DO.

The term SARPODEXAMIDE™ represents an amide of SGL and MEM.

DETAILED DESCRIPTION OF THE INVENTION

An embodiment of the invention is a composition comprising a compound having a formula I:

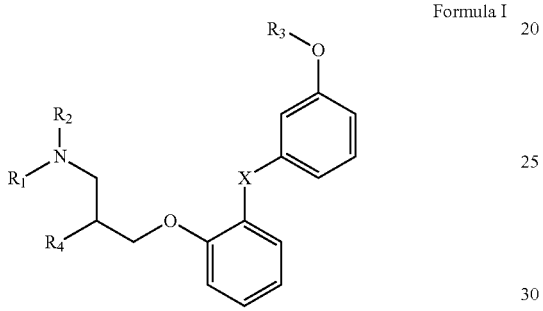

Formula I

Wherein:

$R_1$, $R_2$, and $R_3$ are H, substituted or unsubstituted $C_{1-10}$ alkyl, (halo)$_n$-$C_{1-10}$-alkyl, substituted or unsubstituted $C_{3-10}$ cycloalkyl, substituted or unsubstituted $C_{5-10}$ aryl, substituted or unsubstituted $C_{5-10}$ heteroaryl, or glucuronide (Glu); or $R_1$ and $R_2$ together with the nitrogen form a saturated or unsaturated heterocycle having one or more hetero atoms selected from N, O, and S; wherein halogen is F, Cl, or Br, and n is an integer from 1 to 12 X is a bond, $C_{1-10}$ alkyl, $C_{3-10}$ cycloalkyl, $C_{5-10}$ aryl, —CO—$C_{1-10}$ alkyl, —CO—$C_{3-10}$ cycloalkyl, —COC$_{5-10}$ aryl, CO—$C_{5-10}$ heteroaryl, —CO—NH—$C_{1-10}$ alkyl, —CO—NH—$C_{3-10}$ cycloalkyl, —CO—NH—$C_{5-10}$ aryl, or —CO—NH—$C_{5-10}$ heteroaryl;

$R_4$ is NH—$R_5$, S—$R_5$, —OH, O—$R_5$, —CO—$R_5$, —O—CO—$R_5$, or —CO—O—$R_5$, wherein $R_5$ is an acyl radical, hydrogen, or Glu; or $R_5$ and $R_2$ form a heterocycle; or enantiomers thereof, metabolites thereof, derivatives thereof, deuterated derivatives thereof, prodrugs thereof, pharmaceutically acceptable salts, N-oxides thereof, or a combination thereof.

In another embodiment, the compound is a compound of Formula I wherein R5 is an acyl radical selected from the group consisting of mono, di, and tri carboxylic acid radicals.

In another embodiment, the compound is a compound of Formula I wherein R5 is an acyl radical selected from the group consisting of acetate, acetyl salicylate, adipate, butyrate, caprate, caproate, caprylate, enanthate, formate, glutarate, isophthallate, maleate, malonate, oxalate, pelargonate, pimelate, propionate, phthallate, salicilate, sebacate, succinate, terephthallate, tyrosine, tryptophanate, and valerate.

Another embodiment is a compound of Formula II,

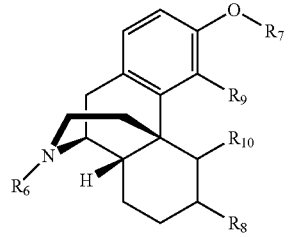

Formula IIa

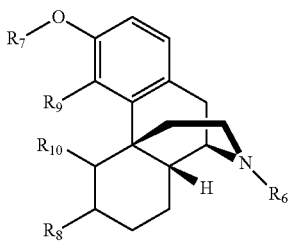

Formula IIb

Wherein, $R_6$, $R_7$, and $R_8$ are independently H, D, substituted or unsubstituted $C_{1-10}$-alkyl, (halo)$_n$$C_{1-10}$-alkyl, wherein halogen is F, Cl, or Br, and n is an integer from 1 to 12;

$R_9$ and $R_{10}$ are independently H; $C_{1-10}$-alkyl; (halo)$_n$-$C_{1-10}$-alkyl wherein halogen is F, Cl, or Br, and n is an integer from 1 to 12; OH; or $R_9$ and $R_{10}$ together form a five-membered heterocycle wherein the hetero atom is O, S, or N.

Another embodiment is a compound of formula I, wherein $R_5$ and $R_2$ form a heterocycle selected from the radicals such as morpholine, dihydrooxazine, oxazine, piperazine, dihydropiperzine, and tetrahydropirazine. Compounds of this embodiment include, but not limited to, the following compounds 10-24:

Compound 10

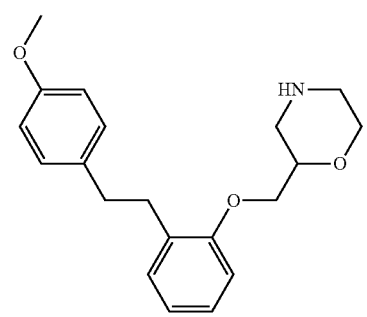

Compound 11

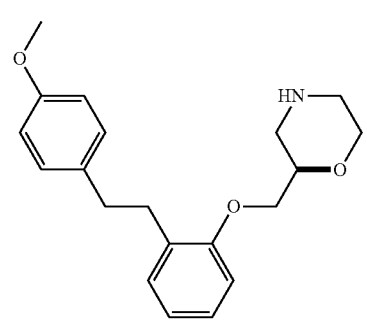

Compound 12
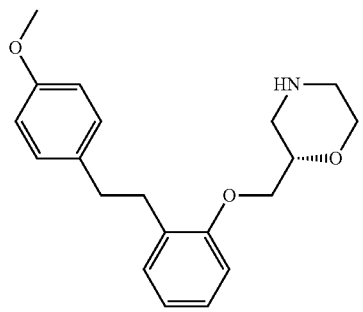
Compound 13
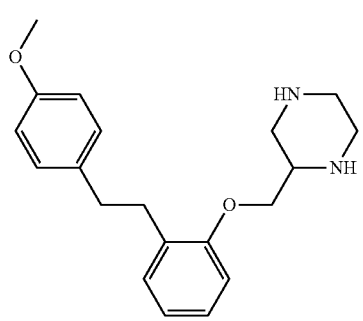
Compound 14
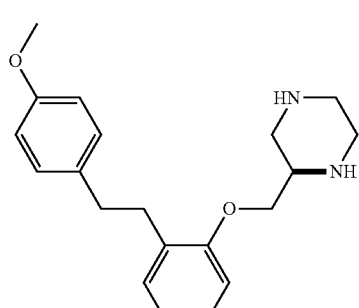
Compound 15
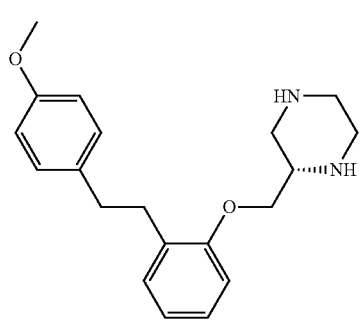
Compound 16
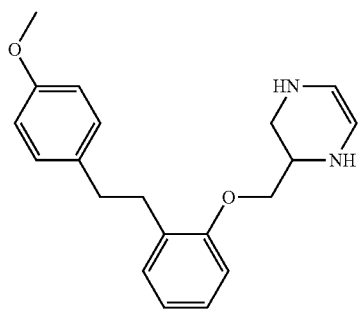
Compound 17
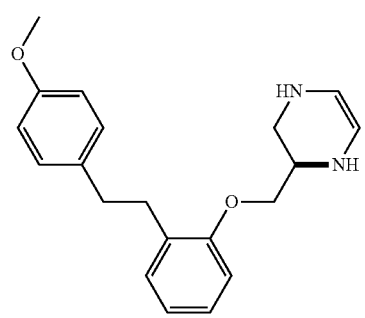
Compound 18
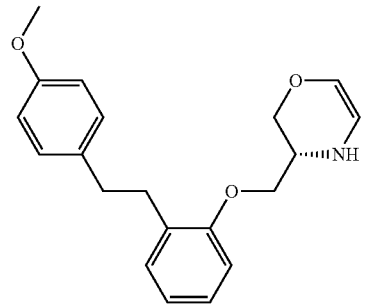
Compound 19
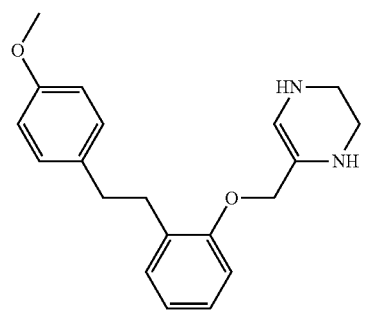
Compound 20

Compound 21

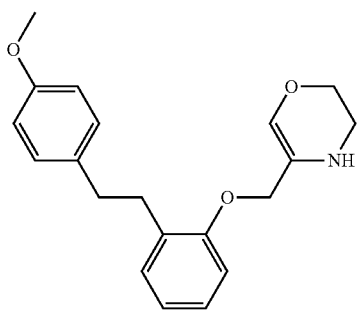

Compound 22

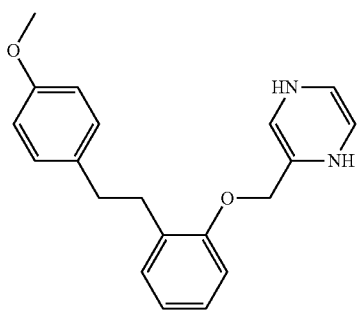

Compound 23

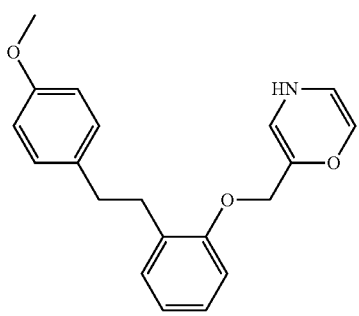

Compound 24

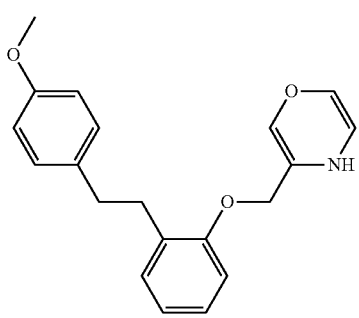

Another embodiment is a pure enantiomer of formula I selected from Formula Ia or Ib.

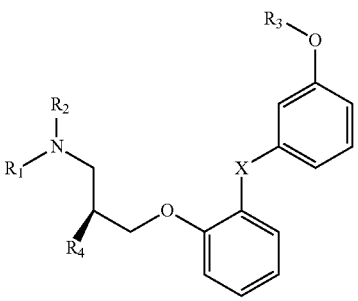

Pure Enantiomer

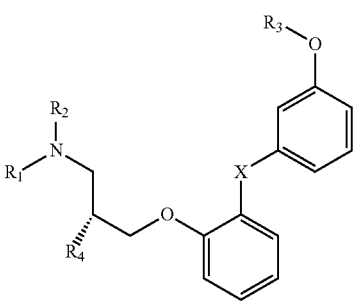

Pure Enantiomer

In another embodiment, the compound of formula I, wherein $R_1$, $R_2$, and $R_3$ are methyl, provided X is not ethyl.

In another embodiment, the composition comprises a compound of formula I, wherein $R_1$, $R_2$, and $R_3$ are methyl, X is ethyl, $R_4$ is $OR_5$, and $R_5$ is succinoyl radical. The compounds of formula I of this embodiment include SGL, SGL-E1, and SGL-E2.

In another embodiment, the composition comprises a compound of formula I, wherein $R_1$, $R_2$, and $R_3$ are methyl, X is ethyl, and $R_4$ is OH. The compounds of Formula I of this embodiment include M1, M1-E1, and M1-E2.

In another embodiment, the composition comprising formula I, wherein $R_1$ and $R_2$ together with the nitrogen form a saturated or unsaturated heterocycle having one or more hetero atoms selected from N, O, and S; and $R_3$ is methyl, X is ethyl, and $R_4$ is OH. In another embodiment, the heterocycle is a five-membered ring. Another embodiment is where the heterocycle is a six-membered ring. In another embodiment, the heterocycle is saturated. Another embodiment has the unsaturated heterocycle. In one embodiment, the heterocycle has one hetero atom. In another, the heterocycle has two hetero atoms.

In another embodiment, the compound of formula I, wherein the heterocycle formed from $R_1$ and $R_2$ together with the nitrogen is selected from the heterocycles listed below:

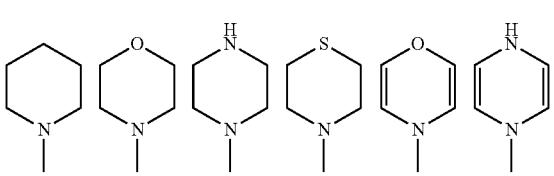

-continued

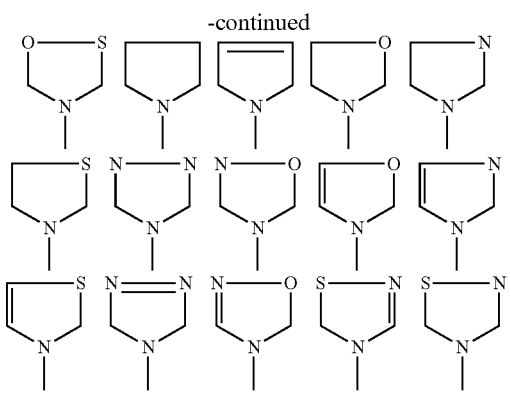

An embodiment of the invention is a composition comprising a compound of formula I, wherein $R_5$ is not citrate radical.

An embodiment of the invention is a composition comprising a compound of formula I and dextromethorphan.

An embodiment of the invention is a composition comprising a compound of formula I and DEX-H$_3$, DEX-D$_3$, DO, or DO-D$_3$.

An embodiment of the invention is a composition comprising: M1, M1-E1, M1-E2, SGL, SGL-E1, or SGL-E2; and DEX-H3, DEX-D3, DO, or DO-D3.

Another embodiment of the invention is a composition comprising a compound of Formula I and a compound of Formula II. Another embodiment of the invention is a composition comprising a compound of Formula I and a compound of Formula IIa or IIb.

Another embodiment of the invention is a composition comprising a compound of Formula I and a compound of Formula IIa.

Another embodiment is a composition comprising a compound of formula I, and at least one compound selected from thioridazine, perphenazine, fluphenazine, haloperidol, zuclopenthixol, risperidone, sertindole, nortriptyline, amitriptyline, imipramine, fluoxetine, paroxetine, ajmaline, amiodarone, amitriptyline, aprindine, azelastine, celecoxib, chlorpheniramine, chlorpromazine, diphenhydramine, doxorubicin, fluphenazine, fluvastatin, haloperidol, imipramine, indinavir, lasoprazole, levomepromazine, lopinavir, loratadine, mequitazine, methadone, metoclopramide, mibefradil, moclobemide, nelfinavir, nevirapine, nicardipine, norfluoxetine, perphenazine, pimozide, terfenadine, thioridazine, cimetidine, quinidine, cisapride, citalopram, clozapine, cocaine, desipramine, ranitidine, risperidone, ritonavir, saquinavir, sertraline, terbinafine, ticlopidine, trifluperidol, yohimbine, clomipramine, doxepin, mianserin, imipramine, 2-chloroimipramine, amitriptyline, amoxapine, protriptyline, trimipramine, nortriptyline, maprotiline, phenelzine, isocarboxazid, tranylcypromine, trazodone, citalopram, sertraline, aryloxy indanamine, benactyzine, escitalopram, fluvoxamine, venlafaxine, desvenlafaxine, duloxetine, mirtazapine, nefazodone, selegiline, sibutramine, milnacipran, tesofensine, brasofensine, moclobemide, rasagiline, nialamide, iproniazid, iproclozide, toloxatone, butriptyline, dosulepin, dibenzepin, iprindole, lofepramine, opipramol, and dapoxetine.

An embodiment of the invention is a composition comprising a compound of formula I, DEX, and at least one compound selected from thioridazine, perphenazine, fluphenazine, haloperidol, zuclopenthixol, risperidone, sertindole, nortriptyline, amitriptyline, imipramine, fluoxetine, paroxetine, ajmaline, amiodarone, amitriptyline, aprindine, azelastine, celecoxib, chlorpheniramine, chlorpromazine, diphenhydramine, doxorubicin, fluphenazine, fluvastatin, haloperidol, imipramine, indinavir, lasoprazole, levomepromazine, lopinavir, loratadine, mequitazine, methadone, metoclopramide, mibefradil, moclobemide, nelfinavir, nevirapine, nicardipine, norfluoxetine, perphenazine, pimozide, terfenadine, thioridazine, cimetidine, quinidine, cisapride, citalopram, clomipramine, clozapine, cocaine, ranitidine, risperidone, ritonavir, saquinavir, sertraline, terbinafine, ticlopidine, trifluperidol, yohimbine, doxepin, mianserin, imipramine, 2-chloroimipramine, amitriptyline, amoxapine, desipramine, protriptyline, trimipramine, nortriptyline, maprotiline, phenelzine, isocarboxazid, tranylcypromine, trazodone, citalopram, sertraline, aryloxy indanamine, benactyzine, escitalopram, fluvoxamine, venlafaxine, desvenlafaxine, duloxetine, mirtazapine, nefazodone, selegiline, sibutramine, milnacipran, tesofensine, brasofensine, moclobemide, rasagiline, nialamide, iproniazid, iproclozide, toloxatone, butriptyline, dosulepin, dibenzepin, iprindole, lofepramine, opipramol, and dapoxetine.

In the above embodiment of the invention, the compound of formula I is M1, M1-E1, M1-E2, SGL, SGL-E1, or SGL-E2.

In the above embodiment of the invention, the compound of formula I is M1, M1-E1, M1-E2, SGL, SGL-E1, or SGL-E2; and DEX is DEX-H3.

In another embodiment, a compound of formula I or sarpogrelate analogs made using the following carboxylic acids:

TABLE 1

| Carboxylic Acid | Compound |
|---|---|
| Malic Acid HO$_2$C—CH$_2$—CH(OH)—CO$_2$H | Compounds 25-29 |
| Methionine H$_3$C—S—(CH$_2$)$_2$—CH(NH$_2$)—CO$_2$H | Compounds 30-34 |
| Phthallic Acid C$_6$H$_4$(CO$_2$H)$_2$ | Compounds 35-37 |
| Malonic Acid HO$_2$C—CH$_2$—CO$_2$H | Compounds 38-40 |
| Tyrosine HO—C$_6$H$_4$—CH$_2$—CH(NH$_2$)—CO$_2$H | Compounds 41-43 |
| Tryptophan C$_8$H$_6$N—CH$_2$—CH(NH$_2$)—CO$_2$H | Compounds 44-46 |
| Maleic Acid HO$_2$C—CH=CH—CO$_2$H | Compounds 47-49 |
| Succinic Acid HO$_2$C—(CH$_2$)$_2$—CO$_2$H | Compounds 50-52 |
| Glutaric acid HO$_2$C—(CH$_2$)$_3$—CO$_2$H | Compounds 53-55 |
| Adipic Acid HO$_2$C—(CH$_2$)$_4$—CO$_2$H | Compounds 56-58 |
| Pimelic acid HO$_2$C—(CH$_2$)$_5$—CO$_2$H | Compounds 59-61 |
| Sebacic acid HO$_2$C—(CH$_2$)$_6$—CO$_2$H | Compounds 62-64 |
| Formic acid HCO$_2$H | Compounds 65-67 |
| Acetic acid CH$_3$CO$_2$H | Compounds 68-70 |
| Propionic acid CH$_3$CH$_2$CO$_2$H | Compounds 71-73 |
| Butyric acid CH$_3$(CH$_2$)$_2$CO$_2$H | Compounds 74-76 |
| Valeric acid CH$_3$(CH$_2$)$_3$CO$_2$H | Compounds 77-79 |
| Caproic acid CH$_3$(CH$_2$)$_4$CO$_2$H | Compounds 80-82 |
| Enanthic acid CH$_3$(CH$_2$)$_5$CO$_2$H | Compounds 83-85 |
| Caprylic acid CH$_3$(CH$_2$)$_6$CO$_2$H | Compounds 86-88 |
| Pelargonic acid CH$_3$(CH$_2$)$_7$CO$_2$H | Compounds 89-91 |
| Capric acid CH$_3$(CH$_2$)$_8$CO$_2$H | Compounds 92-94 |
| Oxalic Acid HO—CO—CO$_2$H | Compounds 95-97 |
| Isophthallic Acid C$_6$H$_4$(CO$_2$H)$_2$ | Compounds 98-100 |
| Terephthallic Acid C$_6$H$_4$(CO$_2$H)$_2$ | Compounds 101-103 |
| Salicilic Acid HO—C$_6$H$_4$—CO$_2$H | Compounds 104-106 |
| Acetyl Salicilic Acid CH$_3$—CO—O—C$_6$H$_4$—CO$_2$H | Compounds 107-109 |

An embodiment of the invention is a compound of formula I, wherein the compound is selected from the group consisting of compounds 25 to 49 and 53 to 109; or enantiomers thereof, metabolites thereof, derivatives thereof, deuterated derivatives thereof, prodrugs thereof, pharmaceutically acceptable salts, N-oxides thereof, or a combination thereof.

An embodiment of the invention is a compound of formula I, wherein the compound is selected from the group consisting of compounds 25 to 49 and 53 to 109, and a compound of Formula II; or enantiomers thereof, metabolites thereof, derivatives thereof, deuterated derivatives thereof, prodrugs thereof, pharmaceutically acceptable salts, N-oxides thereof, or a combination thereof.

An embodiment of the invention is a compound of formula I, wherein the compound is sarpomalate, wherein $R_1$, $R_2$, and $R_3$ are methyl, X is ethyl, and $R_4$ is malate; compounds 25-29; or enantiomers thereof, metabolites thereof, derivatives thereof, deuterated derivatives thereof, prodrugs thereof, pharmaceutically acceptable salts, N-oxides thereof, or a combination thereof.

An embodiment of the invention is a compound of formula I, wherein the compound is sarpomethionate, wherein $R_1$, $R_2$, and $R_3$ are methyl, X is ethyl, and $R_4$ is methionate; compounds 30-34; or enantiomers thereof, metabolites thereof, derivatives thereof, deuterated derivatives thereof, prodrugs thereof, pharmaceutically acceptable salts, N-oxides thereof, or a combination thereof.

An embodiment of the invention is a compound of formula I, wherein the compound is sarpophthallate, wherein $R_1$, $R_2$, and $R_3$ are methyl, X is ethyl, and $R_4$ is phthalate; compounds 35-37; or enantiomers thereof, metabolites thereof, derivatives thereof, deuterated derivatives thereof, prodrugs thereof, pharmaceutically acceptable salts, N-oxides thereof, or a combination thereof.

An embodiment of the invention is a compound of formula I, wherein the compound is sarpomalonate, wherein $R_1$, $R_2$, and $R_3$ are methyl, X is ethyl, and $R_4$ is malonate compounds 38-40; or enantiomers thereof, metabolites thereof, derivatives thereof, deuterated derivatives thereof, prodrugs thereof, pharmaceutically acceptable salts, N-oxides thereof, or a combination thereof.

An embodiment of the invention is a compound of formula I, wherein the compound is sarpotyrosinate, wherein $R_1$, $R_2$, and $R_3$ are methyl, X is ethyl, and $R_4$ is tyrosinate; compounds 41-43; or enantiomers thereof, metabolites thereof, derivatives thereof, deuterated derivatives thereof, prodrugs thereof, pharmaceutically acceptable salts, N-oxides thereof, or a combination thereof.

An embodiment of the invention is a compound of formula I, wherein the compound is sarpotryptophanate, wherein $R_1$, $R_2$, and $R_3$ are methyl, X is ethyl, and $R_4$ is tryptophanate; Compounds 44-46; or enantiomers thereof, metabolites thereof, derivatives thereof, deuterated derivatives thereof, prodrugs thereof, pharmaceutically acceptable salts, N-oxides thereof, or a combination thereof.

In an embodiment, the composition is a combination of DEX and at least one compound selected from the group consisting of compounds 10-46, SGL, SGL-E1, SGL-E2, M1, M1-E1, and M1-E2; or enantiomers thereof, metabolites thereof, derivatives thereof, deuterated derivatives thereof, prodrugs thereof, pharmaceutically acceptable salts, N-oxides thereof, or a combination thereof.

An embodiment of the invention is a composition comprising a compound of formula I, wherein the compound is sarpogrelate, and dextromethorphan; or enantiomers thereof, metabolites thereof, derivatives thereof, deuterated derivatives thereof, prodrugs thereof, pharmaceutically acceptable salts, N-oxides thereof, or a combination thereof.

An embodiment of the invention is a composition comprising a compound of formula I, wherein the compound is sarpogrelate, and dextromethorphan, wherein sarpogrelate and dextromethorphan form diastereomeric mixture.

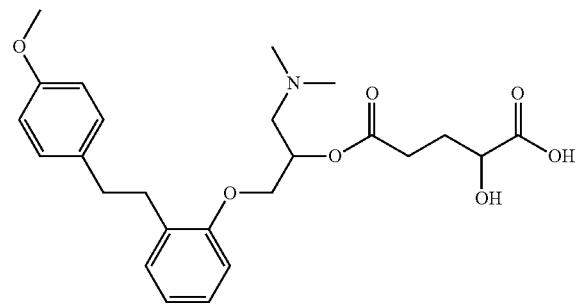

Compound 25


Compound 26

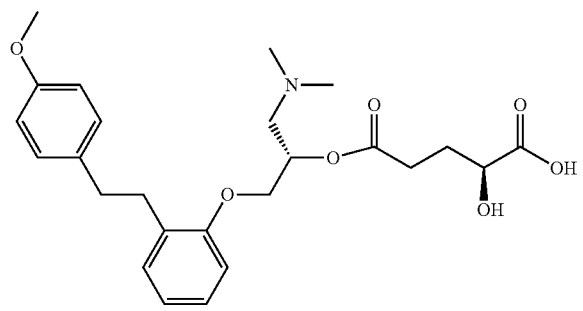

Compound 27

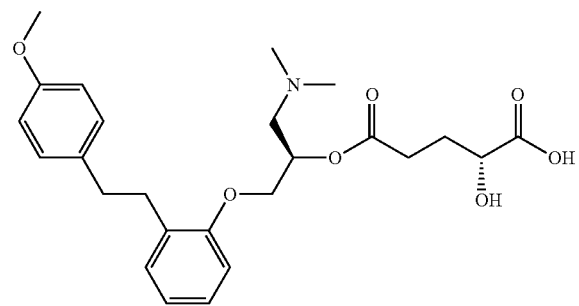

Compound 28

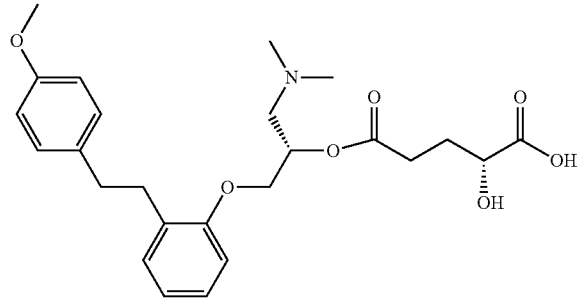

Compound 29

Compound 30
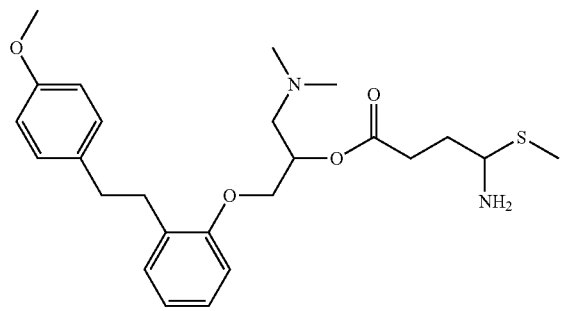

Compound 31
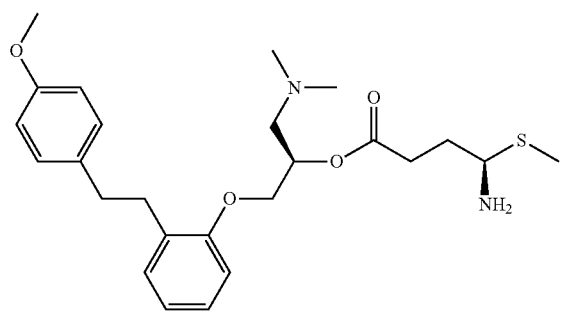

Compound 32
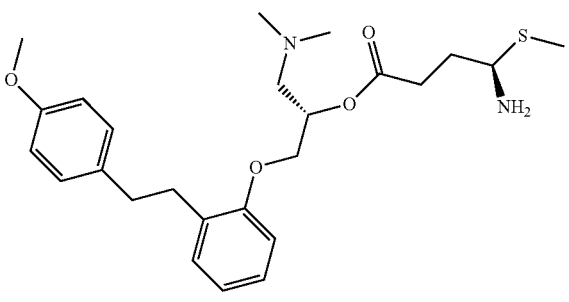

Compound 33
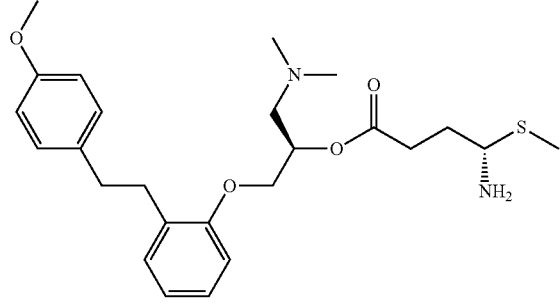

Compound 34
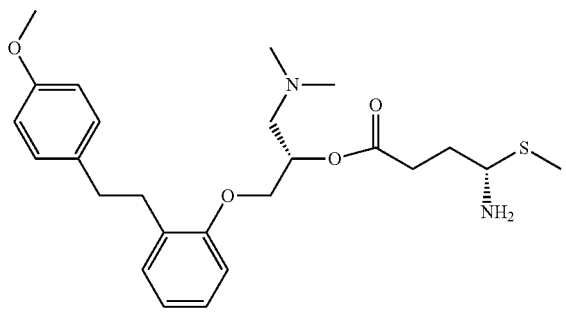

Compound 35
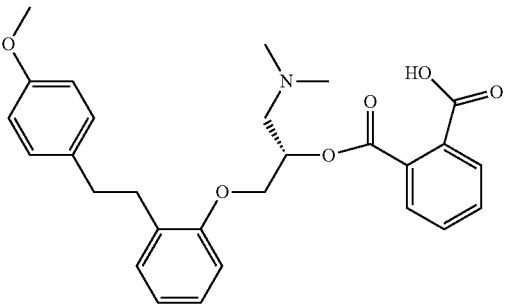

Compound 36
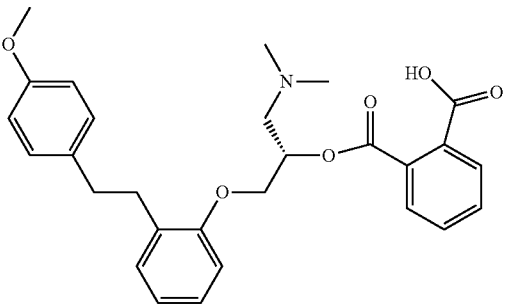

Compound 37
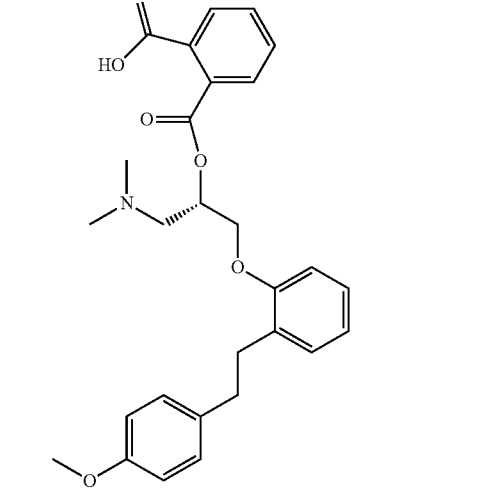

An embodiment of the invention is a composition comprising a compound of formula I, wherein the compound is sarpogrelate, and dextromethorphan, wherein sarpogrelate and dextromethorphan form a salt, wherein the salt is a diastereomeric mixture.

An embodiment of the invention is a composition comprising a compound of formula I, wherein the compound is sarpogrelate, and dextromethorphan, wherein sarpogrelate and dextromethorphan form a salt, wherein the salt is a pure diastereomer; or derivatives thereof, deuterated derivatives thereof, prodrugs thereof, pharmaceutically acceptable salts, N-oxides thereof, or a combination thereof.

An embodiment of the invention is a composition comprising a compound of formula I, wherein the compound is sarpogrelate metabolite M1, and dextromethorphan; or enantiomers thereof, metabolites thereof, derivatives thereof, deuterated derivatives thereof, prodrugs thereof, pharmaceutically acceptable salts, N-oxides thereof, or a combination thereof.

An embodiment of the invention is a composition comprising dextromethorphan and a compound of formula I, wherein the compound is sarpomalate, forming a salt comprising diastereomeric mixture or a pure diastereomer thereof; or derivatives thereof, deuterated derivatives thereof, prodrugs thereof, pharmaceutically acceptable salts, N-oxides thereof, or a combination thereof.

An embodiment of the invention is a composition comprising a compound of formula I, wherein the compound is sarpomethionate, and dextromethorphan, forming a salt comprising diastereomeric mixture or a pure diastereomer thereof; or derivatives thereof, deuterated derivatives thereof, prodrugs thereof, pharmaceutically acceptable salts, N-oxides thereof, or a combination thereof.

An embodiment of the invention is a composition comprising a compound of formula I, wherein the compound is sarpophthallate, and dextromethorphan, forming a salt comprising diastereomeric mixture or a pure diastereomer thereof; or derivatives thereof, deuterated derivatives thereof, prodrugs thereof, pharmaceutically acceptable salts, N-oxides thereof, or a combination thereof.

An embodiment of the invention is a composition comprising a compound of formula I, wherein the compound is sarpomalonate, and dextromethorphan, forming a salt comprising diastereomeric mixture or a pure diastereomer thereof; or derivatives thereof, deuterated derivatives thereof, prodrugs thereof, pharmaceutically acceptable salts, N-oxides thereof, or a combination thereof.

An embodiment of the invention is a composition comprising a compound of formula I, wherein the compound is sarpotyrosinate, and dextromethorphan, forming a salt comprising diastereomeric mixture or a pure diastereomer thereof; or derivatives thereof, deuterated derivatives thereof, prodrugs thereof, pharmaceutically acceptable salts, N-oxides thereof, or a combination thereof.

An embodiment of the invention is a composition comprising a compound of formula I, wherein the compound is sarpotryptophanate, and dextromethorphan, forming a salt comprising diastereomeric mixture or a pure diastereomer thereof; or derivatives thereof, deuterated derivatives thereof, prodrugs thereof, pharmaceutically acceptable salts, N-oxides thereof, or a combination thereof.

An embodiment of the invention is a composition comprising a compound of formula I, wherein the compound is SGL, and dextromethorphan HCl, forming a salt comprising diastereomeric mixture or a pure diastereomer thereof; or derivatives thereof, deuterated derivatives thereof, prodrugs thereof, pharmaceutically acceptable salts, N-oxides thereof, or a combination thereof.

An embodiment of the invention is a composition comprising a compound of formula I, wherein the compound is SGL, and dextromethorphan HBr, forming a salt comprising diastereomeric mixture or a pure diastereomer thereof; or derivatives thereof, deuterated derivatives thereof, prodrugs thereof, pharmaceutically acceptable salts, N-oxides thereof, or a combination thereof.

Compound 38

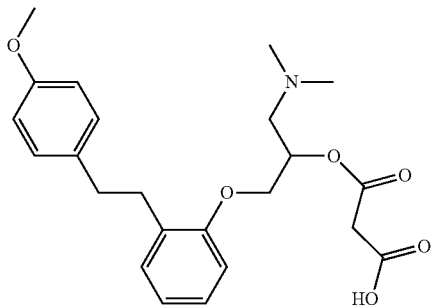

Compound 39

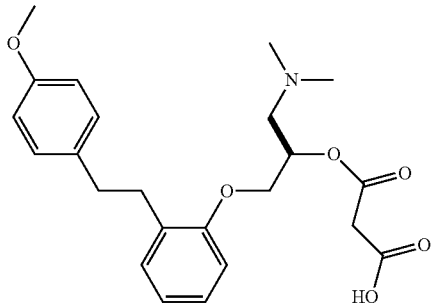

Compound 40

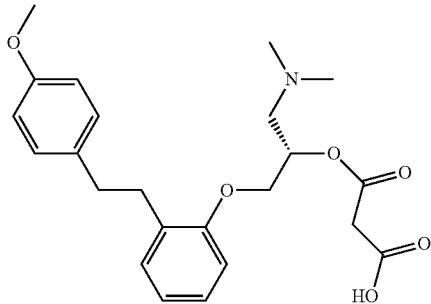

Compound 41

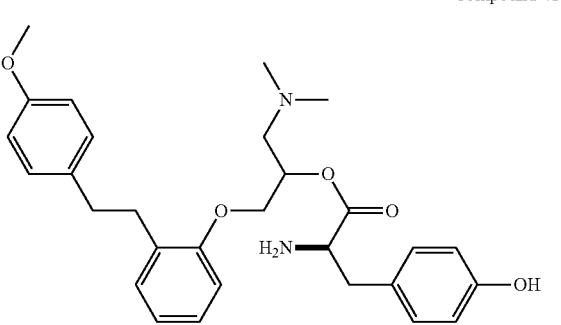

Compound 42

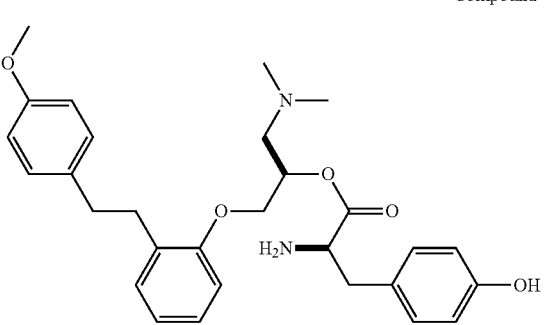

-continued
Compound 43
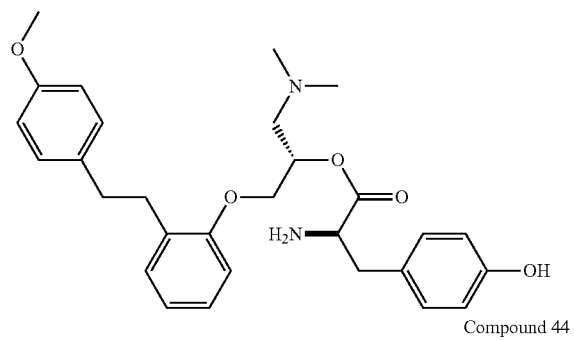
Compound 44
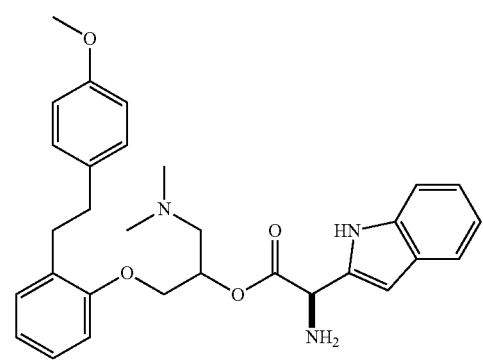
Compound 45
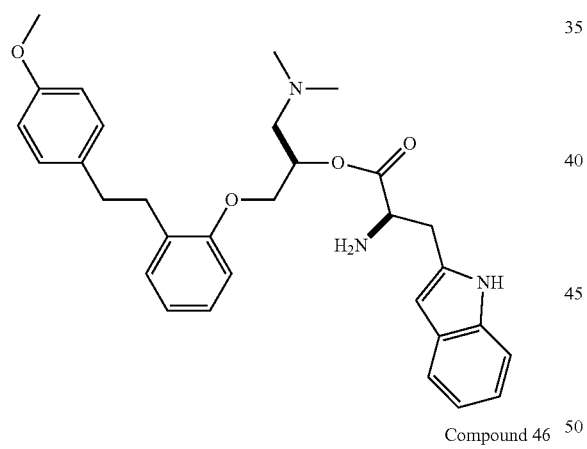
Compound 46
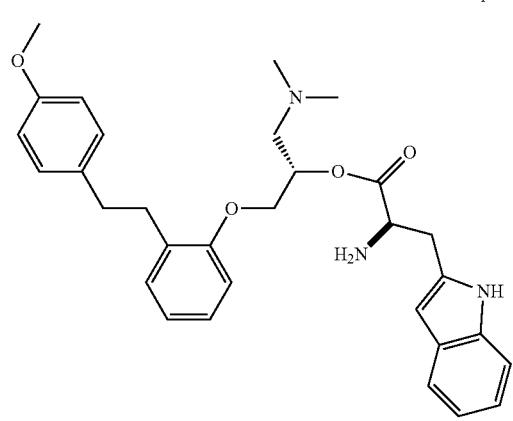
-continued
Compound 47
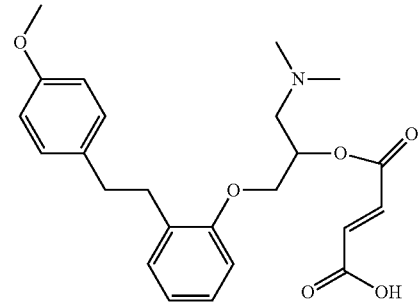
Compound 48
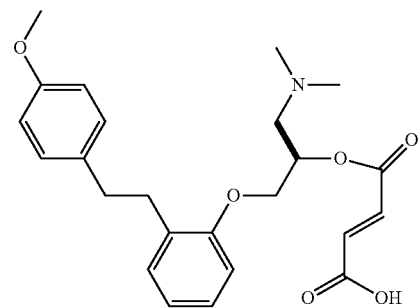
Compound 49
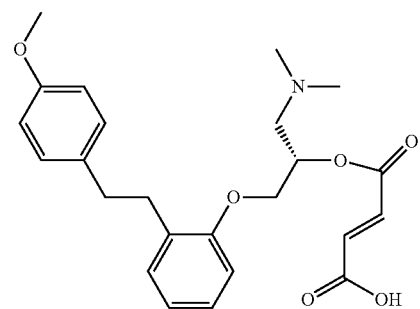
Compound 50
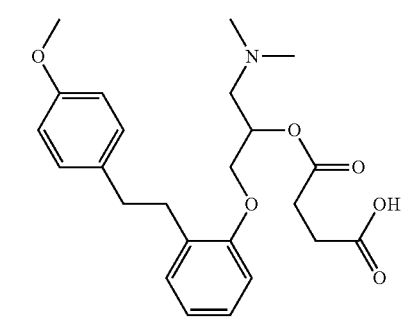
Compound 51

Compound 52
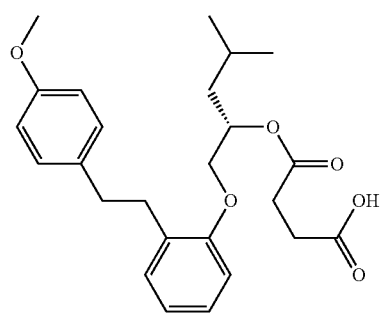
Compound 53
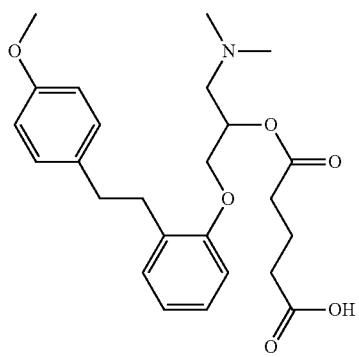
Compound 54
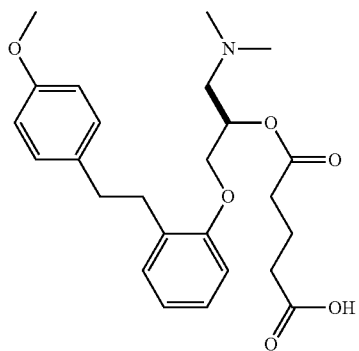
Compound 55
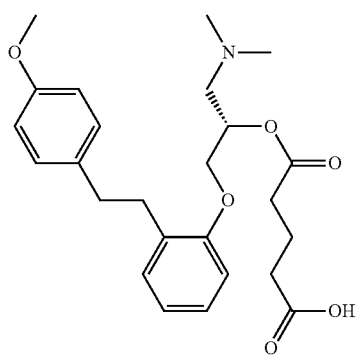
Compound 56
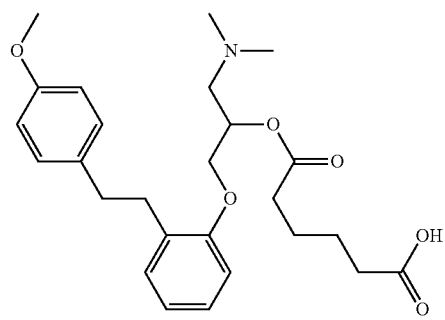
Compound 57
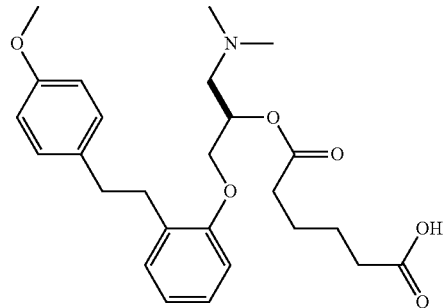
Compound 58
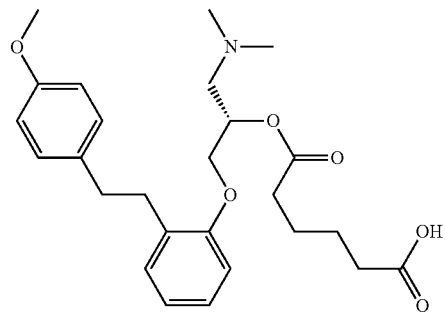
Compound 59
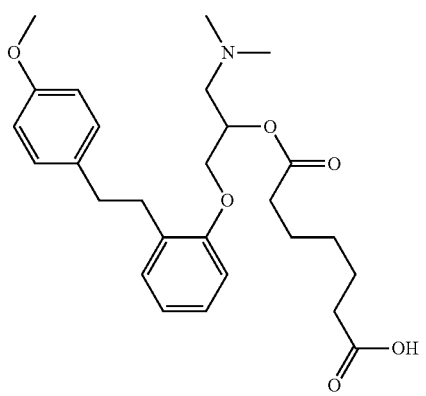

Compound 60
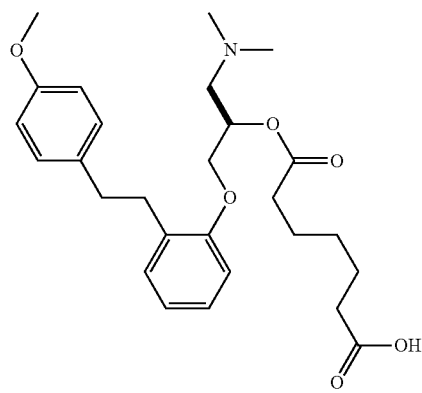
Compound 61
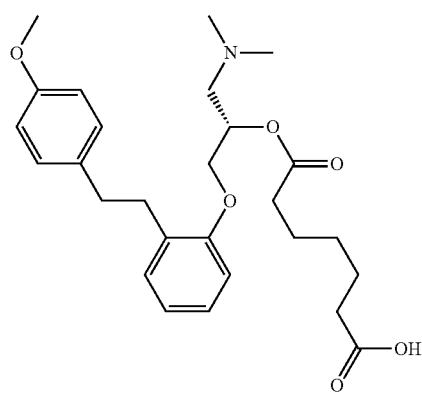
Compound 62
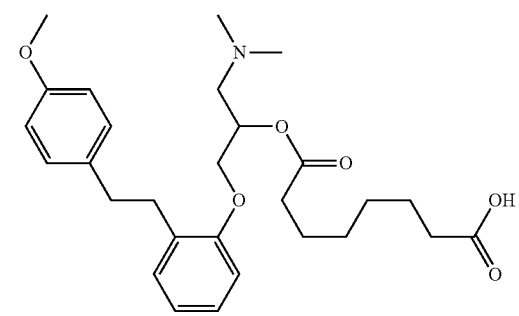
Compound 63
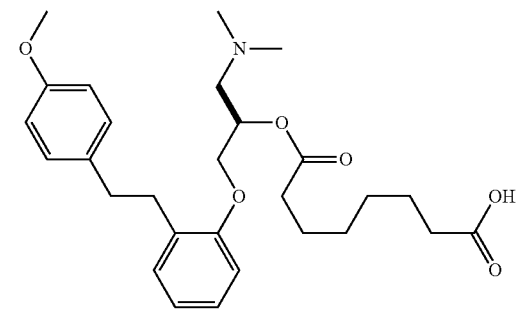
Compound 64
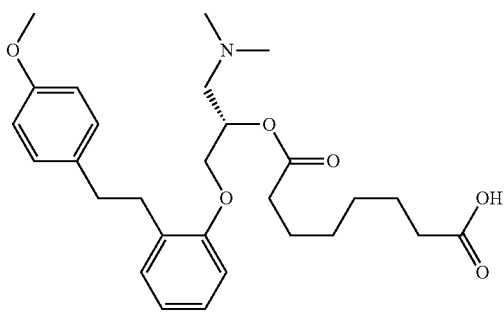
Compound 65
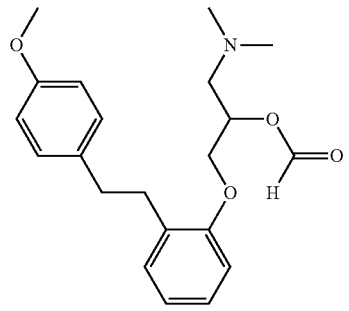
Compound 66
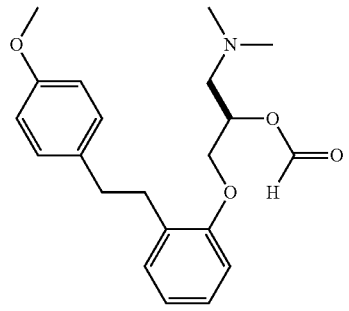
Compound 67
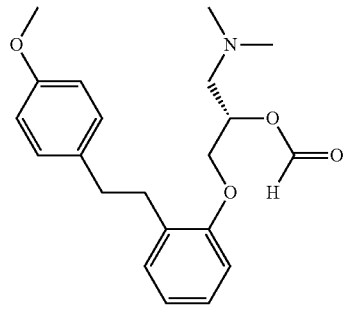
Compound 68
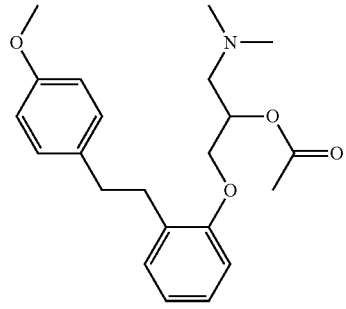

Compound 69
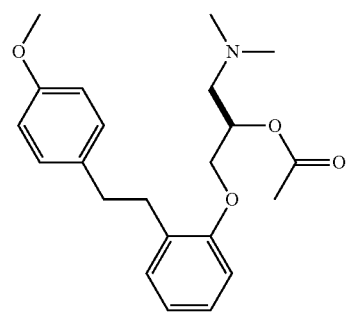
Compound 70
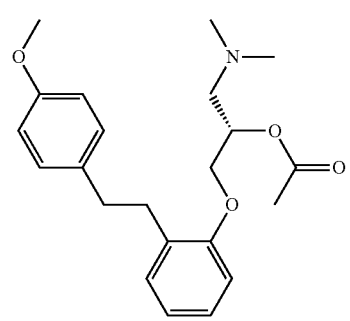
Compound 71
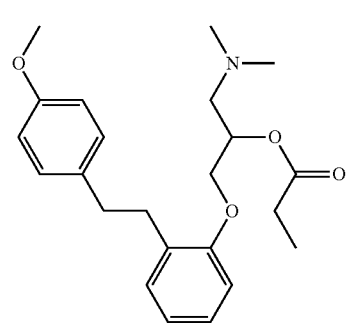
Compound 72
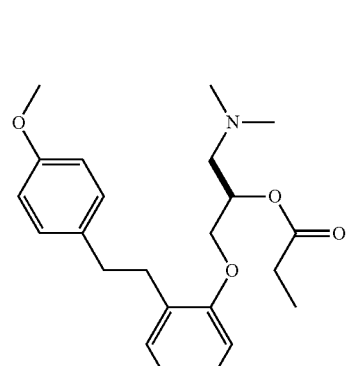
Compound 73
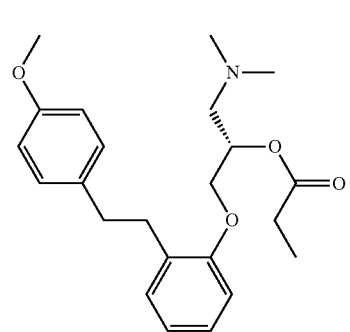
Compound 74
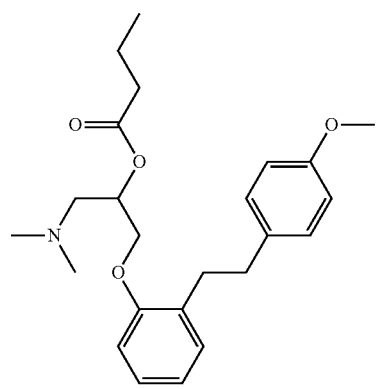
Compound 75
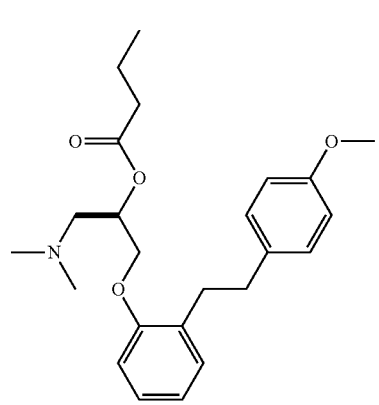
Compound 76
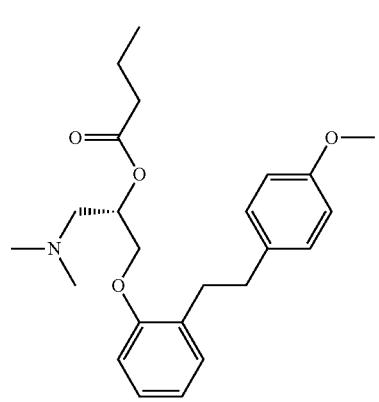
Compound 77
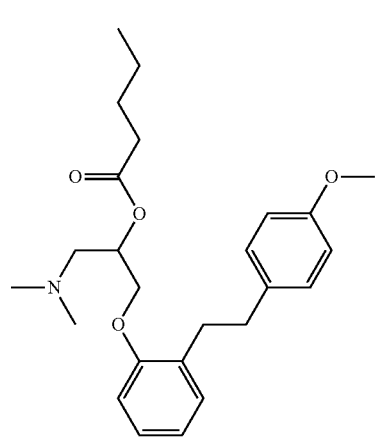

Compound 78
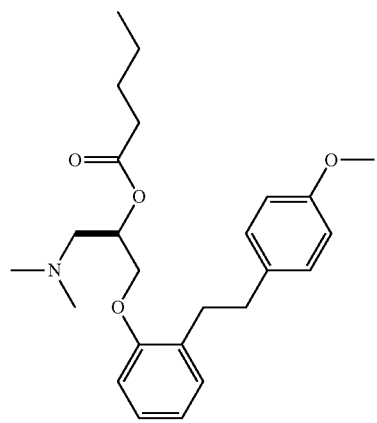
Compound 79
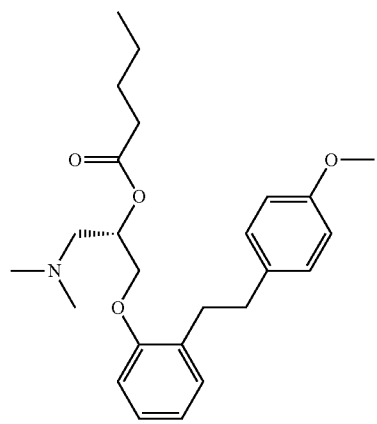
Compound 80
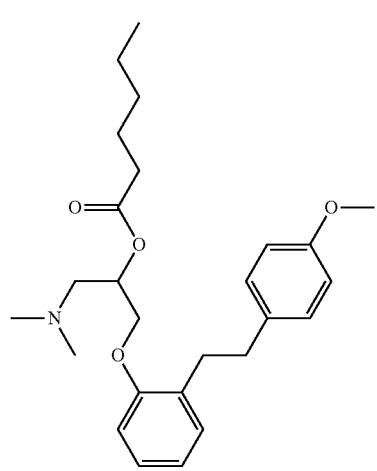
Compound 81
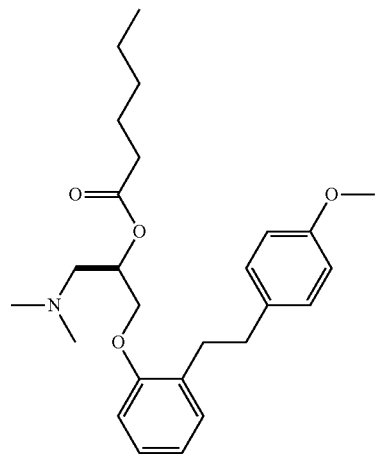
Compound 82
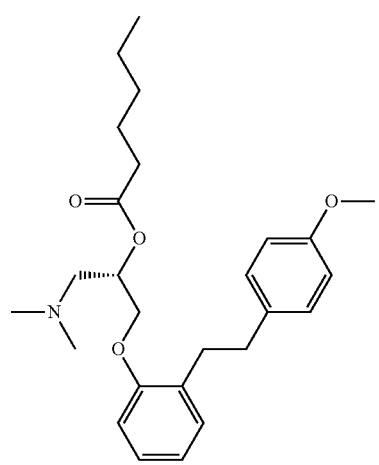
Compound 83
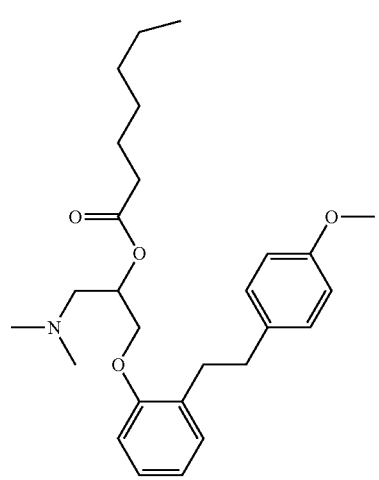

Compound 84
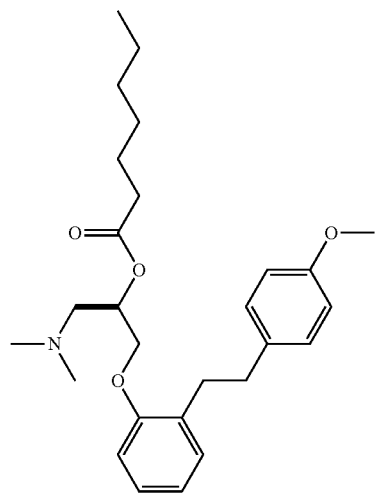
Compound 85
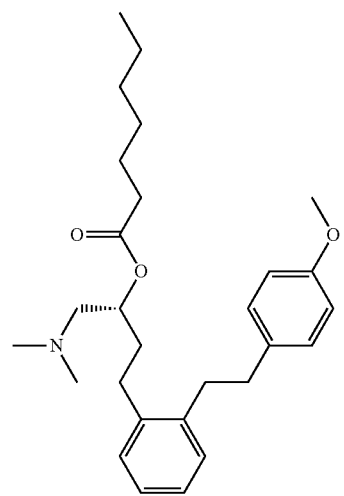
Compound 86
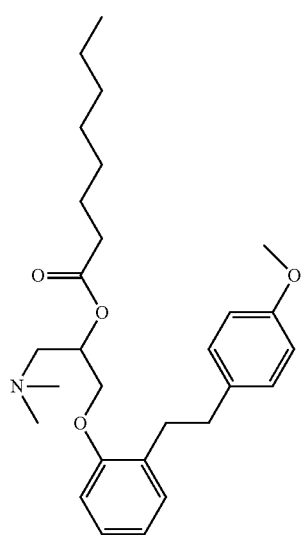
Compound 87
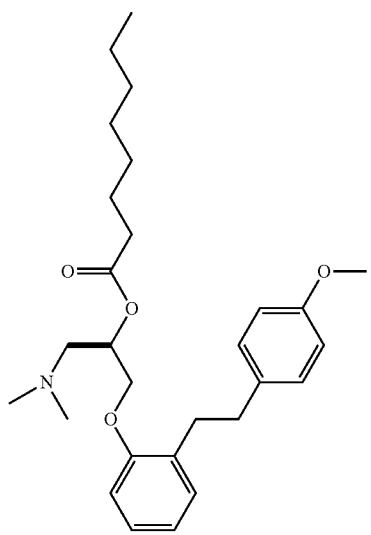
Compound 88
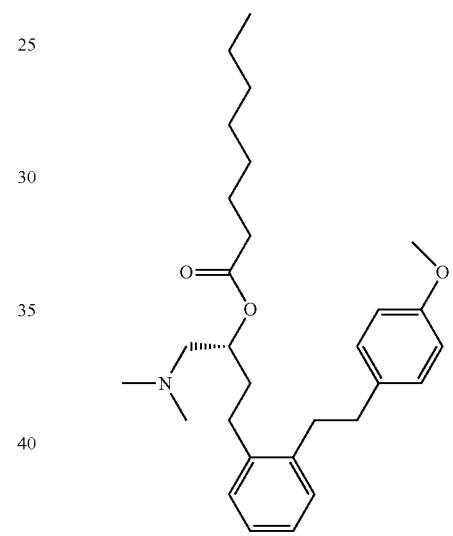
Compound 89
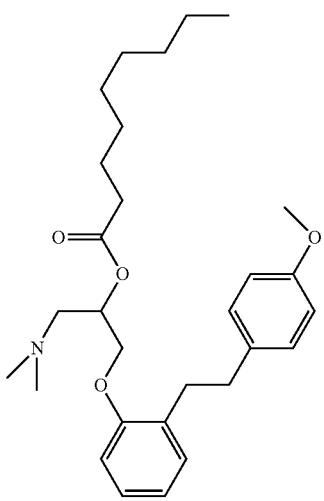

Compound 90
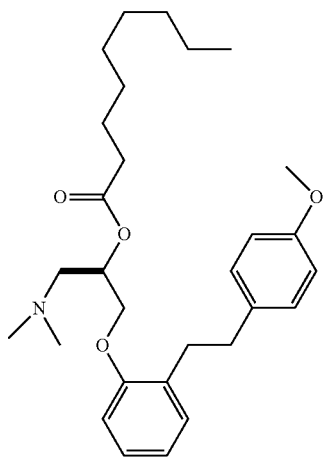
Compound 91
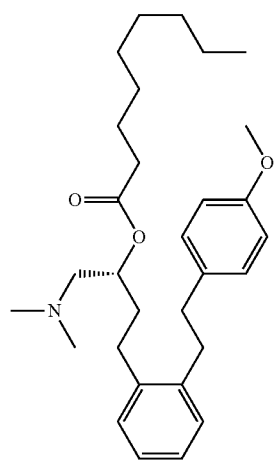
Compound 92
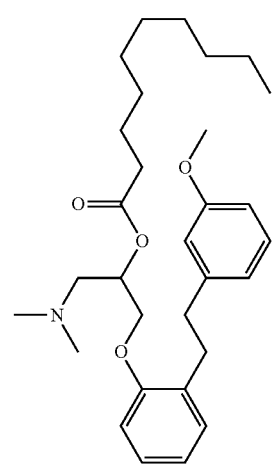
Compound 93
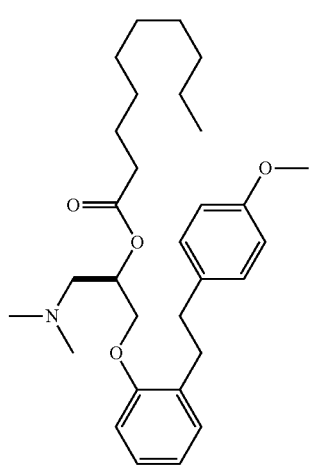
Compound 94
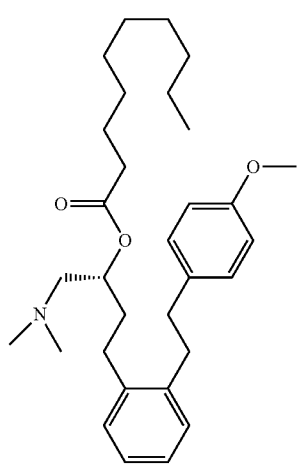
Compound 95
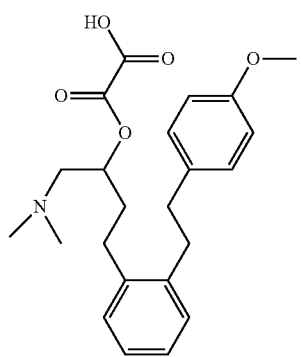
Compound 96
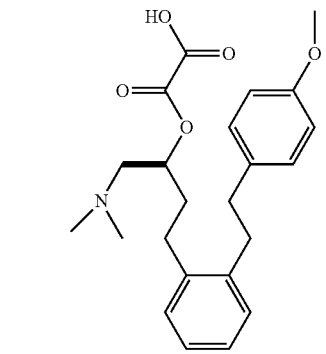

Compound 97
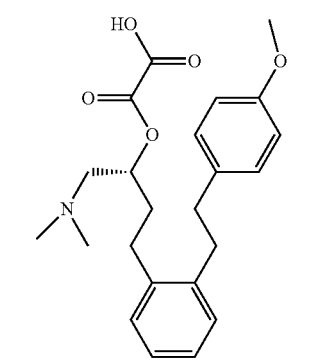
Compound 98
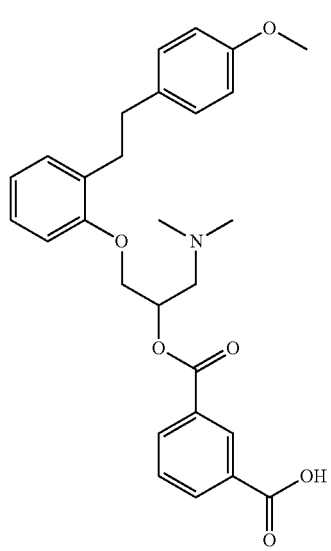
Compound 99
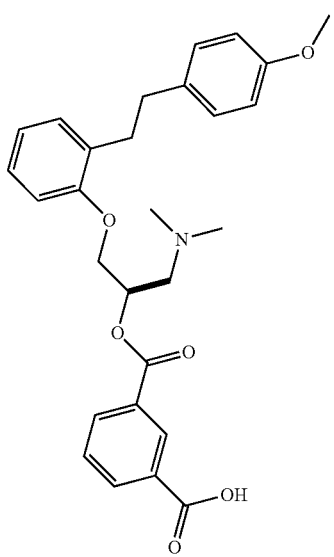
Compound 100
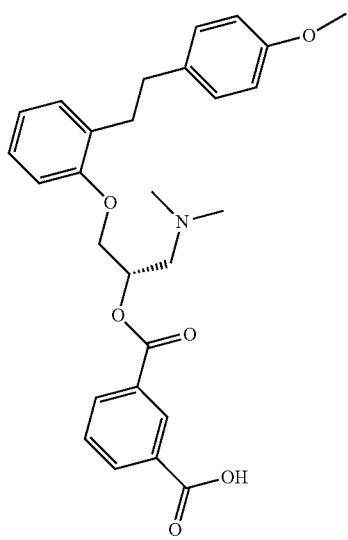
Compound 101
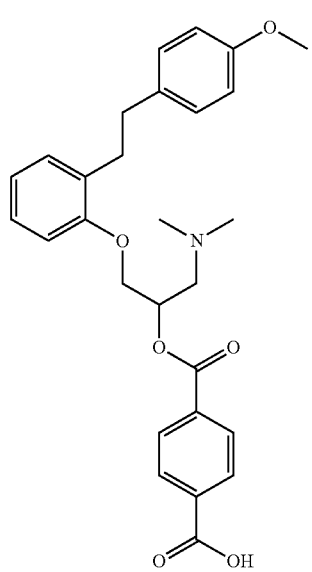
Compound 102

Compound 103
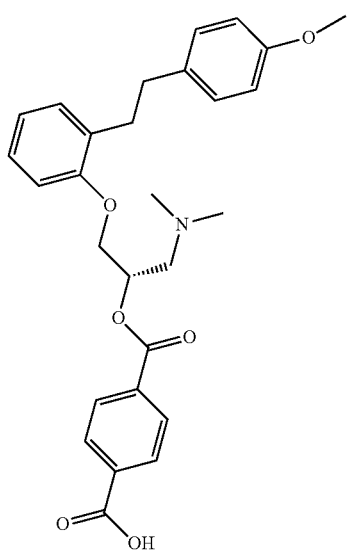
Compound 104
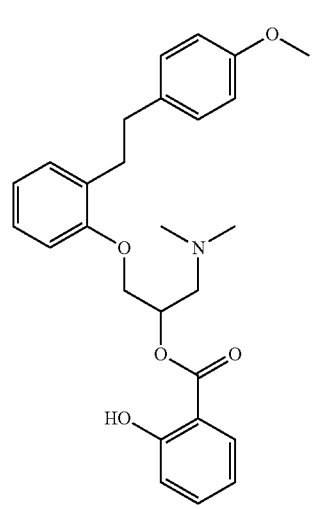
Compound 105
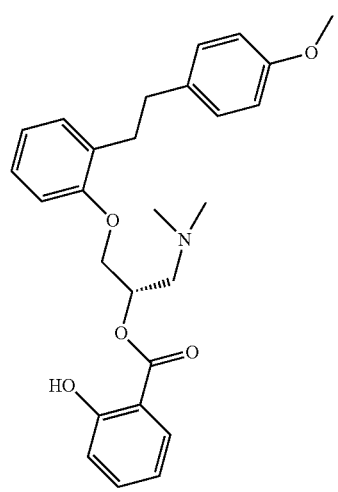
Compound 106
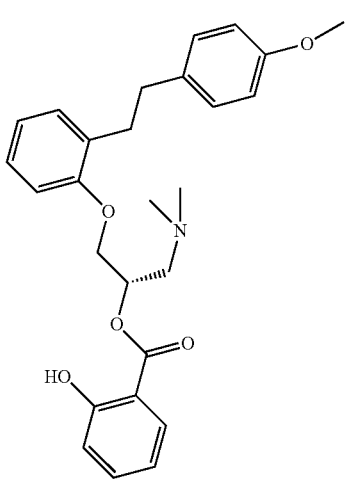
Compound 107
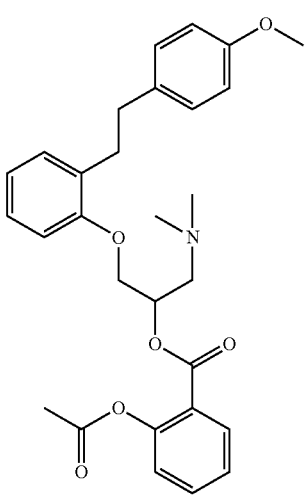
Compound 108
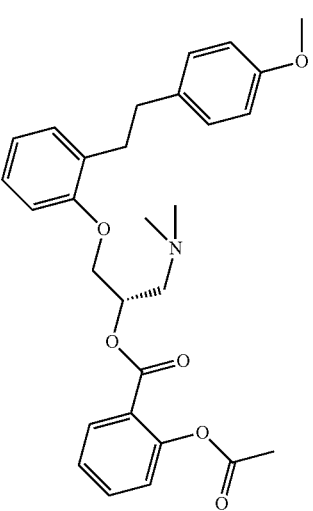

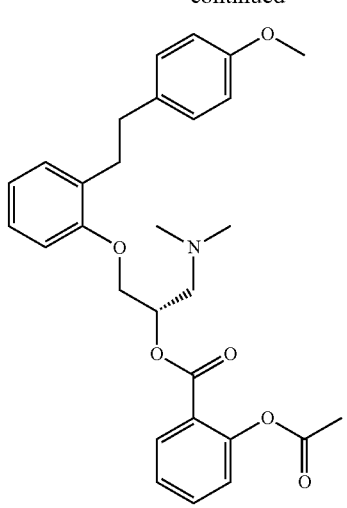

Compound 109

An embodiment of the invention is a composition comprising a compound selected from the group consisting of SGL, M1, SG1, SG2, SMG1, SMG2, SMG3; or enantiomers thereof, metabolites thereof, derivatives thereof, deuterated derivatives thereof, prodrugs thereof, pharmaceutically acceptable salts, N-oxides thereof, or a combination thereof.

An embodiment of the invention is a composition comprising a compound selected from the group consisting of SGL, M1, SG1, SG2, SMG1, SMG2, SMG3; or enantiomers thereof, metabolites thereof, derivatives thereof, deuterated derivatives thereof, prodrugs thereof, pharmaceutically acceptable salts, N-oxides thereof, or a combination thereof; and dextromethorphan or enantiomers thereof, metabolites thereof, derivatives thereof, deuterated derivatives thereof, prodrugs thereof, pharmaceutically acceptable salts, N-oxides thereof, or a combination thereof.

Another embodiment is a compound of formula 1, wherein the Ra and R2 form a five- or six-membered heterocyclic moiety, exemplary compounds are compounds 110-145; or enantiomers thereof, metabolites thereof, derivatives thereof, deuterated derivatives thereof, prodrugs thereof, pharmaceutically acceptable salts, N-oxides thereof, or a combination thereof.

An embodiment of the invention is a composition comprising a compound selected from the group consisting of SGL, enantiomers thereof, a metabolite thereof, M1, SG1, SG2, SMG1, SMG2, SMG3; or enantiomers thereof, metabolites thereof, derivatives thereof, deuterated derivatives thereof, prodrugs thereof, pharmaceutically acceptable salts, N-oxides thereof, or a combination thereof, and a compound of Formula II or dextromethorphan and/or a compound selected from the group consisting of thioridazine, perphenazine, fluphenazine, haloperidol, zuclopenthixol, risperidone, sertindole, nortriptyline, amitriptyline, imipramine, fluoxetine, paroxetine, ajmaline, amiodarone, amitriptyline, aprindine, azelastine, celecoxib, chlorpheniramine, chlorpromazine, diphenhydramine, doxorubicin, fluphenazine, fluvastatin, haloperidol, imipramine, indinavir, lasoprazole, levomepromazine, lopinavir, loratadine, mequitazine, methadone, metoclopramide, mibefradil, moclobemide, nelfinavir, nevirapine, nicardipine, norfluoxetine, perphenazine, pimozide, terfenadine, thioridazine, cimetidine, quinidine, cisapride, citalopram, clomipramine, clozapine, cocaine, desipramine, ranitidine, risperidone, ritonavir, saquinavir, sertraline, terbinafine, ticlopidine, trifluperidol, yohimbine, doxepin, mianserin, imipramine, 2-chloroimipramine, amitriptyline, amoxapine, protriptyline, trimipramine, nortriptyline, maprotiline, phenelzine, isocarboxazid, tranylcypromine, trazodone, citalopram, sertraline, aryloxy indanamine, benactyzine, escitalopram, fluvoxamine, venlafaxine, desvenlafaxine, duloxetine, mirtazapine, nefazodone, selegiline, sibutramine, milnacipran, tesofensine, brasofensine, moclobemide, rasagiline, nialamide, iproniazid, iproclozide, toloxatone, butriptyline, dosulepin, dibenzepin, iprindole, lofepramine, opipramol, and dapoxetine; or enantiomers thereof, metabolites thereof, derivatives thereof, deuterated derivatives thereof, prodrugs thereof, pharmaceutically acceptable salts, N-oxides thereof, or a combination thereof.

In another embodiment, the composition comprises a compound of Formula II or DEX and a compound of formula I and/or prehexiline, flecainide, quinidine, (R)-propaphenone, (S)-propaphenone, isoniazid, (R)-fluoxetine, (S)-fluoxetine, nefazodone, paroxetine, ketoconazole, chloroquine, oxamniquine, primaquine, quinine, acetbutolol, betaxolol, bufuralol, oxprenolol, pindolol, propranolol, budipine, simavastatin, fluvastatin, lovastatin, pravastatin, perazine, ajamlicine, corynanthine, lobeline; or enantiomers thereof, metabolites thereof, derivatives thereof, deuterated derivatives thereof, prodrugs thereof, pharmaceutically acceptable salts, N-oxides thereof, or a combination thereof.

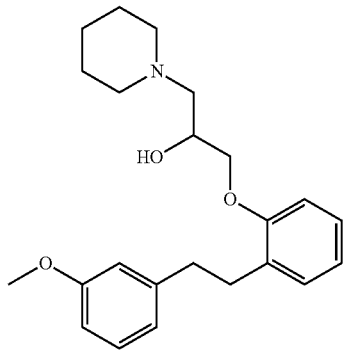

Compound 110

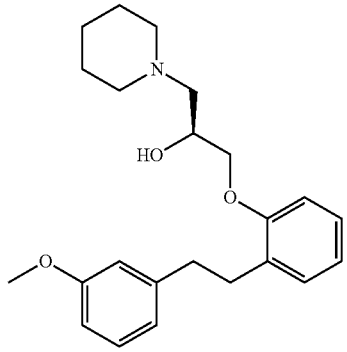

Compound 111

Compound 112
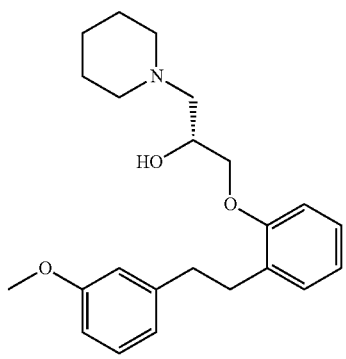
Compound 113
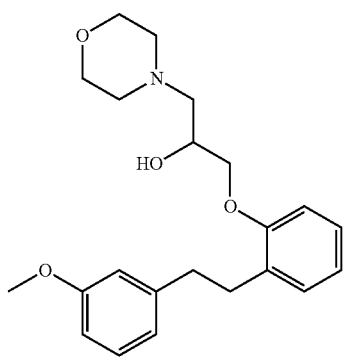
Compound 114
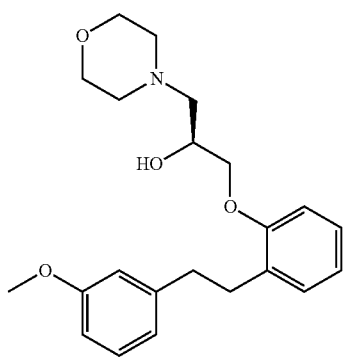
Compound 115
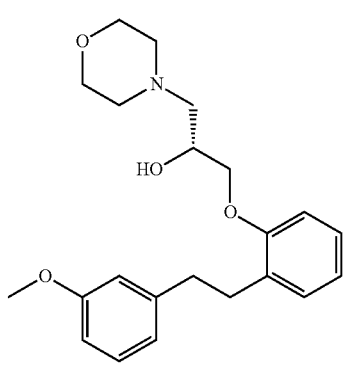
Compound 116
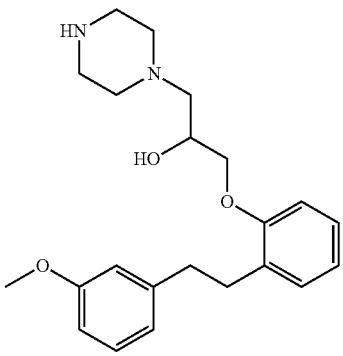
Compound 117
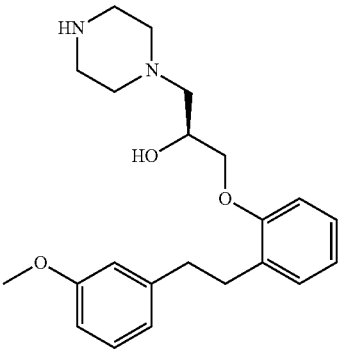
Compound 118
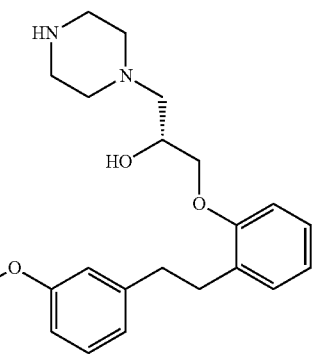
Compound 119
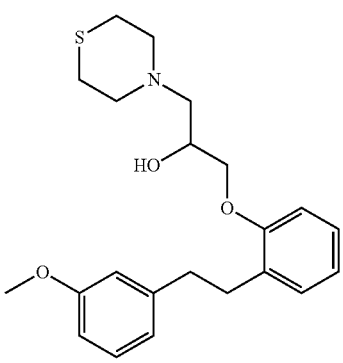

Compound 120
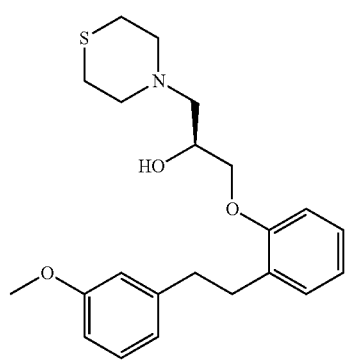
Compound 124
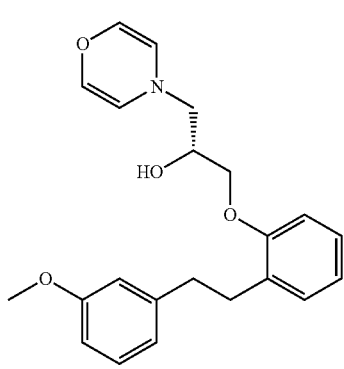
Compound 121
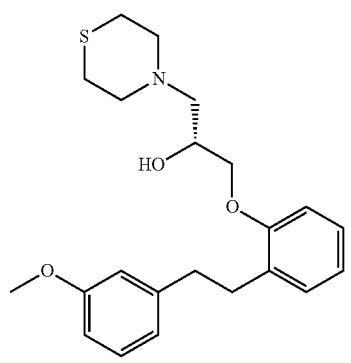
Compound 125
Compound 122
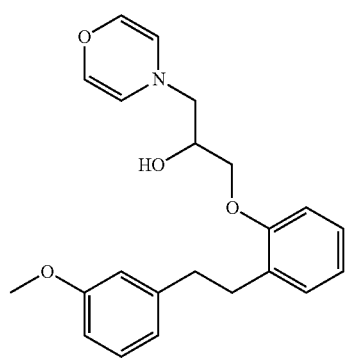
Compound 126
Compound 123
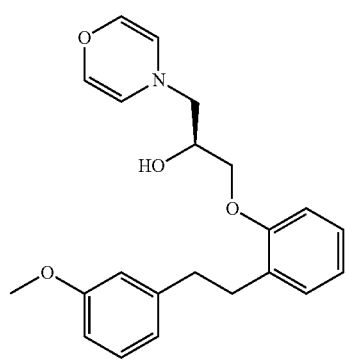
Compound 127
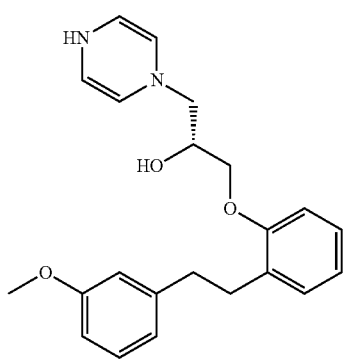

Compound 128
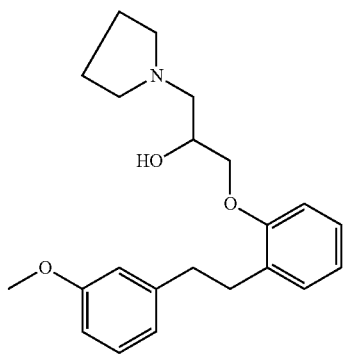
Compound 129
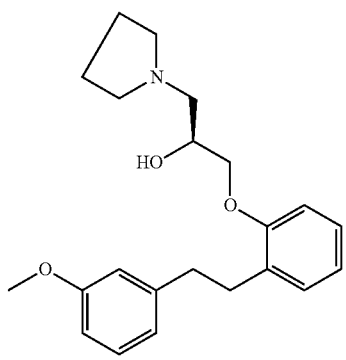
Compound 130
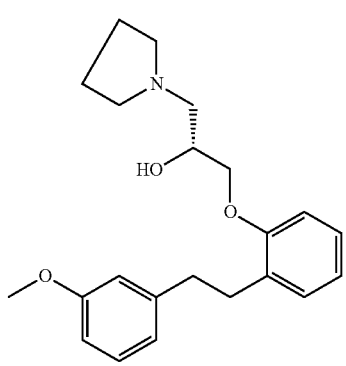
Compound 131
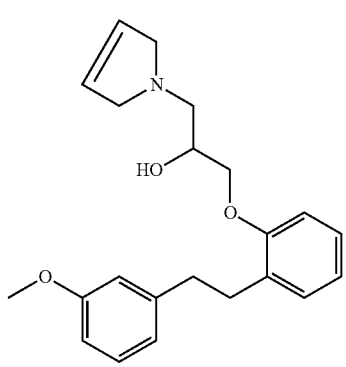
Compound 132
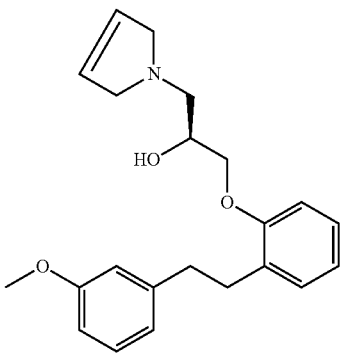
Compound 133
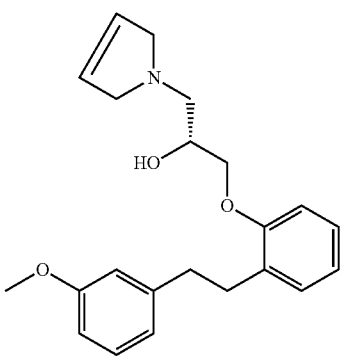
Compound 134
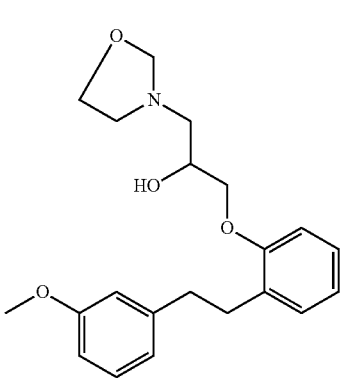
Compound 135
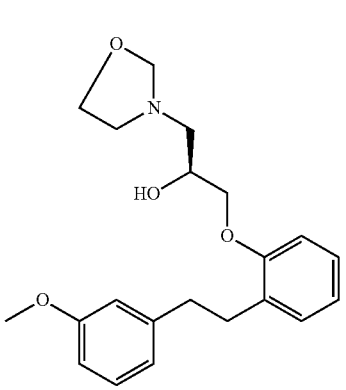

Compound 136
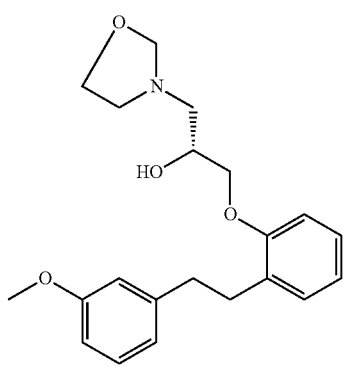
Compound 137
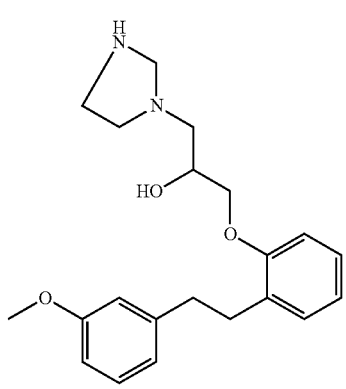
Compound 138
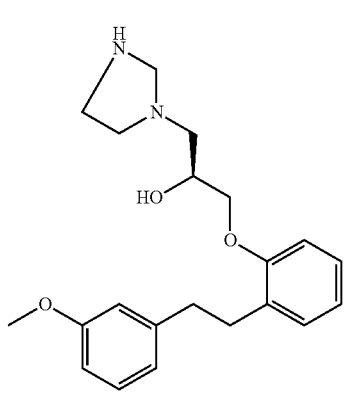
Compound 139
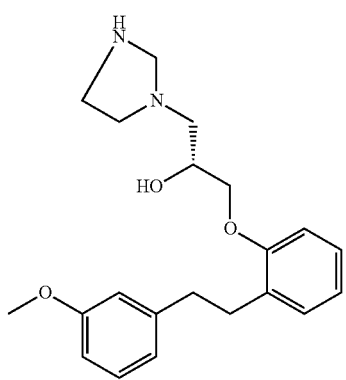
Compound 140
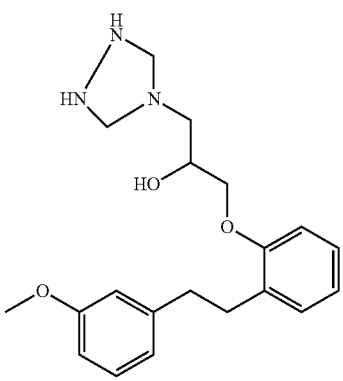
Compound 141
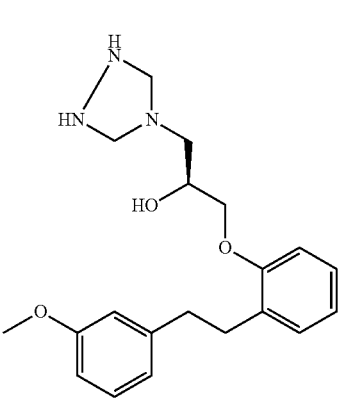
Compound 142
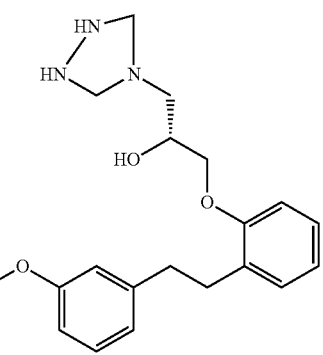
Compound 143
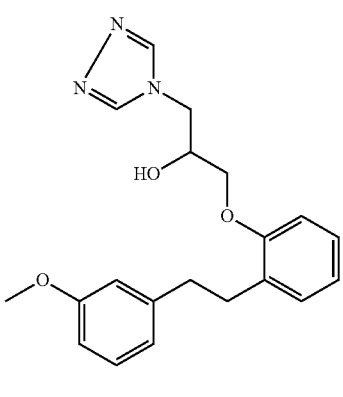

Compound 144
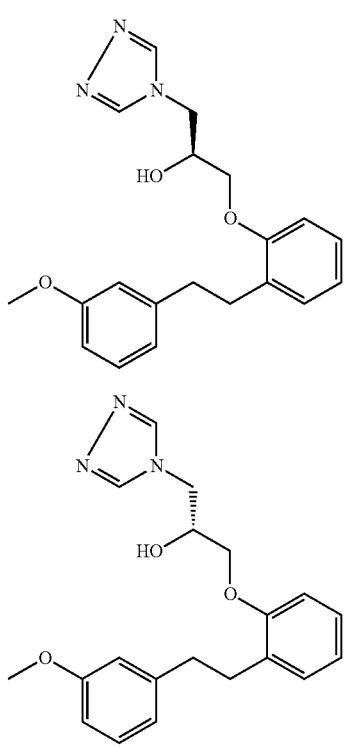
Compound 145
In another embodiment, examples of the compound of formula I, wherein the heterocycle formed from $R_1$ and $R_2$ together with the nitrogen, represented by the compounds having Formulae Ic-Is comprising saturated (shown below) and unsaturated heterocycles:
Formula Ic
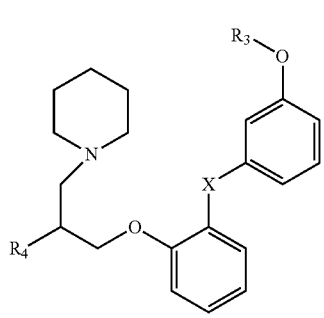
Formula Id
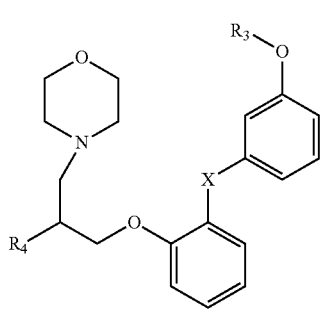
Formula Ie
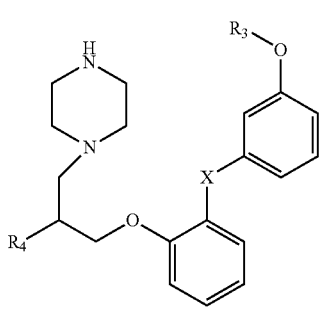
Formula If
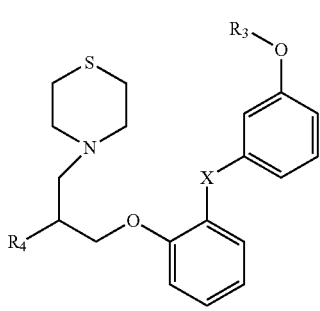
Formula Ik
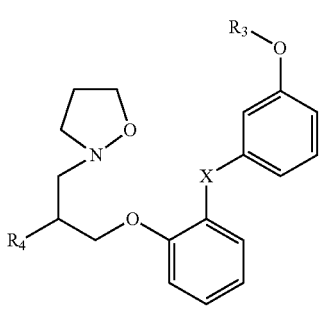
Formula Il
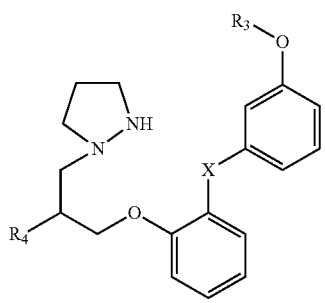
Formula Im
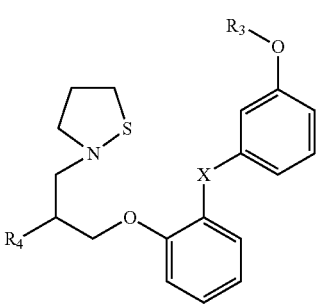

Formula In
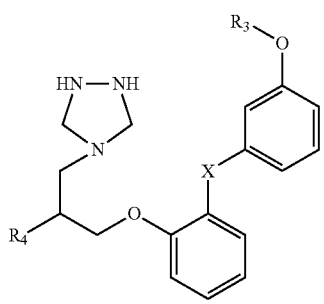

Formula Ig
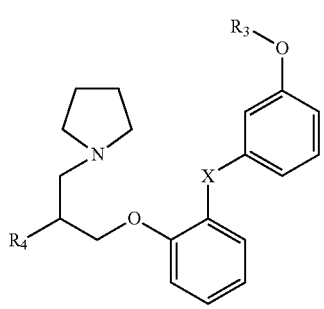

Formula Ih
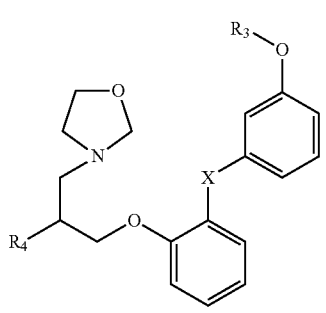

Formula Ii
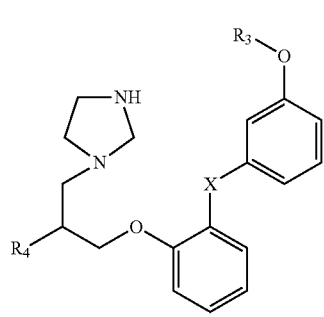

Formula Ij
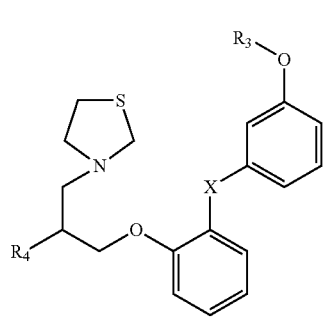

Formula Io
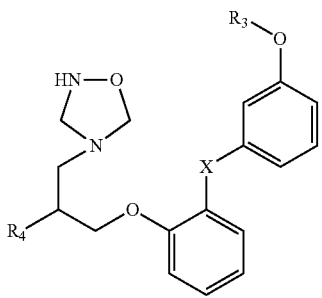

Formula Ip
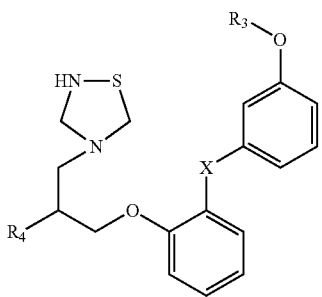

Formula Ir

Formula Is
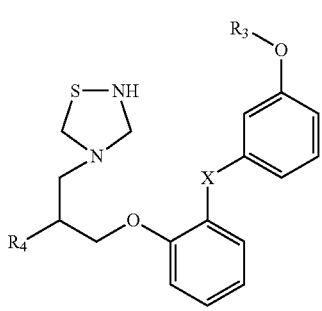

In another embodiment, the compound is a compound of Formulae Ic-Is, wherein the 5-membered heterocycle is unsaturated.

In another embodiment, the composition comprising formula I, wherein $R_1$, $R_2$, and $R_3$ are methyl, X is ethyl, and $R_4$ is OH, represented by the following compounds M1, M1-E1, and M1-E2; or enantiomers thereof, metabolites thereof, derivatives thereof, deuterated derivatives thereof, prodrugs thereof, pharmaceutically acceptable salts, N-oxides thereof, or a combination thereof.

Compound 146

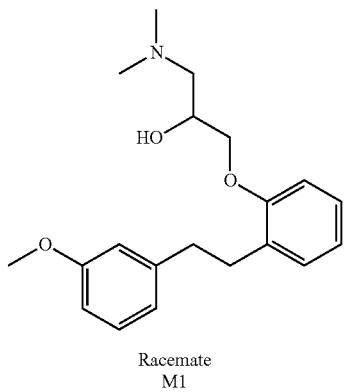

Racemate
M1

Compound 50

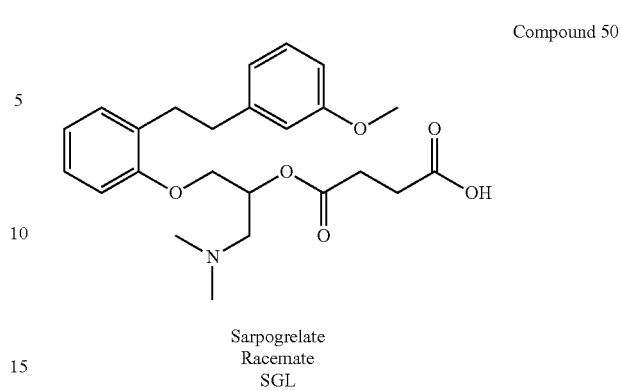

Sarpogrelate
Racemate
SGL

Compound 147

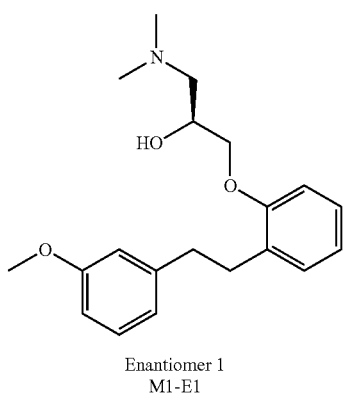

Enantiomer 1
M1-E1

Compound 51

Sarpogrelate
Enantiomer 1
SGL-E1

Compound 148

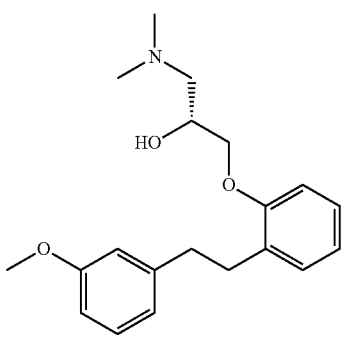

Enantiomer 2
M1L-E2

1-(dimethylamino)-3-(2-(3-methoxyphenethyl)phenoxy)propan-2-ol

Compound 52

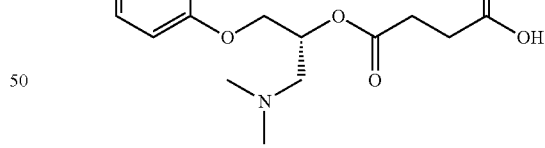

Sarpogrelate
Enantiomer 2
SGL-E2

4-((1-dimethylamino)-3-(2-(3-methoxyphenethyl)phenoxy)propan-2-yl)oxy)-4-oxobutanoic acid In another embodiment, the composition comprising formula I, wherein $R_1$, $R_2$, and $R_3$ are methyl, X is ethyl, and $R_4$ is succinoyl radical, represented by the following compounds SGL, SGL-E1, and SGL-E2; or enantiomers thereof, metabolites thereof, derivatives thereof, deuterated derivatives thereof, prodrugs thereof, pharmaceutically acceptable salts, N-oxides thereof, or a combination thereof.

In one embodiment, the composition comprises DEX-H3, DEX-D3, DO, DO-D3, levomethorphan, morphine, codeine, thebaine, benzocaine, tropane alkaloids such as cocaine, atropine, scopolamine, etc.; or enantiomers thereof, metabolites thereof, derivatives thereof, deuterated derivatives thereof, prodrugs thereof, pharmaceutically acceptable salts, N-oxides thereof, or a combination thereof.

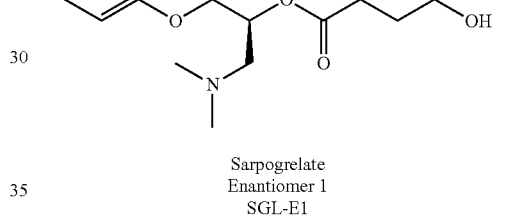

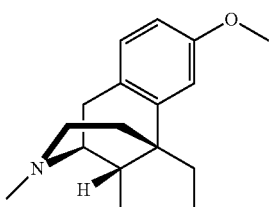

Dextromethorphan
DEX-H₃
Compound 149

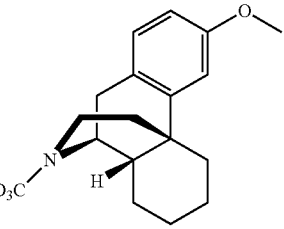

Dextromethorphan
DEX-D₃
Compound 150

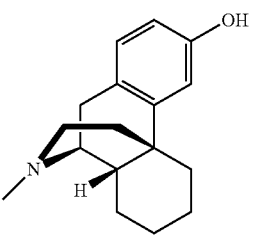

Dextrorphan
DO-H₃
Compound 151

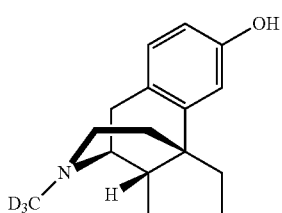

Dextrorphan
DO-D₃
Compound 153

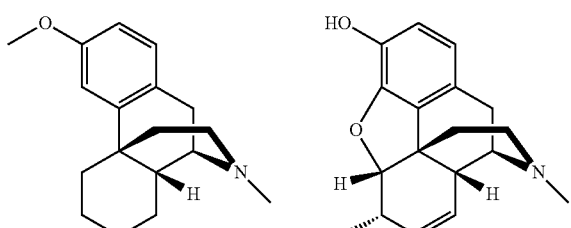

Levomethorphan           Morphine
Compound 154             Compound 155

-continued

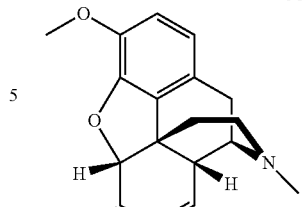

Codeine
Compound 156

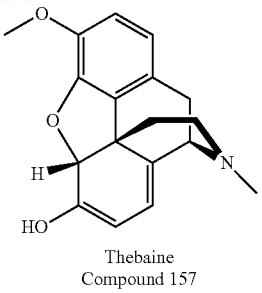

Thebaine
Compound 157

In another embodiment, the composition comprises a compound selected from compounds 149 to 157, or enantiomers thereof, metabolites thereof, derivatives thereof, deuterated derivatives thereof, prodrugs thereof, pharmaceutically acceptable salts, N-oxides thereof, or a combination thereof In another embodiment, the composition comprises an NMDA receptor antagonist such as ketamine, methadone, memantine, amantadine, dextropropoxyphene, ketobemidone and dextromethorphan (Jamero et al., The Emerging Role of NMDA Antagonists in Pain Management, *US Pharm*. 36(5):HS4-HS8 (2011); Sang, NMDA-receptor antagonists in neuropathic pain: experimental methods to clinical trials, J Pain Symptom Manage 19 (1 Suppl) S21-5 (2000); incorporated in entirety herein by reference). DEX is an agonist of the O2 receptor, an N-methyl-D-aspartate (NMDA) antagonist, and an α3β4 nicotinic receptor antagonist. Uptake of norepinephrine and serotonin are also inhibited. Several neuropsychiatric diseases and syndromes such as Alzheimer's disease and behavioral and psychological symptoms of dementia involve dis-regulation of glutamatergic, cholinergic, serotoninergic and norepinephrinergic neurotransmitter systems.

In another embodiment, the pharmaceutical composition comprises SARPODEX™.

Another embodiment is an agent having properties of both 5-HT2A receptor inverse agonist and CYP2D6 inhibitor. In another embodiment, the agent is a compound of formula I or SARPO. In another embodiment, the pharmaceutical composition comprises SARPODEX™.

Another embodiment is a composition comprising one or more agents of the invention, a compound of formula I, SARPO, DEX, or SARPODEX™ alone or in combination with other drugs such as analgesics (e.g. acetaminophen), antihistamines (e.g., chlorpheniramine), decongestants (e.g., pseudoephedrine) and/or expectorants (e.g., guaifenesin).

An embodiment is a compound selected from Compounds 10 to 170. Another embodiment is a composition comprising at least one compound from Compounds 10-170.

Another embodiment is a compound selected from the group consisting of compounds from 10 to 148, and from 158 to 170, or enantiomers thereof, metabolites thereof, derivatives thereof, deuterated derivatives thereof, prodrugs thereof, pharmaceutically acceptable salts, N-oxides thereof, or a combination thereof; and a compound selected from the group consisting of compounds from 149 to 157, or enantiomers thereof, metabolites thereof, derivatives thereof, deuterated derivatives thereof, prodrugs thereof, pharmaceutically acceptable salts, N-oxides thereof, or a combination thereof.

Another embodiment is a pharmaceutical composition comprising at least one compound selected from the group consisting of compounds from 10 to 148, and from 158 to 170, or enantiomers thereof, metabolites thereof, derivatives thereof, deuterated derivatives thereof, prodrugs thereof, pharmaceutically acceptable salts, N-oxides thereof, or a combination thereof; and at least one compound selected from the group consisting of compounds from 149 to 157 or enantiomers thereof, metabolites thereof, derivatives thereof, deuterated derivatives thereof, prodrugs thereof, pharmaceutically acceptable salts, N-oxides thereof, or a combination thereof.

In an embodiment, the pharmaceutically acceptable salts of compounds of Formula I and Formula II prepared from pharmaceutically acceptable non-toxic acids when the pharmaceutically active compound of the present invention is basic, or salts prepared from pharmaceutically acceptable non-toxic bases when the pharmaceutically active compound of the present invention is acidic. Pharmaceutically acceptable organic and inorganic acid salts include, but not limited to, salts formed with acids such as acetic, benzenesulfonic, benzoic, camphorsulfonic, citric, ethane-sulfonic, fumaric, gluconic, glutamic, hydrobromic, hydrochloric, isethionic, lactic, maleic, mandelic, methanesulfonic, mucic, nitric, pamoic, pantothenic, phosphoric, succinic, sulfuric, tartaric, p-toluenesulfonic, etc. Salts may be prepared from pharmaceutically acceptable non-toxic bases. Pharmaceutically acceptable non-toxic basic salts include, but not limited to, salts derived from all stable forms of inorganic bases include aluminum, ammonium, calcium, copper, iron, lithium, magnesium, manganese, potassium, sodium, zinc, etc., and salts derived from pharmaceutically acceptable organic non-toxic bases include salts of primary, secondary, tertiary amines, and substituted amines including naturally occurring substituted amines, cyclic amines and basic ion-exchange resins such as arginine, betaine, caffeine, choline, N,N dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, isopropylamine, lysine, methyl-glucosamine, morpholine, piperazine, piperidine, polyamine resins, procaine, purine, theobromine, triethylamine, trimethylamine, tripropylamine, etc.

In another embodiment, the prodrugs of the invention are Compounds 10 to 148 and 160 to 178, which are prodrugs of the active metabolite M1.

In another embodiment, the prodrugs of the invention are Compounds 149 to 159, which are prodrugs of dextrorphan.

Fluorine can provide many beneficial properties when incorporated into a molecule. Modulation of the pKaH of functional groups proximal to fluorine substitution[2a, 15] can result in increased membrane penetration at physiological pH. Fluorinated arenes are more lipophilic than their non-fluorinated counterparts, which can be used to advantage in drug development. Fluorine is sometimes used as an isostere for hydrogen in medicinal chemistry, but the van der Waals radius of fluorine is more similar to oxygen (1.47 Å for fluorine versus 1.52 Å for oxygen and 1.20 Å for hydrogen).

Fluorinated compounds can be strategically used as transition state inhibitors. The high electronegativity of fluorine contributes to the high carbon-fluorine bond strength due to coulombic attraction between carbon and fluorine due to the polarized covalent bond; the large bond polarization results in attractive interactions of the C—F fragment with hydrogen bond donors, other fluorinated compounds, polar functional groups such as carbonyls, and hydrophobic moieties. Fluorinated molecules can show increased binding affinity to proteins likely due to attractive polar interactions; however, in many cases this phenomenon is empirically observed and rationalized ex post facto and is difficult to predict or design a priori. Most fluorinated compounds also exhibit increased metabolic stability by impeding undesired oxidative metabolism pathways (Liang et al., Introduction of Fluorine and Fluorine-Containing Functional Groups, Angewandte Chemie International Edition 52, no. 32: 8214-8264 (2013); incorporated in entirety by reference). Accordingly, in an embodiment, the compound of the invention is a compound formula I, Formula I

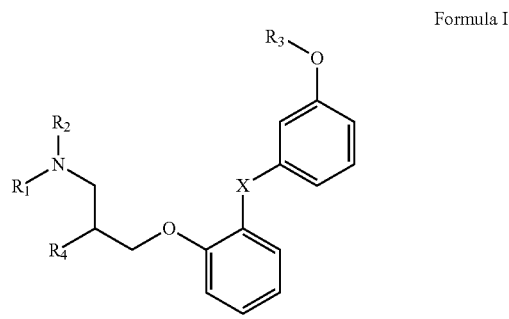

Wherein,

R1, R2, and R3 are independently $C_{1-10}$-alkyl group substituted with one, two or three halogens, wherein the halogen is F, Cl, or Br. Examples of fluorine derivatives of Formula I:

Compound 171

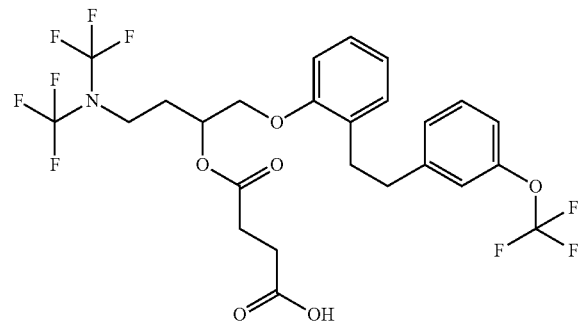

Compound 172

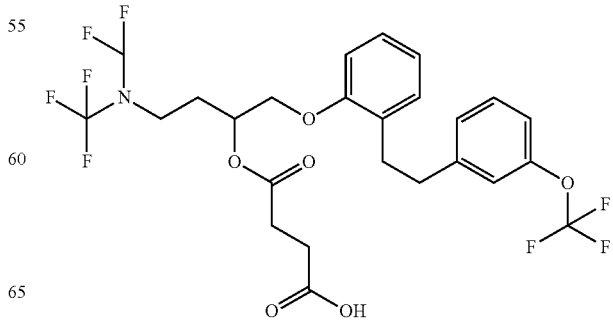

Compound 173
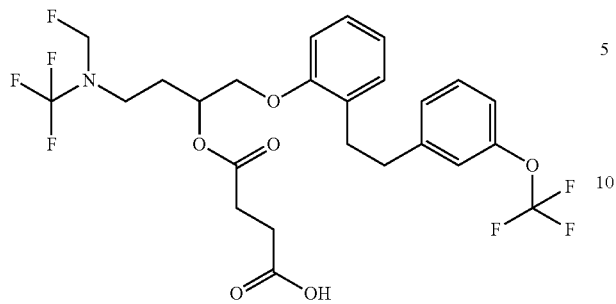

Compound 174
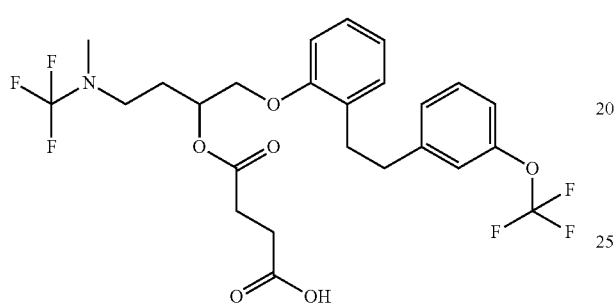

Compound 175
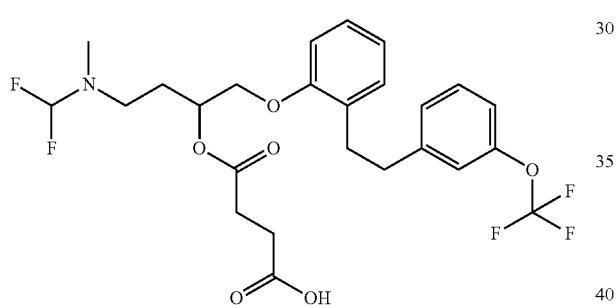

Compound 175
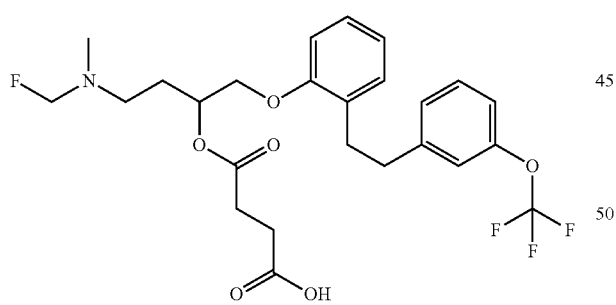

Compound 176
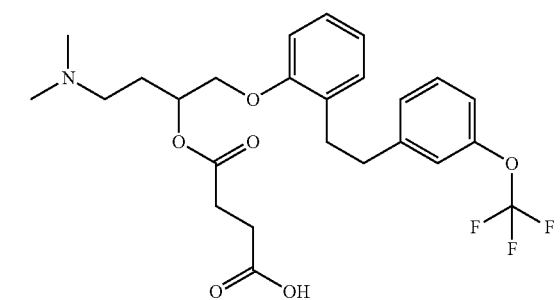

Compound 177
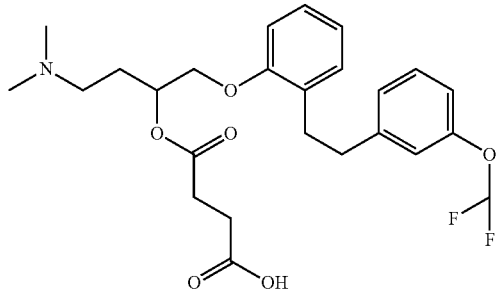

Compound 178
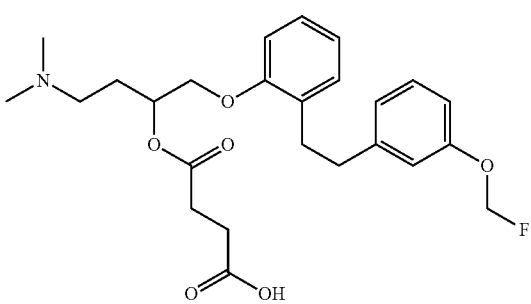

Compound 179
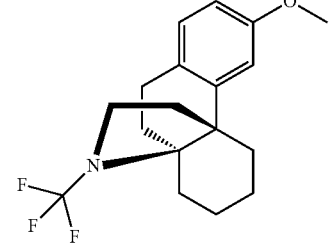

Compound 180
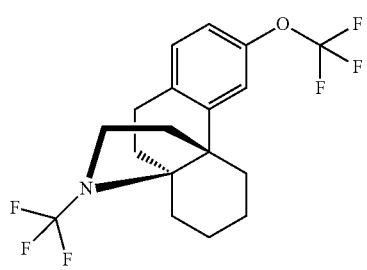

Compound 181
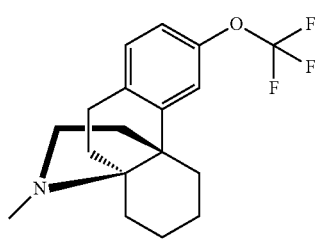

In one embodiment, the invention relates to N-oxides of compounds of Formula I and II. N-oxides are metabolites of many tertiary amines, and in most cases are also intermediates between tertiary amines and their N-dealkylated analogs. The N-oxides of the invention are synthesized from the corresponding tertiary amines (WO 97/036893, WO 00/029397, U.S. Pat. No. 7,750,013 B2, and WO 01/085725; incorporated herein by reference).
Compound 182
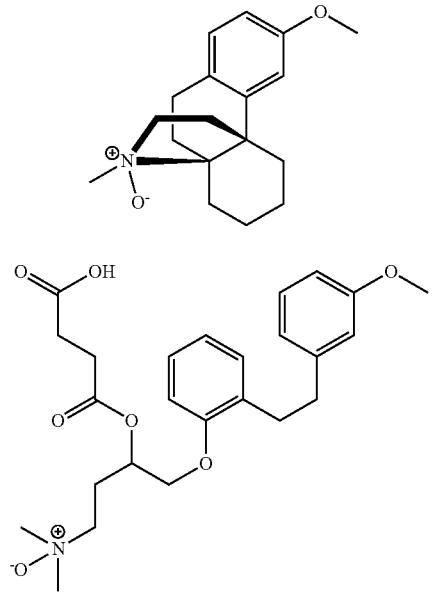
Compound 183
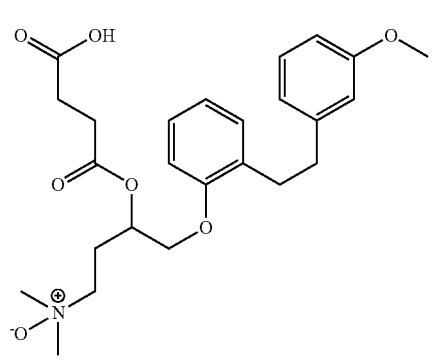
In another embodiment, deuterated compounds of Formula I include, but not limited to, Compounds 184-190 and enantiomers thereof.
Compound 184
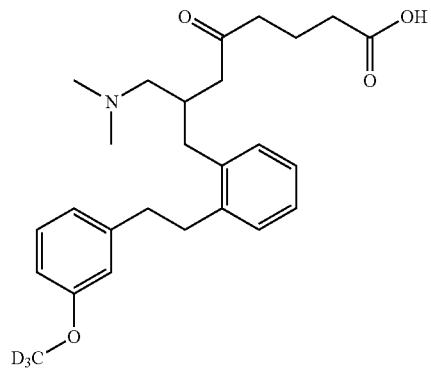
Compound 185
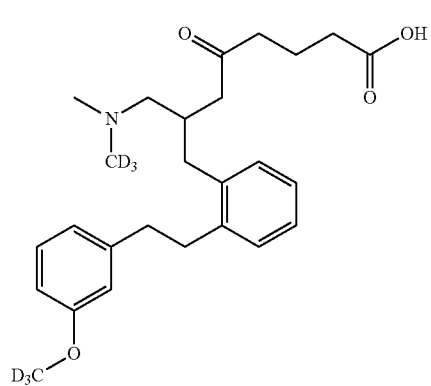
Compound 186
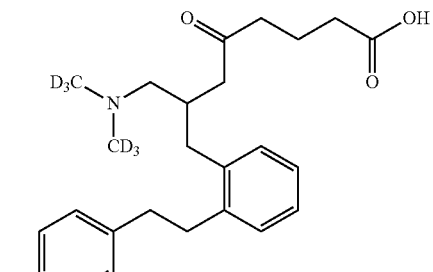
Compound 187
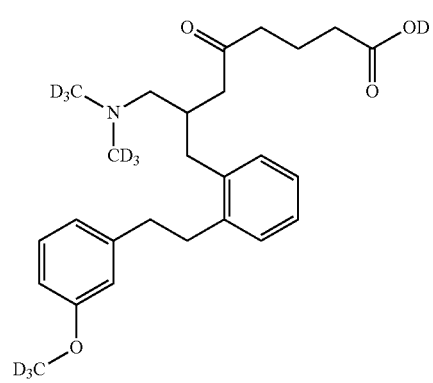
Compound 188
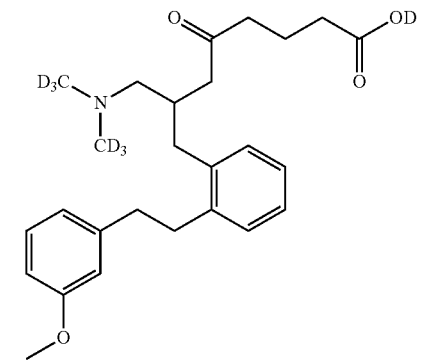
Compound 189
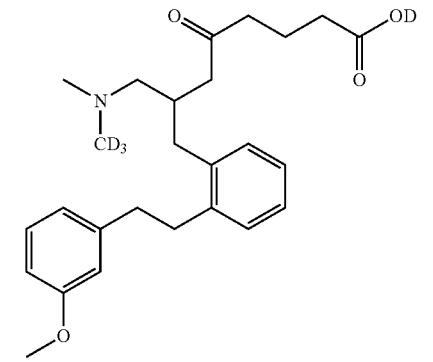

Compound 190
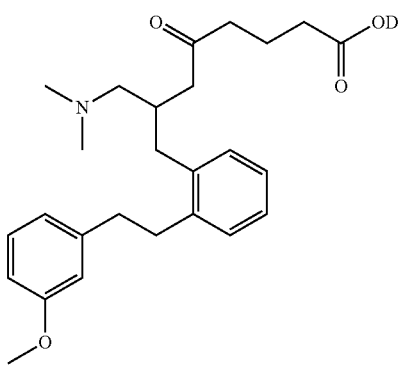
In some embodiments, the invention is a compound of Formula I, wherein X is —(CH$_2$)$_n$—, wherein n is 0-10, examples of which include, but not limited to, the following:
Compound 191
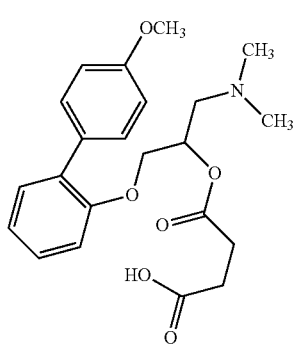
Compound 192
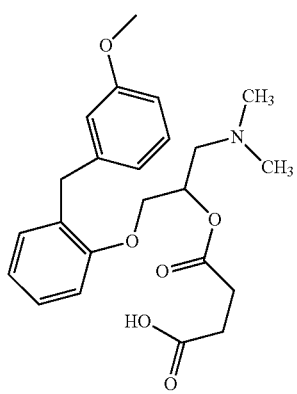
Compound 193
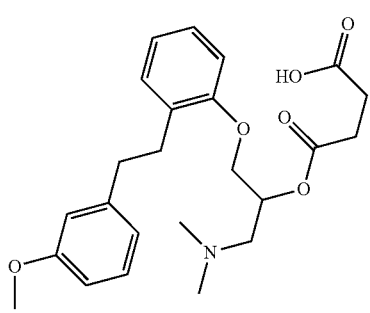
Compound 194
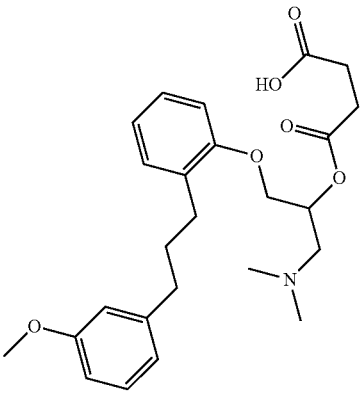
Compound 195
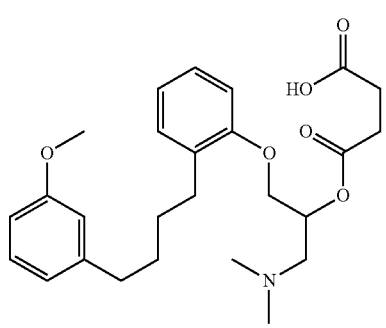
Compound 196
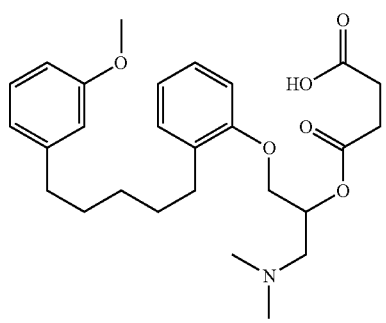
Compound 197
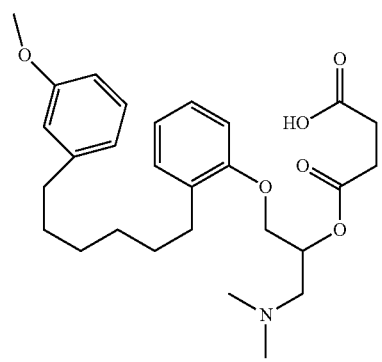

Compound 198
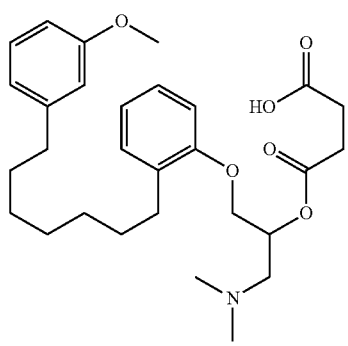
Compound 199
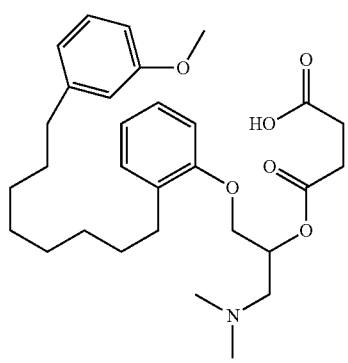
Compound 200
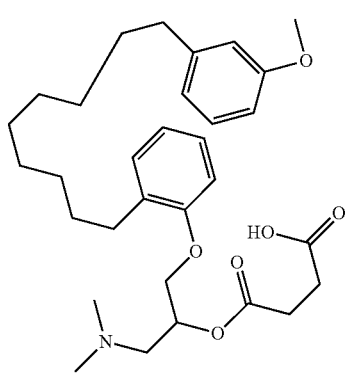
Compound 201
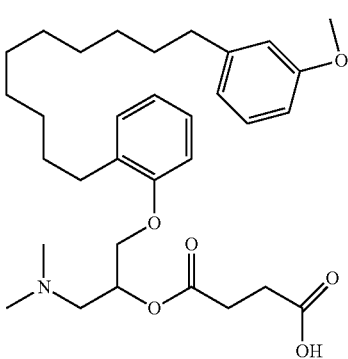
Compound 202
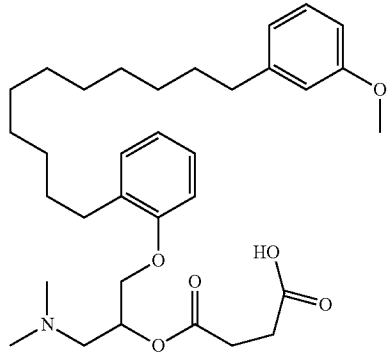
In some embodiments, the compounds of the invention are the positional isomers of compound 191, examples of which include, but not limited to, the following, and similar positional isomers can be prepared for compounds having Formula I.
Compound 203
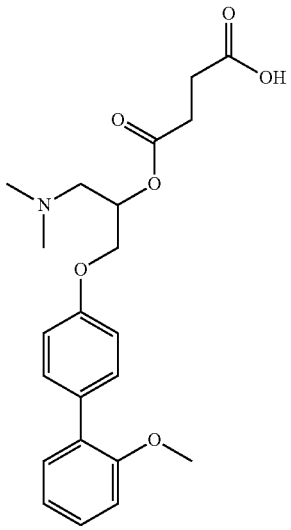
Compound 204
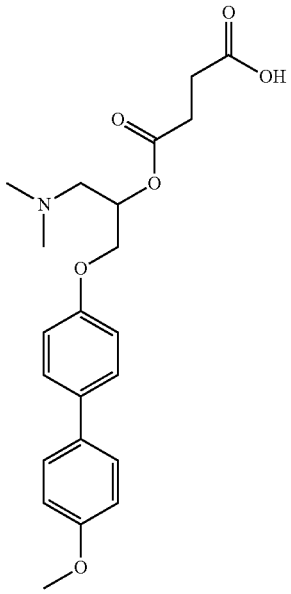

Compound 205
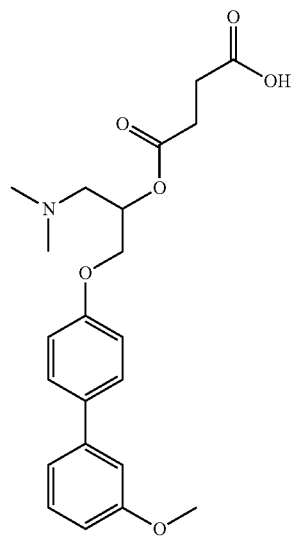
Compound 206
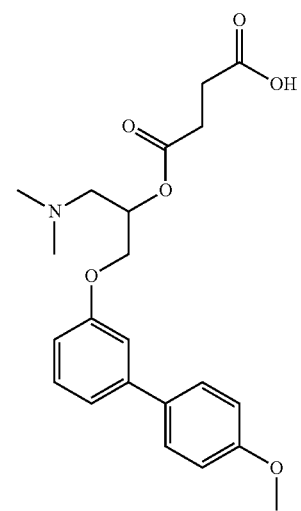
Compound 207
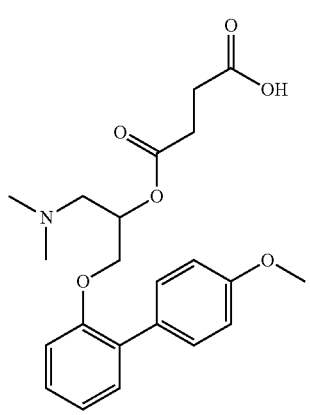
Compound 208
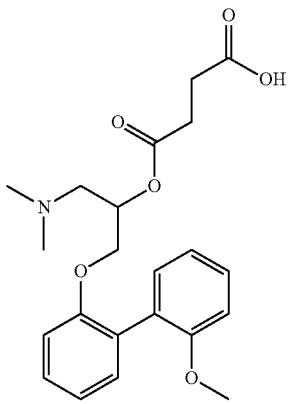
Compound 209
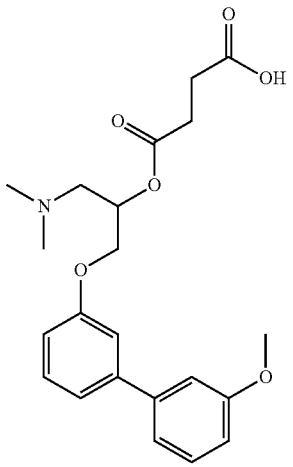
Compound 210
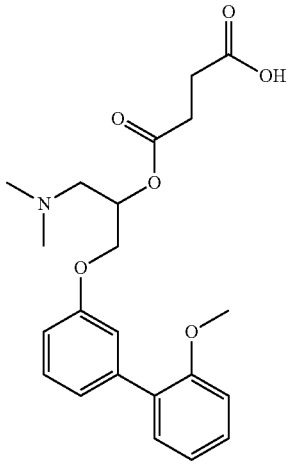
Another embodiment is a compound from the group of formulae Ic-Is.
Another embodiment is the compound of formulae Ic-Is selected from the following:

Compound 211
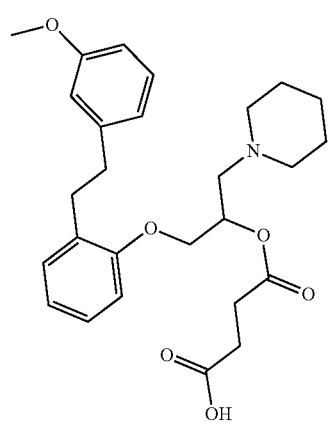
Compound 214
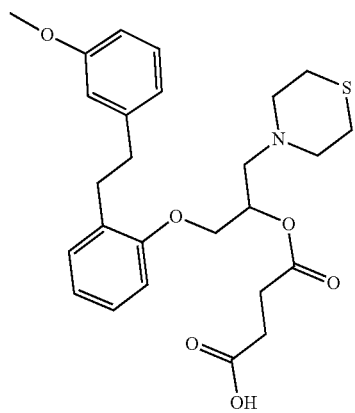
Compound 215
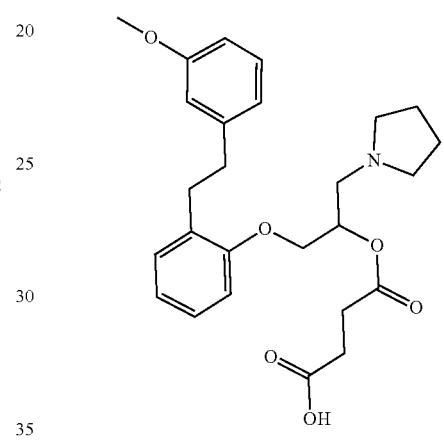
Compound 212
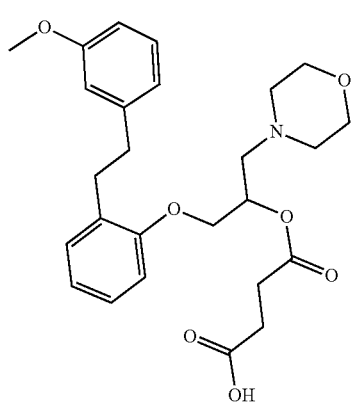
Compound 216
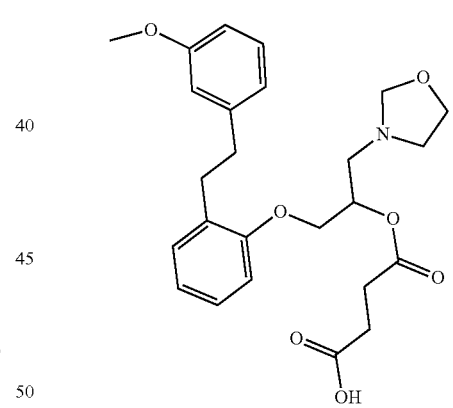
Compound 213
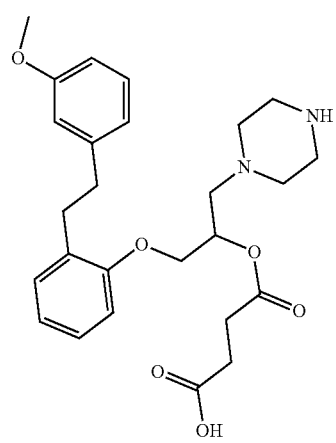
Compound 217
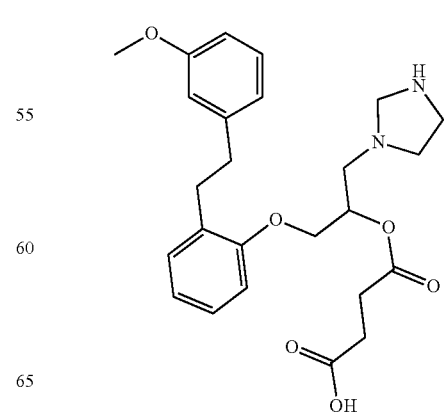

-continued

Compound 218
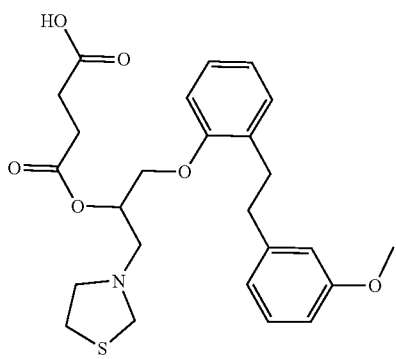

Compound 219
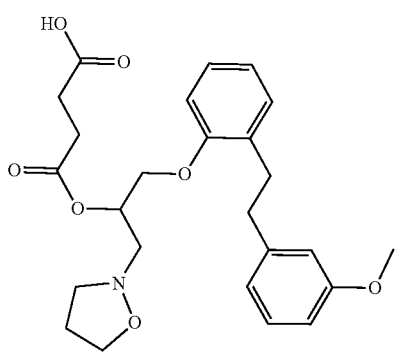

Compound 220
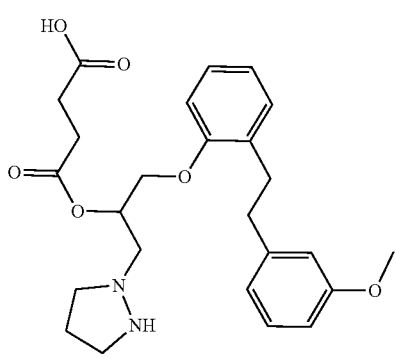

Compound 221
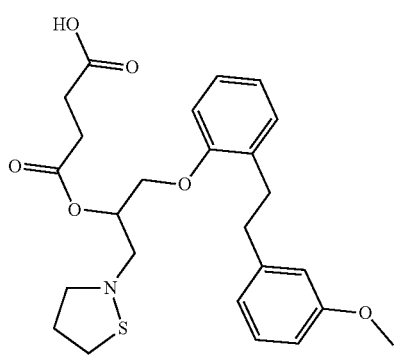

-continued

Compound 222
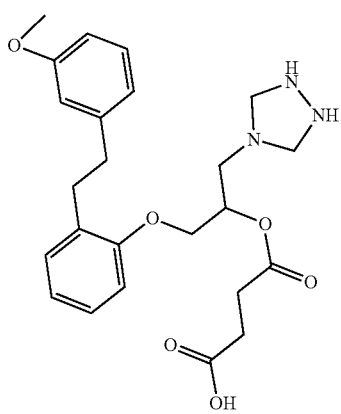

Compound 223
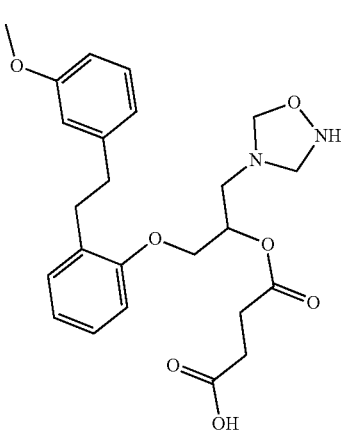

Compound 224
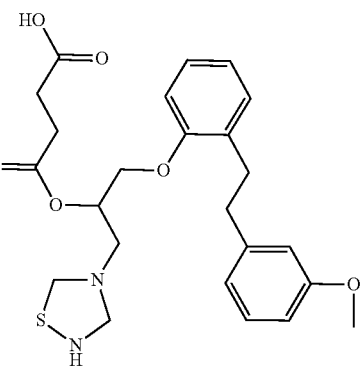

Methods of Use

Antioxidative aromatic alcohols, such as estrogens, donate hydrogen atoms from their phenolic hydroxyl groups to hydroxyl radicals or lipid peroxyradicals prevent oxidative neuronal death. Different aromatic alcohols can prevent oxidative cell death induced by glutamate in clonal hippocampal HT22 cells and in primary cortical neurons. Lipophilicity is an enhancer of neuroprotective action because, for example, the transition from mere phenol to 4-dodecylphenol results in a significant increase in lipophilicity of the molecule and also in a significantly increased neuro-protective activity. 4-dodecylphenol and 4,4'-bi-phenol derivatives were highly protective against glutamate-induced HT22 cell death (Moosmann et al., Neuroprotective potential of aromatic alcohols against oxidative cell death, FEBS Letters 413, 467-472 (1997), incorporated in entirety by reference). Accordingly, an embodiment is a compound Formula I. Another embodiment is a compound selected from the group of Compounds 10-210.

Behavioral and psychological symptoms of dementia (BPSD), also known as neuropsychiatric symptoms, represent a heterogeneous group of non-cognitive symptoms and behaviors occurring in subjects with dementia. BPSD constitute a major component of the dementia syndrome irrespective of its subtype. They are as clinically relevant as cognitive symptoms as they strongly correlate with the degree of functional and cognitive impairment. BPSD include agitation, aberrant motor behavior, anxiety, elation, irritability, depression, apathy, disinhibition, delusions, hallucinations, and sleep or appetite changes. It is estimated that BPSD affect up to 90% of all dementia subjects over the course of their illness, and is independently associated with poor outcomes, including distress among patients and caregivers, long-term hospitalization, misuse of medication, and increased health care costs. Although these symptoms can be present individually it is more common that various psychopathological features co-occur simultaneously in the same patient. Thus, categorization of BPSD in clusters taking into account their natural course, prognosis, and treatment response may be useful in the clinical practice.

Recent studies have emphasized the role of neurochemical, neuropathological, and genetic factors underlying the clinical manifestations of BPSD. Combination of non-pharmacological and careful use of pharmacological interventions is the recommended therapeutic for managing BPSD. Given the modest efficacy of current strategies, there is an urgent need to identify novel pharmacological targets and develop new non-pharmacological approaches to improve the adverse outcomes associated with BPSD. BPSD are highly prevalent in patients with dementia and are associated with distress for patients and caregivers, greater risk of institutionalization, and accelerated progression to severe dementia and death. The core features of dementia consist of gradual onset of multiple cognitive deficits (involving memory and at least one additional cognitive domain) not occurring exclusively during delirium and representing a decline from a previous level of functioning. The presence or absence of a clinically significant behavioral disturbance can be coded, but no guidance is provided about the diagnostic criteria of these symptoms. It is also possible to code dementia (e.g., Alzheimer's disease (AD) in axis III and specific mental disorders (e.g., mood or psychotic disorder) in axis I with the advantage of better characterizing prominent clinical features related to dementia. The assessment of neuropsychiatric symptoms of BPSD requires a thorough examination to collect specific and detailed information about the clinical history, patient's subjective experiences, and objective behavior (Cerejeira et al., Behavioral and psychological symptoms of dementia, Frontiers in Neurology, Volume 3, Article 73 (7 May 2012); DSM-IV-TR: numerical listing of codes and diagnoses; ICD-10-CM Official Guidelines for Coding and Reporting, F Y 2018 (Oct. 1, 2017-Sep. 30, 2018); incorporated in its entirety by reference).

Nonpharmacological interventions are recommended as first-line therapy, but many patients fail to respond, and pharmacotherapy is often needed. Currently marketed dementia therapies leave much room for improvement when it comes to treat BPSD but also other non-cognitive areas of concern. In the continued absence of a disease-modifying therapy, this is of increasing importance, as symptoms like hostility, aggression, wandering, sexually inappropriate behavior or incontinence pose major problems for caregivers and families, and often are a predictor for (costly) nursing home placement. It is common practice to prescribe ("typical or atypical") neuroleptics to facilitate nursing and caregiving. In all dementias, lowering the seizure threshold is another infrequent but highly unwanted potential adverse effect of neuroleptics. Links between a chronic diabetic metabolic situation, metabolic syndrome and the risk and emergence of AD pathophysiology have been substantiated (Goldwaser et al., Breakdown of the Cerebrovasculature and Blood-Brain Barrier: A Mechanistic Link between Diabetes Mellitus and Alzheimer's Disease. *J Alzheimers Dis* 54(2): 445-56 (2016 Aug. 1); incorporated by reference in its entirety).

In several large post-mortem series, more than a third of all subjects clinically diagnosed with typical AD showed evidence of cerebrovascular disease (Grandal Leiros et al., Prevalence and concordance between the clinical and the post-mortem diagnosis of dementia in a psychogeriatric clinic, *Neurologia* S0213-4853(16)30070-6 (2016); incorporated by reference in its entirety). From a clinical perspective, it is therefore desirable to address the cognitive impairment by optimizing a latent diabetic metabolic situation or the fairly frequent Type 2 diabetes in the elderly subjects, because glycemic control impacts the severity of cognitive impairment (Zilliox et al., Diabetes and Cognitive Impairment. *Curr Diab Rep* 16 (9):87 (2016); incorporated by reference in its entirety). Therefore, an embodiment of the invention is a method of treatment of a patient in need thereof comprising administering a composition comprising one or more agents of the invention for the treatment of BPSD. Due to the specific anti-diabetic actions of sarpogrelate, an embodiment of the invention is a method of treatment of cognitive symptoms and disease progression in AD, BPSD of AD, and cognitive and non-cognitive impairment of mainly vascular origin (multi-infarct dementia, vascular dementia, vascular cognitive impairment) comprising administering a composition comprising one or more agents of the invention to a patient in need thereof.

About 10 million people worldwide have Parkinson's disease. Parkinson's disease is a synucleinopathy resulting in progressive neurodegeneration marked by motor dysfunction and non-motor symptoms including psychosis. More than 50% of patients with Parkinson's disease have psychosis at some time. Psychosis affects up to 75% of patients with Parkinson's disease dementia, and symptoms are more intractable in this group. Such psychosis is expressed primarily as hallucinations and delusions, which can cause great distress for patients and their caregivers. These episodes present a major challenge for treatment and care, increase the likelihood of placement in nursing homes, and are associated with increased mortality. Best-practice treatment guidelines promote initial consideration of comorbidities and reduction of dopaminergic therapy. However, these approaches are often insufficient, and few other therapeutic options exist. Antipsychotics can cause profound dopamine D2 antagonism and worsen parkinsonism and/or are poorly tolerated. Accordingly, an embodiment of the invention is a method of treatment of a patient in need thereof comprising administering a composition comprising one or more agents of the invention having high affinity to sites associated with sigma ligands and low affinity to the phencyclidine (PCP) channel of the N-methyl-D-aspartate (NMDA) receptor for the treatment of behavioral and psychological symptoms of Parkinson's disease.

Drug and alcohol dependence is a severe public health problem. It is estimated that between 26.4 million and 36 million people abuse opioids worldwide (UNODC, World Drug Report 2012), with an estimated 2.1 million people in the United States suffering from substance use disorders related to prescription opioid pain relievers in 2012 and an estimated 467,000 addicted to heroin (Substance Abuse and Mental Health Services Administration, Results from the 2012 National Survey on Drug Use and Health: Summary of National Findings, NSDUH Series H-46, HHS Publication No. (SMA) 13-4795. Rockville, Md.: Substance Abuse and Mental Health Services Administration, 2013; incorporated by reference in its entirety). The consequences of this abuse have been devastating and are on the rise. For example, the number of unintentional overdose deaths from prescription pain relievers has soared in the United States, more than quadrupling since 1999. There is also growing evidence to suggest a relationship between increased non-medical use of opioid analgesics and heroin abuse in the United States (Pradip et al., Associations of Nonmedical Pain Reliever Use and Initiation of Heroin Use in the US, Center for Behavioral Health Statistics and Quality Data Review, *SAMHSA* (2013); incorporated by reference in its entirety). Current efforts to taper individuals off opioid medications often lead to limited results due to a high relapse rate and troublesome subjective symptoms. Opioid tolerance, dependence, and addiction are all manifestations of brain changes resulting from chronic opioid abuse. The opioid abuser's struggle for recovery is in great part a struggle to overcome the effects of these changes. Brain abnormalities resulting from chronic use of alcohol and drugs such as heroin, oxycodone, and other morphine-derived drugs are underlying causes of opioid dependence (the need to keep taking drugs to avoid a withdrawal syndrome) and addiction (intense drug craving and compulsive use).

The abnormalities that produce dependence, well understood by science, appear to resolve after detoxification, within days or weeks after opioid use stops. The abnormalities that produce addiction, however, are more wide-ranging, complex, and long-lasting. They may involve an interaction of environmental effects, for example, stress, the social context of initial opiate use, and psychological conditioning, and a genetic predisposition in the form of brain pathways that were abnormal even before the first dose of opioid was taken. Such abnormalities can produce craving that leads to relapse months or years after the individual is no longer opioid dependent. Despite the availability of medications such as naltrexone, their effectiveness is limited, and they often must be used in conjunction with appropriate psychosocial treatments (Kosten et al., The Neurobiology of Opioid Dependence: Implications for Treatment, *Sci Pract Perspect* 1(1): 13-20 (2002 July), incorporated by reference in its entirety).

Dextromethorphan produces PCP-like stimulus effects in rats and partial substitution for PCP in monkeys. Dextrorphan produced full substitution for PCP in both rats and monkeys. Both dextromethorphan and dextrorphan produced self-administration in rhesus monkeys trained to previously self-administer PCP (Nicholson et al., Evaluation of the reinforcing and discriminative stimulus properties of the low-affinity N-methyl-D-aspartate channel blocker memantine. Behav Pharmacol 9(3):231-43 (1998), incorporated by reference in its entirety).

Dextromethorphan can alter self-administration of several drugs of abuse such as morphine, cocaine, and methamphetamine. It attenuates methamphetamine conditioned place preference and behavioral sensitization but has a biphasic effect on cocaine self-administration, locomotor effects and conditioned place preference (Shin et al., Neuropsychotoxicity of abused drugs: potential of dextromethorphan and novel neuroprotective analogs of dextromethorphan with improved safety profiles in terms of abuse and neuroprotective effects. J Pharmacol Sci 106(1):22-7 (2008), incorporated by reference in its entirety). Accordingly, an embodiment of the invention is a method of treatment of a patient in need thereof comprising administering a composition comprising one or more agents of the invention having high affinity to sites associated with sigma ligands and low affinity to the phencyclidine (PCP) channel of the N-methyl-D-aspartate (NMDA) receptor for the treatment of drug abuse and addiction.

Depression currently ranks fourth among the major causes of disability worldwide, after lower respiratory infections, perinatal conditions, and HIV/AIDS. Seventeen percent of people will suffer from depression during their lifetime; making matters worse, people already suffering either from acute or chronic illness are even more likely to suffer from depression, where the incidence of depression is 30% to 50% in patients depending on the specific medical condition. By 2020, it is estimated that unipolar major depression will rank second as a source of lost disability-adjusted life years (DALYs) worldwide. In the United States, depression is the second highest source of disability (DALYs) among women, and antidepressant non-responders are among the heaviest users of health care resources. Despite the clear decrease in quality of life and decreased productivity associated with depression, it is often underdiagnosed and inadequately treated. Depression is associated with reduced monoamine function. The selective 5-HT reuptake inhibitors (SSRIs) and 5-HT and NE reuptake inhibitors (SNRIs) are currently first line treatment options for major depressive disorder (MDD). Monoaminergic mechanisms can be refined by targeting monoaminergic receptors and additional transporters with multimodal drugs and triple re-uptake inhibitors or by adding atypical antipsychotics to SSRI or SNRI treatment.

Glutamate receptors can be targeted with intravenous infusions of the N-methyl-D-aspartate (NMDA) receptor antagonist ketamine. Simultaneous modulation of several neurotransmitter and neuromodulator systems such as cholinergic and gamma-aminobutyric acid (GABA)ergic transmission, neuronal plasticity, stress/hypothalamic pituitary adrenal (HPA)-axis, the reward system, and neuroinflammation can be achieved by using methods of therapy and treatment comprising administering an agent that modulates several neurotransmitter and neuromodulator systems. Accordingly, an embodiment of the invention is a method of treatment of a patient in need thereof comprising administering a composition comprising an agent that modulates several neurotransmitter and neuromodulator systems. In another embodiment, the method of treatment of a patient in need thereof comprising administering a composition comprising one or more agents of the invention that modulates several neurotransmitter and neuromodulator systems.

It was estimated that the total cost of bipolar disorder (BP), also known as manic-depressive illness, made more than a decade ago was as high as $45 billion per year. Most of this cost is accounted for by indirect costs related to reduced functional capacity and lost work. Patients with BP have higher rates of utilization of healthcare resources compared with the general population and compared with patients with other types of psychiatric conditions. Comorbidity contributes to the heavy burden that BP imposes on society. BP frequently occurs together with other psychiatric disorders, especially anxiety disorders and substance abuse. In addition, BP has been associated with a variety of general medical conditions, which further complicate management of the psychiatric disorder (Hirschfeld, Vornik, Bipolar Disorder—Costs and Comorbidity. *Am J Manag Care,* 11: S85-S90 (2005); incorporated by reference in its entirety). BP is a brain disorder that causes unusual shifts in mood, energy, activity levels, and the ability to carry out day-to-day tasks. BP is characterized by a dysregulation of mood, impulsivity, risky behavior and interpersonal problems. BP is a recurrent and often chronic psychiatric illness, associated with functional impairment, elevated suicide rates and utilization of mental health systems. BP is commonly under-recognized and as many as 40% of patients with BPs are initially misdiagnosed, resulting in increased risk for suicide, mania and chronic psychosocial suffering. When correctly diagnosed, successful treatment is possible <50% of diagnosed patients and as many as 10-15% of patients eventually die as a result of suicide (NIMH 2002).

There are four basic types of BP: Bipolar I Disorder, Bipolar II Disorder, Cyclothymic Disorder, and Other Specified and Unspecified Bipolar and Related Disorders. All of BPs involve clear changes in mood, energy, and activity levels. These moods range from periods of extremely up, elated, and energized behavior (known as manic episodes) to very sad, down, or hopeless periods (known as depressive episodes). Less severe manic periods are known as hypomanic episodes. Bipolar I Disorder is defined by manic episodes that last at least 7 days, or by manic symptoms that are so severe that the person needs immediate hospital care. Usually, depressive episodes occur as well, typically lasting at least 2 weeks. Episodes of depression with mixed features (having depression and manic symptoms at the same time) are also possible. Bipolar II Disorder is defined by a pattern of depressive episodes and hypomanic episodes, but not the full-blown manic episodes described above. Cyclothymic Disorder (also called cyclothymia) is defined by numerous periods of hypomanic symptoms as well numerous periods of depressive symptoms lasting for at least two years (1 year in children and adolescents). However, the symptoms do not meet the diagnostic requirements for a hypomanic episode and a depressive episode. Other Specified and Unspecified Bipolar and Related Disorders are defined by BP symptoms that do not match the three categories listed above (Bipolar Disorder, Mental Health Information, National Institute of Mental Health (April 2016), incorporated in entirety by reference). While the pharmacological guidelines for treatment are well established, treatment for BP remains less than ideal. Most individuals still have breakthrough episodes or significant residual symptoms while on medication. In addition, functional deficits often remain even when patients are in remission (NIMH 2002, incorporated in entirety by reference). Because many patients with BP remain symptomatic, even while fully adherent to their medication regimens, the need for greater understanding of the pathogenesis of this illness from the research on the pharmacological mechanisms of bipolar medications is all the more urgent. Common neuroprotective effects of mood stabilizers play a role of brain cell dysfunction in BP, and the dysfunction may eventually cause neuron loss. Volumetric neuroimaging, now increasingly assessing potential involvement of different brain structures in mood regulation, could be applied to test neuroanatomical models of mood disorders. Imaging studies suggested that ongoing neuronal atrophy accompanies BP. For instance, PET images of the cerebral blood flow and the rate of glucose metabolism regarding as brain activity detected the reduced activity in the subgenual prefrontal cortex during the bipolar depression. This decrement in activity was, in part, at least explained by a corresponding reduction of cortical volume, as same as magnetic resonance imaging demonstration of the mean gray matter volume. In BP, abnormalities of the third ventricle, frontal lobe, cerebellum, and possibly the temporal lobe are also noted. Accordingly, an embodiment of the invention is a method of treatment of a patient in need thereof comprising administering a composition comprising one or more agents of the invention that modulates one or several neurotransmitter and neuromodulator systems, wherein the patient is suffering from BP symptoms.

Brain tumors are formed by abnormal growths and can appear in different areas of the brain. Benign (not cancerous) tumors may grow and press on nearby areas of the brain, but rarely spread into other tissues. Malignant (cancerous) tumors are likely to grow quickly and spread into other brain tissue. A tumor that grows into or presses on an area of the brain may stop that part of the brain from working the way it should, whether the tumor itself is benign or malignant, and will then require treatment. The most common type of brain tumor seen does not originate from the brain tissue itself, but rather are metastases from extracranial cancers such as lung cancer and breast cancer. Brain tumors include neurofibromatosis type 1 or 2, von Hippel-Lindau disease, tuberous sclerosis, Li-Fraumeni syndrome, Turcot syndrome type 1 and type 2, Klinefelter syndrome, and Nevoid basal cell carcinoma syndrome. Neuroblastoma is cancer found in developing nerve cells, usually in children under 10 years of age. Almost 90% of cases are diagnosed by the age of 5. Different factors can affect the type of neuroblastoma a child has and their prognosis.

Specific treatment for neurological cancer is based on several factors including a patient's overall health and medical history; the type, location, and size of the tumor; the extent of the condition; and other individual factors. Generally, treatment for patients with cancer of the brain or spinal cord includes surgery, chemotherapy, radiation therapy, and/or steroids to treat and prevent swelling, especially in the brain; anti-seizure medication to treat and prevent seizures associated with intracranial pressure; placement of a shunt (to help drain excess fluid in the brain); lumbar puncture/spinal tap (to measure pressure in the spinal cord and brain); bone marrow transplantation; rehabilitation (to regain lost motor skills and muscle strength); and/or antibiotics (to treat and prevent infections). Chemotherapy is the use of anticancer drugs to treat cancerous cells. In most cases, chemotherapy works by interfering with the cancer cell's ability to grow or reproduce. These drugs may be given into a vein or by mouth, as a tablet.

There were approximately 45 million cases of brain disorders in the UK, with a cost of €134 billion per annum. The most prevalent were headaches, anxiety disorders, sleep disorders, mood disorders and somatoform disorders. However, the five most costly disorders (f million) were: dementia: €22,164; psychotic disorders: €16,717; mood disorders: €19,238; addiction: €11,719; anxiety disorders: €11,687. Apart from psychosis, these five disorders ranked amongst those with the lowest direct medical expenditure per subject (€3000). The approximate breakdown of costs was: 50% indirect costs, 25% direct non-medical and 25% direct healthcare costs (Feinberg et al., The size, burden and cost of disorders of the brain in the UK, J Psychopharmacol. 27(9): 761-770 (2013 September), incorporated in entirety by reference). It was projected that there were 13.8 million cancer survivors in 2010 and 18.1 million cancer survivors i2020, with associated costs of cancer care of 124.57 and 157.77 billion 2010 US dollars, respectively. The total cost in 2020 is projected to be $173 billion (Mariotto et al., Projections of the Cost of Cancer Care in the United States: 2010-2020, J Natl Cancer Inst. 103(2): 117-128 (2011 Jan.

19), incorporated in entirety by reference). Brain diseases represent a considerable social and economic burden in Europe. With yearly costs of about 800 billion euros and an estimated 179 million people afflicted in 2010, brain diseases are an unquestionable emergency and a grand challenge for neuroscientists (DiLuca, The Cost of Brain Diseases: A Burden or a Challenge? Neuron 82(6):1205-8 (2014) incorporated by reference in its entirety).

The Global Burden of Disease study measures burden in "disability-adjusted life years" (DALYs), which is a way of quantifying the health gap between current and ideal health status. The DALY combines years of life lost from an earlier-than-expected death as well as years of healthy life lost from disability, weighted by severity of the disability. One DALY is equivalent to one lost year of healthy life, e.g., dying one year earlier than life expectancy as a result of disease or injury or living two years of life at 50 percent disability. In 2010, mental and behavioral disorders accounted for 183,912,000 DALYs globally, or 2,669 out of every 100,000 DALYs. Neurological disorders made up 73,814,100 DALYs globally, or 1,071 out of every 100,000 DALYs. Although DALYs aren't directly translatable into monetary cost, other methods can give us insight into the cost of these disorders.

The global cost of mental health conditions alone was estimated at US$2.5 trillion in 2010, with a projected increase to over US $6 trillion in 2030. In Europe, the cost of all brain disorders was estimated at €798 billion in 2010. In America, neurological illnesses and mental disorders cost the US more than $760 billion a year (Global Burden of Neurological and Mental Disorders, 10 Nov. 2014; World Health Organization: Neurological Disorders: Public Health Challenges. (2006) Institute for Health Metrics and Evaluation; World Health Organization: The global burden of disease: 2004 update (2004); World Economic Forum. The Global Economic Burden of Non-communicable Diseases (2011); Olesen et al., The economic cost of brain disorders in Europe. European Journal of Neurology. 19: 155-162 (2012); Brain Facts: A Primer on the Brain and Nervous System. Society for Neuroscience (2012); The Numbers Count: Mental Disorders in America. National Institute of Mental Health (2010), incorporated by reference in its entirety). Glioblastoma multiforme is the most common malignant primary brain tumor in adults, with an estimated incidence of 4.43 per 100,000 person-years in the United States and a median age at presentation of 64 years. Symptoms often include headaches; nausea and vomiting; and progressive memory, personality, or neurologic deficits. The treatment remains a challenge, and despite the approval of multiple new therapies in the past decade, survival has not improved. The total expenditures in this patient population were estimated at $6364 per month (GBD 2010 Results by Cause 1990-2010; The Global Burden of Disease: Generating Evidence, Guiding Policy, 2013 Institute for Health Metrics and Evaluation; incorporated by reference in its entirety).

Brain disorders can represent a ticking bomb under global economy due to their enormous societal costs, which are set to grow with the aging of the populations. A huge amount of about 798 billion euros per year is estimated to cost in Europe alone. In every year over a third of the total EU population suffers from mental disorders. The true size of "disorders of the brain" including neurological disorders is even considerably larger. Disorders of the brain are the largest contributor to the all cause morbidity burden as measured by DALY in the EU.

Neurological disorders contribute to 92 million DALYs in 2005 projected to increase to 103 million in 2030 (approximately a 12% increase). While Alzheimer and other dementias are projected to show a 66% increase from 2005 to 2030 (Neurological disorders: public health challenges, Chapter 2. global burden of neurological disorders estimates and projections, pp 27-39).

TABLE 2

| Cause category | 2005 DALYs | 2005 % DALYs | 20015 DALYs | 20015 % DALYs | 2030 DALYs | 2030 % DALYs |
|---|---|---|---|---|---|---|
| Epilepsy | 7 308 | 0.50 | 7 419 | 0.50 | 7 442 | 0.49 |
| Alzheimer/Dementias | 11 078 | 0.75 | 13 540 | 0.91 | 18 394 | 1.20 |
| Parkinson's disease | 1 617 | 0.11 | 1 762 | 0.12 | 2 015 | 0.13 |
| Multiple sclerosis | 1 510 | 0.10 | 1 586 | 0.11 | 1 648 | 0.11 |
| Migraine | 7 660 | 0.52 | 7 736 | 0.52 | 7 596 | 0.50 |

Accordingly, an embodiment of the invention is a method of treatment of a patient in need thereof comprising administering a composition comprising one or more agents of the invention having high affinity to sites associated with sigma ligands and low affinity to the phencyclidine (PCP) channel of the N-methyl-D-aspartate (NMDA) receptor for the treatment of behavioral and psychological symptoms of dementia.

Dextromethorphan binds with high affinity to sites associated with sigma ligands and low affinity to the phencyclidine (PCP) channel of the N-methyl-D-aspartate (NMDA) receptor, forming pentametric or tetrametric complexes of the NR1 subunit and one or more of four NR2 subunits (NR2A-2D). After oral administration, dextromethorphan is quickly absorbed in the gastrointestinal tract with peak serum levels reached within 2-2.5 h. Dextromethorphan is absorbed from the bloodstream and crosses the blood-brain into the cerebral spinal fluid by approximately 33-80% (Hollander et al., High-dose dextromethorphan in amyotrophic lateral sclerosis: phase I safety and pharmacokinetic studies. Ann Neurol 36(6):920-4 (1994), incorporated by reference in its entirety). The activity of dextromethorphan lasts for approximately 5-6 hours with a plasma half-live of 2-4 hours (Pender, et al., Toxicity with dextromethorphan-containing preparations: a literature review and report of two additional cases. Pediatr Emerg Care 7(3):163-5 (1991), incorporated by reference in its entirety). Accordingly, an embodiment of the invention is a method of treatment of a patient in need thereof comprising administering a composition comprising one or more agents of the invention having high affinity to sites associated with sigma ligands and low affinity to the phencyclidine (PCP) channel of the N-methyl-D-aspartate (NMDA) receptor for the treatment of behavioral and psychological symptoms of dementia, wherein the patient has behavioral and psychological symptoms of dementia, and wherein the agent is a compound of Formula II.

Cytochrome P450 in the 2D6 isoenzyme family inactivates dextromethorphan. Dextromethorphan is eliminated renally unchanged or as a demethylated metabolite. Approximately 5-10% of people of white European ethnicity lack CYP2D6, which is necessary to demethylate dextromethorphan to dextrorphan. This can lead to acute toxic levels of dextromethorphan when 'megadoses' (5-10 times the recommended doses) are given (Motassim et al., Direct determination of dextromethorphan and its three metabolites in urine by high-performance liquid chromatography using a precolumn switching system for sample clean-up, J Chromatogr 422:340-5 (1987)). Dextrorphan, the main metabolite, is pharmacologically active with a half-life of approximately 3.5 to 6 h and is a potent NMDA antagonist (Church et al., Dextromethorphan and phencyclidine receptor ligands: differential effects on K(+)- and NMDA-evoked increases in cytosolic free Ca2+ concentration. Neurosci Lett 124(2):232-4 (1991), incorporated by reference in its entirety). Dextromethorphan is rapidly metabolized by the liver and is O-demethylated to produce its active metabolite dextrorphan, and then further N-demethylated and partially conjugated with glucuronic acid and sulfate ions (Woodworth et al., The polymorphic metabolism of dextromethorphan. J Clin Pharmacol 27(2):139-43 (1987), incorporated in entirety by reference). Dextromethorphan is an NR1/NR2A-containing NMDA receptor-preferred antagonist (Avenet et al., Antagonist properties of eliprodil and other NMDA receptor antagonists at rat NR1A/NR2 Å and NR1A/NR2B receptors expressed in *Xenopus* oocytes. Neurosci Lett 223(2):133-6 (1997), incorporated in entirety by reference), while its active metabolite dextrorphan is not and binds with low affinity to sites associated with sigma ligands and high affinity to the PCP-site (Taylor et al., Pharmacology of dextromethorphan: Relevance to dextromethorphan/quinidine (Nuedexta®) clinical use. Pharmacol Ther. 164:170-82 (2016 August); incorporated by reference in its entirety). Accordingly, an embodiment of the invention is a method of treatment of a patient in need thereof comprising administering a composition comprising one or more agents of the invention having high affinity to sites associated with sigma ligands and low affinity to the phencyclidine (PCP) channel of the N-methyl-D-aspartate (NMDA) receptor for the treatment of behavioral and psychological symptoms of dementia, wherein the patient has behavioral and psychological symptoms of dementia, and wherein the composition comprises a compound of Formula II effective in the treatment of behavioral and psychological symptoms of dementia, and an inhibitor of CYP2D6 to prevent rapid metabolism of the compound of Formula II.

Another embodiment is a method of treating behavioral and psychological symptoms of dementia in a patient in need thereof comprising the step of administering a pharmaceutical composition comprising DEX and one or more agents selected from the group comprising 5-HT2A receptor antagonist, 5-HT2A receptor inverse agonist, and CYP2D6 inhibitor. In another embodiment, the agent is an agent having properties of both 5-HT2A receptor antagonist and CYP2D6 inhibitor. In another embodiment, the agent is an agent having properties of both 5-HT2A receptor inverse agonist and CYP2D6 inhibitor. In another embodiment, the agent is a compound of formula I.

Another embodiment is a method of treatment of a patient in need thereof comprising the step of administering a pharmaceutical composition comprising DEX and one or more agents selected from the group comprising 5-HT2A receptor antagonist, 5-HT2A receptor inverse agonist, and CYP2D6 inhibitor. In another embodiment, the agent is an agent having properties of both 5-HT2A receptor antagonist and CYP2D6 inhibitor.

Dextrorphan (DO) is a substance most notable for its psychoactive effects that likely arise from blockade of NMDA receptors. DO has a substantially higher affinity for NMDA receptors compared to that of DEX. Adverse psychoactive effects of DEX have been associated with its metabolism to DO (Taylor, et al., Pharmacology of dextromethorphan: Relevance to dextromethorphan/quinidine (Nuedexta®) clinical use. Pharmacol Ther. 164:170-82 (2016 August); incorporated by reference in its entirety). Accordingly, another embodiment is a method of reducing adverse effects of DEX during treatment of a patient in need thereof comprising the step of administering a pharmaceutical composition comprising DEX and one or more agents selected from the group comprising 5-HT2A receptor antagonist or inverse agonist, 5-HT2A receptor inverse agonist, and CYP2D6 inhibitor. In another embodiment, the agent is an agent having properties of both 5-HT2A receptor antagonist or inverse agonist and CYP2D6 inhibitor. In another embodiment, the agent is an agent having properties of both 5-HT2A receptor inverse agonist and CYP2D6 inhibitor. In another embodiment, the agent is a compound of formula I or SARPO.

Psychological symptoms of dementia involve disregulation of glutamatergic, cholinergic, serotoninergic and norepinephrinergic neurotransmitter systems. Therefore, an embodiment is a method of treating behavioral and psychological symptoms of dementia. Another embodiment is the treatment with a compound of formula I or SARPO, DEX, or SARPODEX™ to improve EEG abnormalities, behavior, cognition, and reduce seizures, as well as improve breathing abnormalities, motor capabilities, bone density, and GI dysfunction. Another embodiment is the treatment with one or more agents of the invention, a compound of formula I or SARPO, DEX, or SARPODEX™ in the treatment of other diseases and conditions, including involuntary emotional expression disorder (IEED) or pseudobulbar affect (PBA), neurodegenerative diseases, neuropathic pain, and brain injuries.

Dextromethorphan is metabolized into active metabolites in the liver starting with O- and N-demethylation to form primary metabolites DO and 3-methoxy-morphinan are further N- and O-demethylated, respectively, to 3-hydroxymorphinan. A major metabolic catalyst is the cytochrome P450 enzyme 2D6 (CYP2D6), which is responsible for the O-demethylation reactions of dextromethorphan and 3-methoxymorphinan. N-demethylation of dextromethorphan and DO are catalyzed by enzymes in the related CYP3A family. Conjugates of DO and 3-hydroxymorphinan can be detected in human plasma and urine within hours of its ingestion. DO is a substance most notable for its psychoactive effects. Therefore, another embodiment is a method of treatment of a patient in need thereof comprising administering dextromethorphan, DO, 3-hydroxymorphinan, or 3-methoxy-morphinan, or a combination thereof.

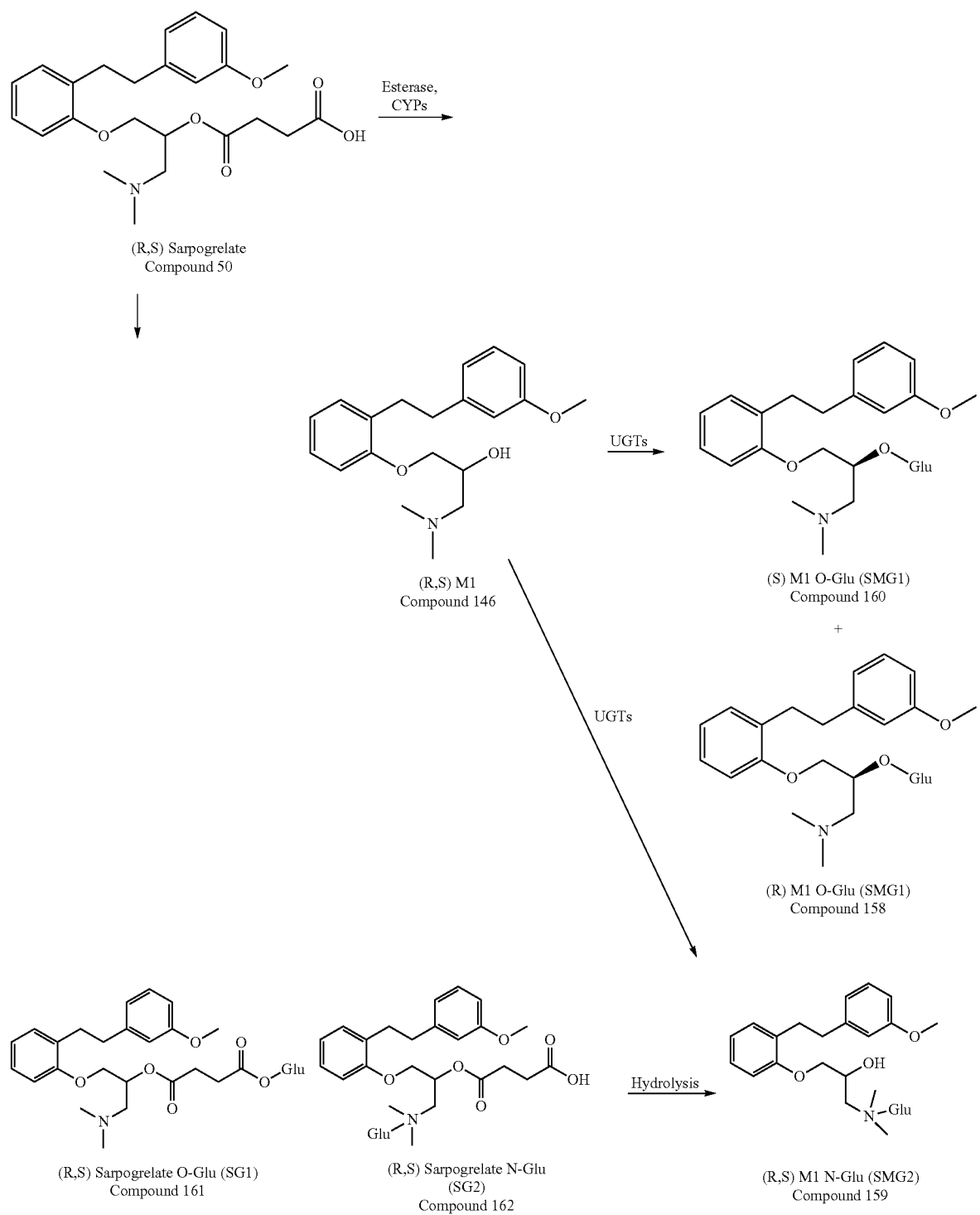

SGL is a 5-HT2A receptor inverse agonist and CYP2D6 inhibitor. SGL inhibits responses to 5-HT mediated by 5-HT2A receptors such as platelet aggregation, vasoconstriction and vascular smooth muscle proliferation. SGL was shown to have the same affinity as ritanserin for 5-HT2A receptors (Nishio et al., Binding affinity of sarpogrelate to 5-HT2A receptor ligand recognition sites in rat renal cortical and mesangial cells in culture. *Gen Pharmacol* 33: 51-57 (1999 March-April); incorporated in entirety by reference).

The blockade of 5-HT2A receptors can inhibit thrombus formation suppresses platelet aggregation and inhibits vascular smooth muscle cell proliferation (Pertz et al., In-vitro pharmacology of sarpogrelate and the enantiomers of its major metabolite: 5-HT2A receptor specificity, stereoselectivity and modulation of ritanserin-induced depression of 5-HT contractions in rat tail artery. *J Pharm Pharmacol.* 47(4):310-6 (1995 April); incorporated in entirety by reference). Accordingly, an embodiment is a method of treatment of a patient in need thereof comprising administering a composition comprising a compound of formula I or SARPO.

In vitro: The main metabolite (R,S)-M-1 blocked 5-HT at 5-HT2A receptors. Reportedly, the stereochemical configuration of M1 did not play a key role at binding to the 5-HT2A receptor (Pertz et al., In-vitro pharmacology of sarpogrelate and the enantiomers of its major metabolite: 5-HT2A receptor specificity, stereoselectivity and modulation of ritanserin-induced depression of 5-HT contractions in rat tail artery. *J Pharm Pharmacol.* 47(4):310-6 (1995 April); incorporated in entirety by reference).

In vivo: PAD patients were divided into two groups. One group treated with 100 mg a compound of formula I or SARPO, per os 3 times one day for 12 weeks (n=10), while the other group who remained on conventional therapy as control group (n=11). Forearm blood flow (FBF) and leg blood flow (LBF) responses to reactive hyperemia (RH) and sublingual administration of nitroglycerin (NTG) were measured by strain-gauge plethysmography. After twelve weeks of its administration, FBF and LBF responses during RH exhibited significant increases from 13.2 6 1.7 to 18.1 6 2.2 mL/min every 100 mL tissue (P 0.01) and from 8.2 6 0.9 to 14.2 6 2.1 mL/min every 100 mL tissue (P 0.05), respectively. Augmentation of FBF and LBF induced by a compound of formula I or SARPO, responses to RH was maintained at 24 weeks. The control group had no change observed in at each follow-up time point. The changes in FBF and LBF after sublingual NTG were similar during follow-up periods in the two groups. These findings suggest that long-term oral administration of a compound of formula I or SARPO, improves vascular function in patients with PAD (Miyazaki et al., Sarpogrelate hydrochloride, a selective 5-HT2A antagonist, improves vascular function in patients with peripheral arterial disease. *J Cardiovasc Pharmacol.* 49(4):221-7 (2007 April); incorporated in entirety by reference).

A method of treating a disease or disorder in a subject in need thereof comprising administering the composition of the invention, wherein the method is a symptomatic and disease-modifying treatment wherein the disease or disorder is a neurodegenerative disease, brain injury and sequelae thereof, organic brain syndrome, chronic traumatic encephalopathy, chronic or intractable pain, ophthalmologic indications associated with retinopathy, anxiety disorder, post-traumatic stress disorder, depression, diabetes mellitus, peripheral neuropathy with or without neuropathic pain, Buerger's disease, Raynaud's disease, coronary artery disease, angina pectoris, atherosclerosis, multi-infarct dementia, Vascular Cognitive Impairment, Vascular Dementia, Binswanger's Disease, nephropathy, Alzheimer's disease (AD), aggression in AD, apathy in AD, Parkinson's disease, vascular cognitive impairment (VCI), Vascular Dementia (VaD), Dementia with Lewy Bodies (DLB), Fronto-Temporal Lobar Degeneration (FTLD), behavioral variant fronto-temporal dementia (bvFTD), anxiety disorders, phobias, generalized anxiety disorder, social anxiety disorder, panic disorder, agoraphobia, obsessive-compulsive disorder, and post-traumatic stress disorder (PTSD), mania, manic depressive illness, hypomania, unipolar depression, depression, stress disorders, somatoform disorders, personality disorders, psychosis, schizophrenia, delusional disorder, schizoaffective disorder, schizotypy, aggression, aggression, agitation, apathy, and aggression, apathy, hostility, aggression, wandering, sexually inappropriate behavior or incontinence in AD, headaches, sleep disorders, mood disorders, somatoform disorders, Bipolar I Disorder, Bipolar II Disorder, Cyclothymic Disorder, and Other Specified and Unspecified Bipolar and Related Disorders, drug abuse and addiction, diabetic and metabolic syndrome, neurofibromatosis type 1 or 2, von Hippel-Lindau disease, tuberous sclerosis, Li-Fraumeni syndrome, Turcot syndrome type 1 and type 2, Klinefelter syndrome, Nevoid basal cell carcinoma syndrome, and neuroblastoma.

Another embodiment is the method of treatment wherein the patient is suffering from a disease or disorder comprising peripheral arterial disease (e.g. Raynaud's Disease, and claudicatio intermittens, Norgen et al. Sarpogrelate, a 5-HT2A receptor antagonist in intermittent claudication. A Phase II European study. Vascular Medicine 11: 75-83 (2006)), pulmonary hypertension (Saini et al., Therapeutic Potentials of Sarpogrelate in Cardiovascular Disease. Cardiovascular Drug Reviews 22: 27-54 (2004); incorporated by reference), angina pectoris (Kinugawa et al., Effectiveness of a novel serotonin blocker, sarpogrelate, for patients with angina pectoris. Am Heart J 144(2):E1 (2002); incorporated by reference), and/or diabetes mellitus (Pietraszek et al., The effect of MCI-9042 on serotonin-induced platelet aggregation in type 2 diabetes mellitus. Thromb Res 70(2): 131-8 (1993); Ogawa et al., Reduced Albuminuria with Sarpogrelate Is Accompanied by a Decrease in Monocyte Chemoattractant Protein-1 Levels in Type 2 Diabetes. Clin J Am Soc Nephrol 3: 362-368 (2008); incorporated by reference). In another embodiment, the method of treatment of a patient after coronary stenting comprising a compound of Formula I or SARPO, to and is useful in restenosis (Doggrell S A. Sarpogrelate: cardiovascular and renal clinical potential. Expert Opinion Invest Drugs 13: 865-874 (2004); incorporated in its entirety by reference).

DO is a substance most notable for its psychoactive effects that likely arise from blockade of NMDA receptors. DO has a substantially higher affinity for NMDA receptors compared to that of DEX. Adverse psychoactive effects of DEX have been associated with its metabolism to DO (Taylor et al., Pharmacology of dextromethorphan: Relevance to dextromethorphan/quinidine (Nuedexta®) clinical use. Pharmacol Ther. 164:170-82 (2016 August); incorporated by reference in its entirety). Therefore, another embodiment is a method of reducing adverse effects of DEX during treatment of a patient in need thereof comprising the step of administering a pharmaceutical composition comprising DEX and one or more agents selected from the group comprising 5-HT2A receptor antagonist or inverse agonist, 5-HT2A receptor inverse agonist, and CYP2D6 inhibitor. In another embodiment, the agent is an agent having properties of both 5-HT2A receptor antagonist or inverse agonist and CYP2D6 inhibitor. In another embodiment, the agent is an agent having properties of both 5-HT2A receptor inverse agonist and CYP2D6 inhibitor. In another embodiment, the agent is a compound of formula I or SARPO.

Another embodiment is a composition comprising (6)-1-{2-[2-(3-methoxyphenil) ethyl]-phenoxy}-3-(dimethylamino)-2-propanol (M-1)), a 5-HT2A receptor inverse agonist and CYP2D6 inhibitor.

Another embodiment is a composition comprising one or more enantiomers of SGL, M1, SG1, SG2, SMG1, SMG2, SMG3 or a combination thereof.

The genetically polymorphic cytochrome CYP2D6 has been implicated in the metabolism of many antipsychotic agents, including thioridazine, perphenazine, chlorpromazine, fluphenazine, haloperidol, zuclopenthixol, risperidone, and sertindole (Michalets, Update: clinically significant cytochrome P-450 drug interactions. Pharmacotherapy 18(1):84-112 (1998), incorporated by reference in its entirety). This enzyme is also important in the metabolism of other drugs that are commonly prescribed to patients with psychiatric disorders, e.g., tricyclic antidepressants (nortriptyline, desipramine, amitriptyline, imipramine, and clomipramine) and selective serotonin reuptake inhibitors, including fluoxetine and paroxetine (Taylor, Cytochromes and psychotropic drug interactions. Br J Psychiatry 168(5):529-32 (1996); Sproule et al., Selective serotonin reuptake inhibitors and CNS drug interactions. A critical review of the evidence. Clin Pharmacokinet 33(6): 454-71 (1997); incorporated by reference in its entirety). Drugs that inhibit these enzymes would be expected to cause increases in the plasma concentration of co-administered antipsychotic drugs (Michalets, Update: clinically significant cytochrome P-450 drug interactions. Pharmacotherapy 18(1):84-112 (1998); incorporated in entirety by reference). These increases may, in turn, lead to the development or aggravation of antipsychotics-induced side effects including cardiac toxicity, anticholinergic side effects, or orthostatic hypotension (Ereshefsky, Pharmacokinetics and drug interactions: update for new antipsychotics. J Clin Psychiatry 57 (Suppl 11): 12-25 (1996); incorporated in entirety by reference).

A number of antipsychotic drugs inhibit CYP2D6-catalyzed DEX O-demethylation compared with other CYP isoform catalyzed reactions. Among the antipsychotic drugs tested, thioridazine and perphenazine were the most potent inhibitors and decreased the DO formation rate to 26.5 and 19.7% of control activity at 10 microM, and 11.4 and 10.7% of control activity at 25 microM, respectively. The inhibitory potency of these drugs on DEX O-demethylation was comparable to the inhibitory effect of 10 to 25 microM quinidine. The estimated mean IC50 values for thioridazine and perphenazine were 2.7±0.5 and 1.5±0.3 micro M, respectively. The IC50 of quinidine, a potent CYP2D6 inhibitor, was estimated to be 0.52±0.2 microM under these conditions. The estimated IC50s of chlorpromazine, fluphenazine, and haloperidol were 9.7, 16.3, and 14.4 microM, respectively. Cisthiothixene, clozapine, and risperidone exhibited weaker inhibition than the other drugs tested, with mean $IC_{50}s$ estimated to be 136.6, 92.2, and 39.1 microM, respectively (Shin et al., Effect Of Antipsychotic Drugs on Human Liver Cytochrome P-450 (CYP) Isoforms in Vitro: Preferential Inhibition of CYP2D6, Drug Metab Dispos 27 (9): 1078-84 (1999); incorporated by reference in its entirety).

In one embodiment, the pharmaceutical composition of the invention comprise one or more of the CYP2D6 inhibitors such as, but are not limited to, Ajmaline, Amiodarone, Amitriptyline, Aprindine, Azelastine, Celecoxib, Chlorpheniramine, Chlorpromazine, Diphenhydramine, Doxorubicin, Fluoxetine, Fluphenazine, Fluvastatin, Fluvoxamine, Haloperidol, Imipramine, Indinavir, Lasoprazole, Levomepromazine, Lopinavir, Loratadine, Mequitazine, Methadone, Metoclopramide, Mibefradil, Moclobemide, Nelfinavir, Nevirapine, Nicardipine, Norfluoxetine, Paroxetine, Perphenazine, Pimozide, Terfenadine, Thioridazine, Cimetidine, Quinidine, Cisapride, Citalopram, Clomipramine, Clozapine, Cocaine, Desipramine, Ranitidine, Risperidone, Ritonavir, Saquinavir, Sertraline, Terbinafine, Ticlopidine, Trifluperidol, Venlafaxine, and Yohimbine.

In one embodiment, the invention is a combination of a 5HT2A receptor antagonist and a CYP2D6 inhibitor providing a therapeutic advantage of the simultaneous 5HT2A receptor antagonism and 2D6 inhibition. In another embodiment, the invention is a combination of a 5HT2A receptor inverse agonist and a CYP2D6 inhibitor providing a therapeutic advantage of the simultaneous 5HT2A receptor inverse agonism and 2D6 inhibition. A compound of formula I or SARPO provides a unique therapeutic advantage by combining both CYP2D6 inhibition and 5HT2A receptor inverse agonism to improve the magnitude of the therapeutic response to DEX. Thus, agents of the invention avoid potential health risks associated with the concomitant use of an anti-arrhythmic drug quinidine with DEX. Accordingly, an embodiment is a composition comprising SARPO-DEX™.

Some embodiments include a method of decreasing the number of doses and/or total daily dose of dextromethorphan, a metabolite, a derivative or a prodrug thereof (DEX) that can be administered while increasing efficacy and safeguarding tolerability and safety, comprising orally administering an effective amount of one or more agents of the invention, a compound of formula I or SARPO, a compound of Formula II or DEX, or SARPODEX™.

Some embodiments include a method of reducing an adverse event associated with treatment by DEX, comprising co-administering one or more agents of the invention, a compound of formula I or SARPO, to a subject in need of a treatment, wherein the subject is at risk of experiencing the adverse event as a result of being treated with DEX or a compound of formula II.

Some embodiments include a method of decreasing DO plasma levels comprising co-administering a compound of formula I or SARPO, to a subject in need of treatment with DEX, wherein the compound of formula I or SARPO is administered on the first day of at least two days of treatment with DEX, wherein a decrease in the DO plasma level occurs on the first day that a compound of formula I or SARPO, and DEX are co-administered, as compared to the same amount of DEX administered without one or more agents of the invention comprising a compound of formula I, or SARPO.

Another embodiment is a method of decreasing DO plasma levels comprising co-administering a compound of formula I or SARPO, and DEX, for at least eight consecutive days, to a subject in need of treatment with DEX, wherein, on the eighth day, the DO plasma level is lower than the DO plasma level that would have been achieved by administering the same amount of DEX administered without a compound of formula I or SARPO, for eight consecutive days.

Another embodiment is a method of using a 5-HT2A receptor antagonist or inverse agonists, such as a compound of formula I or SARPO to improve the therapeutic properties of DEX such as in the treatment of neurological disorders. A compound of formula I, regardless of stereochemistry, can be effective in inhibiting or reducing the metabolism of DEX in some subjects, accomplished by co-administering a compound of formula I.

Another embodiment is a method of treating a neurological disorder comprising administering a 5-HT2A receptor antagonist or inverse agonist and DEX to a subject in need thereof, wherein the subject is an extensive metabolizer of DEX.

Another embodiment is a method of treating a neurological disorder comprising administering a 5-HT2A receptor inverse agonist, antagonist, and DEX to a subject in need thereof, wherein the subject is an extensive metabolizer of DEX.

Another embodiment is a method of increasing DEX plasma levels in a subject in need of treatment with DEX, wherein the subject is an extensive metabolizer of DEX, comprising co-administering a compound of formula I or SARPO, with DEX to the subject.

Another embodiment is a method of inhibiting the metabolism of DEX, comprising administering a compound of formula I or a compound of formula I or SARPO, to a subject, wherein the subject is an extensive metabolizer of DEX, and wherein DEX is present in the body of the subject at the same time as a compound of formula I or SARPO.

Another embodiment is a method of increasing the metabolic lifetime of DEX, comprising administering a compound of formula I to a subject in need of treatment with DEX, wherein the subject is an extensive metabolizer of DEX, and wherein DEX is present in the body of the subject at the same time as a compound of formula I or SARPO.

Another embodiment is a method of correcting extensive metabolism of DEX, comprising administering a compound of formula I to a subject in need thereof.

Another embodiment is a method of improving the antitussive properties of DEX comprising administering a compound of formula I in conjunction with administration of DEX to a subject in need of treatment for a cough.

Another embodiment is a method of treating cough comprising administering a combination of a compound of formula I and Formula II to a subject in need thereof.

Another embodiment is a method of treating a neurological disorder comprising administering a compound of formula I or SARPO, and DEX to a subject in need thereof, wherein the compound of formula I or SARPO, and DEX are administered at least once a day for at least eight days.

Another embodiment is a method of treating a neurological disorder comprising administering about 5 mg/day to about 600 mg/day, about 5 mg/day to about 300 mg/day, about 5 mg/day to about 400 mg/day, about 5 mg/day to about 500 mg/day, about 5 mg/day to about 600 mg/day, about 5 mg/day to about 1,000 mg/day, about 50 mg/day to about 1000 mg/day, about 100 mg/day to about 1000 mg/day, about 150 mg/day to about 1000 mg/day, about 150 mg/day to about 5000 mg/day, about 150 mg/day to about 300 mg/day, or about 150 mg/day to about 100 mg/day, or an amount as required of a compound of formula I or SARPO, and about 0.1 mg/day to about 1 mg/day, about 0.5 mg/day to about 15 mg/day, about 15 mg/day to about 60 mg/day, about 15 mg/day to about 120 mg/day, about 0.1 mg/day to about 200 mg/day, or an amount as required of DEX to a subject in need thereof.

Another embodiment is a method of increasing DEX plasma levels in a subject in need of treatment with DEX, wherein the subject is an extensive metabolizer of DEX, comprising co-administering a compound of formula I or SARPO, with DEX to the subject.

Another embodiment is a method of inhibiting the metabolism of DEX, comprising administering a compound of formula I or SARPO, to a subject, wherein the subject is an extensive metabolizer of DEX, and wherein DEX is present in the body of the subject at the same time as a compound of formula I or SARPO.

Another embodiment is a method of increasing the metabolic lifetime of DEX, comprising administering a compound of formula I or SARPO, to a subject in need of treatment with DEX, wherein the subject is an extensive metabolizer of DEX, and wherein DEX is present in the body of the subject at the same time as a compound of formula I or SARPO.

Another embodiment is a method of increasing DEX plasma levels comprising co-administering a compound of formula I or SARPO, and DEX to a subject in need of treatment with DEX, wherein the compound of formula I or SARPO, is administered on the first day of at least two days of co-administration of a compound of formula I or SARPO, with DEX, wherein an increase in the DEX plasma level occurs on the first day that a compound of formula I or SARPO, and DEX are co-administered, as compared to the same amount of DEX administered without a compound of formula I or SARPO.

Another embodiment is a method of increasing DEX plasma levels comprising co-administering a compound of formula I or SARPO, and DEX, for at least five consecutive days, to a subject in need of treatment with DEX, wherein, on the fifth day, the DEX plasma level is higher than the DEX plasma level that would have been achieved by administering the same amount of DEX administered without a compound of formula I or SARPO, for five consecutive days.

Another embodiment is a method of increasing DEX plasma levels comprising co-administering a compound of formula I or SARPO, and DEX, for at least six consecutive days, to a subject in need of treatment with DEX, wherein, on the sixth day, the DEX plasma level is higher than the DEX plasma level that would have been achieved by administering the same amount of DEX administered without a compound of formula I or SARPO, for six consecutive days.

Another embodiment is a method of reducing a trough effect of DEX comprising, co-administering a compound of formula I or SARPO, with DEX to a subject in need of treatment with DEX, wherein DEX has a plasma level 12 hours after co-administering a compound of formula I or SARPO, with DEX that is at least twice the plasma level that would be achieved by administering the same amount of DEX without a compound of Formula I or SARPO.

Another embodiment is a method of reducing a trough effect of DEX comprising, co-administering a compound of formula I or SARPO, with DEX to a subject in need of treatment with DEX, wherein DEX has a plasma level 12 hours after co-administering a compound of formula I or SARPO, with DEX that is at least twice the plasma level that would be achieved by administering the same amount of DEX without a compound of formula I or SARPO.

Another embodiment is a method of reducing a trough effect of DEX comprising, co-administering a compound of formula I or SARPO, with DEX to a subject in need of treatment with DEX, wherein DEX has a plasma level 12 hours after co-administering a compound of formula I or SARPO, with DEX that is at least twice the plasma level that would be achieved by administering the same amount of DEX without a compound of formula I or SARPO.

Another embodiment is a method of reducing an adverse event or other unwanted consequences such as addiction, abuse, physical or psychological dependence, associated with treatment by DEX, comprising co-administering a compound of formula I or SARPO, and DEX to a subject in need of DEX treatment, wherein the subject is at risk of experiencing the adverse event as a result of being treated with DEX.

Another embodiment is a method of reducing an adverse event associated with treatment by a compound of formula I or SARPO, comprising co-administering DEX and a compound of formula I or SARPO, to a subject in need of a compound of formula I or SARPO, treatment, wherein the subject is at risk of experiencing the adverse event as a result of being treated with a compound of formula I or SARPO.

Another embodiment is a method of improving antitussive properties of DEX comprising administering a compound of formula I or SARPO, in conjunction with administration of DEX to a subject in need of treatment for cough.

Another embodiment is a method of treating cough comprising administering a combination of a compound of formula I or SARPO, and DEX to a subject in need thereof.

Another embodiment is a method of treating a neurological disorder comprising administering a compound of formula I or SARPO, and DEX to a subject in need thereof, wherein the compound of formula I or SARPO, and DEX are administered at least once a day for at least 8 days.

Another embodiment is a method of treating a neurological disorder comprising administering a composition comprising DEX, SARPODEX™ or a compound of formula I or SARPO, to a subject in need thereof, wherein the DEX, SARPODEX™, or a compound of formula I or SARPO, is administered at least once a day for at least 8 days.

Another embodiment is a method of treating a neurological disorder comprising administering a composition comprising DEX, SARPODEX™ or a compound of formula I or SARPO, to a subject in need thereof, wherein the compound of formula I or SARPO, and DEX are administered at least once a day for at least 8 days.

Another embodiment is an oral sustained release delivery system for DEX, comprising a composition comprising DEX, SARPODEX™, a compound of formula I or SARPO, and a water-soluble vehicle. The oral sustained release delivery system is a drug-resin complex to prepare different drug-resin complexes to be combined in the suspension, or where one or more drugs are provided as drug-resin complexes and one or more drugs are dissolved in the liquid carrier. Another embodiment is a pharmaceutical sustained release oral suspension comprising ion exchange resin particles coated with a compound of Formula I or SARPO and suspended in a liquid carrier comprising a compound of Formula II or DEX. Another embodiment is a pharmaceutical sustained release oral suspension comprising ion exchange resin particles coated with a compound of Formula II or DEX and suspended in a liquid carrier comprising a compound of Formula I or SARPO (Savjani et al., Drug Solubility: Importance and Enhancement Techniques, International Scholarly Research Network ISRN Pharmaceutics Volume 2012, Article ID 195727, 10 pages; U.S. Pat. Nos. 2,780,355 A; 4,999,189 A; 5,128,142 A; incorporated in entirety by reference).

Another embodiment provides a controlled release formulation comprising an adsorbate of a mixture of 1 part by weight of a pharmaceutically useful active ingredient comprising a compound of Formula I or SARPO and/or a compound of Formula II or DEX, or SARPODEX™ and from 0.1 to 100 parts by weight of an inactive substance adsorbed on a cross-linked polymer in a ratio of 1 part by weight of the mixture to 0.5-200 parts by weight of cross-linked polymer, said inactive substance being selected to modify the dissolution of the active drug from the cross-linked polymer in vivo, with the proviso that the active ingredient is not a dihydropyridine when the inactive substance is polyvinylpyrrolidone with an average molecular weight in the range 15,000 to 50,000 and the cross-linked polymer is cross-linked polyvinylpyrrolidone. In another embodiment, the polymer to active drug ratio is about 3:1, about 4:1, about 5:1, about 6:1, about 7:1, about 8:1, about 9:1, or about 10:1. Examples of swelling agents that may be used in the present invention include cross-linked polyvinylpyrrolidone, cross-linked carboxymethylcellulose sod sodium, sodium starch glycolate, and the like. The swelling agent may be present in an amount from about 5% to about 50%, preferably from about 10% to about 30%, and more preferably from about 10% to about 20%, by weight of the total weight of the composition. The pharmaceutical composition further contains a viscolyzing agent such as xanthan gum, tragacanth gum, gum karaya, guar gum, acacia, etc. Additionally, the pharmaceutical composition may contain a gel forming polymer such as a water-soluble salt of a polyuronic acids such as mannuoronic acid, guluronic acid, alginic acid, etc., wherein the salt is formed with a metal such as sodium or potassium, or an ammonium salt thereof in an amount from about 0.1% to about 20% by weight of the total weight of the composition. In addition, the pharmaceutical composition may also contain a hydrophilic water-soluble polymer such as hydroxypropyl methylcellulose, hydroxypropylcellulose, polyacrylic acid, or cross-linked polyacrylic acid (U.S. Pat. Nos. 5,128,142 A; 6,261,601 B1; 4,777,033; 5,651,985 incorporated in entirety by reference).

Another embodiment is a method of decreasing the number of doses of DEX that can be administered without loss of efficacy, comprising orally administering an effective amount of a composition comprising DEX, SARPODEX™ or a compound of formula I or SARPO, to a subject in need of treatment with DEX.

Another embodiment is a pharmaceutical composition, dosage form, or medicament comprising a therapeutically effective amount of DEX, a therapeutically effective amount of a compound of formula I or SARPO, and a pharmaceutically acceptable excipient.

In an aspect, provided is a method of increasing the metabolic lifetime of DEX, comprising administering 5-HT2A receptor antagonist or inverse agonist to a subject in need of treatment with DEX, wherein 5-HT2A receptor antagonist or inverse agonist is an inhibitor of a CYP2D6 enzyme and wherein DEX is present in the body of the subject at the same time as the inhibitor of a CYP2D6. In another embodiment, the composition comprises DEX, SARPODEX™ or a compound of formula I or SARPO.

In another aspect, provided is a method of preventing adverse events associated with treatment by DEX, comprising co-administering 5-HT2A receptor antagonist or inverse agonist or inverse agonist such as a compound of formula I or SARPO, to a subject in need of treatment with DEX, wherein the subject is at risk of experiencing the adverse event as a result of being treated with DEX.

In another aspect, provided is a method for using 5HT2A receptor antagonists such as a compound of formula I or SARPO, to improve the therapeutic properties of DEX in the treatment of neurological disorders.

In another aspect, provided is a method of treating a disorder or disease comprising administering a composition comprising 5HT2A receptor antagonist and DEX to a subject in need thereof. In another embodiment, the composition comprises DEX, SARPODEX™ or a compound of formula I or SARPO.

In another aspect, provided is a method for selecting a 5-HT2A receptor antagonist or inverse agonist for the use in combination with DEX in a subject in need thereof.

Another embodiment, NMDA receptor antagonists reduce the physical aspects of the expression of morphine dependence as measured by naloxone-precipitated withdrawal (Popik et al., Inhibition of reinforcing effects of morphine and motivational aspects of naloxone-precipitated opioid withdrawal by N-methyl-D-aspartate receptor antagonist, memantine. *J. Pharmacol. Exp. Ther.* 280: 854-865 (1997); Popik et al., Inhibition of reinforcing effects of morphine and naloxone-precipitated opioid withdrawal by novel glycine site and uncompetitive NMDA receptor antagonists. *Neuropharmacology.* 37: 1033-1042 (1998); U.S. Pat. No. 8,785, 472 B2; US 20060167032 A1; incorporated by reference in its entirety) and may attenuate not only the physical but also affective and motivational components of abstinence states, as well as craving (Cornish et al., A randomized, double-blind, placebo-controlled safety study of high-dose dextromethorphan in methadone-maintained male inpatients. *Drug & Alcohol Dependence.* 67(2): 177-83(2002); incorporated by reference in its entirety). By reducing withdrawal symptoms, such medications should be beneficial for the patients during the acute detoxification phase of treatment for opioid dependence (Cornish et al., A randomized, double-blind, placebo-controlled safety study of high-dose dextromethorphan in methadone-maintained male inpatients. *Drug & Alcohol Dependence.* 67(2): 177-83 (2002); incorporated by reference in its entirety).

Accordingly, an embodiment is a method of treating a subject in need of treatment for disorders or diseases associated with addiction and substance abuse comprising administration of DEX, SARPODEX™ or a compound of formula I or SARPO.

In another embodiment, NMDA antagonists inhibit morphine self-administration and inhibit both the development and expression of morphine conditioned place preference (Popik et al., Inhibition of reinforcing effects of morphine and naloxone-precipitated opioid withdrawal by novel glycine site and uncompetitive NMDA receptor antagonists. *Neuropharmacology.* 37: 1033-1042 (1998); Kim et al., Inhibition by MK-801 of morphine-induced conditioned place preference and postsynaptic dopamine receptor supersensitivity in mice. *Pharmacol. Biochem. Behav.* 55: 11-17 (1996); incorporated by reference in its entirety). Therefore, DEX prevents the development and expression of conditioned drug dependence effects.

Chronic exposure to morphine results in a number of biochemical adaptations of the glutamatergic receptor system in the limbic system (Fitzgerald et al., Drugs of abuse and stress increase the expression of GluR1 and NMDAR1 glutamate receptor subunits in the rat ventral tegmental area: common adaptations among cross-sensitizing agents. *J. Neurosci.* 16: 274-282 (1996); incorporated by reference in its entirety). Excitatory amino acids are involved in the mediation of many neurochemical and behavioral effects resulting from chronic exposure to abusing drugs, some of which can be prevented or reversed using glutamatergic antagonists (Inturrisi, Preclinical evidence for a role of glutamatergic systems in opioid tolerance and dependence. *Semin. Neurosci.* 9: 110-119 (1997); incorporated by reference in its entirety). Continued self-administration of abusive drugs, including opioid, results in an overstimulation of dopamine in the brain reward centers and an increased release of excitatory amino acids including glutamate leading to the development of tolerance and dependence which could be blocked by glutamate antagonists (Herman et al., Clinical medication development for opiate addiction: focus on nonopioids and opioid antagonists for the amelioration of opiate withdrawal symptoms and relapse prevention. *Semin. Neurosci.* 9: 158-172 (1997); incorporated by reference in its entirety). Accordingly, an embodiment is a method of treating a subject in need of treatment for disorders or diseases associated with addiction and substance abuse resulting from opioid tolerance and dependence by amelioration of opiate withdrawal symptoms and relapse prevention comprising administration of DEX, SARPODEX™ or a compound of formula I or SARPO.

DEX affords neuroprotection on dopamine neurons in several inflammation-based animal Parkinson's disease models (Li et al., Protective effect of dextromethorphan against endotoxic shock in mice. *Biochemical Pharmacology.* 69(2): 233-40 (2005); Liu et al., Dextromethorphan protects dopaminergic neurons against inflammation-mediated degeneration through inhibition of microglial activation. *Journal of Pharmacology & Experimental Therapeutics.* 305(1):212-8 (2003); Zhang et al., 3-hydroxymorphinan is neurotrophic to dopaminergic neurons and is also neuroprotective against LPS-induced neurotoxicity. *FASEB Journal.* 19(3): 395-7 (2005); incorporated by reference in its entirety). 1-10 microM DEX protected dopamine neurons against lipopolysaccharide (LPS)-induced reduction of dopamine uptake in rat primary mixed mesencephalic neuron-glia cultures. Morphologically, in LPS-treated cultures, besides the reduction of an abundance of dopamine neurons, the dendrites of the remaining dopamine neurons were significantly less than those in the controls. In cultures pretreated with DEX (10 microM) before LPS stimulation, dopamine neurons were significantly more numerous and the dendrites less affected. Significant neuroprotection was observed in cultures with DEX added up to 60 minutes after the addition of LPS. Thus, DEX significantly protects monoamine neurons not only with pretreatment but also with post-treatment (Zhang et al., 3-hydroxymorphinan is neurotrophic to dopaminergic neurons and is also neuroprotective against LPS-induced neurotoxicity. *FASEB Journal.* 19(3): 395-7 (2005); incorporated by reference in its entirety). Animal studies using both LPS and MPTP PD models also show potent protective effect of DEX (Zhang et al., 3-hydroxymorphinan is neurotrophic to dopaminergic neurons and is also neuroprotective against LPS-induced neurotoxicity. *FASEB Journal.* 19(3): 395-7 (2005); incorporated by reference in its entirety). Accordingly, an embodiment is a method of treating a subject in need of a treatment for Parkinson's disease comprising administration of DEX, SARPODEX™, a compound of Formula I or a compound of formula II, or a combination thereof.

The neuroprotective effect of DEX is associated with the inhibition of microglia over-activation by inhibition of superoxide anion production from NADPH-oxidase, and this neuroprotective effect of DEX is not associated with its NMDA receptor antagonist property. Zhang et al. (Zhang et al., 3-hydroxymorphinan is neurotrophic to dopaminergic neurons and is also neuroprotective against LPS-induced neurotoxicity. *Faseb Journal.* 19(3): 395-7 (2005)) examined several NMDA receptor antagonists, including MK801, AP5 and memantine. They found no correlation between the affinity of NMDA receptor antagonist activity and potency of the neuroprotective effect on dopamine neurons. On the contrary, a better correlation was observed between the anti-inflammatory potency and neuroprotection. These results suggest that the dopamine neuroprotection provided by DEX in the inflammation-related neurodegenerative models is not mediated through the NMDA receptor. This conclusion is not in conflict with previous reports, indicating that NMDA receptor blockade is associated with the neuroprotective effects of DEX in the acute glutamate-induced excitotoxicity models. Accordingly, an embodiment is a method of treating a subject in need of treatment for a disorder or disease thereof comprising administration of DEX, SARPODEX™ or a compound of formula I, wherein the disorder or disease is an inflammation-related neurodegenerative disorder.

Opioid agonists have been reported to modulate the immune system through opioid receptors in the central nervous system (CNS). Direct actions of opiates on immune cells were observed in vitro studies (Madden et al., Opiate binding sites in the cellular immune system: expression and regulation. *J Neuroimmunol* 83(1-2): 57-62 (1998); incorporated by reference in its entirety). Opioid receptors, including micro3 and delta isoforms, were found in immune cells. Indirect actions of morphine also can be demonstrated in the immunological system. Morphine induces thymocyte apoptosis in vivo (Fuchs et al., Morphine induces apoptosis in murine thymocytes in vivo but not in vitro: involvement of both opiate and glucocorticoid receptors. *J Pharmacol Exp Ther* 266(1): 417-23 (1993); incorporated by reference in its entirety). Thymus hypoplasia was shown to be glucocorticoid (GC)-dependent (Sei et al., Morphine-induced thymic hypoplasia is glucocorticoid-dependent. *J. Immunol.* 146(1): 194-8 (1991); incorporated by reference in its entirety). Accordingly, an embodiment is a method of treating a subject in need of treatment for a disorder or disease thereof comprising administration of DEX, SARPODEX™, a compound of formula I or a compound of formula II, or a combination thereof, wherein the disorder or disease is thymic hypoplasia.

GC-dependent effects of morphine activate the hypothalamic-pituitary-adrenal (HPA) axis. The activation of the HPA axis increases the products of GC as potent immunomodulatory hormones (Freier et al., A mechanism of action for morphine-induced immunosuppression: corticosterone mediates morphine-induced suppression of natural killer cell activity. *J Pharmacol Exp Ther* 270(3): 1127-33 (1994); Mellon et al., Role of central opioid receptor subtypes in morphine-induced alterations in peripheral lymphocyte activity. *Brain Res* 789(1): 56-67 (1998); incorporated by reference in its entirety). Accordingly, an embodiment is a method of treating a subject in need of treatment for a disorder or disease thereof comprising administration of SARPODEX™, wherein the disorder or disease is opioid dependence. The dosage of up to about 500 mg/day DEX is suggested, including doses of 120, 240, and 480 mg/day of DEX for heroin addicts undergoing withdrawal. DEX at high doses caused mild elevations of heart rate, blood pressure, temperature, and plasma bromide (Cornish et al., A randomized, double-blind, placebo-controlled safety study of high-dose dextromethorphan in methadone-maintained male inpatients. *Drug & Alcohol Dependence*. 67(2): 177-83 (2002); incorporated by reference in its entirety). In some ethnic groups such as Han Chinese in Taiwan, DEX metabolism profile can be different from that of Western population due to differences in the expression and/or activity of CYP2D6 (Yeh et al., Analysis of pharmacokinetic parameters for assessment of dextromethorphan metabolic phenotypes. *J. Biomed. Sci.* 10: 552-564 (2003); incorporated by reference in its entirety).

Significantly higher interleukin-6, interleukin-8, and TNF-alpha-levels are manifested in bipolar disorder (BP) patients during manic and depressive episodes than normal controls (Kim et al., Alexithymia and Stress Response Patterns among Patients with Depressive Disorders in Korea. *Psychiatry Investig.* 6(1): 13-8 (2009); O'Brien et al., Cytokine profiles in bipolar affective disorder: focus on acutely ill patients. *J Affect Disord.* 90(2-3): 263-7 (2006); Brietzke et al., Comparison of cytokine levels in depressed, manic and euthymic patients with bipolar disorder. *J Affect Disord.* 116(3): 214-7 (2009); incorporated by reference in its entirety).

In postmortem frontal cortex from BP patients, the significantly higher protein and mRNA levels of IL-1 beta receptor and neuroinflammatory markers inducible nitric oxide synthase (iNOS) and c-fos were found (Rao et al., Increased excitotoxicity and neuroinflammatory markers in postmortem frontal cortex from bipolar disorder patients. *Mol. Psychiatry.* 15(4): 384-92 (2010); incorporated by reference in its entirety). Taken together, the imbalance of the immune system, subsequently leading to the neuronal inflammatory response, might be related to the progression of the brain atrophy and aggravated BP symptoms. BP treatment with immune-targeted therapies showed antidepressant effects. For example, open-label acetylsalicylic acid when added to fluoxetine led to increased remission rates in individuals with major depression who were previously non-responsive to fluoxetine monotherapy (Mendlewicz et al., Shortened onset of action of antidepressants in major depression using acetylsalicylic acid augmentation: a pilot open-label study. *Int. Clin. Psychopharmacol.* 21(4): 227-31 (2006); incorporated by reference in its entirety).

Thus, using an anti-inflammatory agent combined with a mood stabilizer improves the treatment effect on BP. Mood stabilizers have been shown to activate interconnected intracellular signaling pathways that promote neurogenesis and synaptic plasticity. A reduction in brain volume in BP patients was found to be largely suppressed by chronic treatment with Valproate (VPA) resulting in neuroprotective effects, as VPA renders neurons less susceptible to a variety of insults (Chen et al., Valproate protects dopaminergic neurons in midbrain neuron/glia cultures by stimulating the release of neurotrophic factors from astrocytes. *Mol Psychiatry.* 11(12):1116-1125 (December 2006); incorporated by reference in its entirety) and even stimulates neurogenesis in the adult rodent brain. VPA induces cytoprotective proteins like Bcl-2, glucose-regulated protein 78 (Grp78), brain-derived neurotrophic factor (BDNF) and heat shock protein 70. Moreover, VPA promotes neurite outgrowth, while VPA at therapeutic levels was reported to inhibit histone deacetylase (HDAC), an enzyme that catalyzes the removal of the acetyl group from lysine residues of histones, promoting local, neuronal BDNF biosynthesis. Accordingly, an embodiment is a method of treating a subject in need of treatment for a disorder or disease thereof comprising administration of DEX, SARPODEX™ a compound of formula I, a compound of formula II, or a combination thereof, wherein the disorder or disease is BP.

Another embodiment is a method of reducing adverse events of DEX in a subject in need thereof comprising:
a. administering DEX; and
b. administering a compound of formula I or SARPO, to the subject.

Some embodiments include a method of treating neuropsychiatric disorders comprising administering a therapeutically effective amount of DEX and a therapeutically effective amount of an antidepressant, such as a compound of formula I or SARPO, to a person in need thereof.

Some embodiments include a method of enhancing the therapeutic properties of DEX in treating neuropsychiatric disorders, comprising co-administering DEX and an antidepressant, such as a compound of formula I or SARPO.

Some embodiments include a method of increasing DEX plasma levels in a subject that is an extensive metabolizer of DEX, comprising co-administering a 5-HT2A receptor antagonist or inverse agonist, such as a compound of formula I or SARPO, and DEX to the subject.

Some embodiments include a method of inhibiting the metabolism of DEX, comprising administering a 5-HT2A receptor antagonist or inverse agonist, such as a compound of formula I or SARPO, to a subject, wherein the subject is an extensive metabolizer of DEX, and wherein DEX is present in the body of the subject at the same time as the 5-HT2A receptor antagonist or inverse agonist.

Some embodiments include a method of increasing the metabolic lifetime of DEX, including increasing the elimination half-life ($T_1/2$) of DEX. These embodiments may comprise administering a 5-HT2A receptor antagonist or inverse agonist, such as a compound of formula I or SARPO, to a subject, wherein the subject is an extensive metabolizer of DEX, and wherein DEX is present in the body of the subject at the same time as the 5-HT2A receptor antagonist or inverse agonist or inverse agonist.

Some embodiments include a method of correcting extensive metabolism of DEX, comprising administering a 5-HT2A receptor antagonist or inverse agonist or inverse agonist, such as a compound of formula I or SARPO, to a subject in need thereof, such as a subject in need of treatment for pain.

Some embodiments include a method of improving the therapeutic properties of DEX in treating neuropsychiatric disorders comprising administering a 5-HT2A receptor antagonist or inverse agonist or inverse agonist, such as a compound of formula I or SARPO, in conjunction with administration of DEX to a subject in need of treatment for a neuropsychiatric disorder.

Some embodiments include a method of treating neuropsychiatric disorders comprising administering a combination of a 5-HT2A receptor antagonist or inverse agonist, such as a compound of formula I or SARPO, and DEX to a subject in need thereof.

In one embodiment, the method of treatment comprises a dosage regimen comprising administration of DEX to a subject in need thereof 6 times a day (every 4 hours), 4 times a day (every 6 hours), or 3 times a day (every 8 hours) (OTC Monograph [21CFR341.74]). DEX is rapidly metabolized in the human liver. This rapid hepatic metabolism may limit systemic drug exposure in individuals who are extensive metabolizers. Subjects can be: 1) extensive metabolizers of DEX—those who rapidly metabolize DEX; 2) poor metabolizers of DEX—those who only poorly metabolize DEX; or 3) intermediate metabolizers of DEX—those whose metabolism of DEX is somewhere between that of an extensive metabolizer and a poor metabolizer. Extensive metabolizers can also be ultra-rapid metabolizers. Extensive metabolizers of DEX are a significant portion of the human population. DEX can, for example, be metabolized to DO.

When given the same oral dose of DEX, plasma levels of DEX are significantly higher in poor metabolizers or intermediate metabolizers as compared to extensive metabolizers of DEX. The low plasma concentrations of DEX can limit its clinical utility as a single agent for extensive metabolizers, and possibly intermediate metabolizers, of DEX. Some antidepressants, such as a compound of formula I or SARPO, inhibit the metabolism of DEX, and can thus improve its therapeutic efficacy. Similarly, antidepressants may allow DEX to be given less often, such as once a day instead of twice a day, once a day instead of three times a day, once a day instead of four times a day, twice a day instead of three times a day, or twice a day instead of four times a day, without loss of therapeutic efficacy.

Accordingly, an embodiment of the invention is a method of treatment of pain or other neuropsychiatric disorders comprising administering a therapeutically effective amount of DEX and a therapeutically effective amount of a 5-HT2A receptor antagonist or inverse agonist, such as a compound of formula I or SARPO, to a person in need thereof.

Another embodiment of the invention is a method of treatment or treatment of increased efficacy of neuropsychiatric disorders that include, but are not limited to: affective disorders, psychiatric disorders, cerebral function disorders, movement disorders, dementias, traumatic brain injury, chronic traumatic encephalopathy, PTSD, motor neuron diseases, neurodegenerative diseases, seizure disorders, and headaches, comprising administering a therapeutically effective amount of DEX and a therapeutically effective amount of a 5-HT2A receptor antagonist or inverse agonist, such as a compound of formula I or SARPO, to a person in need thereof.

Another embodiment of the invention is a method of treatment or treatment of increased efficacy of affective disorders that include, but are not limited to, depression, major depression, treatment-resistant depression and treatment-resistant bipolar depression, BPs including cyclothymia, seasonal affective disorder, mania, anxiety disorders, attention deficit disorder (ADD), attention deficit disorder with hyperactivity (ADDH), and attention deficit/hyperactivity disorder (ADHD), bipolar and manic conditions, obsessive-compulsive disorder, bulimia, anorexia, obesity or weight gain, narcolepsy, chronic fatigue syndrome, premenstrual syndrome, substance addiction or abuse, nicotine addiction, psycho-sexual dysfunction, pseudobulbar affect, and emotional lability, comprising administering a therapeutically effective amount of DEX and a therapeutically effective amount of a 5-HT2A receptor antagonist or inverse agonist, such as a compound of formula I or SARPO, to a person in need thereof.

Depression is manifested by changes in mood, feelings of intense sadness, despair, mental slowing, sleep disturbances, loss of concentration, pessimistic worry, agitation, and self-depreciation. Physical symptoms of depression may include insomnia, anorexia, weight loss, decreased energy and libido, apathy, and abnormal hormonal circadian rhythms.

Another embodiment of the invention is a method of treatment or treatment of increased efficacy of psychiatric disorders that include, but are not limited to, anxiety disorders, including but not limited to, phobias, generalized anxiety disorder, social anxiety disorder, panic disorder, agoraphobia, obsessive-compulsive disorder, and post-traumatic stress disorder (PTSD); mania, manic depressive illness, hypomania, unipolar depression, depression, stress disorders, somatoform disorders, personality disorders, psychosis, schizophrenia, delusional disorder, schizoaffective disorder, schizotypy, aggression, aggression in Alzheimer's disease, agitation, and apathy in Alzheimer's disease, comprising administering a therapeutically effective amount of DEX and a therapeutically effective amount of a 5-HT2A receptor antagonist or inverse agonist, such as a compound of formula I or SARPO, to a person in need thereof.

Apathy, or loss of motivation, is the most common change in behavior in Alzheimer's disease (AD). It is common throughout the spectrum of cognitive decline from mild cognitive impairment to severe Alzheimer's disease (AD), as well as in a variety of other neuropsychiatric disorders. Apathy represents a form of executive cognitive dysfunction. Patients with apathy suffer from decreased daily function and specific cognitive deficits and rely on families to provide more care, which results in increased stress for families. Apathy is one of the primary syndromes associated with frontal and subcortical pathology, and apathy in AD appears to have multiple neuroanatomical correlates that implicate components of frontal subcortical networks. Despite the profound effects of this common syndrome, only a few instruments have been designed to specifically assess apathy, and these instruments have not been directly compared. Assessment of apathy in AD requires clinicians to distinguish loss of motivation from loss of ability due to cognitive decline. Although apathy may be misdiagnosed as depression because of an overlap in symptoms, current research has shown apathy to be a discrete syndrome.

Distinguishing apathy from depression has important treatment implications, because these disorders respond to different interventions.

The Apathy Inventory (IA), a rating scale for global assessment of apathy and separate assessment of emotional blunting, lack of initiative, and lack of interest, is a reliable method for assessing in demented and non-demented elderly subjects several dimensions of the apathetic syndrome, and also the subject's awareness of these symptoms. The IA assesses apathy as effectively as the Neuro Psychiatric Inventory apathy domain (Robert et al., The Apathy Inventory: assessment of apathy and awareness in Alzheimer's disease, Parkinson's disease and mild cognitive impairment, the Journal of Geriatric Psychiatry, Volume 17, Issue 12, Pages 1099-1105 (December 2002); Landes et al., Apathy in Alzheimer's Disease, the Journal of American Geriatric Society, Volume 49, Issue 12, Pages 1700-1707 (December 2001); Malloy et al., Apathy and Its Treatment in Alzheimer's Disease and Other Dementias, Psychiatric Times, Vol. XXII, Issue 13 (Nov. 1, 2005); incorporated by reference in its entirety). Apathy can be the result of damage to one or more areas of the brain such as the frontal cortex, the thalamus, striatum and the amygdala. In most cases direct damage to the frontal lobes or the subcortical nuclei that have connections to the frontal lobes, cause apathy. Apathy associated with Alzheimer's disease is very difficult to treat. Antidepressants, SSRIs, psychostimulants, acetylcholinesterase inhibitors etc., alleviated apathy only to some degree. Accordingly, an embodiment of the invention is a combination of SARPODEX™ and one or more of antidepressants, SSRIs, psychostimulants, acetylcholinesterase inhibitors, dopaminergic agents. Another embodiment is a combination of SARPODEX™ and one or more of donepezil, memantine, amantanidine, bupropion, ropinirole, methylphenidate, amphetamine, modafinil, metrifonate, tacrine, galantamine, rivastigmine, nefiracetam, *Ginkgo biloba* extract, etc. (Ruthirakuhan et al., Pharmacological interventions for apathy in Alzheimer's disease (Protocol), Cochran Database of Systemic Studies, 2016, Issue 5. Art. No.: CD012197, Published by John Wiley & Sons, Ltd.; Theleritis et al., Pharmacological and Nonpharmacological Treatment for Apathy in Alzheimer Disease: A Systematic Review Across Modalities, Journal of Geriatric Psychiatry and Neurology 30 (1): 26-49 (2017); references are incorporated in entirety by reference).

Neuropsychiatric symptoms are a common burden in patients suffering from Alzheimer's disease (AD), Parkinson's disease dementia (PDD), and many other neurodegenerative disorders, including but not limited to dementia with Lewy bodies (DLB), vascular dementia (VaD), and frontotemporal lobar degeneration (FTLD) (Kazui et al., Differences of Behavioral and Psychological Symptoms of Dementia in Disease Severity in Four Major Dementias. PLoS ONE 11(8): e0161092 (2016); Van der Schyf, Psychotropic Drug Development Strategies that Target Neuropsychiatric Etiologies in Alzheimer's and Parkinson's Diseases. Drug Dev Res. 77: 458-468 (2016)).

Many neuropsychiatric symptoms manifest very early in neurodegenerative disease stages, and are even considered prodromal indicators or indicators for disease progression (Kazui et al., Differences of Behavioral and Psychological Symptoms of Dementia in Disease Severity in Four Major Dementias. PLoS ONE 11(8): e0161092 (2016); Peters et al., Neuropsychiatric Symptoms as Predictors of Progression to Severe Alzheimer's Dementia and Death: The Cache County Dementia Progression Study. Am J Psychiatry 172: 460-465 (2015)).

Behavioral and psychological symptoms of dementia (BPSD), also known as neuropsychiatric symptoms, in neurodegenerative diseases and disease states including but not limited to AD have a multifactorial origin (McClam et al., Interventions for neuropsychiatric symptoms in neurocognitive impairment due to Alzheimer's disease: a review of the literature. Harv Rev Psychiatry 23: 377-393 (2015)). Therefore, a strategy aimed at simultaneously targeting multiple etiologies of a disease (hence, multiple drug targets) constitutes the best approach in the development of treatment strategies for a range of diseases including but not limited to AD (Nikolic et al., Drug design for CNS diseases: polypharmacological profiling of compounds using cheminformatic, 3D-QSAR and virtual screening methodologies. Front Neurosci 10: 265 (2016)).

Individual BPSD symptoms may appear as mutually exclusive but can nevertheless share the underlying mechanisms. This shared mechanism similarity can occur at the neurochemical and/or neuroanatomical levels and serves as a basis for developing targeted, but not mechanism-specific therapies addressing more than one BPSD symptom. Shared mechanisms are illustrated by similar neurochemical organizations of the projections from cortical areas to basal ganglia to thalamus and back to the cortex. For example, the dorsolateral prefrontal cortex projects to the dorsolateral caudate, which in turn targets lateral dorsomedial parts of internal globus pallidus that sends projections to the principal part of the ventral anterior or mediodorsal thalamus, which returns projections to the cortex. In contrast, the orbitofrontal cortex projects to the ventromedial caudate that projects to medial dorsomedial parts of internal globus pallidus that sends projections to the magnocellular part of ventral anterior or mediodorsal thalamus which returns projections to the cortex. Thus, different parts of cortex may be responsible for different functions but there are common principles according to which cortical networks operate (Aouizerate et al., Pathophysiology of obsessive-compulsive disorder: a necessary link between phenomenology, neuropsychology, imagery and physiology. Prog Neurobiol 72(3): 195-221 (2004); incorporated by reference in its entirety). Therefore, impairments in different circuits underlie the emergence of different BPSD symptoms. Heterogeneity of the clinical presentations of neurodegenerative disorders is determined by the predominant location of the pathology (i.e. by affected networks). For example, the dorsal anterior cingulate cortex and dorsolateral prefrontal cortex are more affected in apathetic patients, and the medial orbital frontal cortex in disinhibited patients with bvFTLD (Massimo et al., Dement Geriatr Cogn Disord 27:96-104 (2009); incorporated by reference in its entirety).

For 5-HT2A receptors that are targeted by a compound of formula I or SARPO, it is well established that serotonin via 5-HT2A receptors increases glutamatergic spontaneous excitatory postsynaptic currents in apical dendrites of layer V pyramidal cells of prefrontal cortex (Aghajanian et al., Serotonin, via 5-HT2A receptors, increases EPSCs in layer V pyramidal cells of prefrontal cortex by an asynchronous mode of glutamate release. Brain Res 825:161-71 (1999); incorporated by reference in its entirety). Such excessive asynchronous transmission may be functionally expressed in a variety of forms dependent on which part of the cerebral cortex is affected—from auditory or visual hallucinations to disinhibition and apathy—but in most cases, will be sensitive to manipulations involving 5-HT2A receptors that are present across various cortical areas (van Dyck et al., PET quantification of 5-HT2A receptors in the human brain: a constant infusion paradigm with [$^{18}$F] altanserin. J Nucl Med 41(2):234-41 (2000); incorporated by reference in its entirety).

For glutamatergic signaling that is targeted by dextromethorphan, it is well established that it mediates thalamocortical signaling, causing the activation of corresponding areas of the cortex (Kharazia et al., Glutamate in thalamic fibers terminating in layer IV of primary sensory cortex. J Neurosci 14(10):6021-6032 (1994); Sherman S M. Thalamus plays a central role in ongoing cortical functioning. Nat Neurosci 19(4):533-41 (2016); incorporated by reference in its entirety).

Diseases like Alzheimer's disease are characterized by systematic, progressive, probably trans-synaptic spread of neurodegeneration. That does not only mean more cell loss in a certain area of the brain but also spreading of the pathology to other brain areas. As different brain areas have different functional roles, this explains why more advanced stages of the disease are accompanied by a wider spectrum of symptoms (Kazui et al., Differences of Behavioral and Psychological Symptoms of Dementia in Disease Severity in Four Major Dementias. PLoS ONE 11(8): e0161092 (2016); incorporated by reference in its entirety).

Behavioral and psychological symptoms of dementia, also known as neuropsychiatric symptoms, are commonly studied in the clinic using research tools such as the Neuropsychiatric Inventory (NPI; Cummings, The Neuropsychiatric Inventory: Assessing psychopathology in dementia patients. Neurology 48:S10-S16 (1997)). The NPI scale recognizes 12 sub-domains of behavioral functioning: delusions, hallucinations, agitation/aggression, dysphoria, anxiety, euphoria, apathy, disinhibition, irritability/lability, aberrant motor activity, night-time behavioral disturbances, and appetite and eating abnormalities.

Patients rarely display each and every of these NPI symptoms at once as there are NPI items like euphoria that are rare, even at a clinical dementia rating (CDR) score of 3. Conversely, clinical experience indicates that there is rarely a patient showing just one specific item, and none of the rest. Instead, BPSD symptoms occur in various combinations or clusters. For example, a frequent AD cluster could e.g. be aggression, agitation, wandering, repetitiveness, while a frequent Vascular Dementia cluster could e.g. be confusion and restlessness, but the frequency and severity of NPI items is subject to change, e.g. from day to day, but especially during disease progression (Kazui et al., Differences of Behavioral and Psychological Symptoms of Dementia in Disease Severity in Four Major Dementias. PLoS ONE 11(8): e0161092 (2016); Johnson et al., Neuropsychiatric profiles in dementia. Alzheimer Dis Assoc Disord 25(4): 326-332 (2011); incorporated by reference in its entirety). As a given patient may present such a cluster of several symptoms of clinical relevance at once, there is a high medical need in treatments that can target various clusters of symptoms or the entire range of BPSD symptoms, irrespective of any currently prevailing pathophysiological hypothesis on the disease.

The prevalence of delusions is rather low in general population, in people with normal cognitive aging (0.4-2.4%) but is increased in subjects with mild cognitive impairment (MCI; 3.1-3.4%) and markedly increased in dementia (18.0-31.0%) (Geda et al., The Prevalence of Neuropsychiatric Symptoms in Mild Cognitive Impairment and Normal Cognitive Aging: A Population-Based Study. Arch Gen Psychiatry 65(10): 1193-1198 (2008); Lyketsos et al., Prevalence of neuropsychiatric symptoms in dementia and mild cognitive impairment: results from the cardiovascular health study. JAMA 288(12):1475-83 (2002); Zhao et al., The prevalence of neuropsychiatric symptoms in Alzheimer's disease: Systematic review and meta-analysis. J Affect Disord 190:264-71 (2016); incorporated by reference in its entirety). Prevalence of hallucinations is also low in the general population, in people with normal cognitive aging (0.4-0.6%) but is increased in subjects with MCI (0.6-1.3%) and dementia (10.5-16.0%) (Geda et al., The Prevalence of Neuropsychiatric Symptoms in Mild Cognitive Impairment and Normal Cognitive Aging: A Population-Based Study. Arch Gen Psychiatry 65(10): 1193-1198 (2008); Lyketsos et al., Prevalence of neuropsychiatric symptoms in dementia and mild cognitive impairment: results from the cardiovascular health study. JAMA 288(12): 1475-83 (2002); Zhao et al., The prevalence of neuropsychiatric symptoms in Alzheimer's disease: Systematic review and meta-analysis. J Affect Disord 190:264-71 (2016); incorporated by reference in its entirety).

Both delusions and hallucinations are part or symptoms of psychosis in various neurological and psychiatric diseases and disease states. Neuroleptics have traditionally been used off-label to treat such symptoms faute-de-mieux in dementia; however, with very few exceptions both "typical" and "atypical" neuroleptics increase the incidence of CV adverse events and showed a markedly increased death rate when used off-label in dementia. Hence, the FDA issued a "black box" warning against their off-label use outside schizophrenia that leaves little therapeutic options to treat such BPSD symptoms in dementia. On this background, a completely different class, namely 5-HT2A receptor antagonists and inverse agonists demonstrated an antipsychotic-like efficacy profile in preclinical studies (Weiner et al., 5-hydroxytryptamine2A receptor inverse agonists as antipsychotics. J Pharmacol Exp Ther 299(1):268-76 (2001); incorporated by reference in its entirety). Several 5-HT2A receptor antagonists and inverse agonists have been in development for neuropsychiatric indications and there were reports of beneficial antipsychotic effects obtained with compounds such as eplivanserin (Meltzer et al., Placebo-controlled evaluation of four novel compounds for the treatment of schizophrenia and schizoaffective disorder. Am J Psychiatry 161: 975-84 (2004); incorporated by reference in its entirety). 5-HT2A receptor inverse agonist pimavanserin significantly reduced psychotic symptoms, which includes hallucinations and delusions, in patients with moderate to severe Parkinson's disease (Cummings et al., Pimavanserin for patients with Parkinson's disease psychosis: a randomised, placebo-controlled phase 3 trial. Lancet 383: 533-40 (2014)) and has been FDA approved specifically for the treatment of these symptoms in PDD. In patients with Alzheimer's disease dementia, HTR2A T102C polymorphism is a significant risk factor for psychosis with an allelic OR of 2.191 for C allele that increased to 5.143 for the homozygous CC genotype (Ramanathan et al., Serotonergic system genes in psychosis of Alzheimer dementia: meta-analysis. Am J Geriatr Psychiatry 17(10):839-46 (2009); incorporated by reference in its entirety).

Dextromethorphan is described to have NMDA receptor channel blocking properties and NMDA receptor channel blockers such as phencyclidine or ketamine are known to possess psychotomimetic rather than antipsychotic properties. There are reports of psychosis induced by dextromethorphan in humans (Miller, Dextromethorphan psychosis, dependence and physical withdrawal. Addict Biol 10(4): 325-7 (2005), incorporated by reference in its entirety). These psychoactive properties of dextromethorphan may be a function of its metabolic degradation resulting in production of dextrorphan (Zawertailo et al., Effect of metabolic blockade on the psychoactive effects of dextromethorphan. Hum Psychopharmacol 25(1):71-9 (2010); incorporated by reference in its entirety). Psychoactive effects of dextromethorphan observed in some subjects do not exclude a possibility that dextromethorphan also has antipsychotic properties under certain circumstances. Indeed, dextromethorphan, but not its metabolite dextrorphan, was reported to attenuate phencyclidine-induced motor behaviors in rats (Székely et al., Induction of phencyclidine-like behavior in rats by dextrorphan but not dextromethorphan. Pharmacol Biochem Behav 40(2):381-6 (1991); incorporated by reference in its entirety). Meta-analysis of the randomized controlled studies of another NMDA receptor channel blocker, memantine, in patients with Alzheimer's disease indicated that memantine induces significant improvement in delusions (Kishi et al., The effects of memantine on behavioral disturbances in patients with Alzheimer's disease: a meta-analysis. Neuropsychiatr Dis Treatment 13: 1909-1928 (2017); incorporated by reference in its entirety).

Agitation and aggression are grouped together as one item on the NPI scale. Prevalence of agitation and aggression is low in general population, in people with normal cognitive aging (2.8-2.9%) but is increased in subjects with MCI (9.1-11.3%) and dementia (30.3-40%) (Geda et al., The Prevalence of Neuropsychiatric Symptoms in Mild Cognitive Impairment and Normal Cognitive Aging: A Population-Based Study. Arch Gen Psychiatry 65(10): 1193-1198 (2008); Lyketsos et al., Prevalence of neuropsychiatric symptoms in dementia and mild cognitive impairment: results from the cardiovascular health study. JAMA 288(12): 1475-83 (2002); Zhao et al., The prevalence of neuropsychiatric symptoms in Alzheimer's disease: Systematic review and meta-analysis. *J Affect Disord* 190:264-71 (2016); incorporated by reference in its entirety). So this NPI item is one the most prevalent and at the same time difficult to treat clinical BPSD symptom.

Preclinical studies indicate that blockade of 5-HT2A receptors reduces aggression in laboratory rodents (Sakaue et al., Modulation by 5-hT2A receptors of aggressive behavior in isolated mice. Jpn J Pharmacol 89(1):89-92 (2002); incorporated by reference in its entirety). Human genetics data indicate that scores on three out of four subscales of the Buss-Perry Aggression Questionnaire (Hostility, Anger and Physical Aggression) show significant association with HTR2A rs7322347 T allele (Banlaki et al., Polymorphism in the serotonin receptor 2a (HTR2A) gene as possible predisposal factor for aggressive traits. PLoS One 10(2):e0117792 (2015)). In a case-control study in Chinese subjects with AD, aggression in AD was significantly associated with 5-HT2A receptor polymorphism such as T102C (Lam et al., 5-HT2A T102C receptor polymorphism and neuropsychiatric symptoms in Alzheimer's disease. Int J Geriatr Psychiatry 19(6):523-6 (2004); incorporated by reference in its entirety).

Various NMDA receptor channel blockers have been shown to attenuate aggressive behaviors in mice and these effects may be difficult to separate from sedative action (Belozertseva, Effects of NMDA receptor channel blockade on aggression in isolated male mice. Aggr Behav 25:381-396 (1999)). In patients with probable Alzheimer disease and clinically significant agitation, dextromethorphan-quinidine combination reduced Agitation/Aggression scores of the NPI (Cummings et al., Effect of Dextromethorphan-Quinidine on Agitation in Patients With Alzheimer Disease Dementia: A Randomized Clinical Trial. JAMA 314(12): 1242-54 (2015); incorporated by reference in its entirety); this combination treatment has been approved for the treatment of agitation). A meta-analysis of randomized controlled studies of another nonselective NMDA receptor channel blocker, memantine, in patients with Alzheimer's disease indicated that also memantine induces significant improvement in agitation/aggression (Kishi et al., The effects of memantine on behavioral disturbances in patients with Alzheimer's disease: a meta-analysis. Neuropsychiatr Dis Treatment 13: 1909-1928 (2017); incorporated by reference in its entirety).

The prevalence of dysphoria/depression is moderate in general population, in people with normal cognitive aging (7.2-11.4%) but is increased in subjects with MCI (20.1-27.0%) and it is one of the most prevalent problems in dementia (32.3-42%) (Geda et al., The Prevalence of Neuropsychiatric Symptoms in Mild Cognitive Impairment and Normal Cognitive Aging: A Population-Based Study. Arch Gen Psychiatry 65(10): 1193-1198 (2008); Lyketsos et al., Prevalence of neuropsychiatric symptoms in dementia and mild cognitive impairment: results from the cardiovascular health study. JAMA 288(12):1475-83 (2002); Zhao et al., The prevalence of neuropsychiatric symptoms in Alzheimer's disease: Systematic review and meta-analysis. J Affect Disord 190:264-71 (2016); incorporated by reference in its entirety).

Preclinical studies using brain stimulation reward indicated that 5-HT2A receptor antagonism may counteract dysphoria induced by conventional neuroleptics such as haloperidol (Benaliouad et al., Blockade of 5-HT2a receptors reduces haloperidol-induced attenuation of reward. Neuropsychopharmacology 32(3):551-61 (2007); incorporated by reference in its entirety). 5-HT2A receptor antagonists exert antidepressant-like effects in preclinical models sensitive to clinically used antidepressant drugs (Marek et al., The selective 5-HT2A receptor antagonist M100907 enhances antidepressant-like behavioral effects of the SSRI fluoxetine. Neuropsychopharmacology 30: 2205-2215 (2005); Patel et al., The highly selective 5-hydroxytryptamine (5-HT)2A receptor antagonist, EMD 281014, significantly increases swimming and decreases immobility in male congenital learned helpless rats in the forced swim test. Synapse 52: 73-75 (2004); incorporated by reference in its entirety).

NMDA receptor channel blockers such as dextromethorphan have been shown to possess antidepressant-like properties in preclinical models (Sakhaee et al., The role of NMDA receptor and nitric oxide/cyclic guanosine monophosphate pathway in the antidepressant-like effect of dextromethorphan in mice forced swimming test and tail suspension test. Biomed Pharmacother 85:627-634 (2017); incorporated by reference in its entirety). Of the NMDA receptor channel blockers, ketamine, is proven to have rapid and robust antidepressant activity in patients with treatment-resistant major depressive disorder (Singh et al., A Double-Blind, Randomized, Placebo-Controlled, Dose-Frequency Study of Intravenous Ketamine in Patients With Treatment-Resistant Depression. Am J Psychiatry 173(8):816-26 (2016); incorporated by reference in its entirety). Dextromethorphan given in combination with quinidine also exerts antidepressant action in humans (Murrough et al., Dextromethorphan/quinidine pharmacotherapy in patients with treatment resistant depression: A proof of concept clinical trial. J Affect Disord 218:277-283 (2017); incorporated by reference in its entirety). Dextromethorphan is not a selective NMDA receptor channel blocker and is more potent at serotonin and norephinephrine transporters as well as sigma-1 receptors that may contribute to therapeutic effects of dextromethorphan (Stahl, Mechanism of action of dextromethorphan/quinidine: comparison with ketamine. CNS Spectrums 18: 225-227 (2013); incorporated by reference in its entirety). While monoamine transporters are targeted by most currently used antidepressants, sigma-1 receptors have also been found to contribute to antidepressant-like effects of dextromethorphan in laboratory animals (Nguyen et al., Involvement of sigma-1 receptors in the antidepressant-like effects of dextromethorphan. PLoS One 9(2):e89985 (2014); incorporated by reference in its entirety).

The prevalence of apathy is low in general population, in people with normal cognitive aging (3.2-4.8%) but is increased in subjects with MCI (14.7-18.5%) and dementia (35.9-49%) (Geda et al., The Prevalence of Neuropsychiatric Symptoms in Mild Cognitive Impairment and Normal Cognitive Aging: A Population-Based Study. Arch Gen Psychiatry 65(10): 1193-1198 (2008); Lyketsos et al., Prevalence of neuropsychiatric symptoms in dementia and mild cognitive impairment: results from the cardiovascular health study. JAMA 288(12):1475-83 (2002); Zhao et al., The prevalence of neuropsychiatric symptoms in Alzheimer's disease: Systematic review and meta-analysis. J Affect Disord 190:264-71 (2016); incorporated by reference in its entirety). In a case-control study in Chinese subjects with AD, apathy in AD was significantly associated with 5-HT2A receptor polymorphism such as T102C (Lam et al., 5-HT2A T102C receptor polymorphism and neuropsychiatric symptoms in Alzheimer's disease. Int J Geriatr Psychiatry 19(6): 523-6 (2004); incorporated by reference in its entirety). Apathy is a symptom frequently seen in patients with schizophrenia and belongs to the group of negative symptoms. 5-HT2A receptor antagonists reduce the severity of negative symptoms in patients with schizophrenia (Davidson et al., Efficacy and Safety of MIN-101: A 12-Week Randomized, Double-Blind, Placebo-Controlled Trial of a New Drug in Development for the Treatment of Negative Symptoms in Schizophrenia. Am J Psychiatry DOI: 10.1176/appi.ajp.2017. Ser. No. 17/010,122 (2017); Meltzer et al., Placebo-controlled evaluation of four novel compounds for the treatment of schizophrenia and schizoaffective disorder. Am J Psychiatry 161(6):975-84 (2004); incorporated by reference in its entirety).

NMDA receptor channel blockers such as memantine are reported to reduce apathy in certain patients with neurodegenerative diseases (Links et al., A case of apathy due to frontotemporal dementia responsive to memantine. Neurocase 19(3):256-61 (2013); incorporated by reference in its entirety) or with the negative symptoms in schizophrenia (Paraschakis, Tackling negative symptoms of schizophrenia with memantine. Case Rep Psychiatry 2014:384783 (2014); incorporated by reference in its entirety).

The prevalence of anxiety is low in general population, in people with normal cognitive aging (5.0-5.8%) but is increased in subjects with MCI (9.9-14.1%) and dementia (21.5-39%) (Geda et al., The Prevalence of Neuropsychiatric Symptoms in Mild Cognitive Impairment and Normal Cognitive Aging: A Population-Based Study. Arch Gen Psychiatry 65(10): 1193-1198 (2008); Lyketsos et al. Prevalence of neuropsychiatric symptoms in dementia and mild cognitive impairment: results from the cardiovascular health study. JAMA 288(12):1475-83 (2002); Zhao et al., The prevalence of neuropsychiatric symptoms in Alzheimer's disease: Systematic review and meta-analysis. J Affect Disord 190:264-71 (2016); incorporated by reference in its entirety).

5-HT2A receptor antagonists exert anxiolytic in various preclinical models, particularly models of conditioned fear (Adamec et al., Prophylactic and therapeutic effects of acute systemic injections of EMD 281014, a selective serotonin 2A receptor antagonist on anxiety induced by predator stress in rats. Eur J Pharmacol 504(1-2):79-96 (2004); Millan, The neurobiology and control of anxious states. Progr Neurobiol 70: 83-244 (2003); incorporated by reference in its entirety). In humans, 5-HT2A receptor blockade attenuates emotional processing in the orbitofrontal cortex involved in the evaluation of socially relevant stimuli (Hornboll et al., Acute serotonin 2A receptor blocking alters the processing of fearful faces in the orbitofrontal cortex and amygdala. J Psychopharmacol 27(10):903-14 (2013); incorporated by reference in its entirety). 5-HT2 receptor antagonist serazepine (CGS-15040A) has shown efficacy in clinical trials in patients with generalized anxiety disorder (Katz et al., Serotonergic (5-HT2) mediation of anxiety-therapeutic effects of serazepine in generalized anxiety disorder. Biol Psychiatry 34: 41-44 (1993); incorporated by reference in its entirety).

Like other members of the NMDA receptor antagonist class (Chojnacka-Wójcik et al., Glutamate receptor ligands as anxiolytics. Curr Opin Investig Drugs 2(8):1112-9 (2001); incorporated by reference in its entirety), dextromethorphan was observed to induce anxiolytic-like effects in laboratory animals within a certain dose range (Dere et al., NMDA-receptor antagonism via dextromethorphan and ifenprodil modulates graded anxiety test performance of C57BL/6 mice. Behav Pharmacol 14(3):245-9 (2003); incorporated by reference in its entirety). Preclinical anxiolytic effects of dextromethorphan may be related not only to the inhibition of NMDA receptor function but also to interaction with the sigma-1 receptors (Kamei et al., (+)-SKF-10,047 and dextromethorphan ameliorate conditioned fear stress through the activation of phenytoin-regulated sigma 1 sites. Eur J Pharmacol 299(1-3):21-8 (1996); incorporated by reference in its entirety). In patients with AD, treatment with another nonselective NMDA receptor channel blocker, memantine, significantly decreases in the scores of NPI subscale for anxiety (Ishikawa et al., The effect of memantine on sleep architecture and psychiatric symptoms in patients with Alzheimer's disease. Acta Neuropsychiatr 28(3):157-64 (2016); incorporated by reference in its entirety).

The prevalence of euphoria/elation is very low in general population, and in people with normal cognitive aging (0.3-0.4%) but is increased in subjects with MCI (0.6-1.3%) and dementia (3.1-7%) (Geda et al., The Prevalence of Neuropsychiatric Symptoms in Mild Cognitive Impairment and Normal Cognitive Aging: A Population-Based Study. Arch Gen Psychiatry 65(10): 1193-1198 (2008); Lyketsos et al., Prevalence of neuropsychiatric symptoms in dementia and mild cognitive impairment: results from the cardiovascular health study. JAMA 288(12):1475-83 (2002); Zhao et al., The prevalence of neuropsychiatric symptoms in Alzheimer's disease: Systematic review and meta-analysis. J Affect Disord 190:264-71 (2016); incorporated by reference in its entirety). Human PET studies have established a positive correlation of the psychostimulant drug-induced-induced changes in euphoria analog scale scores with decreases in [11C]raclopride receptor binding potential (BP) in the caudate nucleus and putamen consistent with an increase in endogenous dopamine (Drevets, Amphetamine-induced dopamine release in human ventral striatum correlates with euphoria. Biol Psychiatry 49(2):81-96 (2001)). A nonselective 5-HT2A receptor agonist psilocybin significantly reduced [11C]raclopride BP in the ventral striatum that correlated with depersonalization associated with euphoria (Vollenweider et al., 5-HT modulation of dopamine release in basal ganglia in psilocybin-induced psychosis in man—a PET study with [11C]raclopride. Neuropsychopharmacology 20(5):424-33 (1999)). Preclinical data have indicated that the majority of prefrontal cortical pyramidal neurons that project to the dorsal raphe nuclei and ventral tegmental area express 5-HT2A receptors (Vazquez-Borsetti et al., Pyramidal neurons in rat prefrontal cortex projecting to ventral tegmental area and dorsal raphe nucleus express 5-HT2A receptors. Cereb Cortex 19:1678-86 (2009); incorporated by reference in its entirety). Consequently, blockade of prefrontal 5-HT2A receptors may modulate pyramidal neurons projecting to the midbrain and thereby inhibit the dopaminergic system in the midbrain (Erbdrup et al., Serotonin 2A receptor antagonists for treatment of schizophrenia. Expert Opin Investig Drugs 20(9):1211-1223 (2011); incorporated by reference in its entirety). Dopaminergic midbrain system is also under control of cholinergic projections such as those originating in habenula and activity of these projections are modulated by α3β4-containing nicotinic acetylcholine receptors (McCallum et al., α3β4 nicotinic acetylcholine receptors in the medial habenula modulate the mesolimbic dopaminergic response to acute nicotine in vivo. Neuropharmacology 63(3):434-40 (2012); incorporated by reference in its entirety). Antagonism at α3β4-containing nicotinic acetylcholine receptors is associated with various effects ascribed to reduced dopamine tone (Maisonneuve et al., Anti-addictive actions of an iboga alkaloid congener: a novel mechanism for a novel treatment. Pharmacol Biochem Behav 75(3):607-18 (2003); incorporated by reference in its entirety). α3β4-containing nicotinic acetylcholine receptors are one of the main targets of dextromethorphan (Taylor et al., Pharmacology of dextromethorphan: Relevance to dextromethorphan/quinidine (Nuedexta®) clinical use. Pharmacol Ther 164:170-82 (2016); incorporated by reference in its entirety).

The prevalence of disinhibition is low in general population, in people with normal cognitive aging (0.9-1.6%) but is increased in subjects with MCI (3.1-4.7%) and dementia (12.7-17%) (Geda et al., The Prevalence of Neuropsychiatric Symptoms in Mild Cognitive Impairment and Normal Cognitive Aging: A Population-Based Study. Arch Gen Psychiatry 65(10): 1193-1198 (2008); Lyketsos et al., Prevalence of neuropsychiatric symptoms in dementia and mild cognitive impairment: results from the cardiovascular health study. JAMA 288(12):1475-83 (2002); Zhao et al., The prevalence of neuropsychiatric symptoms in Alzheimer's disease: Systematic review and meta-analysis. J Affect Disord 190:264-71 (2016); incorporated by reference in its entirety).

Alterations in the balance of functional activity within the 5-HT system underlie impulse control and preclinical studies suggest that the 5-HT2A receptor regulates impulsive behavior, including both inherent and induced behavioral disinhibition (Anastasio et al., Serotonin (5-hydroxytryptamine) 5-HT(2A) receptor: association with inherent and cocaine-evoked behavioral disinhibition in rats. Behav Pharmacol 22(3):248-61 (2011); incorporated by reference in its entirety).

In humans, there are significant associations found between high levels of behavioral impulsivity and certain 5-HT2A polymorphisms such as the C/C genotype of rs6313 (Jakubczyk A et al. The CC genotype in HTR2A T102C polymorphism is associated with behavioral impulsivity in alcohol-dependent patients. J Psychiatr Res 46(1):44-9 (2012); incorporated by reference in its entirety). Humans with the A/A genotype of the HTR2A 1438A/G polymorphism have higher scores of maladaptive impulsivity (Tomson et al., Effect of a human serotonin 5-HT2A receptor gene polymorphism on impulsivity: Dependence on cholesterol levels. J Affect Disord 206:23-30 (2016); incorporated by reference in its entirety). From a neuroanatomical perspective, neocortex is known to be rich in 5-HT2A receptors and behavioral disinhibition in neurodegenerative diseases such as behavioral variant frontotemporal dementia is correlated with the cortical thickness of the right parahippocampal gyrus, right orbitofrontal cortex and right insula (Santillo et al., Grey and White Matter Clinico-Anatomical Correlates of Disinhibition in Neurodegenerative Disease. PLoS One 11(10):e0164122 (2016); incorporated by reference in its entirety).

Combination of dextromethorphan and quinidine has positive therapeutic effects in patients with pseudobulbar affect (PBA) (Pioro, Review of Dextromethorphan 20 mg/Quinidine 10 mg (NUEDEXTA®) for Pseudobulbar Affect. Neurol Ther 3(1):15-28 (2014); incorporated by reference in its entirety). PBA may occur in association with a variety of neurological diseases such as amyotrophic lateral sclerosis, extrapyramidal and cerebellar disorders, multiple sclerosis, traumatic brain injury, Alzheimer's disease, stroke, and brain tumors. PBA is a disinhibition syndrome, in which pathways involving serotonin and glutamate are disrupted (Ahmed et al., Pseudobulbar affect: prevalence and management. Ther Clin Risk Manag 9:483-9 (2013); incorporated by reference in its entirety). Meta-analysis of the randomized controlled studies of another nonselective NMDA receptor channel blocker, memantine, in patients with Alzheimer's disease indicated that memantine induces significant improvement in disinhibition (Kishi et al., The effects of memantine on behavioral disturbances in patients with Alzheimer's disease: a meta-analysis. Neuropsychiatr Dis Treatment 13: 1909-1928 (2017); incorporated by reference in its entirety).

The prevalence of irritability/lability is low in general population, in people with normal cognitive aging (4.6-7.6%) but is increased in subjects with MCI (14.7-19.4%) and dementia (27-36%) (Geda et al., The Prevalence of Neuropsychiatric Symptoms in Mild Cognitive Impairment and Normal Cognitive Aging: A Population-Based Study. Arch Gen Psychiatry 65(10): 1193-1198 (2008); Lyketsos et al., Prevalence of neuropsychiatric symptoms in dementia and mild cognitive impairment: results from the cardiovascular health study. JAMA 288(12):1475-83 (2002); Zhao et al., The prevalence of neuropsychiatric symptoms in Alzheimer's disease: Systematic review and meta-analysis. J Affect Disord 190:264-71 (2016); incorporated by reference in its entirety).

Animal and human functional magnetic resonance studies have pointed to a specific involvement of the 5-HT2A receptor in the prefrontal cortical (PFC) feedback regulatory projection onto the amygdala. As this receptor is highly expressed in the prefrontal cortex areas, it affects inhibitory control of emotion-based and emotion-controlled actions, such as various impulse-related behaviors (Aznar et al., Regulating prefrontal cortex activation: an emerging role for the $5-HT_2A$ serotonin receptor in the modulation of emotion-based actions?Mol Neurobiol 48(3):841-53 (2013); incorporated by reference in its entirety).

Combination of dextromethorphan and quinidine has positive therapeutic effects in patients with pseudobulbar affect that is characterized by emotional lability, uncontrolled crying or laughing which may be disproportionate or inappropriate to the social context (Pioro, Review of Dextromethorphan 20 mg/Quinidine 10 mg (NUEDEXTA®) for Pseudobulbar Affect. Neurol Ther 3(1):15-28 (2014); incorporated by reference in its entirety). In patients with AD, treatment with another nonselective NMDA receptor channel blocker, memantine, significantly decreases the scores of NPI item for irritability/lability (Ishikawa et al., The effect of memantine on sleep architecture and psychiatric symptoms in patients with Alzheimer's disease. Acta Neuropsychiatr 28(3):157-64 (2016); incorporated by reference in its entirety). Meta-analysis of the randomized controlled studies of memantine in patients with Alzheimer's disease indicated that memantine was superior to control in irritability/lability (Kishi et al., The effects of memantine on behavioral disturbances in patients with Alzheimer's disease: a meta-analysis. Neuropsychiatr Dis Treatment 13: 1909-1928 (2017); incorporated by reference in its entirety).

The prevalence of aberrant motor activity is low in general population, in people with normal cognitive aging (0.4-0.6%) but is increased in subjects with MCI (1.3-3.8%) and dementia (16-32%) (Geda et al., The Prevalence of Neuropsychiatric Symptoms in Mild Cognitive Impairment and Normal Cognitive Aging: A Population-Based Study. Arch Gen Psychiatry 65(10): 1193-1198 (2008); Lyketsos et al., Prevalence of neuropsychiatric symptoms in dementia and mild cognitive impairment: results from the cardiovascular health study. JAMA 288(12):1475-83 (2002); Zhao et al., The prevalence of neuropsychiatric symptoms in Alzheimer's disease: Systematic review and meta-analysis. J Affect Disord 190:264-71 (2016); incorporated by reference in its entirety).

Aberrant motor behavior in AD is found to be significantly associated with 5-HT2A receptor polymorphism such as T102C (Lam et al., 5-HT2A T102C receptor polymorphism and neuropsychiatric symptoms in Alzheimer's disease. Int J Geriatr Psychiatry 19(6):523-6 (2004); Pritchard et al., Role of 5HT 2A and 5HT 2C polymorphisms in behavioural and psychological symptoms of Alzheimer's disease. Neurobiol Aging 29(3):341-7 (2008)).

Aberrant motor behavior in various neurological disease state such as Parkinson's disease are due to abnormal plasticity processes in basal ganglia that may be expressed as behavioral sensitization that is sensitive to glutamate/NMDA receptor blockade (Chase et al., Striatal glutamatergic mechanisms and extrapyramidal movement disorders. Neurotox Res 5(1-2):139-46 (2003); incorporated by reference in its entirety) and antagonism at α3β4-containing receptors (Maisonneuve et al., Anti-addictive actions of an iboga alkaloid congener: a novel mechanism for a novel treatment. Pharmacol Biochem Behav 75(3):607-18 (2003); incorporated by reference in its entirety), two of the receptor targets of dextromethorphan (Taylor et al., Pharmacology of dextromethorphan: Relevance to dextromethorphan/quinidine (Nuedexta®) clinical use. Pharmacol Ther 164:170-82 (2016); incorporated by reference in its entirety).

The prevalence of night-time behavioral disturbances is moderate in general population, in people with normal cognitive aging (10.9%) but is increased in subjects with MCI (13.8-18.3%) and dementia (27.4-39%) (Geda et al., The Prevalence of Neuropsychiatric Symptoms in Mild Cognitive Impairment and Normal Cognitive Aging: A Population-Based Study. Arch Gen Psychiatry 65(10): 1193-1198 (2008); Lyketsos et al., Prevalence of neuropsychiatric symptoms in dementia and mild cognitive impairment: results from the cardiovascular health study. JAMA 288(12): 1475-83 (2002); Zhao et al., The prevalence of neuropsychiatric symptoms in Alzheimer's disease: Systematic review and meta-analysis. J Affect Disord 190:264-71 (2016); incorporated by reference in its entirety).

5-HT2A receptors play a major role in regulation of sleep (Vanover et al., Role of 5-HT2A receptor antagonists in the treatment of insomnia. Nat Sci Sleep 2:139-50 (2010)). In a clinical trial assessing safety and efficacy of 5-HT2A receptor inverse agonist pimavanserin in patients with moderate to severe Parkinson's disease, participants reported improvements on night-time sleep and daytime wakefulness for pimavanserin compared with placebo (Cummings et al., Pimavanserin for patients with Parkinson's disease psychosis: a randomised, placebo-controlled phase 3 trial. Lancet 383: 533-40 (2014)). Another 5-HT2A receptor inverse agonist, eplivanserin, has demonstrated clinical efficacy in patients with insomnia (European Medicines Agency. Withdrawal Assessment Report for Sliwens (Eplivanserin), Mar. 18, 2010, London. EMA/CHMP/90435/2010; incorporated by reference in its entirety).

Meta-analysis of the randomized controlled studies of another nonselective NMDA receptor channel blocker, memantine, in patients with Alzheimer's disease indicated that memantine induces significant improvement in night-time disturbance/diurnal rhythm disturbances (Kishi et al., The effects of memantine on behavioral disturbances in patients with Alzheimer's disease: a meta-analysis. Neuropsychiatr Dis Treatment 13: 1909-1928 (2017); incorporated by reference in its entirety). In patients with AD, memantine was effective in reducing fragmented sleep and polysomnography revealed longer total sleep, increases in sleep efficiency and time spent in stage II, and decreases in nocturnal awakening, the periodic limb movement index, and time spent in stage I (Ishikawa et al., The effect of memantine on sleep architecture and psychiatric symptoms in patients with Alzheimer's disease. Acta Neuropsychiatr 28(3):157-64 (2016); incorporated by reference in its entirety).

The prevalence of appetite and eating abnormalities is low in general population, in people with normal cognitive aging (5.3%) but is increased in subjects with MCI (10.4-10.7%) and dementia (19.6-34%) (Geda et al., The Prevalence of Neuropsychiatric Symptoms in Mild Cognitive Impairment and Normal Cognitive Aging: A Population-Based Study. Arch Gen Psychiatry 65(10): 1193-1198 (2008); Lyketsos et al., Prevalence of neuropsychiatric symptoms in dementia and mild cognitive impairment: results from the cardiovascular health study. JAMA 288(12):1475-83 (2002); Zhao et al., The prevalence of neuropsychiatric symptoms in Alzheimer's disease: Systematic review and meta-analysis. J Affect Disord 190:264-71 (2016); incorporated by reference in its entirety).

Serotonin plays a major role in emergence and maintenance of various types of eating disorders (Steiger, Eating disorders and the serotonin connection: state, trait and developmental effects. J Psychiatry Neurosci 29(1):20-9 (2004); incorporated by reference in its entirety). The gene encoding 5-HT2A receptor (HTR2A) has been implicated as a functional candidate in many neuropsychiatric phenotypes including eating disorders (Norton et al., HTR2A: association and expression studies in neuropsychiatric genetics. Ann Med 37(2):121-9 (2005); incorporated by reference in its entirety). Eating behavior and appetite are also modulated by one of the receptor targets of dextromethorphan, serotonin transporter, that is affected in patients with eating disorders (Spies et al., The serotonin transporter in psychiatric disorders: insights from PET imaging. Lancet Psychiatry 2(8):743-55 (2015); incorporated by reference in its entirety).

Another embodiment of the invention is a method of treatment of substance use disorders and addiction that includes, but is not limited to, drug dependence, addiction to cocaine, psychostimulants (e.g., crack, cocaine, speed, meth), nicotine, alcohol, opioids, anxiolytic and hypnotic drugs, cannabis (marijuana), amphetamines, hallucinogens, phencyclidine, volatile solvents, and volatile nitrites, comprising administering a therapeutically effective amount of DEX and a therapeutically effective amount of a 5-HT2A receptor antagonist or inverse agonist, such as a compound of formula I or SARPO, to a person in need thereof. Nicotine addiction includes nicotine addiction of all known forms, such as smoking cigarettes, cigars and/or pipes, and addiction to chewing tobacco.

Another embodiment of the invention includes a method of treatment of cerebral function disorders that include, but are not limited to, disorders involving intellectual deficits such as vascular dementia, Alzheimer's type dementia, Lewy Body Dementia, Fronto-Temporal Lobar Degeneration, memory loss, amnesia/amnestic syndrome, epilepsy, disturbances of consciousness, coma, lowering of attention, speech disorders, voice spasms, Parkinson's disease, Lennox-Gastaut syndrome, autism, hyperkinetic syndrome, and schizophrenia, comprising administering a therapeutically effective amount of DEX and a therapeutically effective amount of a 5-HT2A receptor antagonist or inverse agonist, such as a compound of formula I or SARPO, to a person in need thereof. Cerebral function disorders also include disorders caused by cerebrovascular diseases including, but not limited to, stroke, cerebral infarction, cerebral bleeding, cerebral arteriosclerosis, cerebral venous thrombosis, head injuries, and the like where symptoms include disturbance of consciousness, dementia, coma, lowering of attention, apathy, and speech disorders. Intrahippocampal injection of 2.0 microL dextromethorphan (DEX, 100 micromol/L) 5 min before ischemia quickened the recovery of EEG changes, the total power spectra of EEG, and the power of dominant frequency following reperfusion. The total power of EEG was increased to 92+/−30 ($P<0.01$) at 240 min following reperfusion. DEX substantially reduced the severe ischemic neuronal damage after 10 min of cerebral ischemia and 24 h of reperfusion. DEX has neuroprotective effects against transient cerebral ischemia and reperfusion injury in gerbils (Ying et al., Neuroprotective effects of dextromethorphan against transient cerebral ischemia/reperfusion injury in gerbils, Acta Pharmacol Sinica 16(2):133-6 (March 1995)).

Another embodiment of the invention includes a method of treatment of movement disorders that include, but are not limited to, akathisia, akinesia, associated movements, athetosis, ataxia, ballismus, hemiballismus, bradykinesia, cerebral palsy, chorea, Huntington's disease, rheumatic chorea, Sydenham's chorea, dyskinesia, tardive dyskinesia, dystonia, blepharospasm, spasmodic torticollis, dopamine-responsive dystonia, Parkinson's disease, restless legs syndrome (RLS), tremor, essential tremor, Tourette's syndrome, and Wilson's disease, comprising administering a therapeutically effective amount of DEX and a therapeutically effective amount of a 5-HT2A receptor antagonist or inverse agonist, such as a compound of formula I or SARPO, to a person in need thereof.

Another embodiment of the invention includes a method of treatment of dementias that include, but are not limited to, Alzheimer's disease, Parkinson's disease, vascular dementia, dementia with Lewy bodies, mixed dementia, fronto-temporal dementia, Creutzfeldt-Jakob disease, normal pressure hydrocephalus, Huntington's disease, Wernicke-Korsakoff Syndrome, and Fronto-Temporal Lobar Degeneration (FTLD), comprising administering a therapeutically effective amount of DEX and a therapeutically effective amount of a 5-HT2A receptor antagonist or inverse agonist, such as a compound of formula I or SARPO, to a person in need thereof.

Another embodiment of the invention includes a method of treatment of motor neuron diseases that include, but are not limited to, amyotrophic lateral sclerosis (ALS), progressive bulbar palsy, primary lateral sclerosis (PLS), progressive muscular atrophy, post-polio syndrome (PPS), spinal muscular atrophy (SMA), spinal motor atrophies, Tay-Sach's disease, Sandhoff disease, and hereditary spastic paraplegia, comprising administering a therapeutically effective amount of DEX and a therapeutically effective amount of a 5-HT2A receptor antagonist or inverse agonist, such as a compound of formula I or SARPO, to a person in need thereof.

Another embodiment of the invention includes a method of treatment of neurodegenerative diseases that include, but are not limited to Alzheimer's disease, prion-related diseases, cerebellar ataxia, spinocerebellar ataxia (SCA), spinal muscular atrophy (SMA), bulbar muscular atrophy, Friedrich's ataxia, Huntington's disease, Lewy body disease, Parkinson's disease, amyotrophic lateral sclerosis (ALS or Lou Gehrig's disease), multiple sclerosis (MS), multiple system atrophy, Shy-Drager syndrome, corticobasal degeneration, progressive supranuclear palsy, Wilson's disease, Menkes disease, adrenoleukodystrophy, cerebral autosomal dominant arteriopathy with subcortical infarcts and leukoencephalopathy (CADASIL), muscular dystrophies, Charcot-Marie-Tooth disease (CMT), familial spastic paraparesis, neurofibromatosis, olivopontine cerebellar atrophy or degeneration, striatonigral degeneration, Guillain-Barre syndrome, and spastic paraplegia, comprising administering a therapeutically effective amount of DEX and a therapeutically effective amount of a 5-HT2A receptor antagonist or inverse agonist, such as a compound of formula I or SARPO, to a person in need thereof.

Another embodiment of the invention includes a method of treatment of seizure disorders that include, but are not limited to, epileptic seizures, nonepileptic seizures, epilepsy, febrile seizures; partial seizures including, but not limited to, simple partial seizures, Jacksonian seizures, complex partial seizures, and epilepsia partialis continua; generalized seizures including, but not limited to, generalized tonic-clonic seizures, absence seizures, atonic seizures, myoclonic seizures, juvenile myoclonic seizures, and infantile spasms; and status epilepticus, comprising administering a therapeutically effective amount of DEX and a therapeutically effective amount of a 5-HT2A receptor antagonist or inverse agonist, such as a compound of formula I or SARPO, to a person in need thereof.

Another embodiment of the invention includes a method of treatment of headaches that include, but are not limited to, migraine, trigeminal cephalgia, tension, and cluster headaches including Bing-Horton-Syndrome, comprising administering a therapeutically effective amount of DEX and a therapeutically effective amount of a 5-HT2A receptor antagonist or inverse agonist, such as a compound of formula I or SARPO, to a person in need thereof.

Another embodiment of the invention includes a method of treatment of other neurological disorders that include Rett Syndrome, autism, tinnitus, disturbances of consciousness disorders, sexual dysfunction, intractable coughing, narcolepsy, cataplexy; voice disorders due to uncontrolled laryngeal muscle spasms, including, but not limited to, abductor spasmodic dysphonia, adductor spasmodic dysphonia, muscular tension dysphonia, and vocal tremor; diabetic neuropathy, chemotherapy-induced neurotoxicity, such as methotrexate neurotoxicity; incontinence including, but not limited, stress urinary incontinence, urge urinary incontinence, and fecal incontinence; and erectile dysfunction, comprising administering a therapeutically effective amount of DEX and a therapeutically effective amount of a 5-HT2A receptor antagonist or inverse agonist, such as a compound of formula I or SARPO, to a person in need thereof.

In some embodiments, a combination of DEX and a 5-HT2A receptor antagonist or inverse agonist such as a compound of formula I or SARPO, a metabolite, a derivative, a metabolite or prodrug of any of these compounds, may be used to treat pain, pseudobulbar affect, depression (including treatment resistant depression), disorders related to memory and cognition, schizophrenia, Parkinson's disease, amyotrophic lateral sclerosis (ALS), Rett's syndrome, seizures, cough (including chronic cough), etc.

In some embodiments, a combination of DEX and a 5-HT2A receptor antagonist or inverse agonist such as a compound of formula I or SARPO, may be used to treat dermatitis.

In some embodiments, pain relieving properties of DEX are enhanced by a method comprising co-administering DEX and a 5-HT2A receptor antagonist or inverse agonist, such as a compound of formula I or SARPO, a metabolite, a derivative, or prodrug of any of these compounds, with DEX.

In some embodiments, these methods are used to treat or provide relief to, any pain including, but not limited to, musculoskeletal pain, neuropathic pain, cancer-related pain, acute pain, nociceptive pain, etc.

Examples of musculoskeletal pain include low back pain (i.e. lumbosacral pain), primary dysmenorrhea, and arthritic pain, such as pain associated with rheumatoid arthritis, juvenile rheumatoid arthritis, osteoarthritis, osteoarthosis, axial spondyloarthritis including ankylosing spondylitis, etc.

In some embodiments, a combination of DEX and a 5-HT2A receptor antagonist or inverse agonist, such as a compound of formula I or SARPO, is used for treating chronic musculoskeletal pain.

Examples of neuropathic pain include idiopathic and diabetic peripheral neuropathy, post-herpetic neuralgia, trigeminal neuralgia, monoradiculopathies, phantom limb pain, central pain, etc. Other causes of neuropathic pain include cancer-related pain, lumbar nerve root compression, spinal cord injury, post-stroke pain, central multiple sclerosis pain, HIV-associated neuropathy, and radio- or chemotherapy associated neuropathy, etc.

The term "treating" or "treatment" includes the diagnosis, cure, mitigation, treatment, or prevention of disease in man or other animals, or any activity that otherwise affects the structure or any function of the body of man or other animals.

In some embodiments, any 5-HT2A receptor antagonist or inverse agonist may be used in combination with DEX to improve the therapeutic properties of DEX. DEX and the 5-HT2A receptor antagonist or inverse agonist may be administered in separate compositions or dosage forms, or may be administered in a single composition or dosage form comprising both.

In some embodiments, 5-HT2A receptor antagonist or inverse agonists that can be co-administered with DEX include, but are not limited to, a compound of formula I or SARPO, clomipramine, doxepin, fluoxetine, mianserin, imipramine, 2-chloroimipramine, amitriptyline, amoxapine, desipramine, protriptyline, trimipramine, nortriptyline, maprotiline, phenelzine, isocarboxazid, tranylcypromine, paroxetine, trazodone, citalopram, sertraline, aryloxy indanamine, benactyzine, escitalopram, fluvoxamine, venlafaxine, desvenlafaxine, duloxetine, mirtazapine, nefazodone, selegiline, sibutramine, milnacipran, tesofensine, brasofensine, moclobemide, rasagiline, nialamide, iproniazid, iproclozide, toloxatone, butriptyline, dosulepin, dibenzepin, iprindole, lofepramine, opipramol, norfluoxetine, dapoxetine, etc., or a metabolite or prodrug of any of these compounds, or a pharmaceutically acceptable salt of any of these compounds.

In some embodiments, combining a compound of formula I or SARPO, with DEX provides greater efficacy, such as greater pain relief, than would otherwise be achieved by administering either component alone. In extensive metabolizers, DEX can be rapidly and extensively metabolized, yielding low systemic exposure even at high doses. In some embodiments, a compound of formula I or SARPO, besides possessing antidepressant and analgesic properties, is an inhibitor of DEX metabolism. Metabolites of a compound of formula I or SARPO, which include a compound of formula I or SARPO, a derivative, a metabolite are also inhibitors of DEX metabolism. Thus, a compound of formula I or SARPO, including a form of a compound of formula I or SARPO, that is rapidly converted in the body (such as a salt, hydrate, solvate, polymorph, etc.), is a prodrug of a compound of formula I or SARPO.

In some embodiments, the method comprises inhibition of DEX metabolism to augment DEX plasma levels, resulting in additive or synergistic efficacy such as relief of neurological disorders including pain, depression, smoking cessation, etc. Inhibition of DEX metabolism with the combination, co-administration of DEX with a compound of formula I or SARPO has many potential benefits. In some embodiments, administration of the combination of SARPO and DEX or co-administration of DEX with a compound of formula I or SARPO enhances the efficacy of a compound of formula I or SARPO, for many conditions. Co-administration of DEX with a compound of formula I or SARPO, may enhance the analgesic properties of a compound of formula I or SARPO, for many conditions. Co-administration of DEX with a compound of formula I or SARPO, may also enhance the antidepressant properties of a compound of formula I or SARPO, for many conditions, including faster onset of action.

In some embodiments, the method of co-administration of DEX and a compound of formula I or SARPO is to reduce the potential for an adverse event, such as drowsiness or confusion, associated with treatment by DEX, in subjects in need thereof such as at risk of experiencing an adverse event as a result being treated with DEX.

In some embodiments, the method of co-administration of DEX and a compound of formula I or SARPO is to reduce an adverse event, such as seizure, associated with treatment by a compound of Formula I or SARPO, in subjects in need hereof, for example, in subjects at risk of experiencing the adverse event as a result being treated with a compound of formula I or SARPO.

In some embodiments, the method of co-administration of DEX and a compound of formula I or SARPO is to reduce a central nervous system adverse event, a gastrointestinal event, or another type of adverse event associated with any of these compounds. Central nervous system (CNS) adverse events include, but are not limited to, nervousness, dizziness, sleeplessness, light-headedness, tremor, hallucinations, convulsions, CNS depression, fear, anxiety, headache, increased irritability or excitement, tinnitus, drowsiness, dizziness, sedation, somnolence, confusion, disorientation, lassitude, incoordination, fatigue, euphoria, nervousness, insomnia, sleeping disturbances, convulsive seizures, excitation, catatonic-like states, hysteria, hallucinations, delusions, paranoia, headaches and/or migraine, and extrapyramidal symptoms such as oculogyric crisis, torticollis, hyperexcitability, increased muscle tone, ataxia, and tongue protrusion.

In some embodiments, the method of co-administration of DEX and a compound of formula I or SARPO is to reduce gastrointestinal adverse events including, but are not limited to, nausea, vomiting, abdominal pain, dysphagia, dyspepsia, diarrhea, abdominal distension, flatulence, peptic ulcers with bleeding, loose stools, constipation, stomach pain, heartburn, gas, loss of appetite, feeling of fullness in stomach, indigestion, bloating, hyperacidity, dry mouth, gastrointestinal disturbances, and gastric pain.

In some embodiments, the method of co-administration of DEX and a 5-HT2A receptor antagonist or inverse agonist of formula I or SARPO comprises administration in a single dosage form, or in two separate dosage forms simultaneously, or sequentially at the same time or at different times as long as both are in the subject together for at least a portion of the time during the treatment.

In some embodiments, the invention is a method of treatment to a subject in need of pain relief, wherein the method comprises co-administration of a combination of a compound of formula I or SARPO, and a compound of Formula II or DEX, whereby the pain is relieved by the treatment with the combination due the improved pain-relieving properties including potentially faster onset of action as compared to a compound of formula I or SARPO alone, or compared to DEX alone.

In some embodiments, the combination method improves pain relieving properties of at least about 0.5%, at least about 1%, at least about 10%, at least about 20%, at least about 30%, at least about 50%, at least 100%, up to about 500% or up to 1000%, about 0.5% to about 1000%, about 10% to about 20%, about 20% to about 30%, about 30% to about 40%, about 40% to about 50%, about 50% to about 60%, about 60% to about 70%, about 70% to about 80%, about 80% to about 90%, about 90% to about 100%, about 100% to about 110%, about 110% to about 120%, about 120% to about 130%, about 130% to about 140%, about 140% to about 150%, about 150% to about 160%, about 160% to about 170%, about 170% to about 180%, about 180% to about 190%, about 190% to about 200%, or any amount of pain relief in a range bounded by, or between, any of these values, as compared to a compound of formula I or SARPO, alone.

In some embodiments, the combination improves pain relieving properties of at least about 0.5%, at least about 1%, at least about 10%, at least about 20%, at least about 30%, at least about 50%, at least 100%, up to about 500% or up to 1000%, about 0.5% to about 1000%, about 10% to about 20%, about 20% to about 30%, about 30% to about 40%, about 40% to about 50%, about 50% to about 60%, about 60% to about 70%, about 70% to about 80%, about 80% to about 90%, about 90% to about 100%, about 100% to about 110%, about 110% to about 120%, about 120% to about 130%, about 130% to about 140%, about 140% to about 150%, about 150% to about 160%, about 160% to about 170%, about 170% to about 180%, about 180% to about 190%, about 190% to about 200%, or any amount of pain relief in a range bounded by, or between, any of these values, as compared to as compared to DEX alone.

Unless otherwise indicated, any reference to a compound herein, such as DEX, a compound of formula I or SARPO, and SARPODEX™, by structure, name, or any other means, includes pharmaceutically acceptable salts; alternate solid forms, such as polymorphs, solvates, hydrates, etc.; tautomers; deuterium-modified compounds, such as deuterium-modified DEX and a compound of formula I or SARPO; or any chemical species that may rapidly convert to a compound described herein under conditions in which the compounds are used as described herein. Examples of deuterium modified DEX and a compound of formula I or SARPO, include, but are not limited to, those shown below.

A dosage form or a composition may be a blend or mixture of DEX and a compound that inhibits the metabolism of DEX, such as a compound of formula I or SARPO, either alone or within a vehicle. For example, DEX and a compound of formula I or SARPO, may be dispersed within each other or dispersed together within a vehicle. A dispersion may include a mixture of solid materials wherein small individual particles are substantially one compound, but the small particles are dispersed within one another, such as might occur if two powders of two different drugs are blended with a solid vehicle material, and the blending is done in the solid form. In some embodiments, DEX and a compound of formula I or SARPO, may be substantially uniformly dispersed within a composition or dosage form. Alternatively, DEX and a compound of formula I or SARPO, may be in separate domains or phases in a composition or dosage form. For example, one drug may be in a coating, and another drug may be in a core within the coating. For example, one drug may be formulated for sustained release and another drug may be formulated for immediate release.

Some embodiments include administration of a tablet that contains a compound of formula I or SARPO, in a form that provides sustained release and DEX in a form that provides immediate release or vice versa. While there are many ways that sustained release of a compound of formula I or SARPO, may be achieved, in some embodiments, a compound of formula I or SARPO, is combined with hydroxypropyl methylcellulose. For example, particles of a compound of formula I or SARPO, hydrochloride could be blended with microcrystalline cellulose and hydroxypropyl methylcellulose (e.g., METHOCEL™) to form an admixture of blended powders. This could then be combined with immediate release DEX in a single tablet.

DEX and/or a 5-HT2A receptor antagonist or inverse agonist such as a compound of formula I or SARPO may be combined with a pharmaceutical carrier selected on the basis of the chosen route of administration and standard pharmaceutical practice (Troy, ed., Remington: The Science and Practice of Pharmacy, $21^{st}$ Edition, 2005). The relative proportions of active ingredient and carrier may be determined, for example, by the solubility and chemical nature of the compounds, chosen route of administration and standard pharmaceutical practice.

Therapeutic compounds may be administered by any means that may result in the contact of the active agent(s) with the desired site or site(s) of action in the body of a patient.

The compounds may be administered by any conventional means available for use in conjunction with pharmaceuticals, either as individual therapeutic agents or in a combination of therapeutic agents. For example, they may be administered as the sole active agents in a pharmaceutical composition, or they can be used in combination with other therapeutically active ingredients.

Therapeutic compounds may be administered to a subject in a variety of forms adapted to the chosen route of administration, e.g., orally or parenterally. Parenteral administration in this respect includes administration by the following routes: intravenous, intramuscular, subcutaneous, intraocular, intrasynovial, transepithelial, including transdermal, ophthalmic, sublingual and buccal; topically including ophthalmic, dermal, ocular, rectal and nasal inhalation via insufflation, aerosol and rectal systemic.

The ratio of DEX to a compound of formula I or SARPO, may vary. In some embodiments, the weight ratio of DEX to a compound of formula I or SARPO, may be about 0.1 to about 10, about 0.1 to about 2, about 0.2 to about 1, about 0.1 to about 0.5, about 0.1 to about 0.3, about 0.2 to about 0.4, about 0.3 to about 0.5, about 0.5 to about 0.7, about 0.8 to about 1, about 0.2, about 0.3, about 0.4, about 0.45, about 0.6, about 0.9, or any ratio in a range bounded by, or between, any of these values. A ratio of 0.1 indicates that the weight of DEX is 1/10 that of a compound of formula I or SARPO. A ratio of 10 indicates that the weight of DEX is 10 times that of a compound of formula I or SARPO.

The amount of DEX in a therapeutic composition may vary. For example, some liquid compositions may comprise about 0.0001% (w/v) to about 50% (w/v), about 0.01% (w/v) to about 20% (w/v), about 0.01% to about 10% (w/v), about 0.001% (w/v) to about 1% (w/v), about 0.1% (w/v) to about 0.5% (w/v), about 1% (w/v) to about 3% (w/v), about 3% (w/v) to about 5% (w/v), about 5% (w/v) to about 7% (w/v), about 7% (w/v) to about 10% (w/v), about 10% (w/v) to about 15% (w/v), about 15% (w/v) to about 20% (w/v), about 20% (w/v) to about 30% (w/v), about 30% (w/v) to about 40% (w/v), or about 40% (w/v) to about 50% (w/v) of DEX.

Some liquid dosage forms may contain about 10 mg to about 500 mg, about 30 mg to about 350 mg, about 50 mg to about 200 mg, about 50 mg to about 70 mg, about 20 mg to about 50 mg, about 30 mg to about 60 mg, about 40 mg to about 50 mg, about 40 mg to about 42 mg, about 42 mg to about 44 mg, about 44 mg to about 46 mg, about 46 mg to about 48 mg, about 48 mg to about 50 mg, about 80 mg to about 100 mg, about 110 mg to about 130 mg, about 170 mg to about 190 mg, about 45 mg, about 60 mg, about 90 mg, about 120 mg, or about 180 mg of DEX, or any amount of DEX in a range bounded by, or between, any of these values.

Some solid compositions may comprise at least about 5% (w/w), at least about 10% (w/w), at least about 20% (w/w), at least about 50% (w/w), at least about 70% (w/w), at least about 80%, about 10% (w/w) to about 30% (w/w), about 10% (w/w) to about 20% (w/w), about 20% (w/w) to about 30% (w/w), about 30% (w/w) to about 50% (w/w), about 30% (w/w) to about 40% (w/w), about 40% (w/w) to about 50% (w/w), about 50% (w/w) to about 80% (w/w), about 50% (w/w) to about 60% (w/w), about 70% (w/w) to about 80% (w/w), or about 80% (w/w) to about 90% (w/w) of DEX.

Some solid dosage forms may contain about 10 mg to about 500 mg, about 30 mg to about 350 mg, about 20 mg to about 50 mg, about 30 mg to about 60 mg, about 40 mg to about 50 mg, about 40 mg to about 42 mg, about 42 mg to about 44 mg, about 44 mg to about 46 mg, about 46 mg to about 48 mg, about 48 mg to about 50 mg, about 50 mg to about 200 mg, about 50 mg to about 70 mg, about 80 mg to about 100 mg, about 110 mg to about 130 mg, about 170 mg to about 190 mg, about 60 mg, about 90 mg, about 120 mg, or about 180 mg of DEX, or any amount of DEX in a range bounded by, or between, any of these values.

The amount of a compound of formula I or SARPO, in a therapeutic composition may vary. If increasing the plasma level of DEX is desired, a compound of formula I or SARPO, should be administered in an amount that increases the plasma level of DEX. For example, a compound of formula I or SARPO, may be administered in an amount that results in a plasma concentration of DEX in the subject, on day 8, that is at least about 2 times, at least about 5 times, at least about 10 times, at least about 15 times, at least about 20 times, at least about 30 times, at least about 40 times, at least about 50 times, at least about 60 times, at least about 70 times, or at least about 80 times, the plasma concentration of the same amount of DEX administered without a compound of formula I or SARPO.

In some embodiments, a compound of formula I or SARPO, is administered to a subject in an amount that results in a 12 hour area under the curve from the time of dosing ($AUC_{0-12}$), or average plasma concentration in the subject for the 12 hours following dosing ($C_{avg}$) of DEX, on day 8, that is at least about 2 times, at least about 5 times, at least about 10 times, at least about 15 times, at least about 20 times, at least about 30 times, at least about 40 times, at least about 50 times, at least about 60 times, at least about 70 times, or at least about 80 times the plasma concentration of the same amount of DEX administered without a compound of formula I or SARPO.

In some embodiments, a compound of formula I or SARPO, is administered to a subject in an amount that results in a maximum plasma concentration ($C_{max}$) of DEX in the subject, on day 8, that is at least about 2 times, at least about 5 times, at least about 10 times, at least about 15 times, at least about 20 times, at least about 30 times, or at least about 40 times the plasma concentration of the same amount of DEX administered without a compound of formula I or SARPO.

For co-administration of a compound of formula I or SARPO, an increase in the DEX plasma level can occur on the first day that a compound of formula I or SARPO, is administered, as compared to the same amount of DEX administered without a compound of formula I or SARPO. For example, the DEX plasma level on the first day that a compound of formula I or SARPO, is administered may be at least about 1.5 times, at least about at least 2 times, at least about 2.5 times, at least about 3 times, at least about 4 times, at least about 5 times, at least about 6 times at least about 7 times, at least about 8 times, at least about 9 times, or at least about 10 times the level that would be achieved by administering the same amount of DEX without a compound of formula I or SARPO.

In some embodiments, the DEX AUC on the first day that a compound of formula I or SARPO, is administered may be at least twice the AUC that would be achieved by administering the same amount of DEX without a compound of formula I or SARPO.

In some embodiments, the DEX $C_{max}$ on the first day that a compound of formula I or SARPO, is administered may be at least twice the $C_{max}$ that would be achieved by administering the same amount of DEX without a compound of formula I or SARPO.

In some embodiments, the DEX trough level (e.g., plasma level 12 hours after administration) on the first day that a compound of formula I or SARPO, is administered may be at least twice the trough level that would be achieved by administering the same amount of DEX without a compound of formula I or SARPO.

In some embodiments, a compound of formula I or SARPO, is administered on the first day of at least two days of treatment with DEX, wherein a decrease in the DO plasma level occurs on the first day that a compound of formula I or SARPO, and DEX are co-administered, as compared to the same amount of DEX administered without a compound of formula I or SARPO. For example, the DO plasma level on the first day may be reduced by at least 5% as compared to the DO plasma level that would be achieved by administering the same amount of DEX without a compound of formula I or SARPO.

In some embodiments, a compound of formula I or SARPO, are co-administered for at least five consecutive days, to a subject in need of treatment with DEX, wherein, on the fifth day, the DEX plasma level is higher than the DEX plasma level that would have been achieved by administering the same amount of DEX administered without a compound of formula I or SARPO, for five consecutive days. For example, the DEX plasma level on the fifth day (for example at 0 hours, 1 hour, 3 hours, 6 hours, or 12 hours after administration) may be at least 5 times, at least 10 times, at least 20 times, at least 40 times, at least 50 times, at least 60 times, at least 65 times, or up to about 500 times, the level that would be achieved by administering the same amount of DEX without a compound of formula I or SARPO, for five consecutive days.

In some embodiments, a compound of formula I or SARPO, and DEX, are co-administered for at least six consecutive days, to a subject in need of treatment with DEX, wherein, on the sixth day, the DEX plasma level is higher than the DEX plasma level that would have been achieved by administering the same amount of DEX administered without a compound of formula I or SARPO, for six consecutive days. For example, the DEX plasma level on the sixth day (for example at 0 hours, 1 hour, 3 hours, 6 hours, or 12 hours after administration) may be at least 5 times, at least 10 times, at least 20 times, at least 30 times, at least 50 times, at least 60 times, at least 70 times, at least 75 times, or up to about 500 times, the level that would be achieved by administering the same amount of DEX without a compound of formula I or SARPO, for six consecutive days.

In some embodiments, a compound of formula I or SARPO, and DEX are co-administered for at least seven consecutive days, to a subject in need of treatment with DEX, wherein, on the seventh day, the DEX plasma level is higher than the DEX plasma level that would have been achieved by administering the same amount of DEX administered without a compound of formula I or SARPO, for seven consecutive days. For example, the DEX plasma level on the seventh day (for example at 0 hours, 1 hour, 3 hours, 6 hours, or 12 hours after administration) may be at least 5 times, at least 10 times, at least 20 times, at least 30 times, at least 50 times, at least 70 times, at least 80 times, at least 90 times, or up to about 500 times, the level that would be achieved by administering the same amount of DEX without a compound of formula I or SARPO, for seven consecutive days.

In some embodiments, a compound of formula I or SARPO, and DEX, are co-administered for at least eight consecutive days, wherein, on the eighth day, DEX has a plasma level, for example at 0 hours, 1 hour, 3 hours, 6 hours, or 12 hours, after co-administering a compound of formula I or SARPO, with DEX that is at least 5 times, at least 10 times, at least 20 times, at least 30 times, at least 50 times, at least 60 times, at least 70 times, at least 80 times, at least 90 times, at least 100 times, or up to about 1,000 times, the plasma level that would be achieved by administering the same amount of DEX without a compound of formula I or SARPO, for eight consecutive days.

In some embodiments, a compound of formula I or SARPO, and DEX are co-administered for at least eight consecutive days, to a subject in need of treatment with DEX, wherein, on the eighth day, the DO plasma level is lower than the DO plasma level that would have been achieved by administering the same amount of DEX administered without a compound of formula I or SARPO, for eight consecutive days. For example, the DO plasma level on the eighth day (for example at 0 hours, 1 hour, 3 hours, 6 hours, or 12 hours after administration) may be reduced by at least 10%, at least 20%, at least 30%, at least 40%, or at least 50%, as compared to the DO plasma level that would be achieved by administering the same amount of DEX without a compound of formula I or SARPO, for eight consecutive days.

In some embodiments, a compound of formula I or SARPO, are administered to a subject in an amount that results in an $AUC_{0-12}$ of a compound of formula I or SARPO, in the subject, on day 8, that is at least about 100 nghr/mL, at least about 200 nghr/mL, at least about 500 nghr/mL, at least about 600 nghr/mL, at least about 700 nghr/mL, at least about 800 nghr/mL, at least about 900 nghr/mL, at least about 1,000 nghr/mL, at least about 1,200 nghr/mL, at least 1,600 nghr/mL, or up to about 15,000 nghr/mL.

In some embodiments, a compound of formula I or SARPO, are administered to a subject in an amount that results in a $C_{avg}$ of a compound of formula I or SARPO, in the subject, on day 8, that is at least about 10 ng/mL, at least about 20 ng/mL, at least about 40 ng/mL, at least about 50 ng/mL, at least about 60 ng/mL, at least about 70 ng/mL, at least about 80 ng/mL, at least about 90 ng/mL, at least about 100 ng/mL, at least 120 ng/mL, or up to about 1,500 ng/mL.

In some embodiments, a compound of formula I or SARPO, are administered to a subject in an amount that results in a $C_{max}$ of a compound of formula I or SARPO, in the subject, on day 8, that is at least about 10 ng/mL, at least about 20 ng/mL, at least about 50 ng/mL, at least about 90 ng/mL, at least about 100 ng/mL, at least about 110 ng/mL, at least about 120 ng/mL, at least about 130 ng/mL, at least about 140 ng/mL, at least 200 ng/mL, or up to about 1,500 ng/mL.

In some embodiments, liquid compositions comprise about 0.0001% (w/v) to about 50% (w/v), about 0.01% (w/v) to about 20% (w/v), about 0.01% to about 10% (w/v), about 1% (w/v) to about 3% (w/v), about 3% (w/v) to about 5% (w/v), about 5% (w/v) to about 7% (w/v), about 5% (w/v) to about 15% (w/v), about 7% (w/v) to about 10% (w/v), about 10% (w/v) to about 15% (w/v), about 15% (w/v) to about 20% (w/v), about 20% (w/v) to about 30% (w/v), about 30% (w/v) to about 40% (w/v), or about 40% (w/v) to about 50% (w/v) of a compound of formula I or SARPO, or any amount of a compound of formula I or SARPO, in a range bounded by, or between, any of these values.

In some embodiments, liquid dosage forms contain about 10 mg to about 1000 mg, about 50 mg to about 1000 mg, about 10 mg to about 50 mg, about 50 mg to about 100 mg, about 40 mg to about 90 mg, about 200 mg to about 300 mg, about 70 mg to about 95 mg, about 100 mg to about 200 mg, about 105 mg to about 200 mg, about 110 mg to about 140 mg, about 180 mg to about 220 mg, about 280 mg to about 320 mg, about 200 mg, about 150 mg, or about 300 mg of a compound of formula I or SARPO, or any amount of a compound of formula I or SARPO, in a range bounded by, or between, any of these values.

In some embodiments, solid compositions comprise at least about 5% (w/w), at least about 10% (w/w), at least about 20% (w/w), at least about 50% (w/w), at least about 70% (w/w), at least about 80%, about 10% (w/w) to about 30% (w/w), about 10% (w/w) to about 20% (w/w), about 20% (w/w) to about 30% (w/w), about 30% (w/w) to about 50% (w/w), about 30% (w/w) to about 40% (w/w), about 40% (w/w) to about 50% (w/w), about 50% (w/w) to about 80% (w/w), about 50% (w/w) to about 60% (w/w), about 70% (w/w) to about 80% (w/w), or about 80% (w/w) to about 90% (w/w) of a compound of formula I or SARPO, or any amount of a compound of formula I or SARPO, in a range bounded by, or between, any of these values.

In some embodiments, solid dosage forms contain about 10 mg to about 1000 mg, about 50 mg to about 1000 mg, about 10 mg to about 50 mg, about 50 mg to about 100 mg, about 40 mg to about 90 mg, about 200 mg to about 300 mg, about 70 mg to about 95 mg, about 100 mg to about 200 mg, about 105 mg to about 200 mg, about 110 mg to about 140 mg, about 50 mg to about 150 mg, about 180 mg to about 220 mg, about 280 mg to about 320 mg, about 200 mg, about 150 mg, or about 300 mg of a compound of formula I or SARPO, or any amount of a compound of formula I or SARPO, in a range bounded by, or between, any of these values.

In some embodiments, a compound of formula I or SARPO, is administered at a dose that results in a a compound of formula I or SARPO, plasma level of about 0.1 μM to about 10 μM, about 0.1 μM to about 5 μM, about 0.2 μM to about 3 μM, 0.1 μM to about 1 μM, about 0.2 μM to about 2 μM, 1 μM to about 10 μM, about 1 μM to about 5 μM, about 2 μM to about 3 μM, or about 2.8 μM to about 3 μM, about 1.5 μM to about 2 μM, about 4.5 μM to about 5 μM, about 2.5 μM to about 3 μM, about 1.8 μM, about 4.8 μM, about 2.9 μM, about 2.8 μM, or any plasma level in a range bounded by, or between, any of these values.

In some embodiments, a compound of formula I or SARPO, is administered at a dose that results in a a compound of formula I or SARPO, plasma level of about 0.1 μM to about 10 μM, about 0.1 μM to about 5 μM, about 0.2 μM to about 3 μM, 0.1 μM to about 1 μM, about 0.2 μM to about 2 μM, 1 μM to about 10 μM, about 1 μM to about 5 μM, about 2 μM to about 3 μM, or about 2.8 μM to about 3 μM, about 1.5 μM to about 2 μM, about 4.5 μM to about 5 μM, about 2.5 μM to about 3 μM, about 1.8 μM, about 4.8 μM, about 2.9 μM, about 2.8 μM, or any plasma level in a range bounded by, or between, any of these values.

In some embodiments, a compound of formula I or SARPO, is administered to a subject in an amount that results in an $AUC_{0-12}$ of a compound of formula I or SARPO, in the subject, on day 8, that is at least about 3,000 nghr/mL, at least about 7,000 nghr/mL, at least about 10,000 nghr/mL, at least about 15,000 nghr/mL, at least about 20,000 nghr/mL, at least about 30,000 nghr/mL, up to about 50,000 nghr/mL, up to about 150,000 nghr/mL, or any AUC in a range bounded by, or between, any of these values.

In some embodiments, a compound of formula I or SARPO, is administered to a subject in an amount that results in a $C_{max}$ of a compound of formula I or SARPO, in the subject, on day 8, that is at least about 300 ng/mL, at least about 700 ng/mL, at least about 1,000 ng/mL, at least about 1,500 ng/mL, at least about 2,000 ng/mL, at least about 4,000 ng/mL, up to about 10,000 ng/mL, up to about 50,000 ng/mL, or any $C_{max}$ in a range bounded by, or between, any of these values.

In some embodiments, a compound of formula I or SARPO, is administered to a subject in an amount that results in a $C_{avg}$ of a compound of formula I or SARPO, in the subject, on day 8, that is at least about 200 ng/mL, at least about 300 ng/mL, at least about 700 ng/mL, at least about 1,000 ng/mL, at least about 1,500 ng/mL, at least about 2,000 ng/mL, at least about 4,000 ng/mL, up to about 10,000 ng/mL, up to about 50,000 ng/mL, or any $C_{avg}$ in a range bounded by, or between, any of these values.

In some embodiments, a compound of formula I or SARPO, metabolite, or a prodrug of a compound of formula I or SARPO, metabolite, is administered at a dose that results in a a compound of formula I or SARPO, metabolite plasma level of about 0.1 μM to about 10 μM, about 0.1 μM to about 5 μM, about 0.2 μM to about 3 μM, 0.1 μM to about 1 μM, about 0.2 μM to about 2 μM, 1 μM to about 10 μM, about 1 μM to about 5 μM, about 2 μM to about 3 μM, or about 2.8 μM to about 3 μM, about 1.5 μM to about 2 μM, about 4.5 μM to about 5 μM, about 2.5 μM to about 3 μM, about 1.8 μM, about 4.8 μM, about 2.9 μM, about 2.8 μM, or any plasma level in a range bounded by, or between, any of these values.

In some embodiments, a compound of formula I or SARPO, is administered to a subject in an amount that results in an $AUC_{0-12}$ of a compound of formula I or SARPO, in the subject, on day 8, that is at least about 1,000 nghr/mL, at least about 2,000 nghr/mL, at least about 4,000 nghr/mL, at least about 5,000 nghr/mL, at least about 8,000 nghr/mL, up to about 10,000 nghr/mL, up to about 40,000 nghr/mL, or any AUC in a range bounded by, or between, any of these values.

In some embodiments, a compound of formula I or SARPO, is administered to a subject in an amount that results in a $C_{max}$ of a compound of formula I or SARPO, in the subject, on day 8, that is at least about 100 ng/mL, at least about 200 ng/mL, at least about 400 ng/mL, at least about 500 ng/mL, at least about 600 ng/mL, at least about 800 ng/mL, up to about 2,000 ng/mL, up to about 10,000 ng/mL, or any $C_{max}$ in a range bounded by, or between, any of these values.

In some embodiments, a compound of formula I or SARPO, is administered to a subject in an amount that results in a $C_{avg}$ of a compound of formula I or SARPO, in the subject, on day 8, that is at least about 100 ng/mL, at least about 300 ng/mL, at least about 400 ng/mL, at least about 600 ng/mL, at least about 800 ng/mL, up to about 2,000 ng/mL, up to about 10,000 ng/mL, or any $C_{avg}$ in a range bounded by, or between, any of these values.

In some embodiments, a compound of formula I or SARPO, is administered at a dose that results in an a compound of formula I or SARPO, plasma level of about 0.1 μM to about 10 μM, about 0.1 μM to about 5 μM, about 0.2 μM to about 3 μM, 0.1 μM to about 1 μM, about 0.2 μM to about 2 μM, 1 μM to about 10 μM, about 1 μM to about 5 μM, about 2 μM to about 3 μM, or about 2.8 μM to about 3 μM, about 1.5 μM to about 2 μM, about 4.5 μM to about 5 μM, about 2.5 μM to about 3 μM, about 1.8 μM, about 4.8 μM, about 2.9 μM, about 2.8 μM, or any plasma level in a range bounded by, or between, any of these values.

In some embodiments, a compound of formula I or SARPO, is administered to a subject in an amount that results in an $AUC_{0-12}$ of a compound of formula I or SARPO, in the subject, on day 8, that is at least about 200 nghr/mL, at least about 400 nghr/mL, at least about 700 nghr/mL, at least about 1,000 nghr/mL, at least about 1,500 nghr/mL, at least about 3,000 nghr/mL, up to about 5,000 nghr/mL, up to about 30,000 nghr/mL, or any plasma level in a range bounded by, or between, any of these values.

In some embodiments, a compound of formula I or SARPO, is administered to a subject in an amount that results in a $C_{max}$ of a compound of formula I or SARPO, in the subject, on day 8, that is at least about 30 ng/mL, at least about 60 ng/mL, at least about 90 ng/mL, at least about 100 ng/mL, at least about 150 ng/mL, at least about 200 ng/mL, at least about 300 ng/mL, up to about 1,000 ng/mL, or any $C_{max}$ in a range bounded by, or between, any of these values.

In some embodiments, a compound of formula I or SARPO, is administered to a subject in an amount that results in a $C_{avg}$ of a compound of formula I or SARPO, in the subject, on day 8, that is at least about 20 ng/mL, at least about 30 ng/mL, at least about 50 ng/mL, at least about 80 ng/mL, at least about 90 ng/mL, at least about 100 ng/mL, at least about 150 ng/mL, at least about 200 ng/mL, at least about 300 ng/mL, up to about 1,000 ng/mL, up to about 5,000 ng/mL, or any $C_{avg}$ in a range bounded by, or between, any of these values.

For compositions comprising both DEX and a compound of formula I or SARPO, some liquids may comprise about 0.0001% (w/v) to about 50% (w/v), about 0.01% (w/v) to about 20% (w/v), about 0.01% to about 10% (w/v), about 1% (w/v) to about 3% (w/v), about 3% (w/v) to about 5% (w/v), about 5% (w/v) to about 7% (w/v), about 5% (w/v) to about 15% (w/v), about 7% (w/v) to about 10% (w/v), about 10% (w/v) to about 15% (w/v), about 15% (w/v) to about 20% (w/v), about 20% (w/v) to about 30% (w/v), about 30% (w/v) to about 40% (w/v), about 40% (w/v) to about 50% (w/v) of DEX and a compound of formula I or SARPO, combined, or any amount in a range bounded by, or between, any of these values. Some solid compositions may comprise at least about 5% (w/w), at least about 10% (w/w), at least about 20% (w/w), at least about 50% (w/w), at least about 70% (w/w), at least about 80%, about 10% (w/w) to about 30% (w/w), about 10% (w/w) to about 20% (w/w), about 20% (w/w) to about 30% (w/w), about 30% (w/w) to about 50% (w/w), about 30% (w/w) to about 40% (w/w), about 40% (w/w) to about 50% (w/w), about 50% (w/w) to about 80% (w/w), about 50% (w/w) to about 60% (w/w), about 70% (w/w) to about 80% (w/w), about 80% (w/w) to about 90% (w/w) of DEX and a compound of formula I or SARPO, combined, or any amount in a range bounded by, or between, any of these values. In some embodiments, the weight ratio of DEX to a compound of formula I or SARPO, in a single composition or dosage form may be about 0.1 to about 2, about 0.2 to about 1, about 0.1 to about 0.3, about 0.2 to about 0.4, about 0.3 to about 0.5, about 0.5 to about 0.7, about 0.8 to about 1, about 0.2, about 0.3, about 0.4, about 0.45, about 0.6, about 0.9, or any ratio in a range bounded by, or between, any of these values.

In some embodiments, a therapeutically effective amount of a therapeutic compound may vary depending upon the circumstances, for example, a daily dose of DEX may in some instances range from about 0.1 mg to about 1000 mg, about 40 mg to about 1000 mg, about 20 mg to about 600 mg, about 60 mg to about 700 mg, about 100 mg to about 400 mg, about 15 mg to about 20 mg, about 20 mg to about 25 mg, about 25 mg to about 30 mg, about 30 mg to about 35 mg, about 35 mg to about 40 mg, about 40 mg to about 45 mg, about 45 mg to about 50 mg, about 50 mg to about 55 mg, about 55 mg to about 60 mg, about 20 mg to about 60 mg, about 60 mg to about 100 mg, about 100 mg to about 200 mg, about 100 mg to about 140 mg, about 160 mg to about 200 mg, about 200 mg to about 300 mg, about 220 mg to about 260 mg, about 300 mg to about 400 mg, about 340 mg to about 380 mg, about 400 mg to about 500 mg, about 500 mg to about 600 mg, about 15 mg, about 30 mg, about 60 mg, about 120 mg, about 180 mg, about 240 mg, about 360 mg, or any daily dose in a range bounded by, or between, any of these values. DEX may be administered once daily; or twice daily or every 12 hours, three times daily, four times daily, or six times daily in an amount that is about half, one-third, one-quarter, or one-sixth, respectively, of the daily dose.

In some embodiments, a daily dose of a compound of formula I or SARPO, may in some instances range from about 10 mg to about 1000 mg, about 50 mg to about 600 mg, about 100 mg to about 2000 mg, about 50 mg to about 100 mg, about 70 mg to about 95 mg, about 100 mg to about 200 mg, about 105 mg to about 200 mg, about 100 mg to about 150 mg, about 150 mg to about 300 mg, about 150 mg to about 200 mg, about 200 mg to about 250 mg, about 250 mg to about 300 mg, about 200 mg about 300 mg, about 300 mg to about 400 mg, about 400 mg to about 500 mg, about 400 mg to about 600 mg, about 360 mg to about 440 mg, about 560 mg to about 640 mg, or about 500 mg to about 600 mg, about 100 mg, about 150 mg, about 200 mg, about 300 mg, about 400 mg, about 600 mg, or any daily dose in a range bounded by, or between, any of these values. a compound of formula I or SARPO, may be administered once daily; or twice daily or every 12 hours, or three times daily in an amount that is about half or one-third, respectively, of the daily dose.

In some embodiments:

1) about 50 mg/day to about 100 mg/day, about 100 mg/day to about 150 mg/day, about 150 mg/day to about 300 mg/day, about 150 mg/day to about 200 mg/day, about 200 mg/day to about 250 mg/day, about 250 mg/day to about 300 mg/day of a compound of formula I or SARPO, or about 300 mg/day to about 500 mg/day of a compound of formula I or SARPO; and/or 2) about 15 mg/day to about 60 mg/day, about 15 mg/day to about 30 mg/day, about 30 mg/day to about 45 mg/day, about 45 mg/day to about 60 mg/day, about 60 mg/day to about 100 mg/day, about 80 mg/day to about 110 mg/day, about 100 mg/day to about 150 mg/day, or about 100 mg/day to about 300 mg/day of DEX, are administered to a subject in need thereof.

In some embodiments, about 150 mg/day of a compound of formula I or SARPO, and about 5 mg/day of DEX, about 10 mg/day of DEX, about 15 mg/day of DEX, about 20 mg/day of DEX, about 30 mg/day of DEX, about 150 mg/day of a compound of formula I or SARPO, and about 60 mg/day of DEX, about 150 mg/day of a compound of formula I or SARPO, and about 90 mg/day of DEX, about 150 mg/day of a compound of formula I or SARPO, and about 120 mg/day of DEX, about 200 mg/day of a compound of formula I or SARPO, and about 30 mg/day of DEX, about 200 mg/day of a compound of formula I or SARPO, and about 60 mg/day of DEX, about 200 mg/day of a compound of formula I or SARPO, and about 90 mg/day of DEX, about 200 mg/day of a compound of formula I or SARPO, and about 120 mg/day of DEX, about 300 mg/day of a compound of formula I or SARPO, and about 30 mg/day of DEX, about 300 mg/day of a compound of formula I or SARPO, and about 60 mg/day of DEX, about 300 mg/day of a compound of formula I or SARPO, and about 90 mg/day of DEX, or about 300 mg/day of a compound of formula I or SARPO, and about 120 mg/day of DEX is administered to the subject.

In some embodiments, about 100 mg/day of a compound of formula I or SARPO, and about 15 mg/day of DEX is administered to the subject for 1, 2, or 3 days, followed by about 200 mg/day of a compound of formula I or SARPO, and about 30 mg/day of DEX. In some embodiments, about 100 mg/day of a compound of formula I or SARPO, and about 30 mg/day of DEX is administered to the subject for 1, 2, or 3 days, followed by about 200 mg/day of a compound of formula I or SARPO, and about 60 mg/day of DEX.

In some embodiments, about 75 mg/day of a compound of formula I or SARPO, and about 15 mg/day of DEX is administered to the subject for 1, 2, or 3 days, followed by about 150 mg/day of a compound of formula I or SARPO, and about 30 mg/day of DEX. In some embodiments, about 75 mg/day of a compound of formula I or SARPO, and about 30 mg/day of DEX is administered to the subject for 1, 2, or 3 days, followed by about 150 mg/day of a compound of formula I or SARPO, and about 60 mg/day of DEX.

In some embodiments, a 5-HT2A receptor antagonist or inverse agonist, such as a compound of formula I or SARPO, may be administered for as long as needed to treat a neurological condition, such as pain, depression or cough. In some embodiments, a 5-HT2A receptor antagonist or inverse agonist, such as a compound of formula I or SARPO, and DEX are administered at least once a day, such as once daily or twice daily, for at least 1 day, at least 3 days, at least 5 days, at least 7 days, at least 8 days, at least 14 days, at least 30 days, at least 60 days, at least 90 days, at least 180 days, at least 365 days, or longer.

In some embodiments, therapeutic compounds may be formulated for oral administration, for example, with an inert diluent or with an edible carrier, or it may be enclosed in hard or soft shell gelatin capsules, compressed into tablets, or incorporated directly with the food of the diet. For oral therapeutic administration, the active compound may be incorporated with an excipient and used in the form of ingestible tablets, buccal tablets, troches, capsules, elixirs, suspensions, syrups, wafers, and the like.

In some embodiments, tablets, troches, pills, capsules and the like may also contain one or more of the following: a binder such as gum tragacanth, acacia, cornstarch, or gelatin; an excipient, such as dicalcium phosphate; a disintegrating agent such as corn starch, potato starch, alginic acid, and the like; a lubricant such as magnesium stearate; a sweetening agent such as sucrose, lactose, or saccharin; or a flavoring agent such as peppermint, oil of wintergreen, or cherry flavoring. When the dosage unit form is a capsule, it may contain, in addition to materials of the above type, a liquid carrier. Various other materials may be present as coating, for instance, tablets, pills, or capsules may be coated with shellac, sugar or both. A syrup or elixir may contain the active compound, sucrose as a sweetening agent, methyl and propylparabens as preservatives, a dye and flavoring, such as cherry or orange flavor. It may be desirable for material in a dosage form or pharmaceutical composition to be pharmaceutically pure and substantially nontoxic in the amounts employed.

In some embodiments, compositions or dosage forms may be a liquid, or may comprise a solid phase dispersed in a liquid.

In some embodiments, therapeutic compounds may be formulated for parenteral or intraperitoneal administration. Solutions of the active compounds as free bases or pharmacologically acceptable salts can be prepared in water suitably mixed with a surfactant, such as hydroxypropylcellulose. A dispersion can also have an oil dispersed within, or dispersed in, glycerol, liquid polyethylene glycols, and mixtures thereof. Under ordinary conditions of storage and use, these preparations may contain a preservative to prevent the growth of microorganisms.

Although dementias such as Alzheimer's disease (AD) are characterized by cognitive deficits, neuropsychiatric symptoms (behavioral and psychological symptoms of dementia, BPSD) are among the main drivers for caregiver burden and hospitalization. Frequency of BPSD symptoms increases with the disease progression (e.g. up to 60% in mild and moderate AD and up to 90% in severe AD). Currently marketed dementia therapies leave much room for improvement when it comes to treat BPSD but also other non-cognitive areas of concern. In the continued absence of a disease-modifying therapy, this is of increasing importance, as symptoms like hostility, aggression, wandering, sexually inappropriate behavior or incontinence pose major problems to caregivers and families, and are predictors for (costly) nursing home placement. It is common global practice to prescribe (typical or atypical) neuroleptics to facilitate nursing and caregiving. However, the FDA has determined that off-label prescription of neuroleptics poses a major threat to the health of demented subjects, and has issued a black box warning, citing severe cardiovascular adverse events and an increased risk for death. EU approval of risperidone allows for short-term use in moderate-severe AD patients only in case of harm to self or others. In Parkinson's Disease, the anticholinergic effects of neuroleptics are highly unwanted as they inevitably worsen, in addition, the motor condition and symptoms of the vegetative nervous system. In all dementias, lowering the seizure threshold is another infrequent but highly unwanted potential adverse effect of neuroleptics. These concerns about the use of neuroleptic drugs in dementias result in decreased use of neuroleptics in this category of patients leaving BPSD symptoms in the vast majority of mild-to-moderate AD patients essentially untreated.

Accordingly, several embodiments are novel compositions and methods useful in the symptomatic and disease-modifying treatment of neurodegenerative diseases and brain injuries including sequelae thereof like organic brain syndrome and chronic traumatic encephalopathies; chronic or intractable pain, ophthalmologic indications associated with retinopathies, anxiety disorders, post-traumatic stress disorder, depression, diabetes mellitus and it's complications like peripheral neuropathies with or without neuropathic pain, Buerger's disease, Raynaud's disease, coronary artery disease, angina pectoris, atherosclerosis including CNS like multi-infarct dementia, Vascular Cognitive Impairment, Vascular Dementia or Binswanger's Disease, and nephropathies.

In a first aspect, provided is a method of increasing the metabolic lifetime of DEX, comprising administering 5-HT2A receptor antagonist or inverse agonist such as M1 to a subject in need of treatment with DEX, wherein 5-HT2A receptor antagonist or inverse agonist is an inhibitor of a CYP2D6 enzyme and wherein DEX is present in the body of the subject at the same time as M1.

In a second aspect, provided is a method of preventing adverse events associated with treatment by DEX, comprising co-administering 5-HT2A receptor antagonist or inverse agonist such as M1 to a subject in need of treatment with DEX, wherein the subject is at risk of experiencing the adverse event as a result of being treated with DEX.

In a third aspect, provided is a method for using 5HT2A receptor antagonists such as M1 to improve the therapeutic properties of DEX in the treatment of neuropsychiatric disorders.

In a fourth aspect, provided is a method of treating a neuropsychiatric disorder comprising administering a 5HT2A receptor antagonist such as M1 and DEX to a subject in need thereof.

In an embodiment of the first, second, third and fourth aspects, the 5-HT2A receptor antagonist or inverse agonist is a prodrug of M1 such as a compound of formula I or SARPO, or pharmaceutically acceptable salts thereof.

In an embodiment of the first, second, third and fourth aspects, 5-HT2A receptor antagonist or inverse agonist is an enantiomer of M1 such as (R)-1-(dimethylamino)-3-(2-(3-methoxyphenethyl) phenoxy) propan-2-ol) or (S)-1-(dimethylamino)-3-(2-(3-methoxyphenethyl)phenoxy)propan-2-ol), or pharmaceutically acceptable salts thereof.

In an embodiment of the first, second, third and fourth aspects, 5-HT2A receptor antagonist or inverse agonist the 5-HT2A receptor antagonist or inverse agonist is a prodrug of (R)-1-(dimethylamino)-3-(2-(3-methoxyphenethyl) phenoxy) propan-2-ol) or (S)-1-(dimethylamino)-3-(2-(3-methoxyphenethyl)phenoxy)propan-2-ol), or pharmaceutically acceptable salts thereof.

In an embodiment of the third and fourth aspects, the neuropsychiatric disorder is Alzheimer's disease.

In a fifth aspect, provided is a method for selecting a 5-HT2A receptor antagonist or inverse agonist for the use in combination with DEX in subjects in need thereof.

In an embodiment of the fifth aspect, a specific enantiomer of a 5HT2A receptor antagonist with potent CYP2D6 inhibitory activity has higher blood-brain barrier penetration.

In an embodiment of the fifth aspect, a specific enantiomer of an 5HT2A receptor antagonist with potent CYP2D6 inhibitory activity has a better ratio of central vs peripheral effects when administered in combination with DEX, wherein central effects are assessed by direct or indirect 5HT2A receptor engagement methods while peripheral effects are assessed by methods based on blood glucose measurement.

In an embodiment of the fifth aspect, DEX and the selected 5-HT2A antagonist are administered in a combined dose, and wherein the amount of DEX administered comprises from about 20 mg/day to about 80 mg/day.

In an embodiment of the fifth aspect, DEX is administered in a combined dose with a selected enantiomer of M1, wherein the amount of the M1 enantiomer administered comprises from about 0.1 mg/day to about 1000 mg/day.

An embodiment of the invention is a method to augment therapeutic properties of DEX by administering it with a 5HT2A receptor antagonist that has potent CYP2D6 inhibitory activity, and multiple therapeutic benefits of its own.

Some embodiments include a method of treating a disease or disorder comprising administering about 5 mg/day to about 600 mg/day, about 5 mg/day to about 300 mg/day, about 5 mg/day to about 400 mg/day, about 5 mg/day to about 500 mg/day, about 5 mg/day to about 600 mg/day, about 5 mg/day to about 1,000 mg/day, about 50 mg/day to about 1000 mg/day, about 100 mg/day to about 1000 mg/day, about 150 mg/day to about 1000 mg/day, about 150 mg/day to about 5000 mg/day, about 150 mg/day to about 300 mg/day, or about 150 mg/day to about 100 mg/day, or an amount as required of a compound of formula I or SARPO, and about 0.1 mg/day to about 1 mg/day, about 0.5 mg/day to about 15 mg/day, about 15 mg/day to about 60 mg/day, about 15 mg/day to about 120 mg/day, about 0.1 mg/day to about 200 mg/day, or any amount of a compound of formula I or SARPO, in a range bounded by, or between, any of these values, or an amount as required of DEX to a subject in need thereof.

The invention also provides the use of M1, as a racemate or specific enantiomers, for the preparation of pharmaceutical compositions for the treatment of neuropsychiatric disorders in combination with DEX, whereby the combination covers a wider range of symptoms and/or is therapeutically more effective than either component given alone, resulting in additive or synergistic therapeutic benefit.

In all embodiments of methods, the compound of Formula is selected from the compounds Pharmaceutical Compositions and Formulations The present invention is based on the finding that the stability of a drug-resin complex improves significantly when the resin is treated with an inorganic alkaline material prior to use. The stability of the drug-resin complex may further be improved by impregnating the drug-resin complex prior to final formulation. The drug-resin complex may further be coated with a diffusion barrier to obtain a desirable drug dissolution profile.

In one aspect, the present invention provides a pharmaceutical composition with an improved stability that comprises a drug-resin complex, wherein the resin used therein has been treated with an inorganic alkaline material and wherein the drug-resin complex has been impregnated with an alkalizing agent and optionally a solvating agent.

In another aspect, the present invention provides a pharmaceutical composition with an improved stability that comprises a drug-resin complex, wherein the resin used therein has been treated with an inorganic alkaline material and wherein the drug-resin complex has been impregnated with L-methionine, an antioxidant agent, or a combination thereof. The drug stability may further be improved by adding phosphoric acid and by avoiding use of propylene glycol in the formulation.

In yet another aspect, the present invention provides a pharmaceutical composition with an improved stability that comprises a drug-resin complex, wherein the resin used therein has been treated with an inorganic alkaline material and wherein the drug-resin complex has been coated with a diffusion barrier to modify the drug dissolution profile.

In a further aspect, the invention provides a method of preparing a pharmaceutical composition with improved drug stability. The method comprises the steps of: (1) treating a resin with an inorganic alkaline material; (2) combining a drug and the treated resin to form a drug-resin complex; (3) impregnating or coating the drug-resin complex with suitable reagents to either improve the stability or modify the dissolution profile of the drug; and (4) formulating the complex from the previous step to form a pharmaceutical composition.

In accordance with the present invention, any non-toxic resin may be suitable for use as long as a drug can be sufficiently bound or adsorbed into the resin. A resin is ion exchange resin. Ion-exchange resins suitable for use in the present invention are water-insoluble and comprise pharmacologically inert organic and/or inorganic matrix containing functional groups that are ionic or capable of being ionized under the appropriate conditions of pH. The organic matrix may be synthetic (e.g., polymers or copolymers of acrylic acid, methacrylic acid, sulfonated styrene, sulfonated divinylbenzene), or partially synthetic (e.g. modified cellulose and dextrans). The inorganic matrix comprises silica gel modified by the addition of ionic groups. Covalently bound ionic resins may also be used. The covalently bound ionic groups may be strongly acidic (e.g., sulfonic acid, phosphoric acid), weakly acidic (e.g., carboxylic acid), strongly basic (e.g., primary amine), weakly basic (e.g. quaternary ammonium), or a combination of acidic and basic groups (Borodkin, Book chapter: Ion-exchange resin delivery system, in "Polymers for Controlled Drug Delivery", Tarcha, P J, Ed., CRC Press, Boca Raton, 1990; incorporated by reference in its entirety).

An ion exchange resin known to be useful in the present invention is divinylbenzene sulfonic acid cationic exchange resin, in either sodium salt or potassium salt form. In one embodiment, Purolite C 100 E MR/4395 is used which has a particle size less than 150 micron. Other commercially available equivalent resins that can be used are Amberlite IRP-69 and Dow XYS-40010.00. Both are sulfonated polymers composed of polystyrene cross-linked with about 8% of divinylbenzene, with an ion-exchange capacity of about 4.5 to 5.5 meq/g of dry resin ($H^+$ form). Their essential difference is in physical form. Amberlite IRP-69 consists of irregularly shaped particles with a size range of about 5 microns to about 149 microns produced by milling the parent large size spheres of Amberlite IRP-120. The Dow XYS-40010.00 product consists of spherical particles with a size range of 45 microns to 150 microns.

All drugs which exist in an ionic form may be used to bind with ion exchange resins in the present invention. Such drugs include, but are not limited to, many families of drugs such as antibacterials, antivirals, antifungals, anti-parasitics, tumoricidals, anti-metabolites, polypeptides, immunoglobulins, immunomodulators, vasodilators, anti-inflammatories, antiglaucomics, mydriatic compounds, antidepressants, antispasmodics, antiulceratives, anxiolytics, calcium channel blockers, dopamine receptor agonists and antagonists, narcotic antagonists, protease inhibitors, respiratory stimulants, retroviral protease inhibitors, reverse transcriptase inhibitors.

The drugs that in particular are benefited from the present invention are those prone to degradation after complexation, for example, due to oxidation or hydrolysis. In some embodiments, the drug is selected from a group consisting of dextromethorphan, codeine, morphine, hydrocodone, pseudoephedrine, phenylpropanolamine and the salts thereof. In an embodiment, the drug is dextromethorphan.

In accordance with the present invention, the resin, before being complexed with the drug, is treated with an inorganic alkaline material in water. It is observed that a drug-resin complex which is made of the treated resin exhibits significantly improved stability compared to a drug-resin complex using an untreated resin.

The treatment can be conducted by soaking with stirring, the resin in an aqueous solution of an inorganic alkaline material for an extended time. An elevated temperature may be used to increase the effectiveness of the treatment. The concentration of the inorganic alkaline material may vary. In one embodiment, the inorganic alkaline material is 2N sodium hydroxide. The time required for the treatment also vary, depending on the amount of resins to be pretreated, the temperature, the time, the type of the inorganic alkaline material and its concentration.

The treatment can also be conducted in a chromatographic column by repeatedly running an aqueous solution of an inorganic alkaline material through the chromatographic column containing the resin to be treated.

The alkalizing material are pharmaceutically acceptable inorganic salts of alkaline metals and alkaline earth metals such as lithium salts, potassium salts, sodium salts in form of oxide, carbonate, bicarbonate, and the like. An alkalizing agent for the resin is sodium hydroxide.

All water used for the invention is distilled or purified water, free of minerals, ions, and ion exchange components may be used for the invention. In an embodiment, deionized (DI) water is used.

After the alkaline pretreatment, the treated resin is collected by filtration, optionally, the resin is washed with water numerous times. The resin is then dried at about 50 degrees C. until the water content is less than 8%, as measured by the well-known Karl-Fischer method. The dried, treated resin can then be reacted with a drug to form a drug-resin complex using standard techniques.

In one embodiment, a drug-resin complex is formed by adding an aqueous solution of a drug to a container containing the treated resin and stirring for sufficient time. The resulting drug-resin complex suspension is filtered, and optionally is washed with water numerous times, to yield the drug-resin complex. The drug-resin complex is then dried until the water content was below 8%, as measured by the Karl-Fischer method.

The amounts of drug and resin necessary to form an effective drug-resin complex vary greatly. Among the factors to be considered in determining the ratio of drug to resin are the particular drug itself, the resin, the reaction conditions, and the final dosage form. The resin has a high loading capacity for the drug in question. A small loading capacity may make the resulting dosage form overly bulky or expensive to produce. The actual loading of the drug on the resin particles can range from about 1% to 90% by weight but 5% to 30% by weight of the resin.

The stability of the drug-resin complex is also improved by impregnating the drug-resin complex with an alkalizing agent.

Suitable alkaline agents for the present invention can be organic or inorganic agents. Inorganic alkaline agents include, but not limited to, carbonate, alkaline oxide, and hydroxide. Inorganic alkaline agents include MgO, $Mg(OH)_2$, $CaCO_3$, $Ca(OH)_2$, $MgCO_3$. In one embodiment, Inorganic alkaline agent is magnesium oxide (MgO). Organic alkaline agents include, but not limited to, pseudoephedrine and phenylpropanolamine.

The alkalizing agent is present in an amount of about 5% to about 30% by weight of the resin. In one embodiment, the alkalizing agent is about 10% by weight of the resin.

Additionally, the drug-resin complex may be treated with a solvating agent to aid the impregnation of the alkalizing agent. This step can be performed simultaneously with or before the impregnation of magnesium oxide. Solvating agents include polyol, such as polyethylene glycol, glycerol, propylene glycol, polyethylene glycol (PEG), or PEG 3350. The solvating agent may be in an amount of about 5% to about 35% or about 15% by weight of the resin.

It has been observed that the alkalized drug-resin complex, i.e., the complex which has been impregnated with PEG and MgO, exhibits significantly improved stability, compared to the drug-resin complex without such impregnation.

The drug-resin complex made from a resin pre-treated with an inorganic alkaline material can further be impregnated with L-methionine. For better result, a solvating agent is added in this step. It is observed that the impregnation with L-methionine and a solvating agent improves the drug stability of the pharmaceutical composition. In one embodiment, the impregnation is conducted by adding a few drops of water to moisten the mixture of L-methionine, PEG and the alkalized drug-resin complex, thoroughly mixing the ingredients, and then drying. For better result, the L-methionine and PEG are grounded to fine powders prior to use. The L-methionine may be in an amount of about 5% to about 30%, or about 10% by weight of the resin. The PEG amount used is about 5% to about 35%, or about 15% by weight of the resin.

Other ingredients, such as an antioxidant, can also be impregnated simultaneously with L-methionine. Antioxidants are known to improve the chemical stability of resins.

Possible antioxidant agents include, but not limited to, butylated hydroxyanisole (BHA) and butylated hydroxytoluene (BHT). The antioxidant is used in an amount of about 0.05% to about 0.5%, or about 0.2% by weight of the resin. It should be noted that, antioxidant can also be added to the final formulation, rather than being impregnated onto the resin, to improve the stability of the composition.

The drug-resin complex of the present invention can be formulated into any pharmaceutical dosage forms for oral, topical, rectal, vaginal, nasal, or ophthalmic administration. Dosage forms include syrups and suspensions. Commonly known ingredients and procedures to formulate a drug-resin pharmaceutical composition are within the purview of a person skilled in the art. Various methods (U.S. Pat. Nos. 4,221,778, 4,762,709, 4,788,055, 4,959,219, 4,996,047, 5,071,646, and 5,186,930; incorporated herein in their entirety by reference) can be used to formulate the composition.

The stability of drug-resin pharmaceutical suspensions is tested. Of the commonly known ingredients used in formulating a suspension, propylene glycol is found to destabilize the suspension, and phosphoric acid is found to stabilize the suspension.

The present invention further provides a pharmaceutical composition having not only a stabilized drug-resin complex but also a desirable dissolution profile. This is achieved by coating the alkalized drug-resin complex with a film forming polymer prior to the final formulation. The film forming polymer is called a diffusion barrier because it can slow the rate of drug dissolution. Possible coating materials include, but not limited to, hydoxypropyl cellulose (HPC), ethylcellulose, methylcellulose, polyethylene glycol, mannitol, lactose and others, with HPC being the coating material. Additionally, a functional coating may be used to further control the dissolution, for instance, to sustain or delay the release of the drug from the drug-resin complex. Varying the amount of coating or combining coated and uncoated complexes in the same formulation can be used to adjust the dissolution profile as desired.

Conventional coating procedures (U.S. Pat. No. 4,221,778 A, incorporated by reference in its entirety) can be used to coat the particles. In one embodiment, the coating is carried out in a fluid bed coating apparatus equipped with a Wurster Column. Samples are collected at three intervals in order to assess the coating weight gain influenced release. Following coating, the complex is well mixed with colloidal silicon dioxide at 1%, followed by curing in a forced draft oven for 48 hours at 40° C.

The coated drug-resin complex is formulated into a desirable pharmaceutical dosage form. The pharmaceutical composition prepared in accordance with the present invention is able to maintain a sustained release profile that is comparable to a brand name product.

In one embodiment, the oral formulations and the tablet formulations are enteric coating layered formulations that comprise a separating layer to separate the acidic enteric coating material from omeprazole being an acid susceptible substance. HPC or other suitable polymers disclosed herein may be used in a layer that separates the core material from the enteric coating layer in the described formulations.

Synthetic Methods

SGL hydrochloride (CAS NO.: 135159-51-2), with its systematic name of Butanedioic acid, mono(2-(dimethylamino)-1-((2-(2-(3-methoxyphenyl) ethyl) phenoxy) methyl) ethyl) ester, hydrochloride, could be produced through many synthetic methods (Chen et al., A practical synthesis of sarpogrelate hydrochloride and in vitro platelet aggregation inhibitory activities of its analogues, Chinese Chemical Letters, Volume 21, Issue 3, March 2010, Pages 287-28; J Med Chem 33(6) (1990); CN103242179 A; WO2015008973; incorporated by reference herein).

The reaction of 2-hydroxy-3'-methoxybibenzyl with epichlorohydrin by means of a base in a suitable solvent gives 2-(2,3-epoxypropoxy)-3'-methoxybibenzyl, which by reaction with dimethylamine in refluxing in a suitable solvent yields 2-[3-(dimethylamino)-2-hydroxypropoxy]-3'-methoxybibenzyl. Finally, this compound is treated with succinic anhydride while refluxing in a suitable solvent with an acid.

Scheme Ia

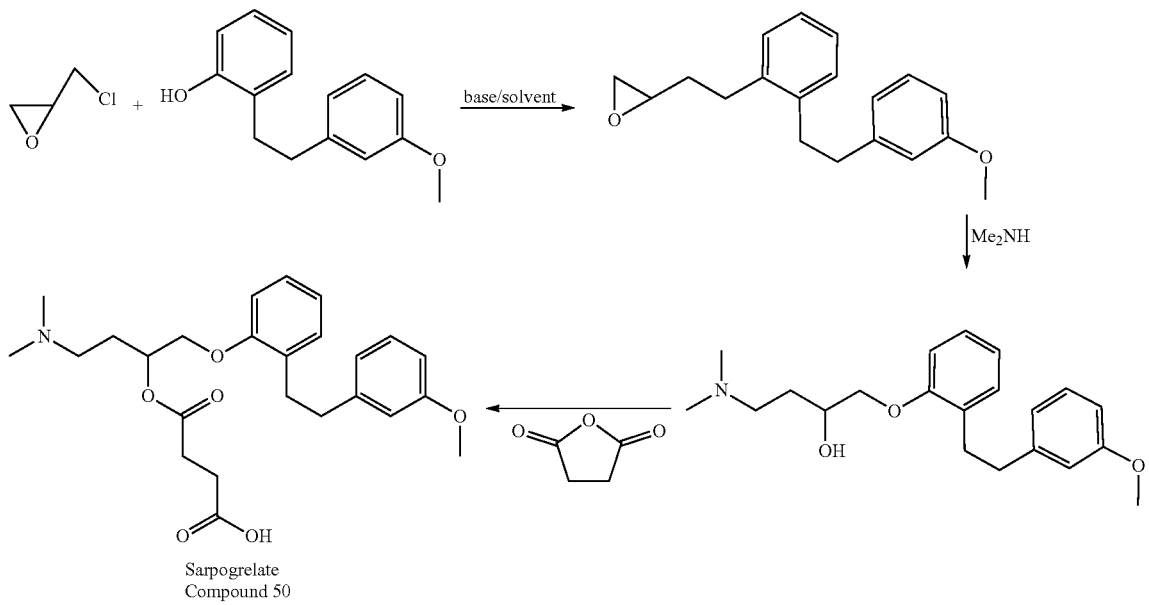

Sarpogrelate
Compound 50

As shown in the scheme below, the reaction of 2-hydroxy-3'-methoxybibenzyl with epichlorohydrin by means of a base NaH in DMF gives 2-(2,3-epoxypropoxy)-3'-methoxybibenzyl, which by reaction with dimethylamine in refluxing THF yields 2-[3-(dimethylamino)-2-hydroxypropoxy]-3'-methoxybibenzyl. Finally, this compound is treated with succinic anhydride in refluxing THF and with HCl in acetone (J Med Chem 33(6) (1990), incorporated by reference herein).

Scheme Ib

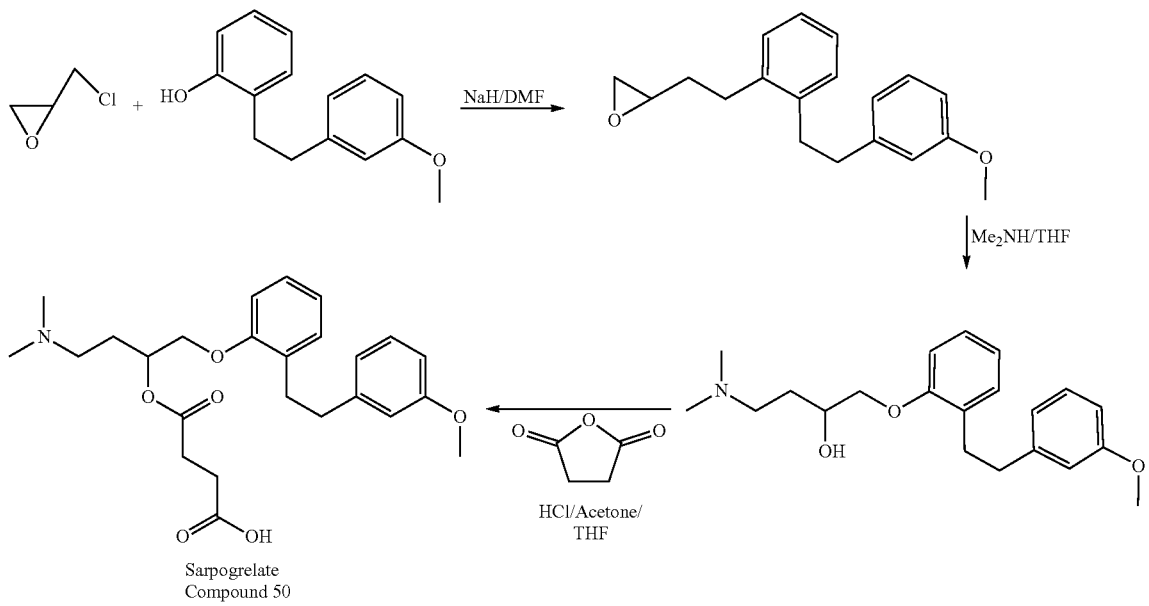

Sarpogrelate
Compound 50

SGL hydrochloride was synthesized from salicylicaldehyde via benzyl protection, reduction, chlorination, Arbuzov reaction, Wittig-Horner reaction, catalytic hydrogenation to give 2-2-(3-methoxyphenyl)ethyl phenol, which was subjected to react with epichlorohydrin, amination, esterification and salt formation.

SGL hydrochloride drug substance used in the preparation SGL hydrochloride tablets achieve acceptable purity, single hetero content meets the corresponding requirements. SGL hydrochloride recrystallized from a suitable solvent system to obtain pure SGL salt. The solvent system comprises at one or more solvents such as acetone, acetonitrile, propionitrile, 1,4-dioxane, tetrahydrofuran, dimethyl formamide, dimethyl acetamide, sulfolane, dimethyl sulfoxide, etc., or a mixture of more than two kinds thereof with methanol, ethanol, acetone, ethyl acetate, diethyl ether, diisopropyl ether or the like can be used as the recrystallization solvent SGL hydrochloride; or $C_{2-10}$ alkanes, $C_{3-10}$ ketones, $C_{2-10}$ carboxylic acid esters, $C_{1-10}$ halogenated alkanes, aromatic hydrocarbons or aromatic derivative at room temperature to the reflux temperature, water as a recrystallization solvent or an organic solvent, an aqueous 5% or more (U.S. Pat. No. 4,485,258 A; CN 101,239,920 A; incorporated in entirety by reference).

Scheme II

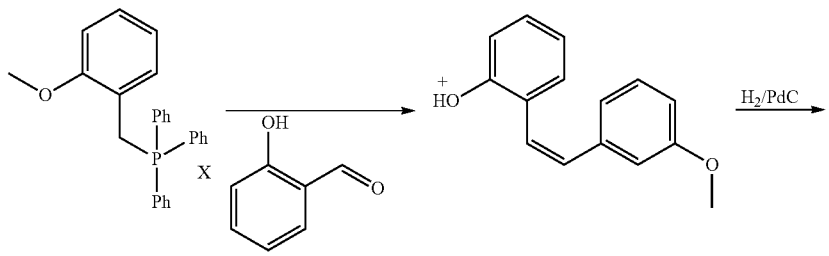

-continued
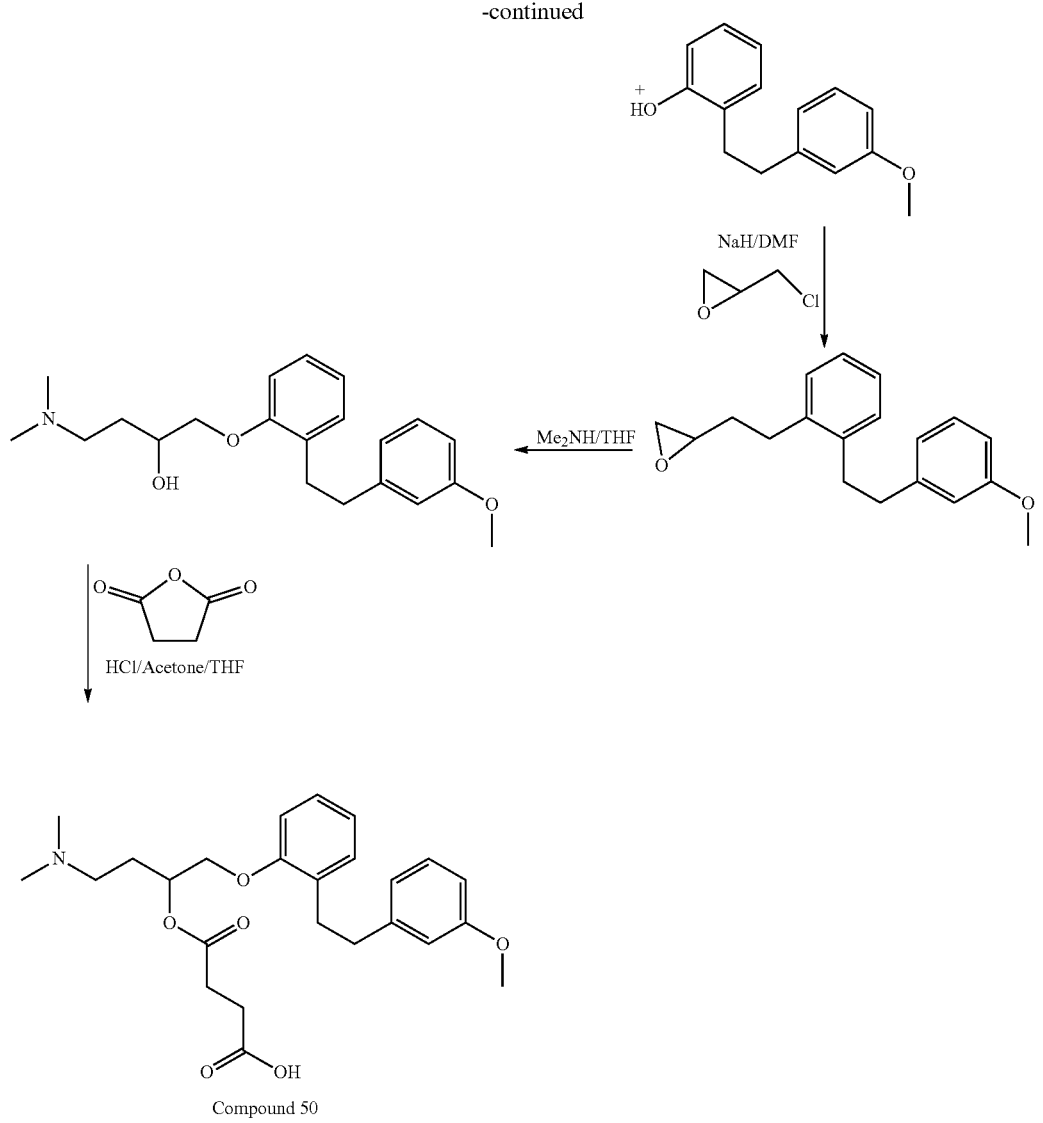
Compound 50
Enantiomerically pure form of SGL can be produced using chiral ligands to induce formation of a single enantiomer of choice as shown below:
Scheme III
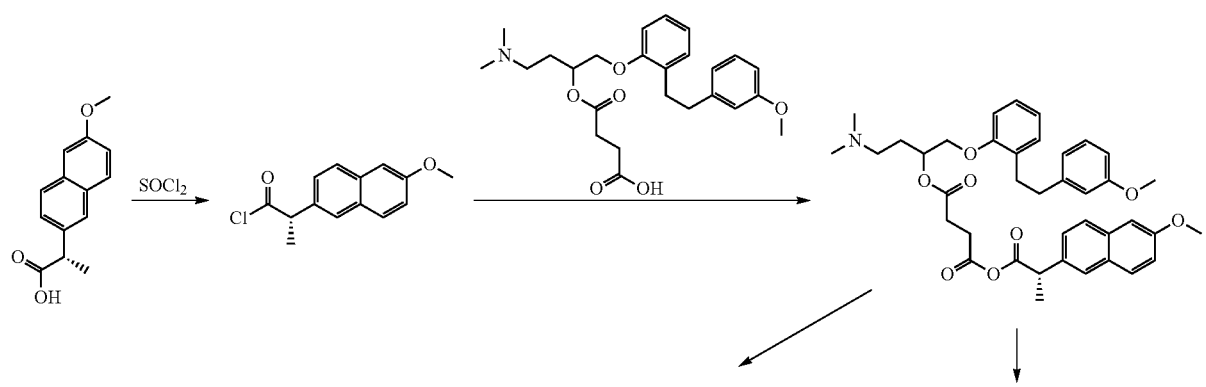

139 140
-continued
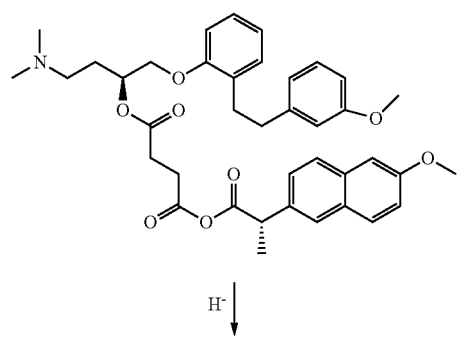
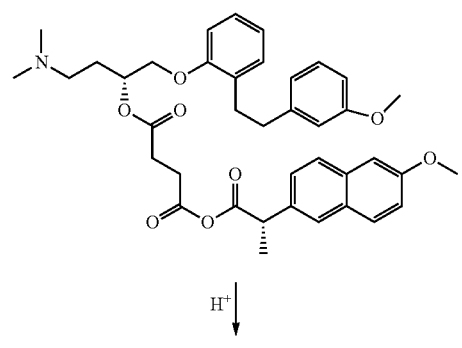
↓ H⁻  ↓ H⁺
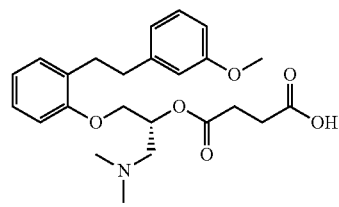
(R)-4-((1-(dimethylamino)-3-(2-(3-methoxyphenethyl)phenoxy)propan-2-yl)oxy)-4-oxobutanoic acid
(R) Sarpogrelate
SGL-E1
Compound 51
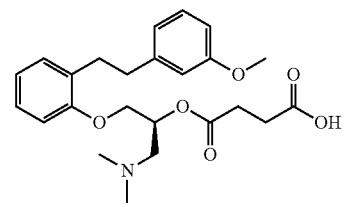
(S)-4-((1-(dimethylamino)-3-(2-(3-methoxyphenethyl)phenoxy)propan-2-yl)oxy)-4-oxobutanoic acid
(S) Sarpogrelate
SGL-E2
Compound 52
Scheme IV
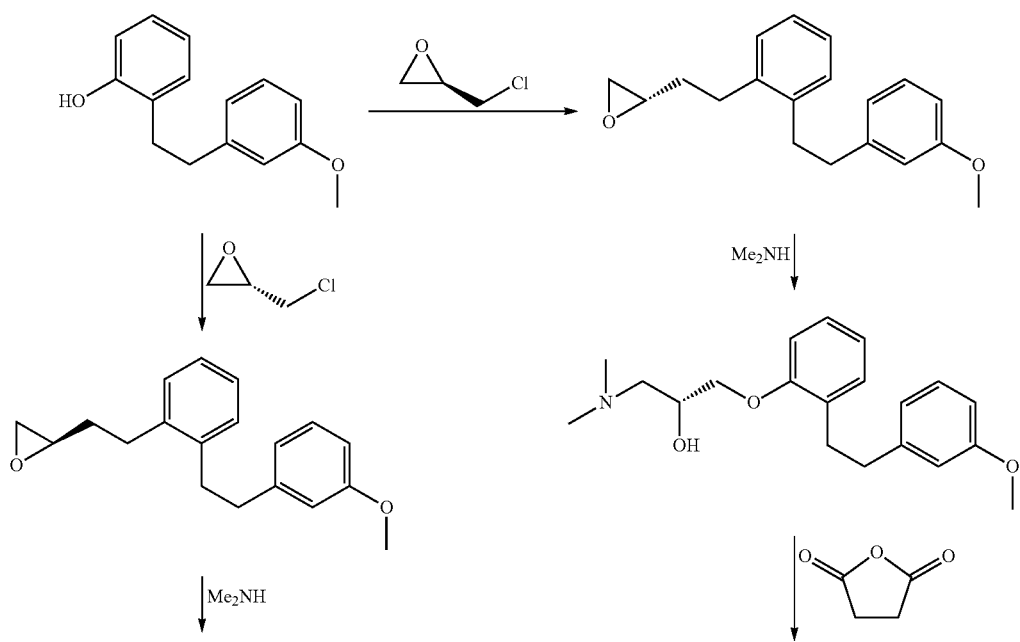

141                                                                142
-continued
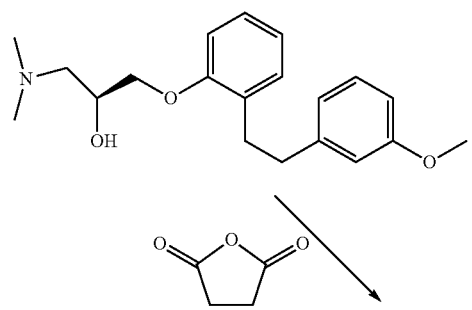
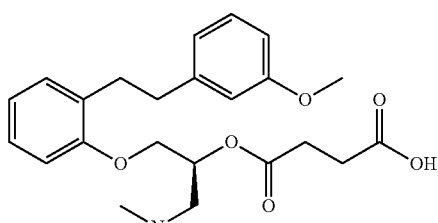
(S)Sarpogrelate
Enantiomer
SGL-E2
Compound 52
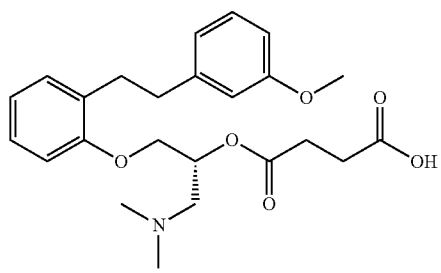
(R)Sarpogrelate
Enantiomer
SGL-E1
Compound 51
Scheme V
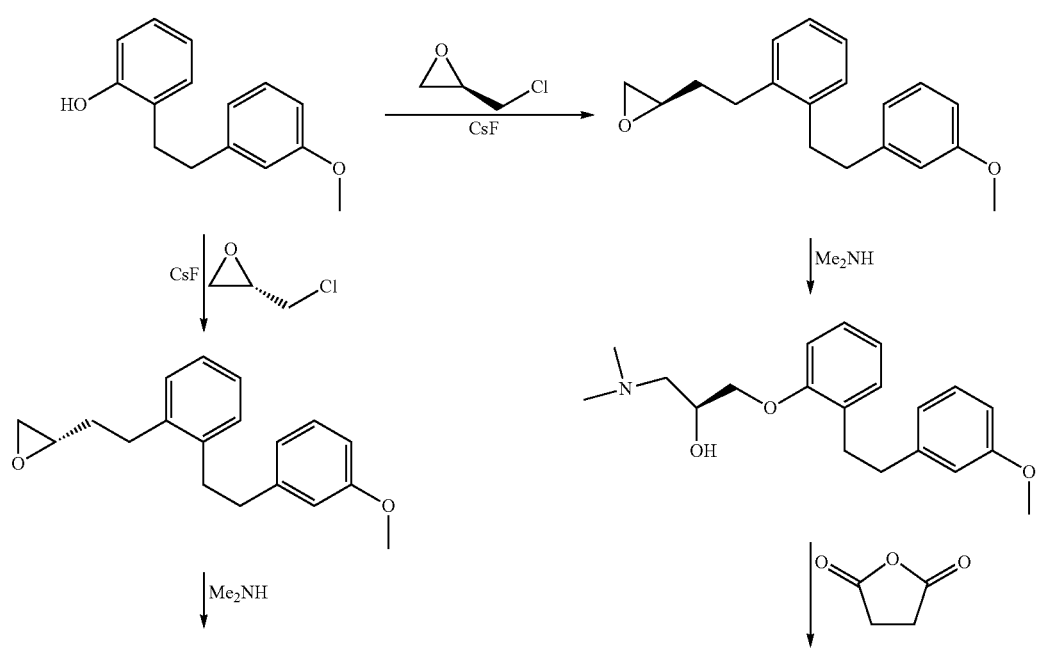

143
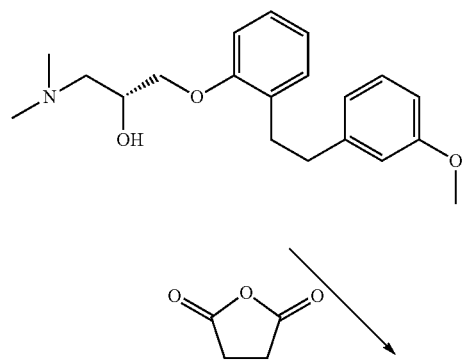
144
-continued
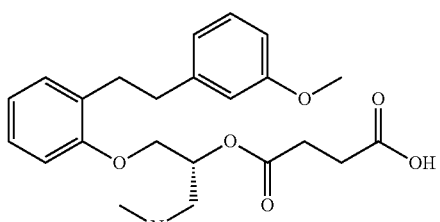
(R)Sarpogrelate
Enantiomer
SGL-E1
Compound 51
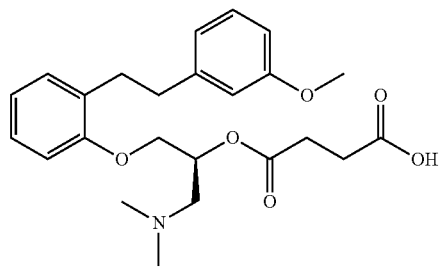
(S)Sarpogrelate
Enantiomer
SGL-E2
Compound 52
Scheme VI
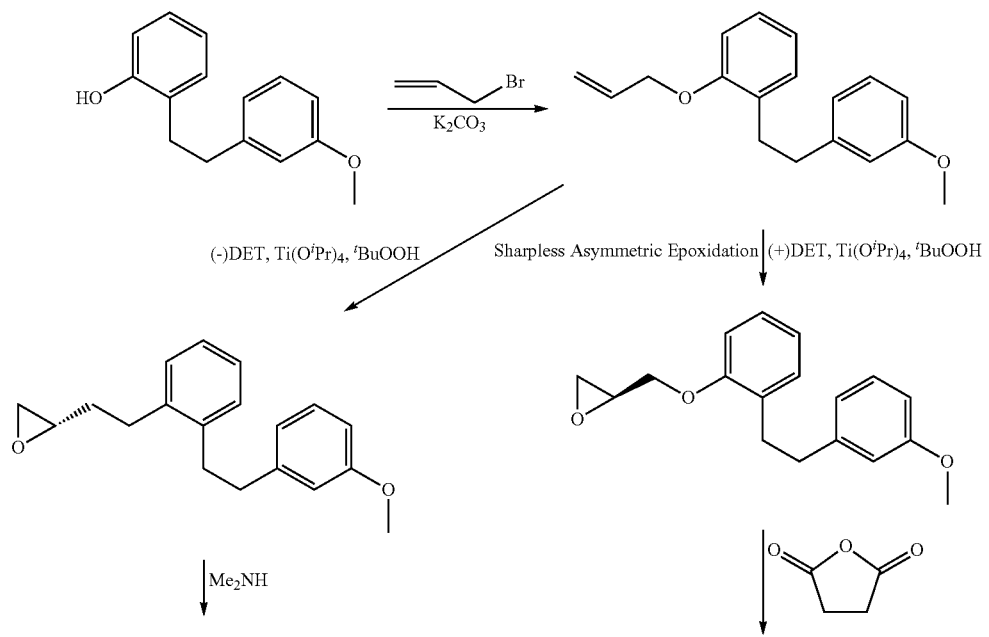

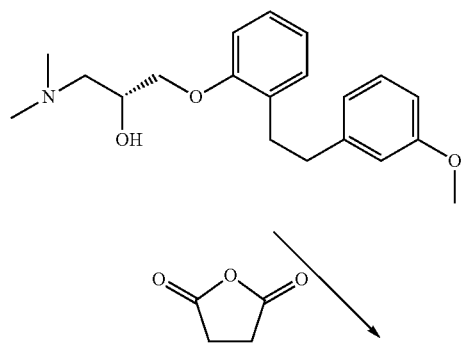

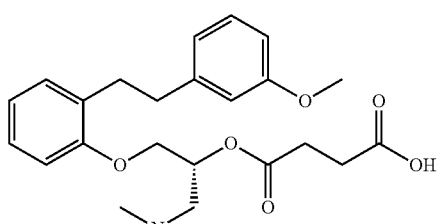

(R)Sarpogrelate
Enantiomer
SGL-E1
Compound 51

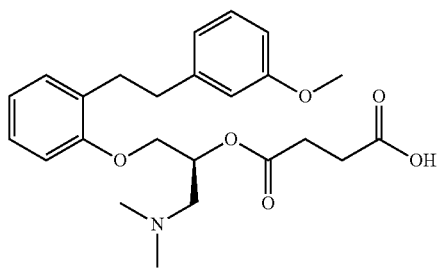

(S)Sarpogrelate
Enantiomer
SGL-E2
Compound 52

Chiral organic compounds play an important role in pharmaceuticals, agrochemicals and other materials which possess useful biological activity. Enzymes and other natural binding sites recognize substrates with particular chirality to generate a variety of biological functions. These enzymes or receptor sites are specific in their action, because the enantiomers may exhibit different properties due to the chirality. Hence for biologically active compounds, it is possible that only one of the enantiomer is active and the other is devoid of activity, both enantiomers are active but they have different potencies or both the enantiomers have similar or equal activities. Therefore, the production of enantiomerically pure molecules of drugs is of interest and the methodology has three basic strategies, 1) resolution (2) use of chiral building blocks and (3) asymmetric synthesis. Asymmetric synthesis provides by far the most efficient use of one chiral material to prepare another.

Scheme VII

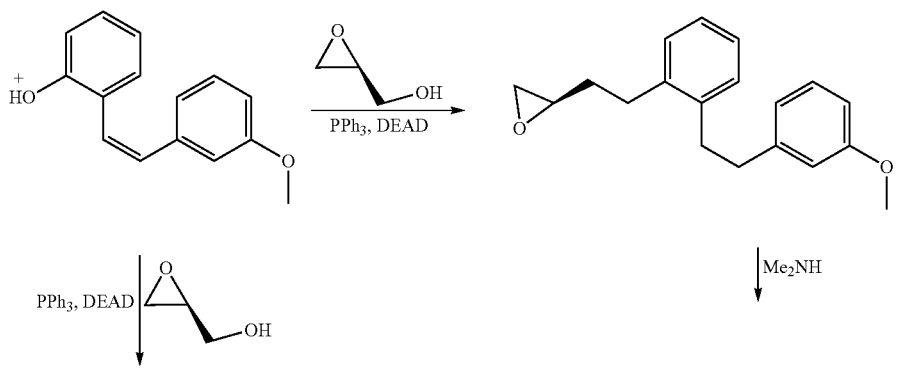

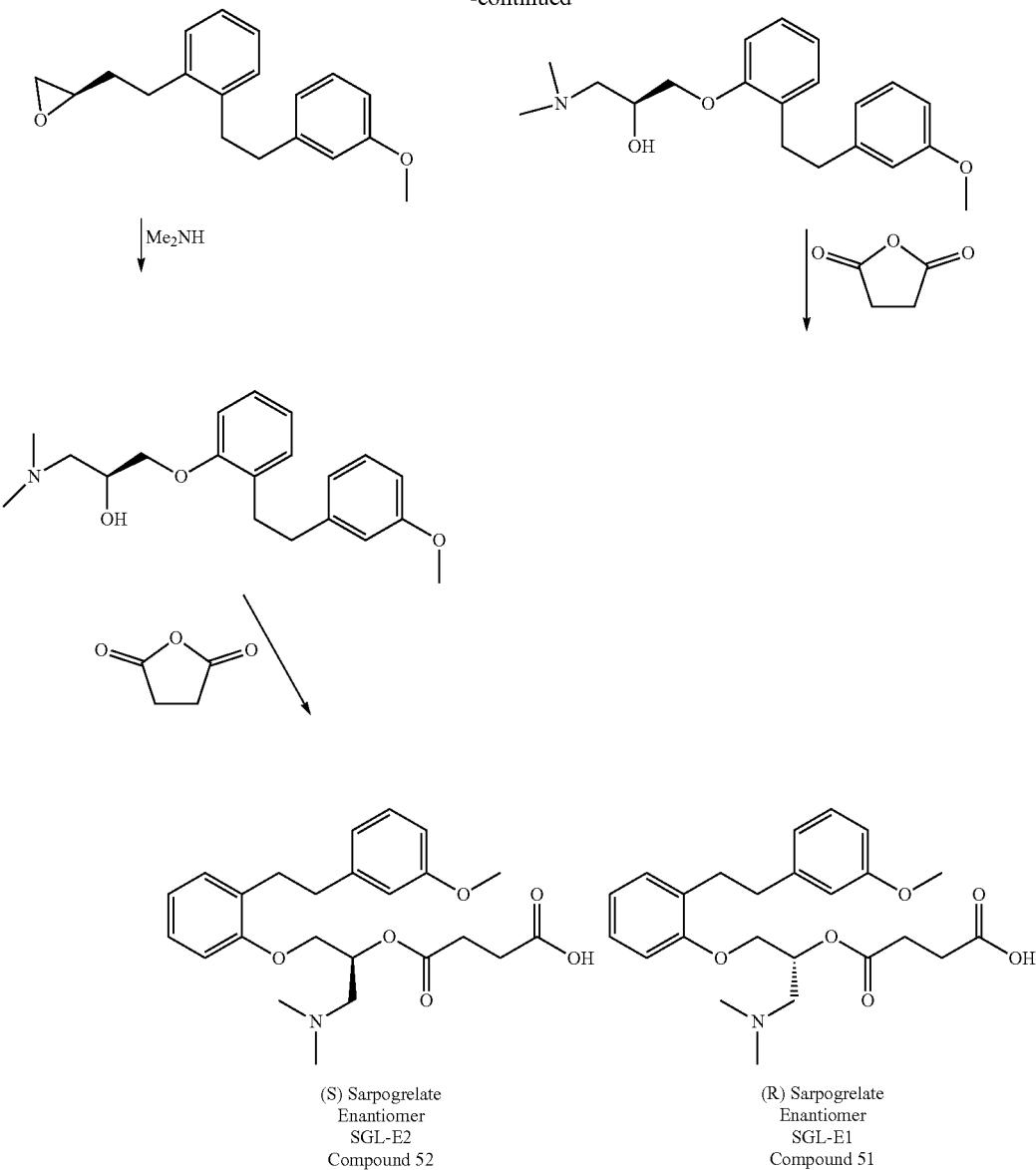

The preparation of enantiomerically pure molecules of biological interest can be effectively achieved by asymmetric synthesis. This method involves the creation of one or more chiral centers from prochiral starting materials under the influence of chiral substrates. The preparation of enantiomerically pure compounds involves use of chiral auxiliaries, chiral reagents or chiral catalysts, or a combination thereof.

In another embodiment, the compounds of the disclosure can be prepared from (2R)-3-(dimethylamino)-1,2-propanediol and (2S)-3-(dimethylamino)-1,2-propanediol (Scheme VIII).

Various versatile and convenient chiral carboxylic acid ligands are available in the literature such as mandelic acid, 2-metylmandelic acid, 2-chloromandelic acid, 3-chloromandelic acid, 4-methoxymandelic acid, O-acetylmandelic acid, α-methoxyphenylacetic acid, malic acid, tartaric acid, etc. The chiral ligands can be prepared from readily available building blocks (Moloney et al., Chiral carboxylic acid ligands derived from camphoric acid, Tetrahedron: Asymmetry, Volume 7, Issue 9, September 1996, Pages 2551-2562; U.S. Pat. No. 7,230,135 B2; Product: (S)-2-Amino-1,2,3,4-tetrahydro-6-methoxy-naphthalene, Chiral Quest Corp; Ager (Ed), CHAPTER I CHIRAL HYDROXY COMPOUNDS AS LIGANDS IN ASYMMETRIC SYNTHESIS, Handbook of Chiral Chemicals, Second Edition; Hu et al., Adventure in Asymmetric Hydrogenation: Synthesis of Chiral Phosphorus Ligands and Asymmetric Hydrogenation of Heteroaromatics, Top Organomet Chem 36:313-354 (2011); Ishihara et al., An extremely simple, convenient, and selective method for acetylating primary alcohols in the presence of secondary alcohols, J. Org. Chem., 58 (15), pp 3791-3793 (1993); Edwards et al., The stereoselective replacement of hydroxyl groups by chlorine, using the mesyl chloride-N,N-dimethylformamide reagent, Carbohydrate Research, Volume 35, Issue 1, Pages 111-129 (July 1974); incorporated by reference herein).

Scheme VIIIa
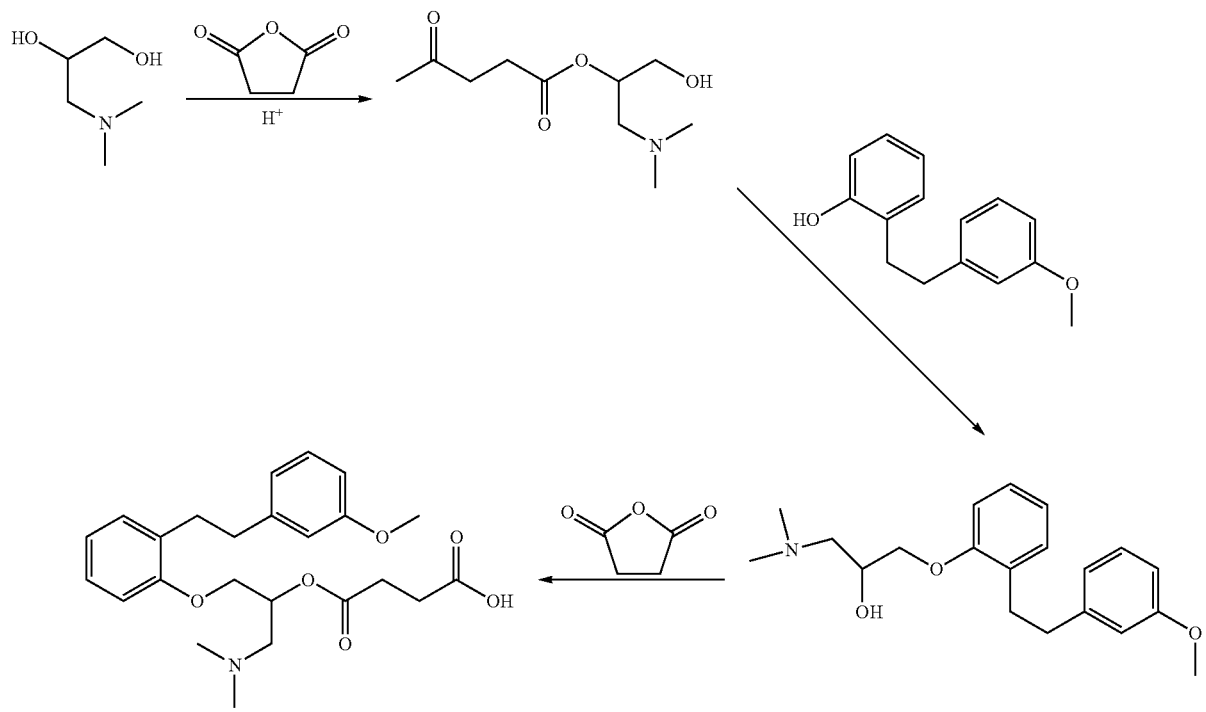
Scheme VIIIb
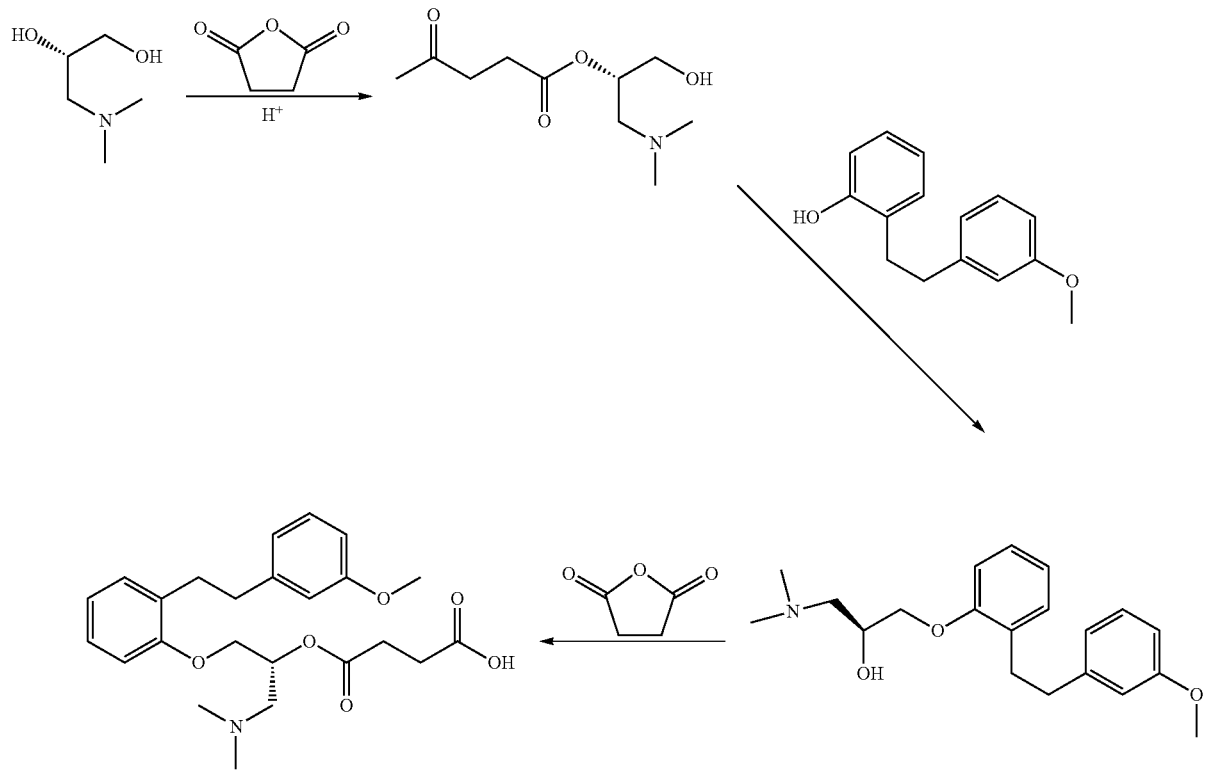
(R)Sarpogrelate
Enantiomer
SGL-E1
Compound 51

-continued
Scheme VIIIc
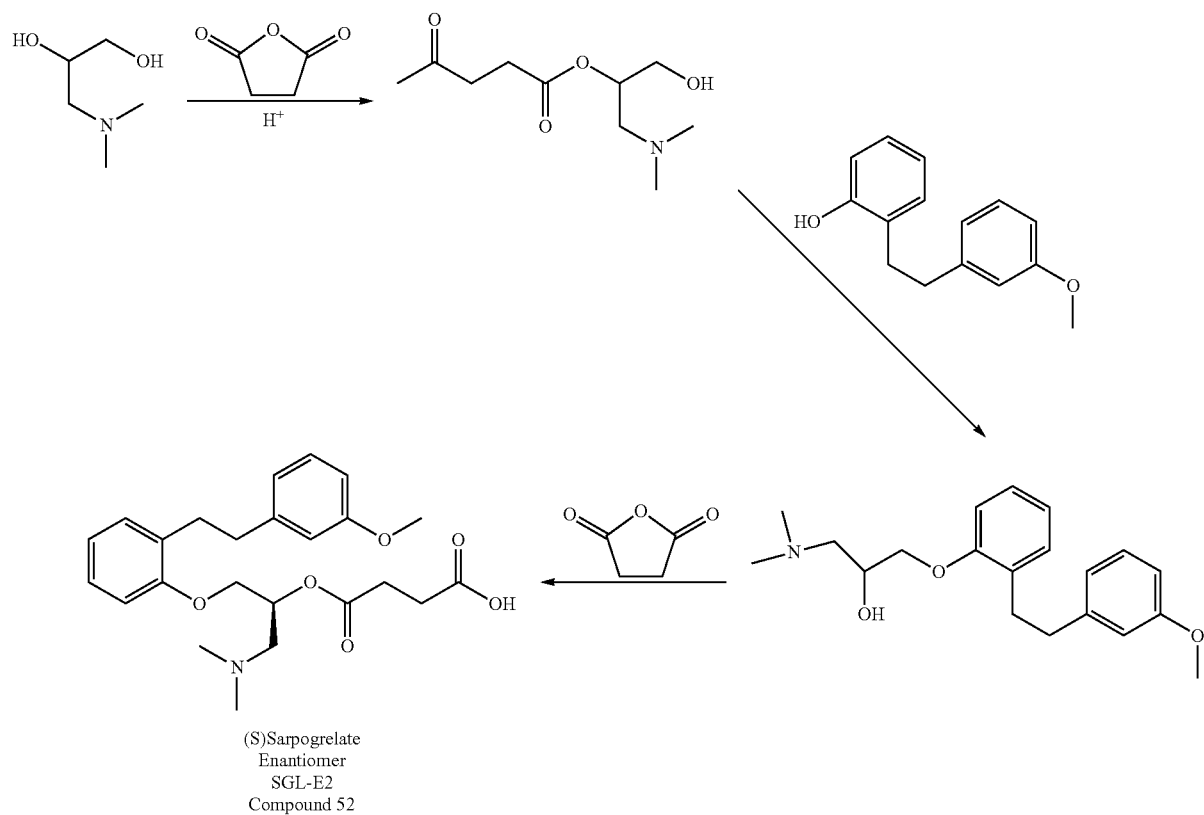
Scheme IX
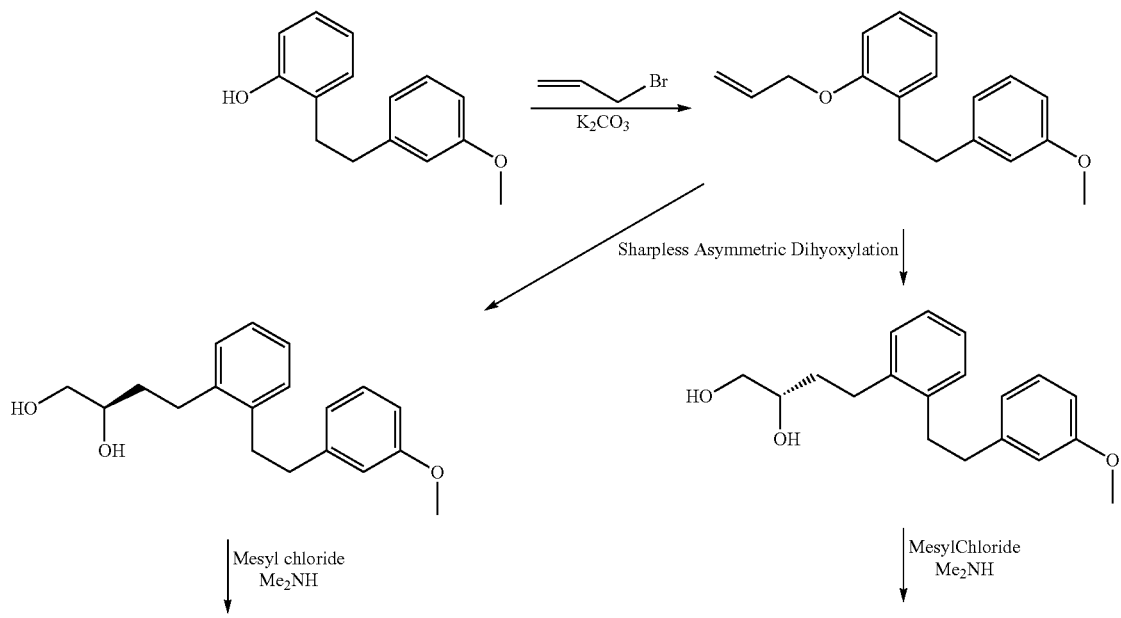

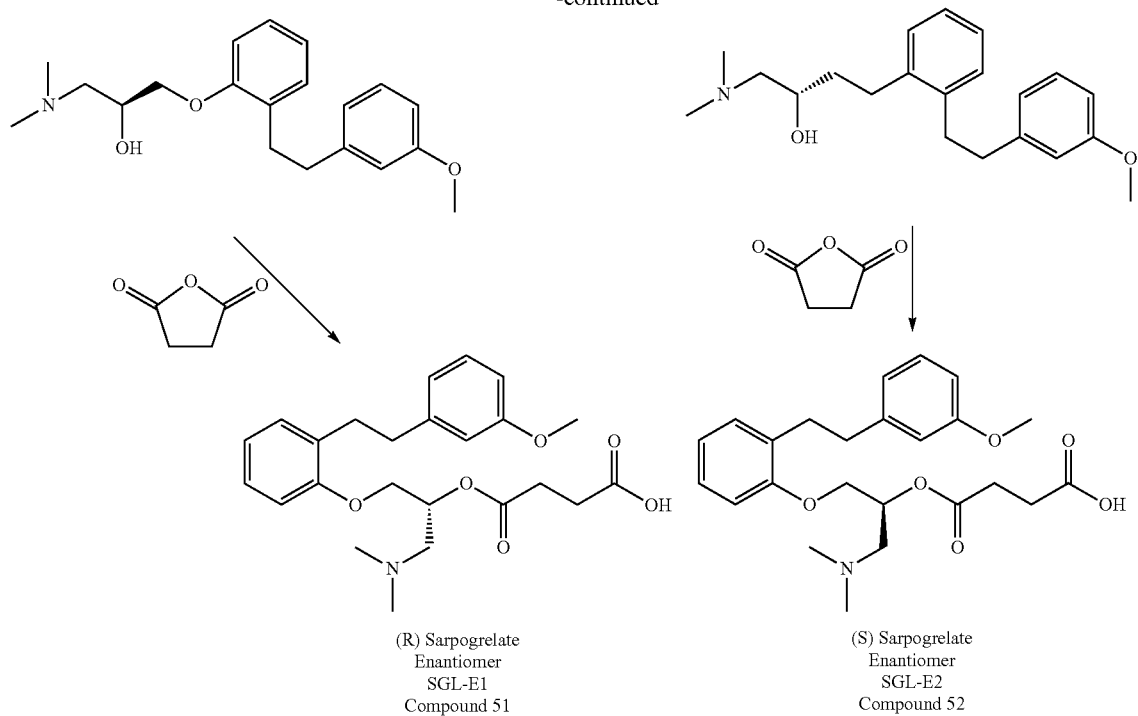

(R) Sarpogrelate
Enantiomer
SGL-E1
Compound 51

(S) Sarpogrelate
Enantiomer
SGL-E2
Compound 52

Enantiomerically pure sarpogrelate can be prepared starting from dimethylamino-propanediol by forming a phenol ether at the primary position on the selectively esterified diol with succinic acid. The sequence of the reactions can be varied by changing order. Enantiomerically pure sarpogrelate can be prepared starting from dimethylamino-propanediol by forming a phenol ether at the primary position selectively and then esterification at the secondary hydroxyl with succinic acid (Scheme X).

Scheme IX

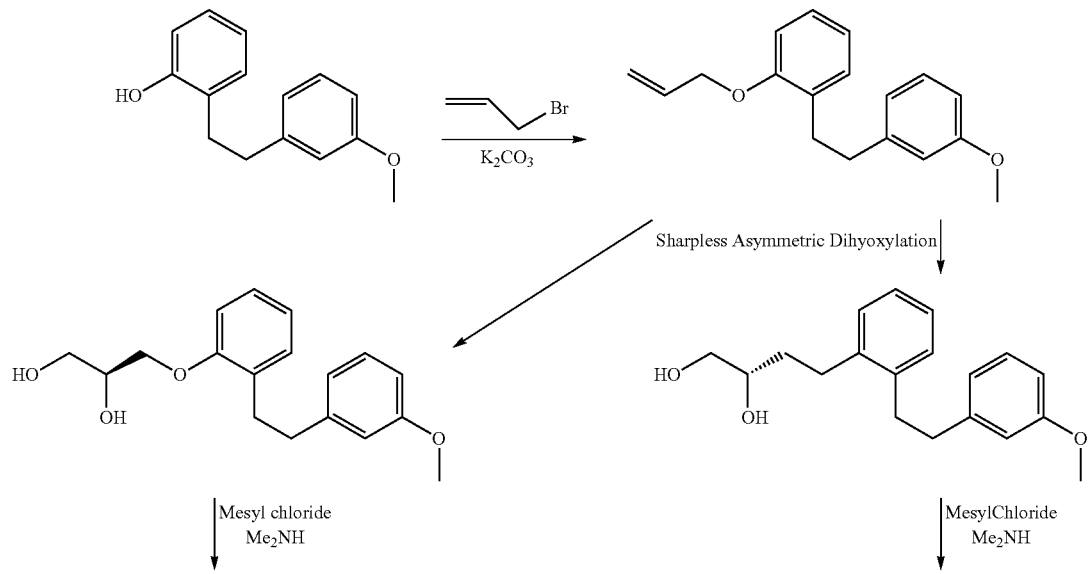

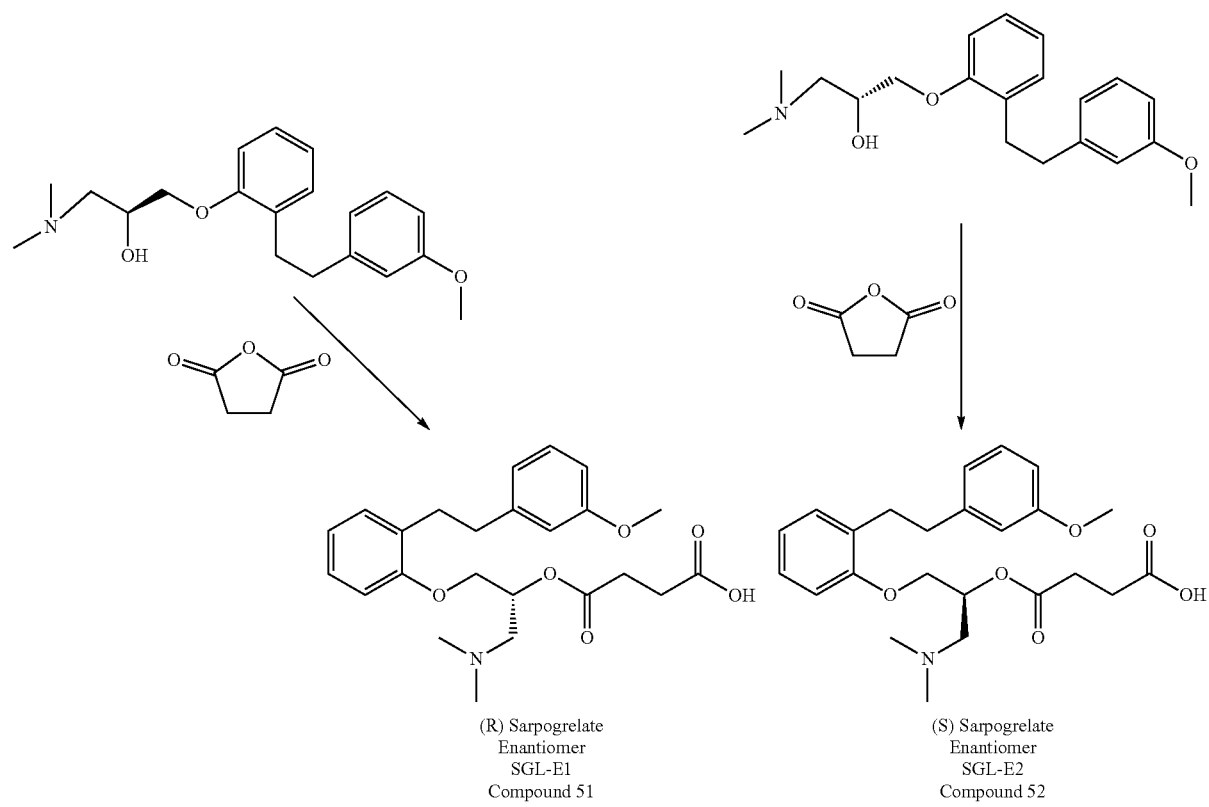
Scheme Xa
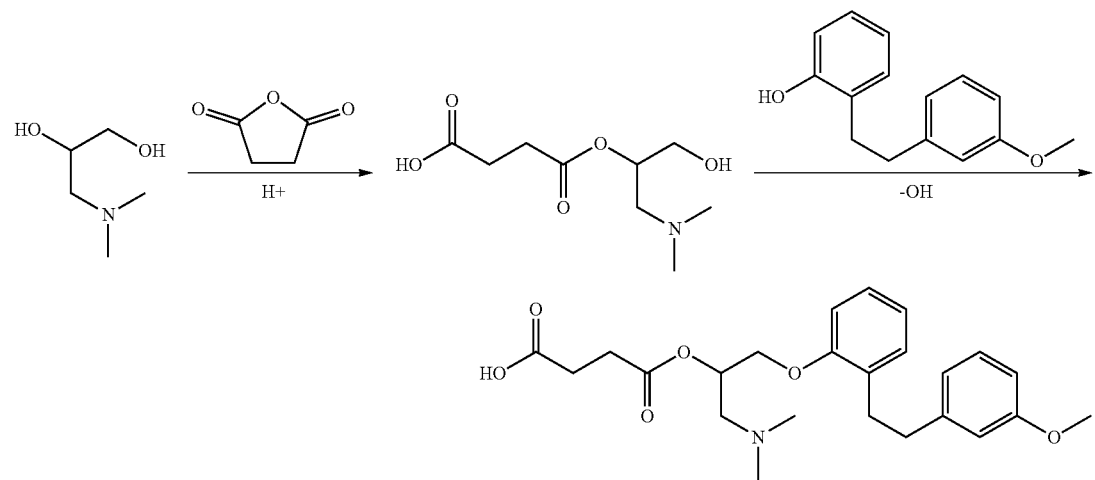
Scheme Xb
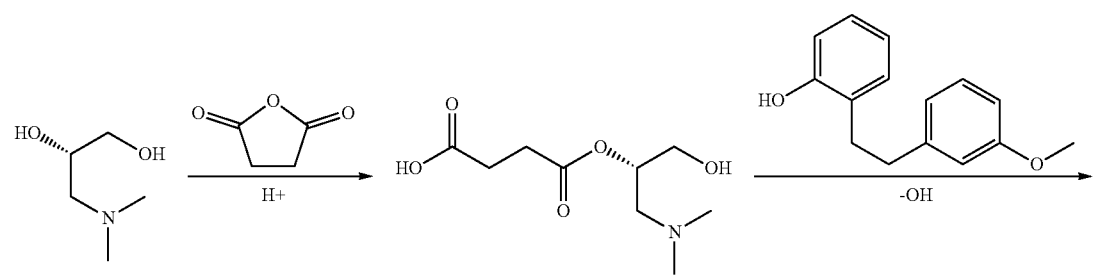

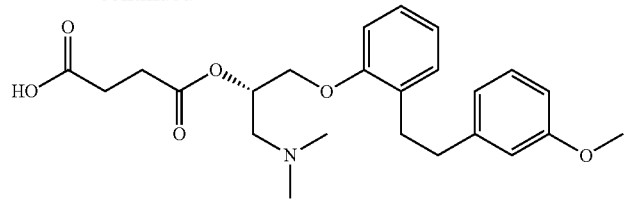

Scheme Xc

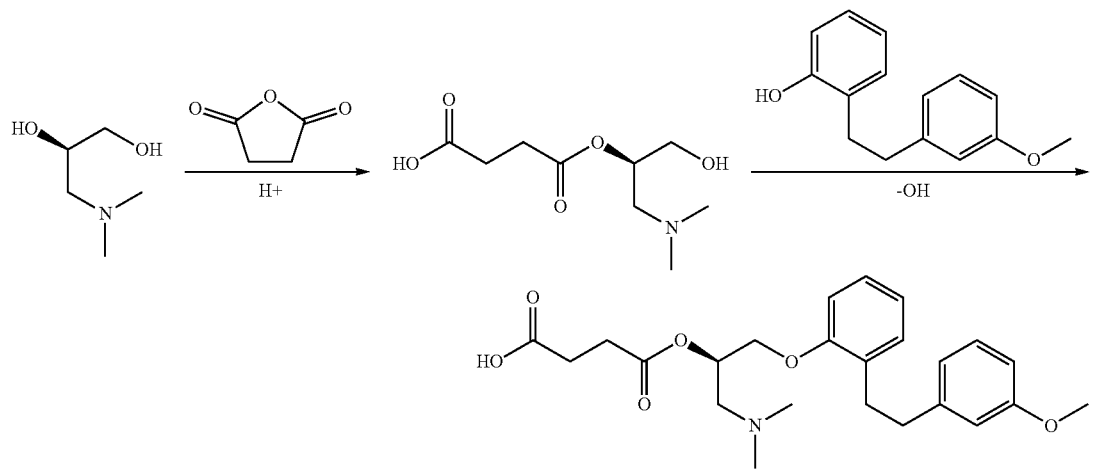

To prepare compounds 197-205, in all the above schemes, 2-(3-methoxyphenethyl)phenol is replaced with an appropriate commercially available phenol derivative such as 4'-methoxy-[1,1'-biphenyl]-4-ol, 3'-methoxy-[1,1'-biphenyl]-4-ol, 2'-methoxy-[1,1'-biphenyl]-4-ol, 4'-methoxy-[1,1'-biphenyl]-3-ol, 4'-methoxy-[1,1'-biphenyl]-2-ol, 3'-methoxy-[1,1'-biphenyl]-3-ol, 3'-methoxy-[1,1'-biphenyl]-2-ol, 2'-methoxy-[1,1'-biphenyl]-3-ol, and 2'-methoxy-[1,1'-biphenyl]-2-ol.

Similarly, to prepare compounds 191-196 and homologs, in all the above schemes, 2-(3-methoxyphenethyl)phenol is replaced with an appropriate commercially available phenol derivative such as 2-(3-methoxybenzyl)phenol, 2-(3-(3-methoxyphenyl)propyl)phenol, 2-(4-(3-methoxyphenyl)butyl)phenol, 2-(5-(3-methoxyphenyl)pentyl)phenol, 2-(6-(3-methoxyphenyl)hexyl)phenol, 2-(7-(3-methoxyphenyl)heptyl)phenol, 2-(8-(3-methoxyphenyl)octyl)phenol, 2-(9-(3-methoxyphenyl)nonyl)phenol, and 2-(10-(3-methoxyphenyl)decyl)phenol.

Chiral Separation

Chiral agents that can be used in the enantiomeric separation and diastereomeric separation of the compounds of the invention include, but not limited to, the following:

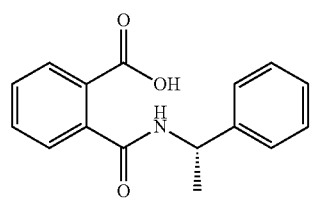

-continued

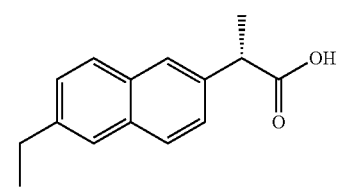

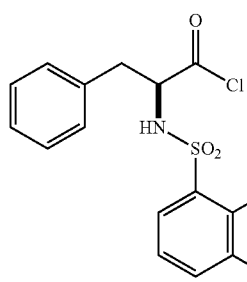

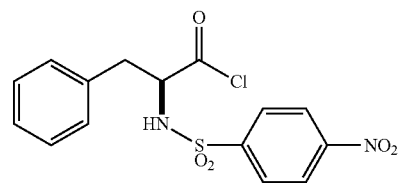

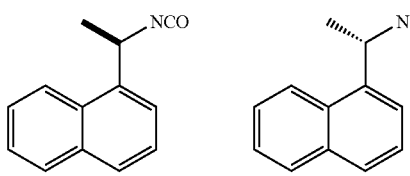

159
-continued
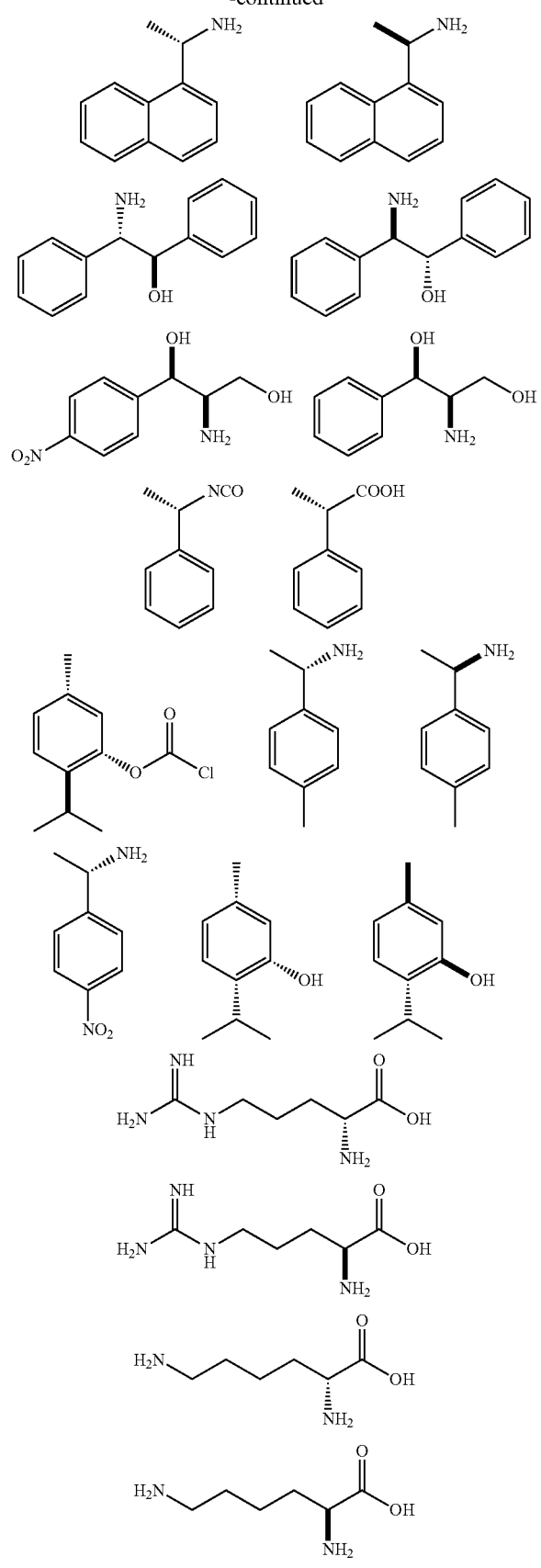
160
-continued
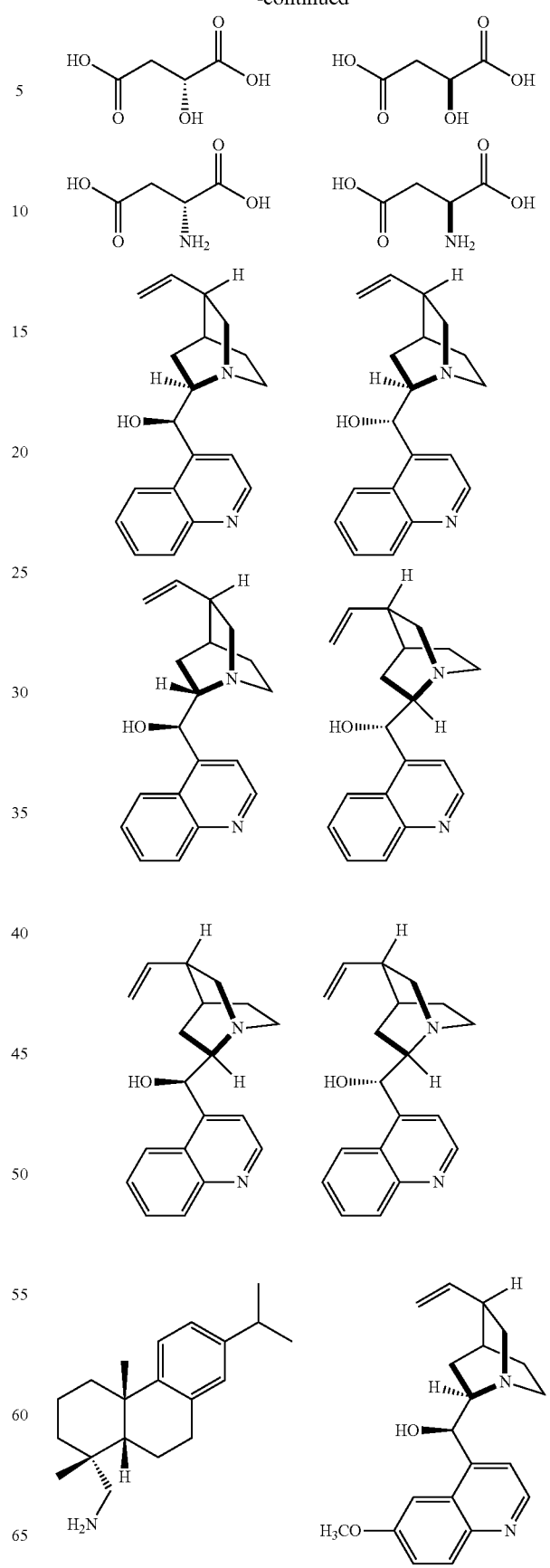

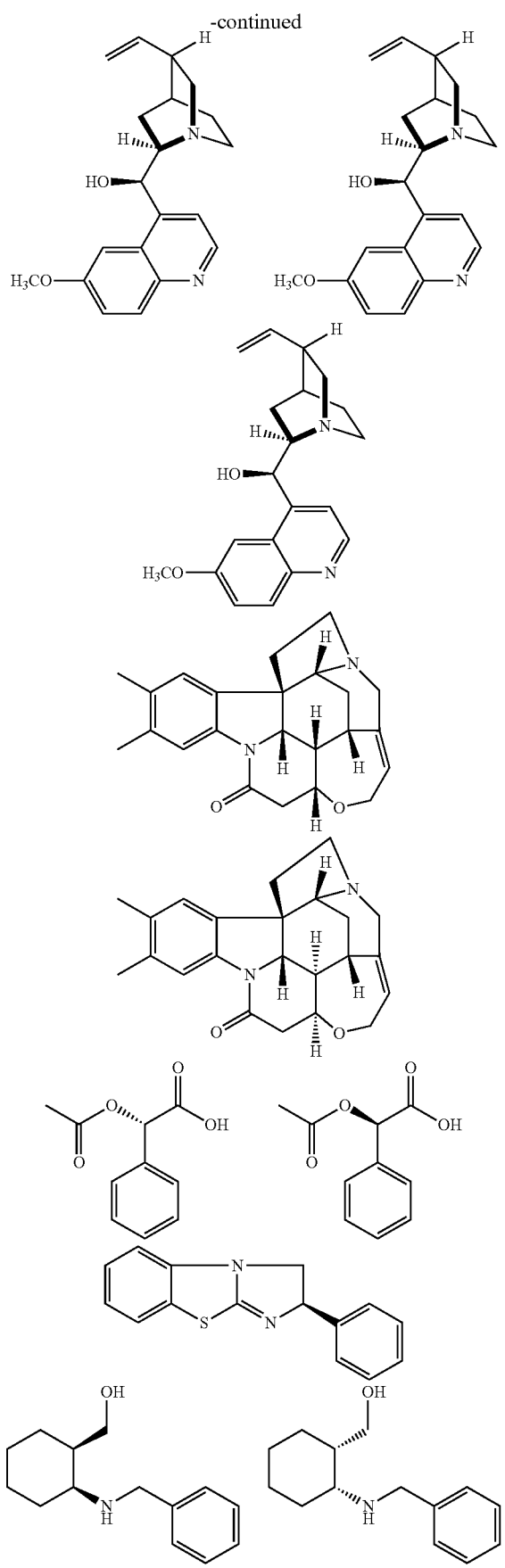
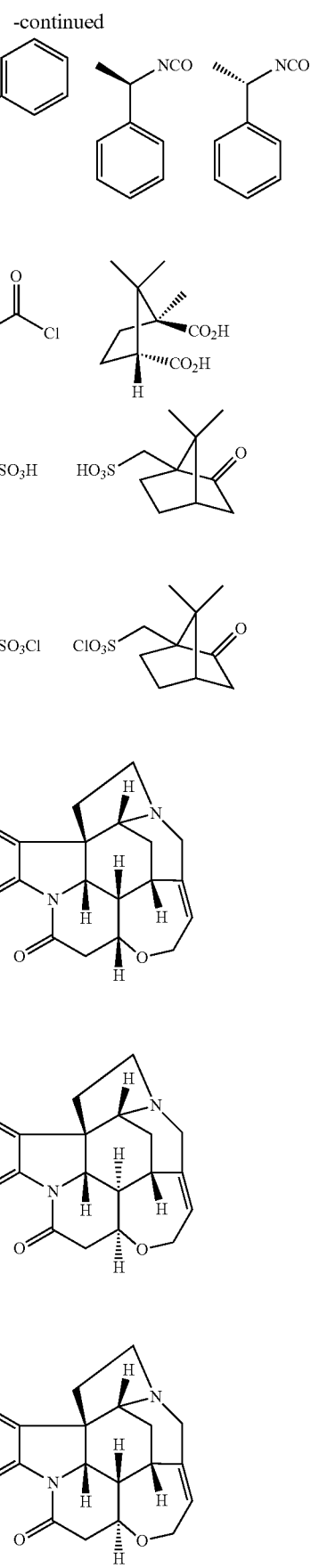

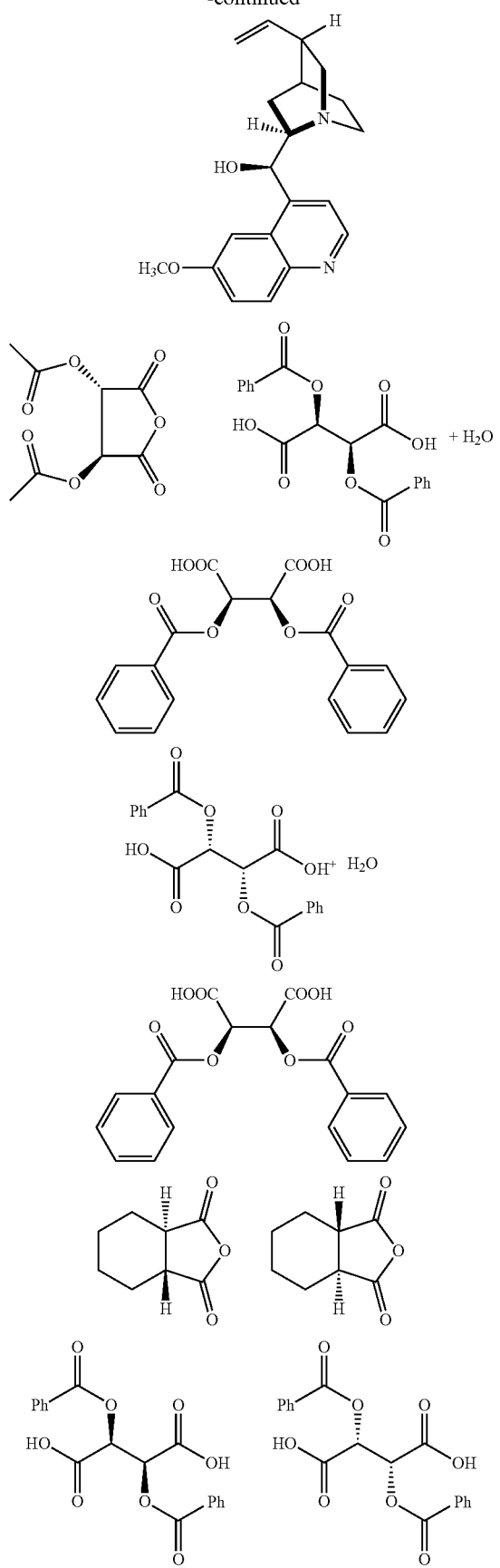
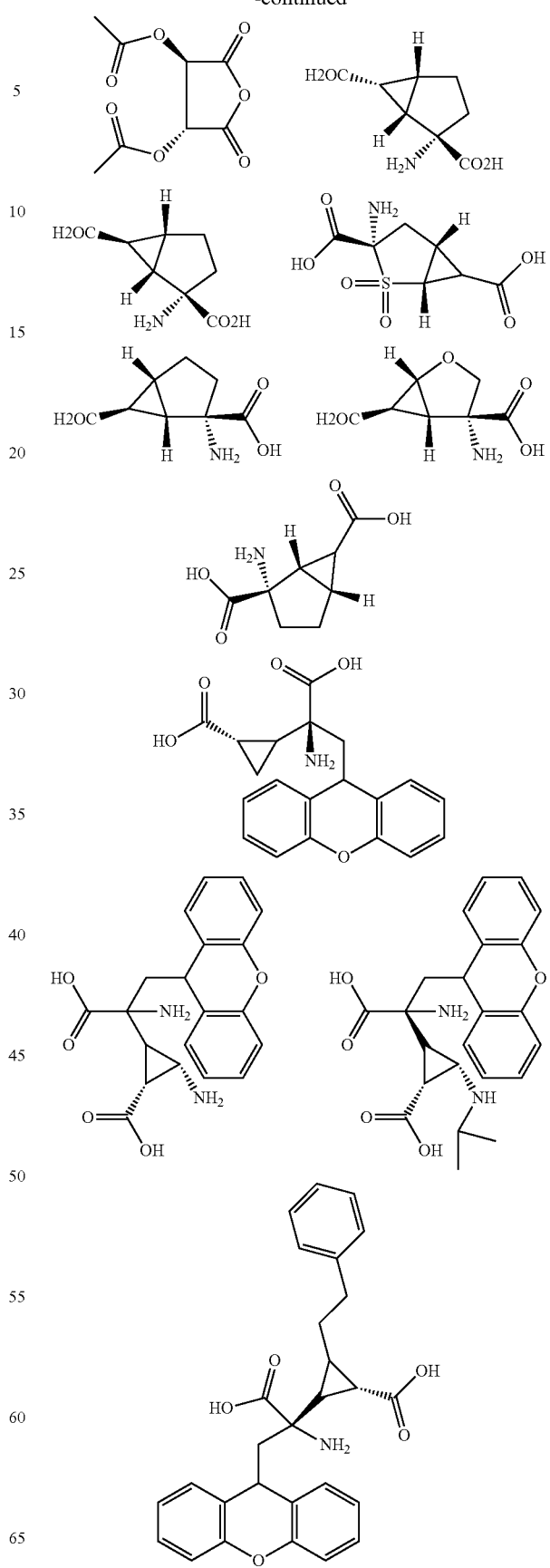

165
-continued

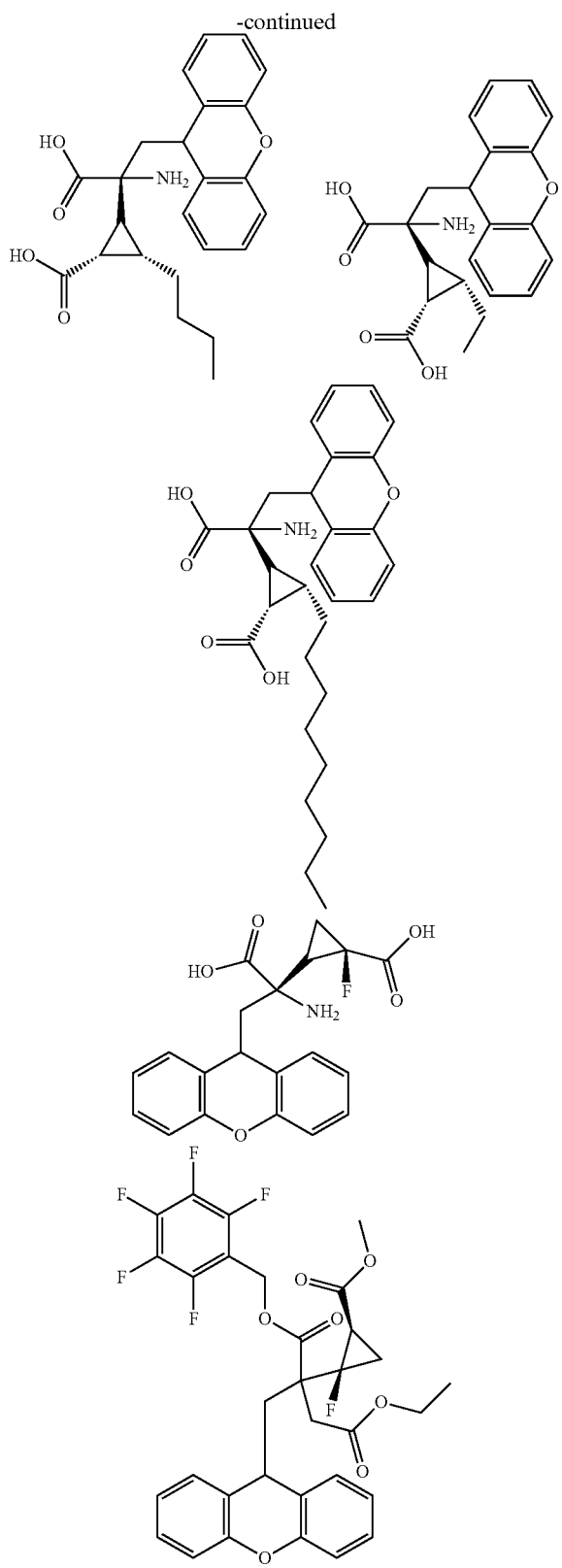

Formation of the diastereomeric compounds and salts is carried out in a suitable reaction medium. Suitable reaction media include water, methanol, ethanol, 1-propanol, 2-propanol, diethyl ether, methyl tert-butyl ether, tetrahydrofuran, acetic acid, methyl acetate, ethyl acetate, isopropyl acetate, butyl acetate, acetone, methyl ethyl ketone, methyl isobutyl ketone, acetonitrile, methylene chloride, chloroform, 1,2-dichloroethane, benzene, toluene and xylenes, and/or mixtures thereof.

Sarpodexter™ and Sarpodexamide™

Linkers that can be used in the synthesis of SARPODEXAMIDE™ derivatives in the above scheme include, but not limited to, linkers described in the literature (Simplicio et al., Prodrugs for Amines, Molecules 13, 519-547 (2008); Mahato et al., Prodrugs for Improving Tumor Targetability and Efficiency, Adv Drug Deliv Rev. 63(8): 659-670 (2011 Jul. 18); Jornada et al., The Prodrug Approach: A Successful Tool for Improving Drug Solubility, Molecules 21, 42 (2016); Jain et al., Mutual prodrugs containing bio-cleavable and drug releasable disulfide linkers, Bioorganic Chemistry 49C:40-48 (July 2013); US20130053301, WO2011089216A1; WO2006136586 A2; U.S. Pat. No. 7,932,294; US 20060046967 A1; U.S. Pat. Nos. 8,357,723; 8,349,901; 8,354,455; 9,550,734; US20160220694; US20160002167; US20150328323; U.S. Pat. No. 9,090,563; US20140058063; US20130158271; U.S. Pat. No. 8,288,557; US20110274695; WO1998043961; incorporated herein by reference) using known amidation and acylation techniques (Synthesis of amides, Organic Chemistry Portal, Making Amides from Acid Anhydrides, Making Amides from Carboxylic Acids, Making Amides from Acyl Chlorides, Making Amides from Nitriles—all available at Chemistry LibreTexts web site; MAKING AMIDES, available at Chemguide.co.uk; WO1998043961; each incorporated in entirety by reference herein).

Esterification: Esters are derived from carboxylic acids. A carboxylic acid contains the —COOH group, and in an ester the hydrogen in this group is replaced by a hydrocarbon group R' such as an alkyl, cycloalkyl, an aryl, and a hetero-aryl group. Esters are produced when carboxylic acids are heated with alcohols in the presence of an acid catalyst. The catalyst is an acid, usually concentrated sulfuric acid. Dry hydrogen chloride gas can be used in some cases. TsOH (tosic acid) is also often used.

The esterification reaction is both slow and reversible. The equation for the reaction between an acid RCOOH and an alcohol R'OH (where R and R' can be the same or different) is:

Scheme XI

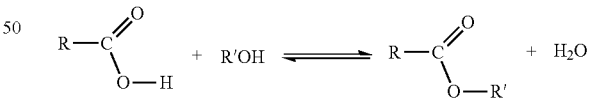

The alcohol is generally used as solvent so is present in large excess (ESTERIFICATION available at websites: Chem Portal, organic chemistry org, master organic chemistry, vigo schools, and science jrank org; WO1998043961; incorporated herein by reference).

Preparation of Sarpodexter™

In another embodiment of preparation of the compositions of the application, the diastereomerically pure SARPODEXTER can be obtained by reacting the racemic sarpogrelate with optically pure dextrorphan (DO-H₃, compound 151) under mild esterification conditions to obtain a mixture of diastereomeric esters, compounds 165-166, which can be separated by crystallization and chromatographic techniques mentioned above and the techniques described in this specification to obtain diastereomerically pure SARPODEXTERs 165 and 166.

Scheme XII

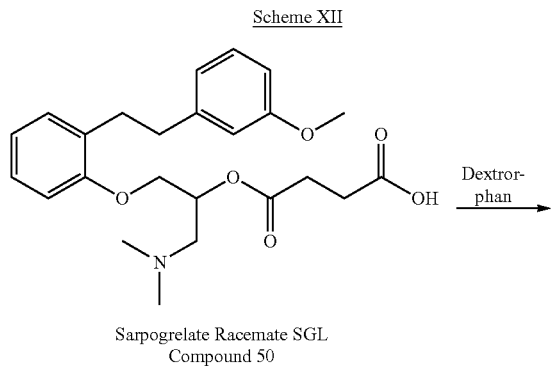

Sarpogrelate Racemate SGL
Compound 50

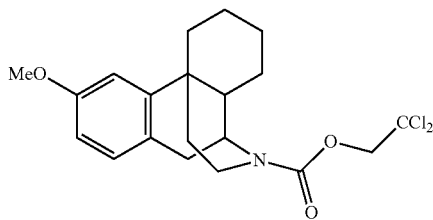

The trichloroethoxycarbonyl above can be converted to N-desmethyl dextromethorphan by heating to reflux in presence of powdered zinc in glacial acetic acid.

The N-desmethyl dextromethorphan obtained as described above or purchased (CAS Number: 125-71-3) can be treated with trifluoromethansulfonic anhydride and pyridine at room temperature (Liebigs Ann. Chem. 1986, 336, and WO1998043961, incorporated herein in its entirety).

Optically Pure Sarpodexamide

Scheme XIII

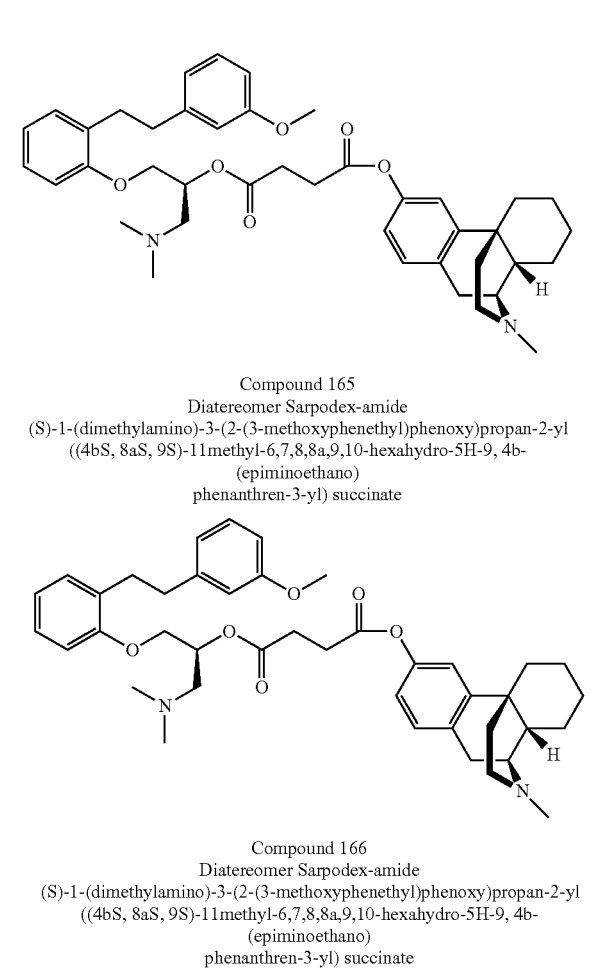

Preparation of Sarpodexamide™ Derivatives

A compound of formula I or Sarpodexamide™ derivatives can be obtained by reacting dextromethorphan either as a single isomer or a mixture thereof with 2,2,2-trichloroethyl chloroformate in refluxing toluene thus obtaining the N-demethylated compound.

As shown in Scheme XIII, amides (S)-1-(dimethylamino)-3-(2-(3-methoxyphenethyl) phenoxy) propan-2-yl 4-((4bS,8aS,9S)-3-methoxy-6,7,8,8a,9,10-hexahydro-5H-9,4b-(epiminoethano) phenanthren-11-yl)-4-oxobutanoate (Compound 167) and (R)-1-(dimethylamino)-3-(2-(3-methoxyphenethyl)phenoxy)propan-2-yl 4-((4bS,8aS,9S)-3-methoxy-6,7,8,8a,9,10-hexahydro-5H-9,4b-(epiminoethano)phenanthren-11-yl)-4-oxobutanoate (compound 168) can be obtained from sarpogrelate by amidation with N-desmethyl dextromethorphan using HBTU in combination with Hünig's base in 1-2 h. Reagents such as uronium salt (1-cyano-2-ethoxy-2-oxoethylidenaminooxy) dimethylamino morpholino carbenium hexafluorophosphate (COMU), ethyl 2-cyano-2-(2-nitrobenzenesulfonyloxyimino) acetate (o-NosylOXY), EDCI and NaHCO$_3$, B(OCH$_2$CF$_3$)$_3$, trimethylaluminium, Lanthanum trifluoromethanesulfonate, ZrOCl$_2$.8H$_2$O, methanesulfonyl chloride and N-methylimidazole, N,N'-carbonyldiimidazole (CDI), etc. can be used.

Optically Pure Sarpodex™ Salt

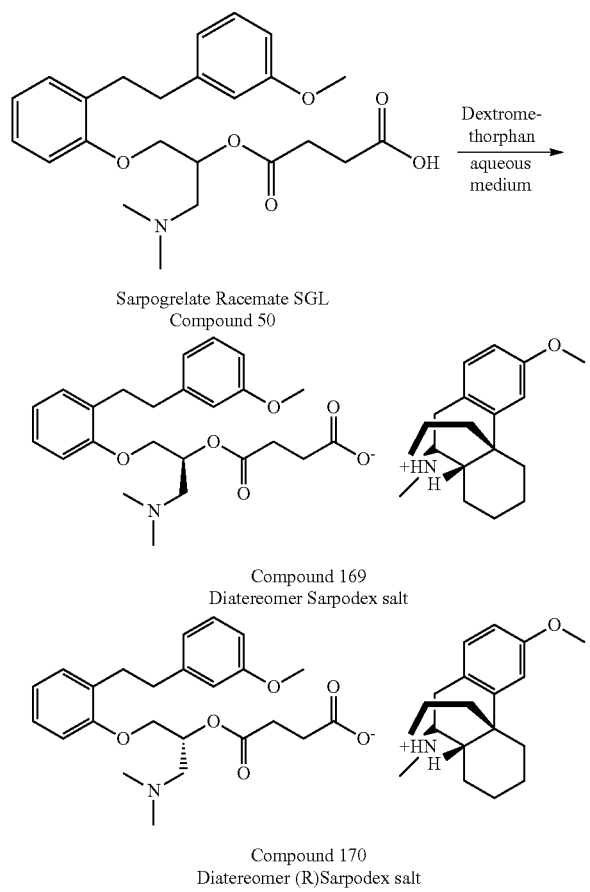

Scheme XIV

Sarpogrelate Racemate SGL
Compound 50

Compound 169
Diatereomer Sarpodex salt

Compound 170
Diatereomer (R)Sarpodex salt

Compound 50 and compound 149 form a diastereomeric salt mixture of dextromethorphan (S)-4-((1-(dimethylamino)-3-(2-(3-methoxyphenethyl)phenoxy)propan-2-yl)oxy)-4-oxobutanoate (S-SARPODEX™) salt and dextromethorphan (R)-4-((1-(dimethylamino)-3-(2-(3-methoxyphenethyl)phenoxy)propan-2-yl)oxy)-4-oxobutanoate (R-SARPODEX™) salt in chloroform or other suitable solvents such as dichloromethane, DMF, etc., which can be separated by crystallization and recrystallization in suitable solvents such DMF and/or chromatographic techniques referred to and described in this specification.

In one embodiment, provided is a process for separating the diastereomers of a compound by using an ionic liquid to increase separation efficiency. When the diastereomers are separated, for example, by a process such as liquid-liquid extraction, one or more ionic liquids may be used as the extractant.

In one embodiment, this separation process may be performed on a compound containing a mixture of at least one pair of diastereomers, and the diastereomers may be separated by contacting the mixture with at least one ionic liquid in which one of the diastereomers is soluble to a greater extent than the other diastereomer, and separating the lower-solubility diastereomer from the mixture. The inventions disclosed herein thus include processes for the separation of diastereomers, the use of such processes, and the products obtained and obtainable by such processes.

In another embodiment, this separation process may be performed on a compound such as a diastereomeric mixture of SARPODEX™ salt wherein, the diastereomers are separated by contacting the mixture with at least one ionic liquid in which one of the diastereomers is soluble to a greater extent than the other diastereomer, and separating the lower-solubility diastereomer from the mixture.

In yet another embodiment, there is provided a process for separating the erythro or threo diastereomers of SARPODEX™ from a mixture comprising both diastereomers by liquid-liquid extraction using at least one ionic liquid as an extractive solvent.

Another embodiment is a process for performing an industrial operation selected from the group consisting of a calibration operation, a cleaning operation, a rinsing operation, a drying operation, a particulate removal operation, a solvent operation, a dispersion operation, a heat transfer operation, and an insulating operation, comprising contacting a mixture comprising a pair of diastereomers of SARPODEX™ with at least one ionic liquid in which one of the diastereomers is soluble to a greater extent than the other diastereomer, separating the lower-solubility diastereomer from the mixture, and employing the separated diastereomer in the operation.

Another embodiment is a process for separating one diastereomer from another diastereomer in a pair of diastereomers in a compound. In such a process, an ionic liquid is used to facilitate the separation, and the diastereomers may be separated by contacting the mixture with at least one ionic liquid in which one of the diastereomers is soluble to a greater extent than the other diastereomer, and separating the lower-solubility diastereomer from the mixture.

The term "ionic liquid" is defined as an organic salt that is fluid at or below about 100° C.

"Liquid-liquid extraction" is a process for separating components in solution by their distribution between two immiscible liquid phases. Liquid-liquid extraction involves the transfer of mass from one liquid phase into a second immiscible liquid phase, and is carried out using an extractant or solvent.

Components in a liquid mixture can be separated by a process such as liquid-liquid extraction using a single equilibrium (or theoretical) stage, or using multiple stages. An equilibrium, or theoretical, stage is a device that allows intimate mixing of a feed with an immiscible liquid such that concentrations approach equilibrium, followed by physical separation of the two immiscible liquid phases. A single stage device can be a separatory funnel, or an agitated vessel, which allows for intimate mixing of the feed with the immiscible extractant. Following intimate mixing, one or both of the liquid phases can be recovered, for example, by decantation.

Multiple stage devices for liquid separation can be cross-current or countercurrent devices. In a multiple stage device, the feed enters a first equilibrium stage and is contacted with an extractant. The two liquid phases are mixed, with droplets of one phase suspended in the second phase, and then the two phases are separated, and SARPODEX™ from the first stage is contacted with additional extractant, and the separation process is repeated. The process of (1) contacting SARPODEX™ with extractant, (2) allowing for equilibrium concentrations to be approached, and (3) separating the liquid phases is repeated until the desired purity of the component of interest is achieved. The number of equilibrium stages will depend on the desired purity, as well as the solubility of the components in the extractant and the flow rates of the feed and extractant.

In a crosscurrent system (or device), the feed is initially contacted with extractant in a first equilibrium stage. SARPODEX™ from this stage then cascades down through one or more additional stages. At each stage, SARPODEX™ is contacted with fresh extractant, and further purification of the desired component in SARPODEX™ is achieved. An example of a crosscurrent system is shown in FIG., where the threo isomer of SARPODEX™ is purified using the ionic liquid 1-butyl-3-methylimidazolium tetrafluoroborate ([bmim][$BF_4$] as the extractant.

In a countercurrent system or device, the extractant enters at the stage farthest from the feed, and the two phases are passed through and across each other, coming from the two different (e.g. opposite) directions. FIG. depicts the countercurrent separation of the threo and erythro isomers of SARPODEX™ from a feed thereof.

Equipment used for liquid-liquid extraction can be classified as "stagewise" or "continuous (differential) contact" equipment. Stagewise equipment is also referred to as "mixer-settlers". Mixing the liquids occurs by contacting the feed with the extractant, and the resultant dispersion is settled as the two phases separate. Mixing can occur with the use of baffles or impellers, and the separation process may be carried out in batch fashion or with continuous flow. Settlers can be simple gravity settlers, such as decanters, or can be cyclones or centrifuges, which enhance the rate of settling.

Continuous contact equipment is typically arranged for multistage countercurrent contact of the immiscible liquids, without repeated separation of the liquids from each other between stages. Instead, the liquids remain in continuous contact throughout their passage through the equipment. Countercurrent flow is maintained by the difference in densities of the liquids and either the force of gravity (vertical towers) or centrifugal force (centrifugal extractors). Gravity-operated extractors can be classified as spray towers, packed towers or perforated-plate (sieve-plate) towers. Gravity-operated towers also include towers with rotating stirrers and pulsed towers as is known in the art.

When the diastereomers of a compound such as SARPODEX™, and in particular the threo and erythro isomers of 2,3-dihydrodecafluoropentane, are separated by a process such as liquid-liquid extraction, any of the equipment described above can be used to perform the separation. In one preferred embodiment, the separation is carried out using a vertical tower with perforated plates. After separation of the phase containing the lower-solubility diastereomer from the phase containing the extractant and the higher-solubility diastereomer, the higher solubility diastereomer may be separated from the extractant by a process such as distillation.

The transfer of mass from one liquid phase into a separate immiscible phase by liquid-liquid extraction, and equipment for use therein (Robbins and Cusack, "Liquid-Liquid Extraction Operations and Equipment" in Perry's Chemical Engineers' Handbook, 7.sup.th Ed., (McGraw-Hill, 1997, Section 15), incorporated by reference). Known liquid-liquid extraction processes that operate on principles that are the same as or similar to those applicable to the separations described herein include the recovery of acetic acid from water using ethyl ether or ethyl acetate as the extractant (Brown, Chem. Engr. Prog. (1963) 59:65), and the recovery of phenolics from water with methyl isobutyl ketone as the extractant (Scheibel, "Liquid-Liquid Extraction," Perry and Weissburg (eds), Separation and Purification, $3^{rd}$ Ed. (1978) Chapter 3, John Wiley & Sons, Inc., Hoboken, N.J.), incorporated by reference).

The dielectrical constant of the solvent (if solvent is used at the resolutions) changes the formation, composition and enantiomer recognition of the crystals (Sakai et al., Tetrahedron: Asymmetry, 14, 3716 (2003), incorporated by reference). The composition of crystalline diastereoisomers is also influenced by the pH of the reaction mixture (Fogassy et al., J. Chem. Res., S 11, 346 (1981); Fogassy et al., J. Chem. Soc. Perkin Trans. 2. (1988), incorporated by reference). The purity (de) of the diastereoisomer can be improved using a mixture of structurally related resolving agents. It is often referred as "Dutch resolution" in the literature (Kellogg et al., Synthesis, 1626 (2003), incorporated by reference). If the diastereoisomeric salt cannot be separated by fractionated precipitation, it is feasible to get its crystalline solvate by fractionated precipitation from a solvate forming solution (Schindler et al., Chirality, 19, 239 (2007), incorporated by reference). When the solvent, unsuitable for separation of the diastereoisomers, contains structurally partly similar compounds to the solvate forming solution, the separation of enantiomers became feasiable by fractionated precipitation of the diastereoisomeric salt (Pilovics et al., Separation of the Mixtures of Chiral Compounds by Crystallization, Advances in Crystallization Processes, pp 1-37 (2012); U.S. Pat. No. 214,720 A; Chem. Abs. 124, 117097 (1995); U.S. Pat. No. 2,133,894 A; Chem. Abs. 139, 90595 (2001), incorporated in entirety by reference).

At the crystallization of melts of racemate forming enantiomeric mixtures the eutectic composition usually determinates the composition of the crystallized mixture and the oily residue. That eutectic composition can be known from the binary melting point phase diagram. When the initial isomeric composition (ee0) is higher than the eutectic composition, the pure optical isomer can be crystallized.

An ionic liquid, or a mixture of two or more thereof, may be used in a process hereof to separate the diastereomers of a compound. Ionic liquids are, quite simply, liquids that are comprised entirely of ions. When, for example, the diastereomers of SARPODEX™ are separated by a process such as liquid-liquid extraction, the extractant used may be an ionic liquid or a mixture of two or more ionic liquids. Ionic liquids are organic compounds that are liquid at room temperature (approximately 25° C.). They differ from most salts in that they have very low melting points, and they generally tend to be liquid over a wide temperature range. They also generally tend to not be soluble in non-polar hydrocarbons; to be immiscible with water (depending on the anion); and to be highly ionizing (but have a low dielectric strength). Ionic liquids have essentially no vapor pressure, most are air and water stable, and they can either be neutral, acidic or basic.

A cation or anion of an ionic liquid useful herein can in principle be any cation or anion such that the cation and anion together form an organic salt that is liquid at or below about 100° C. The properties of an ionic liquid can, however, be tailored by varying the identity of the cation and/or anion. For example, the acidity of an ionic liquid can be adjusted by varying the molar equivalents and type and combinations of Lewis acids used.

Many ionic liquids are formed by reacting a nitrogen-containing heterocyclic ring, preferably a heteroaromatic ring, with an alkylating agent (for example, an alkyl halide) to form a quaternary ammonium salt, and performing ion exchange or other suitable reactions with various Lewis acids or their conjugate bases to form the ionic liquid. Examples of suitable heteroaromatic rings include substituted pyridines, imidazole, substituted imidazole, pyrrole and substituted pyrroles. These rings can be alkylated with virtually any straight, branched or cyclic $C_{1-20}$ alkyl group, but preferably, the alkyl groups are $C_{1-16}$ groups, since groups larger than this may produce low melting solids rather than ionic liquids. Various triarylphosphines, thioethers and cyclic and non-cyclic quaternary ammonium salts may also been used for this purpose. Counter ions that may be used include chloroaluminate, tetrachloroaluminate (III), bromoaluminate, gallium chloride, tetrafluoroborate, tetrachloroborate, hexafluorophosphate, nitrate, trifluoromethane sulfonate, methylsulfonate, p-toluenesulfonate, hexafluoroantimonate, hexafluoroarsenate, tetrachloroaluminate, tetrabromoaluminate, perchlorate, hydroxide anion, copper dichloride anion, iron trichloride anion, zinc trichloride anion, as well as various lanthanum, potassium, lithium, nickel, cobalt, manganese, and other metal-containing anions.

Ionic liquids may also be synthesized by salt metathesis, by an acid-base neutralization reaction or by quaternizing a selected nitrogen-containing compound; or they may be obtained commercially from several companies such as Merck (Darmstadt, Germany) or BASF (Mount Olive, N.J.).

In one embodiment, a library of ionic liquids may be prepared, for example, by preparing various alkyl derivatives of a particular cation (such as the quaternary ammonium cation), and varying the associated anions (US 20090131728 A1, incorporated in entirety by reference). In another embodiment, the diastereomers of the invention can be separated efficiently by cation exchange with mixed-mode sorbent in the solid phase extraction (SPE) procedure.

In one embodiment, diastereomers can be separated by extractive distillation, wherein an auxiliary which changes the partial pressure of the various diastereomers to be separated to a different degree allowing easier separation of the diastereomers by distillation in a good yield. Separation can be accomplished using fractionating columns, and preferably under reduced pressure of about $10^{-3}$ bar to about 1 bar (U.S. Pat. No. 4,874,473 A, US 20070225505 A1, incorporated in entirety by reference).

In one embodiment, reversed (RP-HPLC) and normal phase chromatographic (NP-HPLC) separations can be used to separate the diastereomers of the invention Columns that can be used in the separation of enantiomers can be Primesep C, NUCLEOSIL, cellulose based chiral HPLC columns, SHISEIDO Chiral CD-Ph, etc. (Fekete et al., Comparative Study Separation of Diastereomers by HPLC, Chromatographia, 57, No. ¾ (2003 February), U.S. Pat. No. 7,119,211 B2, incorporated in entireity by reference).

Pharmaceutical Formulations

The compositions of this invention can be prepared A compound of formula I or SARPODEX™ is added to, and dissolved in, a suitable solvent. The solution, thus obtained, is added to the complex magnesium aluminum silicate to form a paste-like mass. While the foregoing steps are carried out at about room temperature, elevated temperatures can be employed if desired. Subsequently, sodium chloride and sodium saccharin are added to, and uniformly distributed throughout, the paste. Edible coloring and flavoring materials can be incorporated into the system at any stage of the ipreparative method. In another embodiment, soluble ingredients are added to the A compound of formula I or SARPODEX™ solution, which is prepared in the first step. The paste which is thus obtained can be incorporated readily into a conventional hard candy-forming mass, which mass, in turn, can be worked up, by conventional procedures, into attractive, pleasant-tasting lozenges each containing therapeutically effective quantities of A compound of formula I or SARPODEX™ uniformly distributed throughout.

Variations in the preparative methods presented here are within the scope of the present invention. For example, in producing the compositions of the invention, one can mix (R,S) compound of formula I or SARPODEX™, R- or S-compound of formula I or SARPODEX™ and the complex magnesium aluminum silicate and subsequently add a suitable solvent thereto to form a paste therewith. Sodium chloride and sodium saccharin can be added to the dextromethorphan-complex magnesium aluminum silicate mixture prior to forming the mixture into a paste. In the alternative, sodium chloride and sodium saccharin can be added to the paste. Furthermore, suitable flavoring agents and coloring agents can be added either to the dry mixture or to the paste. In carrying out this invention, any medicinally acceptable organic solvent which is suitable for pharmaceutical use and in which A compound of formula I or SARPODEX™ is soluble can be employed. Thus, for example, organic solvents, such as propylene glycol, glycerine, 1,3-butylene glycol, benzyl alcohol, etc., can be used. In an embodiment of compositions of the invention, benzyl alcohol is employed as the solvent for the SAPRODEX™.

Edible coloring agents and edible flavoring agents can be used in preparing the present compositions. Flavoring agents which are suitable for use include, for example, licorice, ginger, natural fruit extracts, etc. As the coloring agent one can use any color which is suitable for use in foods and drugs. The quantity of coloring and the quantity of flavoring agents used in formulating the composition of this invention is variable.

In an embodiment, the formulation contains about 0.3 g to about 1.5 g, about 1.0 g, of thickener; about 1 g to about 10 g, about 2.5 g, of 1,2-propylen glycol as a dissolving agent; about 0.12 g to about 0.19 g, or 0.15 g, of at least one paraben preservative such as methyl paraben; about 0.05 g to about 0.2 g, or about 0.1 g, of sorbic acid; about 30 g to about 60 g, or 40 g of a sugar alcohol solution; about 0.05 to about 0.2 g, or 0.1 g of an artificial sweetener; A compound of formula I or SARPODEX™-resin complex in an amount to yield a desired strength of about 2.10 g (the amount of a 1:6 complex needed to deliver equivalent to 60 mg of A compound of formula I or SARPODEX™ in a 20 ml adult 12 hour dose); and sufficient water to bring the volume up to 100 ml.

In another embodiment, suitable thickeners include: tragacanth; bentonite; acacia and lower alkyl ethers of cellulose (including the hydroxy and carboxy derivatives of the cellulose ethers). Exemplary paraben preservatives are C1-C4 alkyl parabens namely methyl, ethyl, propyl, and butyl parabens. In one embodiment, both methyl and propyl paraben are present in the formulation in a ratio of methyl paraben to propyl paraben of from about 2.5:1 to about 7.5:1. In another embodiment the methyl and propyl paraben ratio is 4:1.

In one embodiment, the artificial sweetener is a form of saccharin or aspartame. In one embodiment, saccharin is sacharin sodium. In other embodiments, equivalent sweetening amounts of other known sweetening agents such as the sugar alcohol sorbitol may be substituted therefor.

In another embodiment, the formulation comprises an amount of resinate sufficient to deliver, when administered at one dose every 12 hours, therapeutically effective amount of a compound of formula I and/or a compound of formula II, or SARPODEX™ over a period of approximately 12 hours to a patient in need of such administration.

In an embodiment, the formulation comprises an adult dose of 20 ml contains approximately 420 mg of resinate, to deliver equivalent to 60 mg of A compound of formula I or SARPODEX™ when the drug to resin ratio is 1:6 and 2.10 g of resinate are present per 100 ml of formulation. The dosage can be altered analogously to that known for the administration of dextromethorphan which has not been complexed with resin, i.e. the typical 15 mg-30 mg/dose of dextromethorphan hydrobromide 1 to 4 times daily, becomes S-20 ml once to twice daily.

In another embodiment, the formulation comprises the nontoxic substances that block the NMDA receptor in accordance with this invention are dextromethorphan ((+)-3-hydroxy-N-methylmorphinan), a compound of formula I or SARPODEX™ or derivatives thereof, and Saprodexter™, mixtures and pharmaceutically acceptable salts thereof.

In another embodiment, the formulation comprises substances that block the NMDA receptor include amantadine (1-aminoadamantine), memantine (3,5 dimethylaminoadamantone), pyrroloquinoline quinone and cis-4-(phosphonomethyl)-2-piperidinecarboxylic acid, mixtures and pharmaceutically acceptable salts thereof. Of the NMDA receptor antagonists, a compound of formula I or SARPODEX™ or pharmaceutically acceptable salts thereof. (U.S. Pat. No. 5,891,885, incorporated by reference in its entirety).

In another embodiment, the therapeutic composition comprises at least one other pharmacologically active substance, e.g., caffeine (a stimulant), an antiemetic drug such as metoclopramide, domperidone, belladonna alkaloids and phenothiazines such as chlorpromazine, prochlorperazine, and promethazine, a nonnarcotic analgesic, e.g., acetaminophen or a nonsteroidal anti-inflammatory drug such as aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, nabumetone, naproxen, oxaprozin, phenylbutazone, piroxicam, sulindac, tolmetin, zomepirac, and the like.

Synthesis of Compounds and Compositions of the Invention

All reactions were performed under an argon atmosphere with dry solvents, unless otherwise stated. Dry chloroform ($CH_3Cl$), methylene chloride ($CH_2Cl_2$), tetrahydrofuran (THF), ethyl acetate, DMF, DMSO, methanol, ethanol, and acetonitrile ($CH_3CN$) were purchased or prepared. All commercially available reagents were purchased and used without further purification. Reactions were monitored by thin-layer chromatography (TLC) on silica gel plates (Merck TLC Silica Gel 60 F254) using UV light, PMA (an ethanolic solution of phosphomolybdic acid) or ANIS (an ethanolic solution of para-anisaldehyde) as visualizing agent. Purification of products was conducted by column chromatography through silica gel 60 (0.060-0.200 mm). NMR spectra were obtained on Bruker AVANCE III 500 MHz (Bruker Corporation, Billerica, Mass., USA) using residual undeuterated solvent or TMS (tetramethylsilane) as an internal reference. High-resolution mass spectra (HR-MS) were recorded on a JEOL JMS-700 (JEOL, Tokyo, Japan) using E1 (electron impact).

Example 1

Dextromethorphan has been synthesized from a benzylisoquinoline (with a planar structure) by Grewe's cyclization to give the corresponding morphinan, wherein the 1,2,3,4,5,6,7,8-octahydro-1-(4-methoxybenzyl)isoquinoline is converted into the N-formyl derivative, cyclized to the N-formyl normorphinan, and the formyl group reduced to an N-methyl group, to give 3-methoxy-17-methylmorphinan. Dextromethorphan is freely soluble in ethanol 96% and essentially insoluble in water. Dextromethorphan can be monohydrated hydrobromide salt or bound to an ion exchange resin based on polystyrene sulfonic acid. Dextrometorphan's specific rotation in water is +27.6° (20° C., Sodium D-line).

Example 2

Equimolar sarpogrelate (429.506 g/mol) and dextromethorphan (271.40 g/mol) were mixed in a suitable solvent, agitated and let crystallize. The compound of Formula I or sarpogrelate acid anion and dextromethorphan positive cation would form hydrogen bond to form a complex and crystallize.

Example 3

To a solution of 54.28 g of dextromethorphan in one liter of chloroform is added a solution of 85.9 g of sarpogrelate in chloroform at 70° C. The salt is precipitated from the hot solution by the addition of ethyl acetate. After cooling the salt is collected, washed with ethyl acetate and dried to yield d-3-methoxy-N-methylmorphinan 4-[1-dimethylamino-3-[2-[2-(3-methoxyphenyl) ethyl]phenoxy]propan-2-yl] oxy-4-oxobutanoate salt (A compound of formula I or SARPODEX™). A compound of formula I or SARPODEX™ is recrystallized from aqueous dimethylformamide (DMF) to yield of 135 g of the compound of formula I or SARPODEX™ diastereomeric mixture.

| EXAMPLE 4 | |
| --- | --- |
| Ingredients | Amount |
| A compound of formula I or SARPODEX ™ | 15 g |
| Glyceryl tristearate | 15 g |
| Carbon tetrachloride | 100 ml |

Glyceryl tristearate is dissolved in the warm carbon tetrachloride at 55-60° C. A compound of formula I, derivative thereof, SARPODEX™ or derivative thereof is then added and suspended in the solution. The suspension is then spray dried using an inlet temperature of 90° C. and an outlet temperature of 40° C. The resulting coated A compound of formula I or SARPODEX™ having an average particle size of from about 10 to about 200 microns is then suspended in the following aqueous vehicle.

Tragacanth, USP 10.00 g
Methylparaben, USP 1.20 g

Propylparaben, USP 0.20 g
Saccharin sodium, USP 0.30 g
Sucaryl sodium, USP 3.00 g
Sorbic acid 250.00 mL
Methyl cellulose, 15 cps 1.00 g
Imitation black currant 2.00 mL
Distilled water 1000.00 mL The parabens, saccharin sodium, sucaryl sodium and sorbic acid are dissolved in a portion of the distilled water which has been heated to 85° C. The tragacanth is then added to this solution and dispersed uniformly. The dispersion is again heated, cooled and the sorbitol solution, a solution of the methyl cellulose in water and the imitation black currant are then added with mixing to form the vehicle. The coated A compound of formula I or SARPODEX™ is then added to the above vehicle and mixed until the particles are thoroughly wetted and uniformly dispersed.

The controlled drug-release composition of the present invention is characterized by comprising 100 parts by weight of an organic polymeric material which is soluble in an organic solvent and insoluble in water; 5 to 60 parts by weight of a lipid-soluble, low molecular weight release auxiliary agent; and 1 to 70 parts by weight of a drug.

In one embodiment, the polymeric material is biodegradable or biocompatible, or both, for example, biodegradable aliphatic polyester, or an aliphatic poly(carbonate), poly(lactic acid), lactic acid-glycolic acid copolymer, poly(caprolactone), poly(hydroxybutyric acid) and the like.

In one embodiment, the release auxiliary agent is a carboxylic acid ester, a monoester or diester of glycerin. In another embodiment, the release auxiliary agent is an ester of an organic acid selected from succinic acid, citric acid, tartaric acid, malic acid or the like, or monoacetate ester or diacetate ester of glycerin.

In one embodiment, the composition may further comprise a cell adhesion material or an endothelialization promoting agent on a surface of a medical device.

In one embodiment, in invention is a drug-releasable medical device characterized by containing the compositions of the present disclosure. The drug-releasable medical device forms a layer of the composition on the surface, and contacts with a living body, or is incorporated or indwelled in a living body. The device includes a stent, a catheter, a clip, an organ replacement medical device, a capsule sensor or an artificial organ. The stent in one embodiment is used for treating coronary artery stenosis and gradually releasing the composition from the surface. The release rate is $1/10^3$ mu g/mm$^2$/h to 1 mu g/mm$^2$/h on 21 days after indwelling the stent. In addition, the stent of the present invention is characterized in that the drug to be gradually released is carried in a polymeric material coated on the surface of a metal forming the stent or in a porous stent substrate.

The polymeric material coated on the surface of the stent is amorphous. The polymeric material coated on the surface of the stent is an amorphous biodegradable polymeric material. The polymeric material is a poly(lactic acid) or a lactic acid-glycolic acid copolymer, which is biodegradable. The polymeric material further comprises a release auxiliary agent that promotes the release of a drug to be carried. The auxiliary agent that promotes the release of a drug is a tartrate ester or a malate ester, or a monoester or diester of glycerin. The surface of the metal forming the stent may be a porous body and the above-mentioned drug to be gradually released may be carried in the porous body. In one embodiment, the porous body has a pore size of 0.01 nm to 300 nm in diameter.

Example 5

Optically Pure Sarpomalate

Malic acid is a component of many of the foods that we eat daily. Although it is found as a naturally occurring organic compound in various fruits, many choose to take malic acid supplements to increase their overall health, as well as treat various maladies. Today, the acid is most commonly used as a food additive and preservative. It is a mild and relatively harmless acid when used in appropriate amounts. As a food supplement, it is generally considered beneficial for health and is present in large amounts in apple juice (Hrenchir, Five Unexpected Benefits Delivered to the Body by Malic Acid, Newsmax, page 1 (31 Mar. 2015); incorporated in entirety by reference).

Natural organic compounds having asymmetric carbon usually exist as an optically active material and exhibit physiological activity markedly different from that of enantiomers. Malic acid (0.55 mmol, 1.1 equiv.), dicyclohexylcarbodiimide (DCC, 0.55 mmol, 1.1 equiv.) and 4-dimethylaminopyridine at 0° C. are added to a stirred solution of racemate or enantiomerically pure M1 (0.50 mmol, 1.0 equiv.) in $CH_2Cl_2$ (5 mL), heated over 30 min to 25° C., stirred the mixture at 25° C. for 18 to 24 h, and diluted with $CH_2Cl_2$ (50 mL) and sat. aq. $NaHCO_3$ (30 mL). The organic layer is separated, dried ($Na_2SO_4$), filtered, and concentrated under reduced pressure. The crude residue is purified by column chromatography (silica gel, hexanes:EtOAc) to yield racemic or diasteriomerically pure sarpomalate, respectively depending upon the M1 and malic acid used (compounds 25-29). Racemic sarpomalate can be purified by crystallization and/or chiral chromatography to obtain diasteriomerically pure sarpomalate.

Example 6

Optically Pure Sarpomethionate

Methionine (0.55 mmol, 1.1 equiv.), dicyclohexylcarbodiimide (DCC, 0.55 mmol, 1.1 equiv.) and 4-dimethylaminopyridine at 0° C. are added to a stirred solution of racemate or enantiomerically pure M1 (0.50 mmol, 1.0 equiv.) in $CH_2Cl_2$ (5 mL), heated over 30 min to 25° C., stirred the mixture at 25° C. for 18 to 24 h, and diluted with $CH_2Cl_2$ (50 mL) and sat. aq. $NaHCO_3$ (30 mL). The organic layer is separated, dried ($Na_2SO_4$), filtered, and concentrated under reduced pressure. The crude residue is purified by column chromatography (silica gel, hexanes:EtOAc) to yield racemic or diasteriomerically pure sarpomethionate, respectively depending upon the M1 and methionine used (compounds 30-34). Racemic sarpomethionate can be purified by crystallization and/or chiral chromatography to obtain diasteriomerically pure sarpomethionate.

Example 7

Optically Pure Sarpophthallate

Phthallic acid (0.55 mmol, 1.1 equiv.), dicyclohexylcarbodiimide (DCC, 0.55 mmol, 1.1 equiv.) and 4-dimethylaminopyridine at 0° C. are added to a stirred solution of racemate or enantiomerically pure M1 (0.50 mmol, 1.0 equiv.) in $CH_2Cl_2$ (5 mL), heated over 30 min to 25° C., stirred the mixture at 25° C. for 18 to 24 h, and diluted with $CH_2Cl_2$ (50 mL) and sat. aq. $NaHCO_3$ (30 mL). The organic layer is separated, dried ($Na_2SO_4$), filtered, and concentrated under reduced pressure. The crude residue is purified by column chromatography (silica gel, hexanes:EtOAc) to yield racemic or optically pure sarpophthallate, respectively depending upon the M1 and phthallic acid used to yield compounds 35-37. Racemic sarpophthallate can be purified by crystallization and/or chiral chromatography to obtain diasteriomerically pure sarpomalate.

Example 8

Optically Pure Sarpomalonate

Malonic acid (0.55 mmol, 1.1 equiv.), dicyclohexylcarbodiimide (DCC, 0.55 mmol, 1.1 equiv.) and 4-dimethylaminopyridine at 0° C. are added to a stirred solution of racemate or enantiomerically pure M1 (0.50 mmol, 1.0 equiv.) in $CH_2Cl_2$ (5 mL), heated over 30 min to 25° C., stirred the mixture at 25° C. for 18 to 24 h, and diluted with $CH_2Cl_2$ (50 mL) and sat. aq. $NaHCO_3$ (30 mL). The organic layer is separated, dried ($Na_2SO_4$), filtered, and concentrated under reduced pressure. The crude residue is purified by column chromatography (silica gel, hexanes:EtOAc) to yield racemic or optically pure sarpomalonate, respectively depending upon the M1 to yield compounds 38-40. Racemic sarpomalonate can be purified by crystallization and/or chiral chromatography to obtain optically pure sarpomalonate.

Example 9

Optically Pure Sarpotyrosinate

Tyrosine (0.55 mmol, 1.1 equiv.), dicyclohexylcarbodiimide (DCC, 0.55 mmol, 1.1 equiv.) and 4-dimethylaminopyridine at 0° C. are added to a stirred solution of racemate or enantiomerically pure M1 (0.50 mmol, 1.0 equiv.) in $CH_2Cl_2$ (5 mL), heated over 30 min to 25° C., stirred the mixture at 25° C. for 18 to 24 h, and diluted with $CH_2Cl_2$ (50 mL) and sat. aq. $NaHCO_3$ (30 mL). The organic layer is separated, dried ($Na_2SO_4$), filtered, and concentrated under reduced pressure. The crude residue is purified by column chromatography (silica gel, hexanes:EtOAc) to yield racemic or optically pure sarpotyrosinate, respectively depending upon the M1 to yield compounds 41-43. Racemic sarpotyrosinate can be purified by crystallization and/or chiral chromatography to obtain optically pure sarpotyrosinate.

Example 10

Optically Pure Sarpotryptophanate

Tryptophan (0.55 mmol, 1.1 equiv.), dicyclohexylcarbodiimide (DCC, 0.55 mmol, 1.1 equiv.) and 4-dimethylaminopyridine at 0° C. are added to a stirred solution of racemate or enantiomerically pure M1 (0.50 mmol, 1.0 equiv.) in $CH_2Cl_2$ (5 mL), heated over 30 min to 25° C., stirred the mixture at 25° C. for 18 to 24 h, and diluted with $CH_2Cl_2$ (50 mL) and sat. aq. $NaHCO_3$ (30 mL). The organic layer is separated, dried ($Na_2SO_4$), filtered, and concentrated under reduced pressure. The crude residue is purified by column chromatography (silica gel, hexanes:EtOAc) to yield racemic or optically pure sarpotryptophanate, respectively depending upon the M1 to yield compounds 44-46. Racemic sarpotryptophanate can be purified by crystallization and/or chiral chromatography to obtain optically pure sarpotryptophanate.

Example 11

Optically Pure Sarpomaleate

Maleic acid (0.55 mmol, 1.1 equiv.), dicyclohexylcarbodiimide (DCC, 0.55 mmol, 1.1 equiv.) and 4-dimethylaminopyridine at 0° C. are added to a stirred solution of racemate or enantiomerically pure M1 (0.50 mmol, 1.0 equiv.) in $CH_2Cl_2$ (5 mL), heated over 30 min to 25° C., stirred the mixture at 25° C. for 18 to 24 h, and diluted with $CH_2Cl_2$ (50 mL) and sat. aq. $NaHCO_3$ (30 mL). The organic layer is separated, dried ($Na_2SO_4$), filtered, and concentrated under reduced pressure. The crude residue is purified by column chromatography (silica gel, hexanes:EtOAc) to yield racemic or optically pure sarpomaleate, respectively depending upon the M1 to yield compounds 47-49. Racemic sarpomaleate can be purified by crystallization and/or chiral chromatography to obtain optically pure sarpomaleate.

Example 12

Optically Pure Sarpogrelate (+)-1-(DIMETHYL-AMINO)-3-(2-(3-METHOXYPHENETHYL)PHENOXY)PROPAN-2-OL HYDROCHLORIDE $^1$HNMR, 400 MHz 1H-NMR (CDCl3, ppm) 11.84-11.52 (br s, 1H) 7.22-7.12 (m, 3H) 6.96-6.90 (m, 1H) 6.83 (d, J=8.1 Hz, 1H) 6.76-7.71 (m, 2H) 6.70-6.67 (m, 1H) 5.56-5.17 (br s, 1H) 4.62-4.45 (m, 1H) 4.14 (dd, J=9.2, 4.0 Hz, 1H) 3.89 (dd, J=9.2, 8.1 Hz, 1H) 3.77 (s, 3H) 2.31-3.12 (m, 2H) 2.97-2.76 (m, 10H); ESI-MS, m/z) 330 [M+H]+; NMR purity (%) 96; HPLC purity (%) 99; HPLC conditions—Column: XBridge® C18 3.5 µm, 2.1×50 mm; Mobile phase: gradient elution from 10% MeCN in 0.01% TFA to 95% MeCN in 0.01% TFA; Flow rate: 0.5 ml/min; Detection: UV 254 nm; Sample concentration: 0.5 mg/ml; Molecular formula: $C_{20}H_{28}ClNO_3$; Molecular weight: 365.9041; Melting point (° C.):124-125; Optical rotation, $[\alpha]_D$: +22.2 (c 0.39, MeOH).

(−)-1-(DIMETHYLAMINO)-3-(2-(3-METHOXY-PHENETHYL)PHENOXY)PROPAN-2-OL HYDROCHLORIDE $^1$HNMR, 400 MHz 1H-NMR (CDCl$_3$, ppm) 12.06-11.86 (br s, 1H) 7.23-7.13 (m, 3H) 6.97-6.91 (m, 1H) 6.83 (d, J=8.1 Hz, 1H) 6.76-7.71 (m, 2H) 6.70-6.67 (m, 1H) 5.42-5.08 (br s, 1H) 4.60-4.48 (m, 1H) 4.16-4.10 (m, 1H) 3.91-3.83 (m, 1H) 3.77 (s, 3H) 2.26-3.14 (m, 2H) 2.95-2.76 (m, 10H); ESI-MS, m/z 330 [M$^+$H]$^+$; NMR purity (%) 97; HPLC purity (%) 99; HPLC conditions Column: XBridge® C18 3.5 µm, 2.1×50 mm; Mobile phase: gradient elution from 10% MeCN in 0.01% TFA to 95% MeCN in 0.01% TFA; Flow rate: 0.5 ml/min; Detection: UV 254 nm; Sample concentration: 0.5 mg/ml.

Molecular formula: $C_{20}H2_8ClNO_3$; Molecular weight: 365.9041; Melting point (° C.):124-125; Optical rotation, $[\alpha]_D$: −20.4 (c 0.53, MeOH).

Sarpogrelate Enantiomers

Succinic acid (0.55 mmol, 1.1 equiv.), dicyclohexylcarbodiimide (DCC, 0.55 mmol, 1.1 equiv.) and 4-dimethylaminopyridine at 0° C. are added to a stirred solution of racemate or enantiomerically pure M1 (0.50 mmol, 1.0 equiv.) in $CH_2Cl_2$ (5 mL), heated over 30 min to 25° C., stirred the mixture at 25° C. for 18 to 24 h, and diluted with $CH_2Cl_2$ (50 mL) and sat. aq. $NaHCO_3$ (30 mL). The organic layer is separated, dried ($Na_2SO_4$), filtered, and concentrated under reduced pressure. The crude residue is purified by column chromatography (silica gel, hexanes:EtOAc) to yield racemic or optically pure sarpogrelate, respectively depending upon the M1 to yield compounds 50-52. Racemic sarpogrelate can be purified by crystallization and/or chiral chromatography to obtain optically pure.

Enantiomers of compounds described here can be separated using chromatographic techniques. The preparative separation of enantiomers by chromatography on chiral stationary phases (CSPs) has been recognized as being a useful alternative to the more conventional approaches such as enantioselective synthesis and enzymatically catalyzed transformations (Francotte, Enantioselective chromatography as a powerful alternative for the preparation of drug enantiomers, Journal of Chromatography A, Volume 906, Issues 1-2, Pages 379-397 (12 Jan. 2001); Rajendran, et al., Simulated moving bed chromatography for the separation of enantiomers, Journal of Chromatography A, Volume 1216, Issue 4, Pages 709-738 (23 Jan. 2009); Maier et al., Separation of enantiomers: needs, challenges, perspectives, Journal of Chromatography A, Volume 906, Issues 1-2, Pages 3-33 (12 Jan. 2001); Miller et al., Chromatographic resolution of the enantiomers of a pharmaceutical intermediate from the milligram to the kilogram scale, Journal of Chromatography A, Volume 849, Issue 2, Pages 309-317 (23 Jul. 1999); Andersson et al., Preparative chiral chromatographic resolution of enantiomers in drug discovery, Journal of Biochemical and Biophysical Methods, Volume 54, Issues 1-3, Pages 11-23 (31 Dec. 2002); Pirkle et al., Chapter 6 Separation of Enantiomers by Liquid Chromatographic Methods, Asymmetric Synthesis, pp 87-124, in Volume 1: Analytical Methods covers the major analytical methods used to determine enantiomeric ratios, by Morrison (ed), Elsevier, (Dec. 2, 2012); incorporated in entirety by reference). Racemates of the invention can be resolved from an analytical to a preparative scale by this technique.

Simulated moving-bed chromatography can be used for the separation of the enantiomers of the compounds of the invention, feasible at all production scales, from laboratory to pilot to production plant (Juza et al., Simulated moving-bed chromatography and its application to chirotechnology, Trends in Biotechnology, Volume 18, Issue 3, Pages 108-118 (1 Mar. 2000), incorporated in entirety by reference).

Separation of Enantiomers of Sarpogrelate Hydrochloride ((−)-4-((1-(DIMETHYLAMINO)-3-(2-(3-ETHOXYPHENETHYL)PHENOXY)PROPAN-2-YLOXY)-4-OXOBUTANOIC ACID HYDROCHLORIDE)

Sarpogrelate hydrochloride was separated with the XBridge® C18 3.5 m, 2.1×50 mm column, using a mobile phase: gradient elution from 10% MeCN in 0.01% TFA to 95% MeCN in 0.01% TFA, with a flow rate of 0.5 ml/min, at UV 254 nm, to yield 5.30 mg of enantiomer (99% HPLC purity). NMR: 400 MHz 1H-NMR (C0300, ppm) 7.20-7.14 (m, 2H) 7.11 (dd, J=7.4, 1.6 Hz, 1H) 6.94-6.87 (m, 2H) 6.79-6.71 (m, 3H) 5.70-5.62 (m, 1H) 4.18 (dd, J=10.6, 4.1 Hz, 1H) 4.15 (dd, J=10.6, 4.7 Hz, 1H) 3.75 (S, 3H) 3.70 (dd, J=13.8, 10.1 Hz, 1H) 3.54 (dd, J=13.8, 2.3 Hz, 1H) 2.98 (s, 6H) 2.96-2.77 (m, 4H) 2.76-2.53 (m, 4H). ESI-MS, m/z): 429 [M+H]+. Melting point (° C.): 155-156. Optical rotation, $[\alpha]_D$: −20.0 (c 0.33, MeOH).

(+)-4-((1-(DIMETHYLAMINO)-3-(2-(3-METHOXYPHENETHYL)PHENOXY) PROPAN-2-YL) OXY)-4-OXOBUTANOIC ACID HYDROCHLORIDE

Molecular formula: $C_{24}H_{32}ClNO_6$; Molecular weight: 465.9787; Melting point (° C.):154-155; Optical rotation, $[\alpha]_D$: +20.8 (c 0.53, MeOH); 1HNMR, 400 MHz 1H-NMR (CD3OD, ppm) 7.20-7.14 (m, 2H) 7.11 (dd, J=7.4, 1.6 Hz, 1H) 6.93-6.87 (m, 2H) 6.78-6.71 (m, 3H) 5.70-5.62 (m, 1H) 4.18 (dd, J=10.6, 4.1 Hz, 1H) 4.15 (dd, J=10.6, 4.7 Hz, 1H) 3.75 (s, 3H) 3.70 (dd, J=13.8, 10.1 Hz, 1H) 3.54 (dd, J=13.8, 2.3 Hz, 1H) 2.98 (s, 6H) 2.96-2.77 (m, 4H) 2.76-2.54 (m, 4H); ESI-MS, m/z, 430 [M+H]+; NMR purity (%) 96; HPLC purity (%) 99; HPLC conditions Column: XBridge® C18 3.5 µm, 2.1×50 mm; Mobile phase: gradient elution from 10% MeCN in 0.01% TFA to 95% MeCN in 0.01% TFA; Flow rate: 0.5 ml/min; Detection: UV 254 nm; Sample concentration: 0.5 mg/ml.

(−)-4-((1-(DIMETHYLAMINO)-3-(2-(3-METHOXYPHENETHYL)PHENOXY) PROPAN-2-YL)OXY)-4-OXOBUTANOIC ACID HYDROCHLORIDE

Molecular formula: $C_{24}H_{32}ClNO_6$; Molecular weight: 465.9787; Melting point (° C.): 155-156; Optical rotation, $[\alpha]_D$: −180.1 (c 0.30, MeOH); NMR, 400 MHz 1H-NMR (CD3OD, ppm) 7.20-7.14 (m, 2H) 7.11 (dd, J=7.4, 1.6 Hz, 1H) 6.93-6.87 (m, 2H) 6.78-6.71 (m, 3H) 5.70-5.62 (m, 1H) 4.18 (dd, J=10.6, 4.1 Hz, 1H) 4.15 (dd, J=10.6, 4.7 Hz, 1H) 3.75 (s, 3H) 3.70 (dd, J=13.8, 10.1 Hz, 1H) 3.54 (dd, J=13.8, 2.3 Hz, 1H) 2.98 (s, 6H) 2.96-2.77 (m, 4H) 2.76-2.54 (m, 4H); ESI-MS, m/z, 430 [M+H]+; NMR purity (%) 96; HPLC purity (%) 99; HPLC conditions Column: XBridge® C18 3.5 µm, 2.1×50 mm; Mobile phase: gradient elution from 10% MeCN in 0.01% TFA to 95% MeCN in 0.01% TFA; Flow rate: 0.5 ml/min; Detection: UV 254 nm; Sample concentration: 0.5 mg/ml Example 13

Optically Pure Sarpoglutarate

Glutaric acid (0.55 mmol, 1.1 equiv.), dicyclohexylcarbodiimide (DCC, 0.55 mmol, 1.1 equiv.) and 4-dimethylaminopyridine at 0° C. are added to a stirred solution of racemate or enantiomerically pure M1 (0.50 mmol, 1.0 equiv.) in $CH_2Cl_2$ (5 mL), heated over 30 min to 25° C., stirred the mixture at 25° C. for 18 to 24 h, and diluted with $CH_2Cl_2$ (50 mL) and sat. aq. $NaHCO_3$ (30 mL). The organic layer is separated, dried ($Na_2SO_4$), filtered, and concentrated under reduced pressure. The crude residue is purified by column chromatography (silica gel, hexanes:EtOAc) to yield racemic or optically pure sarpoglutarate, respectively depending upon the M1 to yield compounds 53-55. Racemic sarpoglutarate can be purified by crystallization and/or chiral chromatography to obtain optically pure sarpoglutarate, as explained in Example 12.

Example 14

Optically Pure Sarpoadipate

Adipic acid (0.55 mmol, 1.1 equiv.), dicyclohexylcarbodiimide (DCC, 0.55 mmol, 1.1 equiv.) and 4-dimethylaminopyridine at 0° C. are added to a stirred solution of racemate or enantiomerically pure M1 (0.50 mmol, 1.0 equiv.) in $CH_2Cl_2$ (5 mL), heated over 30 min to 25° C., stirred the mixture at 25° C. for 18 to 24 h, and diluted with $CH_2Cl_2$ (50 mL) and sat. aq. $NaHCO_3$ (30 mL). The organic layer is separated, dried ($Na_2SO_4$), filtered, and concentrated under reduced pressure. The crude residue is purified by column chromatography (silica gel, hexanes:EtOAc) to yield racemic or optically pure sarpoadipate, respectively depending upon the M1 to yield compounds 56-58. Racemic

Example 15

Optically Pure Sarpopimelate

Pimelic acid (0.55 mmol, 1.1 equiv.), dicyclohexylcarbodiimide (DCC, 0.55 mmol, 1.1 equiv.) and 4-dimethylaminopyridine at 0° C. are added to a stirred solution of racemate or enantiomerically pure M1 (0.50 mmol, 1.0 equiv.) in $CH_2Cl_2$ (5 mL), heated over 30 min to 25° C., stirred the mixture at 25° C. for 18 to 24 h, and diluted with $CH_2Cl_2$ (50 mL) and sat. aq. $NaHCO_3$ (30 mL). The organic layer is separated, dried ($Na_2SO_4$), filtered, and concentrated under reduced pressure. The crude residue is purified by column chromatography (silica gel, hexanes:EtOAc) to yield racemic or optically pure sarpopimelate, respectively depending upon the M1 to yield compounds 59-61. Racemic sarpopimelate can be purified by crystallization and/or chiral chromatography to obtain optically pure sarpopimelate, as explained in Example 12.

Example 16

Optically Pure Sarposebacate

Sebacic acid (0.55 mmol, 1.1 equiv.), dicyclohexylcarbodiimide (DCC, 0.55 mmol, 1.1 equiv.) and 4-dimethylaminopyridine at 0° C. are added to a stirred solution of racemate or enantiomerically pure M1 (0.50 mmol, 1.0 equiv.) in $CH_2Cl_2$ (5 mL), heated over 30 min to 25° C., stirred the mixture at 25° C. for 18 to 24 h, and diluted with $CH_2Cl_2$ (50 mL) and sat. aq. $NaHCO_3$ (30 mL). The organic layer is separated, dried ($Na_2SO_4$), filtered, and concentrated under reduced pressure. The crude residue is purified by column chromatography (silica gel, hexanes:EtOAc) to yield racemic or optically pure sarposebacate, respectively depending upon the M1 to yield compounds 62-64. Racemic sarposebacate can be purified by crystallization and/or chiral chromatography to obtain optically pure sarposebacate, as explained in Example 12.

Example 17

Optically Pure Sarpoformate

Formic acid (0.55 mmol, 1.1 equiv.), dicyclohexylcarbodiimide (DCC, 0.55 mmol, 1.1 equiv.) and 4-dimethylaminopyridine at 0° C. are added to a stirred solution of racemate or enantiomerically pure M1 (0.50 mmol, 1.0 equiv.) in $CH_2Cl_2$ (5 mL), heated over 30 min to 25° C., stirred the mixture at 25° C. for 18 to 24 h, and diluted with $CH_2Cl_2$ (50 mL) and sat. aq. $NaHCO_3$ (30 mL). The organic layer is separated, dried ($Na_2SO_4$), filtered, and concentrated under reduced pressure. The crude residue is purified by column chromatography (silica gel, hexanes:EtOAc) to yield racemic or optically pure sarpoformate, respectively depending upon the M1 to yield compounds 65-67. Racemic sarpoformate can be purified by crystallization and/or chiral chromatography to obtain optically pure sarpoformate, as explained in Example 12.

Example 18

Optically Pure Sarpoacetate

Acetic acid (0.55 mmol, 1.1 equiv.), dicyclohexylcarbodiimide (DCC, 0.55 mmol, 1.1 equiv.) and 4-dimethylaminopyridine at 0° C. are added to a stirred solution of racemate or enantiomerically pure M1 (0.50 mmol, 1.0 equiv.) in $CH_2Cl_2$ (5 mL), heated over 30 min to 25° C., stirred the mixture at 25° C. for 18 to 24 h, and diluted with $CH_2Cl_2$ (50 mL) and sat. aq. $NaHCO_3$ (30 mL). The organic layer is separated, dried ($Na_2SO_4$), filtered, and concentrated under reduced pressure. The crude residue is purified by column chromatography (silica gel, hexanes:EtOAc) to yield racemic or optically pure sarpoacetate, respectively depending upon the M1 to yield compounds 68-70. Racemic sarpoacetate can be purified by crystallization and/or chiral chromatography to obtain optically pure sarpoacetate, as explained in Example 12.

Example 19

Optically Pure Sarpopropionate

Propionic acid (0.55 mmol, 1.1 equiv.), dicyclohexylcarbodiimide (DCC, 0.55 mmol, 1.1 equiv.) and 4-dimethylaminopyridine at 0° C. are added to a stirred solution of racemate or enantiomerically pure M1 (0.50 mmol, 1.0 equiv.) in $CH_2Cl_2$ (5 mL), heated over 30 min to 25° C., stirred the mixture at 25° C. for 18 to 24 h, and diluted with $CH_2Cl_2$ (50 mL) and sat. aq. $NaHCO_3$ (30 mL). The organic layer is separated, dried ($Na_2SO_4$), filtered, and concentrated under reduced pressure. The crude residue is purified by column chromatography (silica gel, hexanes:EtOAc) to yield racemic or optically pure sarpopropionate, respectively depending upon the M1 to yield compounds 71-73. Racemic sarpopriopionate can be purified by crystallization and/or chiral chromatography to obtain optically pure sarpopropionate, as explained in Example 12.

Example 20

Optically Pure Sarpobutyrate

Butyric acid (0.55 mmol, 1.1 equiv.), dicyclohexylcarbodiimide (DCC, 0.55 mmol, 1.1 equiv.) and 4-dimethylaminopyridine at 0° C. are added to a stirred solution of racemate or enantiomerically pure M1 (0.50 mmol, 1.0 equiv.) in $CH_2Cl_2$ (5 mL), heated over 30 min to 25° C., stirred the mixture at 25° C. for 18 to 24 h, and diluted with $CH_2Cl_2$ (50 mL) and sat. aq. $NaHCO_3$ (30 mL). The organic layer is separated, dried ($Na_2SO_4$), filtered, and concentrated under reduced pressure. The crude residue is purified by column chromatography (silica gel, hexanes:EtOAc) to yield racemic or optically pure sarpobutyrate, respectively depending upon the M1 to yield compounds 74-76. Racemic sarpobutyrate can be purified by crystallization and/or chiral chromatography to obtain optically pure sarpobutyrate, as explained in Example 12.

Example 21

Optically Pure Sarpovalerate

Valeric acid (0.55 mmol, 1.1 equiv.), dicyclohexylcarbodiimide (DCC, 0.55 mmol, 1.1 equiv.) and 4-dimethylaminopyridine at 0° C. are added to a stirred solution of racemate or enantiomerically pure M1 (0.50 mmol, 1.0 equiv.) in $CH_2Cl_2$ (5 mL), heated over 30 min to 25° C., stirred the mixture at 25° C. for 18 to 24 h, and diluted with $CH_2Cl_2$ (50 mL) and sat. aq. $NaHCO_3$ (30 mL). The organic layer is separated, dried ($Na_2SO_4$), filtered, and concentrated under reduced pressure. The crude residue is purified by column chromatography (silica gel, hexanes:EtOAc) to yield racemic or optically pure sarpovalerate, respectively depending upon the M1 to yield compounds 77-79. Racemic sarpovalerate can be purified by crystallization and/or chiral chromatography to obtain optically pure sarpovalerate, as explained in Example 12.

Example 22

Optically Pure Sarpocaproate

Caproic acid (0.55 mmol, 1.1 equiv.), dicyclohexylcarbodiimide (DCC, 0.55 mmol, 1.1 equiv.) and 4-dimethylaminopyridine at 0° C. are added to a stirred solution of racemate or enantiomerically pure M1 (0.50 mmol, 1.0 equiv.) in $CH_2Cl_2$ (5 mL), heated over 30 min to 25° C., stirred the mixture at 25° C. for 18 to 24 h, and diluted with $CH_2Cl_2$ (50 mL) and sat. aq. $NaHCO_3$ (30 mL). The organic layer is separated, dried ($Na_2SO_4$), filtered, and concentrated under reduced pressure. The crude residue is purified by column chromatography (silica gel, hexanes:EtOAc) to yield racemic or optically pure sarpocaproate, respectively depending upon the M1 to yield compounds 80-82. Racemic sarpocaproate can be purified by crystallization and/or chiral chromatography to obtain optically pure sarpocaproate, as explained in Example 12.

Example 23

Optically Pure Sarpoenanthate

Enanthoic (heptanoic) acid (0.55 mmol, 1.1 equiv.), dicyclohexylcarbodiimide (DCC, 0.55 mmol, 1.1 equiv.) and 4-dimethylaminopyridine at 0° C. are added to a stirred solution of racemate or enantiomerically pure M1 (0.50 mmol, 1.0 equiv.) in $CH_2Cl_2$ (5 mL), heated over 30 min to 25° C., stirred the mixture at 25° C. for 18 to 24 h, and diluted with $CH_2Cl_2$ (50 mL) and sat. aq. $NaHCO_3$ (30 mL). The organic layer is separated, dried ($Na_2SO_4$), filtered, and concentrated under reduced pressure. The crude residue is purified by column chromatography (silica gel, hexanes:EtOAc) to yield racemic or optically pure sarpoenanthoate, respectively depending upon the M1 to yield compounds 62-64. Racemic sarpoenanthoate can be purified by crystallization and/or chiral chromatography to obtain optically pure sarpoenanthoateate, as explained in Example 12.

Example 24

Optically Pure Sarpocaprylate

Caprylic acid (0.55 mmol, 1.1 equiv.), dicyclohexylcarbodiimide (DCC, 0.55 mmol, 1.1 equiv.) and 4-dimethylaminopyridine at 0° C. are added to a stirred solution of racemate or enantiomerically pure M1 (0.50 mmol, 1.0 equiv.) in $CH_2Cl_2$ (5 mL), heated over 30 min to 25° C., stirred the mixture at 25° C. for 18 to 24 h, and diluted with $CH_2Cl_2$ (50 mL) and sat. aq. $NaHCO_3$ (30 mL). The organic layer is separated, dried ($Na_2SO_4$), filtered, and concentrated under reduced pressure. The crude residue is purified by column chromatography (silica gel, hexanes:EtOAc) to yield racemic or optically pure sarpocaprylate, respectively depending upon the M1 to yield compounds 86-88. Racemic sarpocaprylate can be purified by crystallization and/or chiral chromatography to obtain optically pure sarpocaprylate, as explained in Example 12.

Example 25

Optically Pure Sarpopelargonate

Pelargonic acid (0.55 mmol, 1.1 equiv.), dicyclohexylcarbodiimide (DCC, 0.55 mmol, 1.1 equiv.) and 4-dimethylaminopyridine at 0° C. are added to a stirred solution of racemate or enantiomerically pure M1 (0.50 mmol, 1.0 equiv.) in $CH_2Cl_2$ (5 mL), heated over 30 min to 25° C., stirred the mixture at 25° C. for 18 to 24 h, and diluted with $CH_2Cl_2$ (50 mL) and sat. aq. $NaHCO_3$ (30 mL). The organic layer is separated, dried ($Na_2SO_4$), filtered, and concentrated under reduced pressure. The crude residue is purified by column chromatography (silica gel, hexanes:EtOAc) to yield racemic or optically pure sarpopelargonate, respectively depending upon the M1 to yield compounds 89-91. Racemic sarpopelargonate can be purified by crystallization and/or chiral chromatography to obtain optically pure sarpopelargonate, as explained in Example 12.

Example 26

Optically Pure Sarpocaprate

Capric acid (0.55 mmol, 1.1 equiv.), dicyclohexylcarbodiimide (DCC, 0.55 mmol, 1.1 equiv.) and 4-dimethylaminopyridine at 0° C. are added to a stirred solution of racemate or enantiomerically pure M1 (0.50 mmol, 1.0 equiv.) in $CH_2Cl_2$ (5 mL), heated over 30 min to 25° C., stirred the mixture at 25° C. for 18 to 24 h, and diluted with $CH_2Cl_2$ (50 mL) and sat. aq. $NaHCO_3$ (30 mL). The organic layer is separated, dried ($Na_2SO_4$), filtered, and concentrated under reduced pressure. The crude residue is purified by column chromatography (silica gel, hexanes:EtOAc) to yield racemic or optically pure sarpocaprate, respectively depending upon the M1 to yield compounds 92-94. Racemic sarpocaprate can be purified by crystallization and/or chiral chromatography to obtain optically pure sarpocaprate, as explained in Example 12.

Example 27

Optically Pure Sarpooxalate

Oxalic acid (0.55 mmol, 1.1 equiv.), dicyclohexylcarbodiimide (DCC, 0.55 mmol, 1.1 equiv.) and 4-dimethylaminopyridine at 0° C. are added to a stirred solution of racemate or enantiomerically pure M1 (0.50 mmol, 1.0 equiv.) in $CH_2Cl_2$ (5 mL), heated over 30 min to 25° C., stirred the mixture at 25° C. for 18 to 24 h, and diluted with $CH_2Cl_2$ (50 mL) and sat. aq. $NaHCO_3$ (30 mL). The organic layer is separated, dried ($Na_2SO_4$), filtered, and concentrated under reduced pressure. The crude residue is purified by column chromatography (silica gel, hexanes:EtOAc) to yield racemic or optically pure sarpooxalate, respectively depending upon the M1 to yield compounds 95-97. Racemic sarpooxalate can be purified by crystallization and/or chiral chromatography to obtain optically pure sarpooxalate, as explained in Example 12.

Example 28

Optically Pure Sarpoisophthallate

Isophthallic acid (0.55 mmol, 1.1 equiv.), dicyclohexylcarbodiimide (DCC, 0.55 mmol, 1.1 equiv.) and 4-dimethylaminopyridine at 0° C. are added to a stirred solution of racemate or enantiomerically pure M1 (0.50 mmol, 1.0 equiv.) in $CH_2Cl_2$ (5 mL), heated over 30 min to 25° C., stirred the mixture at 25° C. for 18 to 24 h, and diluted with $CH_2Cl_2$ (50 mL) and sat. aq. $NaHCO_3$ (30 mL). The organic layer is separated, dried ($Na_2SO_4$), filtered, and concentrated under reduced pressure. The crude residue is purified by column chromatography (silica gel, hexanes:EtOAc) to yield racemic or optically pure sarpoisophthallate, respectively depending upon the M1 to yield compounds 98-100. Racemic sarpoisophthallate can be purified by crystallization and/or chiral chromatography to obtain optically pure sarpoisophthallate, as explained in Example 12.

Example 29

Optically Pure Sarpoterephthallate

Terephthallic acid (0.55 mmol, 1.1 equiv.), dicyclohexylcarbodiimide (DCC, 0.55 mmol, 1.1 equiv.) and 4-dimethylaminopyridine at 0° C. are added to a stirred solution of racemate or enantiomerically pure M1 (0.50 mmol, 1.0 equiv.) in $CH_2Cl_2$ (5 mL), heated over 30 min to 25° C., stirred the mixture at 25° C. for 18 to 24 h, and diluted with $CH_2Cl_2$ (50 mL) and sat. aq. $NaHCO_3$ (30 mL). The organic layer is separated, dried ($Na_2SO_4$), filtered, and concentrated under reduced pressure. The crude residue is purified by column chromatography (silica gel, hexanes:EtOAc) to yield racemic or optically pure sarpoterephthallate, respectively depending upon the M1 to yield compounds 101-103. Racemic sarpoterephthallate can be purified by crystallization and/or chiral chromatography to obtain optically pure sarpoterephthallate, as explained in Example 12.

Example 30

Optically Pure Sarposalicilate

Salicilic acid (0.55 mmol, 1.1 equiv.), dicyclohexylcarbodiimide (DCC, 0.55 mmol, 1.1 equiv.) and 4-dimethylaminopyridine at 0° C. are added to a stirred solution of racemate or enantiomerically pure M1 (0.50 mmol, 1.0 equiv.) in $CH_2Cl_2$ (5 mL), heated over 30 min to 25° C., stirred the mixture at 25° C. for 18 to 24 h, and diluted with $CH_2Cl_2$ (50 mL) and sat. aq. $NaHCO_3$ (30 mL). The organic layer is separated, dried ($Na_2SO_4$), filtered, and concentrated under reduced pressure. The crude residue is purified by column chromatography (silica gel, hexanes:EtOAc) to yield racemic or optically pure sarposalicilate, respectively depending upon the M1 to yield compounds 104-106. Racemic sarposalicilate can be purified by crystallization and/or chiral chromatography to obtain optically pure sarposalicilate, as explained in Example 12.

Example 31

Optically Pure Sarpoacetylsalicilate

Acetylsalicilic acid (0.55 mmol, 1.1 equiv.), dicyclohexylcarbodiimide (DCC, 0.55 mmol, 1.1 equiv.) and 4-dimethylaminopyridine at 0° C. are added to a stirred solution of racemate or enantiomerically pure M1 (0.50 mmol, 1.0 equiv.) in $CH_2Cl_2$ (5 mL), heated over 30 min to 25° C., stirred the mixture at 25° C. for 18 to 24 h, and diluted with $CH_2Cl_2$ (50 mL) and sat. aq. $NaHCO_3$ (30 mL). The organic layer is separated, dried ($Na_2SO_4$), filtered, and concentrated under reduced pressure. The crude residue is purified by column chromatography (silica gel, hexanes:EtOAc) to yield racemic or optically pure sarpoacetylsalicilate, respectively depending upon the M1 to yield compounds 107-109. Racemic sarpoacetylsalicilate can be purified by crystallization and/or chiral chromatography to obtain optically pure sarpoacetylsalicilate, as explained in Example 12.

(Park et al., Aspirination of α-Aminoalcohol (Sarpogrelate M1), Molecules 21(9), 1126 (2016); incorporated in entirety by reference)

Example 32

To a stirred solution of M1 (0.50 mmol, 1.0 equiv.) in $CH_2Cl_2$ (5 mL) or $CH_3CN$ (5 mL) was added aspirin (0.55 mmol, 1.1 equiv.) and 1,1'-carbonyldiimidazole (CDI, 0.60 mmol, 1.2 equiv.) at 25° C. The mixture was stirred for 12 h, and diluted with $CH_2Cl_2$ (40 mL) and sat. aq. $NH_4Cl$ (25 mL). The organic layer was separated, dried ($Na_2SO_4$), filtered, and concentrated under reduced pressure. The crude residue was purified by column chromatography (silica gel, hexanes:EtOAc) to obtain compound 107. Racemic sarpoacetylsalicilate compound 107 can be purified by crystallization and/or chiral chromatography to obtain optically pure sarpoacetylsalicilates 108 and 109, as explained in Example 12.

Example 33

To a stirred solution of M1 (0.50 mmol, 1.0 equiv.) in THF (5 mL) was added acetylsalicylic acid (0.75 mmol, 1.5 equiv.), triphenylphosphine (0.75 mmol, 1.5 equiv.) and diisopropyl azodicarboxylate (DIAD, 0.75 mmol, 1.5 equiv.) at 0° C. The mixture was stirred at the same temperature for 1 h, and the solvent was removed under reduced pressure. The residue was diluted with EtOAc (30 mL) and sat. aq. $NH_4Cl$ (15 mL). The organic layer was separated, dried ($Na_2SO_4$), filtered, and concentrated under reduced pressure. The crude residue was purified by column chromatography (silica gel, hexanes:EtOAc) to obtain compound 107. Racemic sarpoacetylsalicilate compound 107 can be purified by crystallization and/or chiral chromatography to obtain optically pure sarpoacetylsalicilates 108 and 109, as explained in Example 12.

Example 34

To a stirred solution of acetyl salicylate (1.00 mmol, 2.0 equiv.) in $CH_2Cl_2$ (5 mL) was added oxalyl chloride (2 M in $CH_2Cl_2$, 0.60 mL, 1.20 mmol, 2.4 equiv.) and dimethylformamide (DMF, 8.0 μL, 0.10 mmol, 0.2 equiv.) at 0° C. Then, the temperature was gradually raised to 25° C. The mixture was stirred at the same temperature for 12 h. Then, to another stirred solution of M1 3 (0.50 mmol, 1.0 equiv.) in $CH_2Cl_2$ (5 mL) was added pyridine (0.24 mL, 3.0 mmol, 6.0 equiv.) and the previously prepared aspirinyl chloride solution. The mixture was stirred for another 12 h, and diluted with $CH_2Cl_2$ (50 mL) and sat. aq. $NaHCO_3$ (30 mL). The organic layer was separated, dried ($Na_2SO_4$), filtered, and concentrated under reduced pressure. The crude residue was purified by column chromatography (silica gel, hexanes: EtOAc) to obtain compound 107. Racemic sarpoacetylsalicilate compound 107 can be purified by crystallization and/or chiral chromatography to obtain optically pure sarpoacetylsalicilates 108 and 109, as explained in Example 12.

Example 35

To a stirred solution of salicylate ester (241 mg, 0.536 mmol, 1.0 equiv.) in pyridine (2 mL) was added $Ac_2O$ (76 μL, 0.81 mmol, 1.5 equiv.) at 0° C. The temperature was raised to 25° C. The mixture was stirred at the same temperature for 12 h. Then, the mixture was concentrated under reduced pressure and diluted with ethyl acetate (30 mL) and washed with $H_2O$ (10 mL). The organic layer was separated, dried ($Na_2SO_4$), filtered, and concentrated under reduced pressure. The crude residue was purified by column chromatography (silica gel, hexanes: EtOAc=1:2) to afford compound 107 (239 mg, 90% yield). Racemic sarpoacetylsalicilate compound 107 can be purified by crystallization and/or chiral chromatography to obtain optically pure sarpoacetylsalicilates 108 and 109, as explained in Example 12.

Example 36

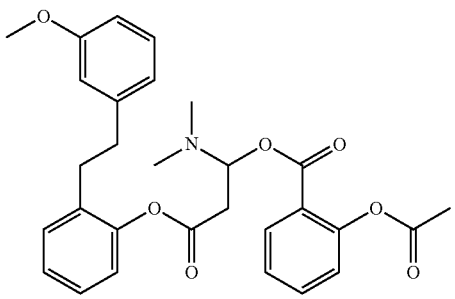

1-(dimethylamino)-3-(2-(3-methoxyphenethyl)phenoxy)-3-oxopropyl 2-acetoxybenzoate 1-(Dimethylamino)-3-(2-(3-methoxyphenethyl)phenoxy)propan-2-yl 2-acetoxy benzoate (compound 163)

Colorless oil; $R_f$=0.25 (silica gel, hexanes: EtOAc 1:1); $^1$H-NMR (500 MHz, CDCl$_3$): δ=7.99 (dd, J$_1$=1.6 Hz, J$_2$=7.9 Hz, 1H), 7.53-7.50 (m, 1H), 7.18 (ddd, J$_1$=1.1 Hz, J$_2$=7.9 Hz, J$_3$=7.9 Hz, 1H), 7.18-7.14 (m, 2H), 7.10-7.06 (m, 2H), 6.89-6.86 (m, 2H), 6.77 (d, J=7.7 Hz, 1H), 6.72-6.71 (m, 2H), 5.56-5.51 (m, 1H), 4.28-4.22 (m, 2H), 3.75 (s, 3H), 2.92-2.71 (m, 6H), 2.32 (s, 6H), 2.30 (s, 3H) ppm; $^{13}$C-NMR (125 MHz, CDCl$_3$): δ=169.7, 163.9, 159.7, 156.5, 150.9, 144.1, 134.0, 131.9, 130.5, 130.3, 129.3, 127.4, 126.1, 123.9, 123.4, 121.0, 120.9, 114.2, 111.39, 111.37, 71.2, 67.6, 59.4, 55.2, 46.4, 36.5, 32.8, 21.1 ppm; HRMS (EI): calcd for C$_{29}$H$_{33}$NO$_6$ [M$^+$]: 491.2308, found 491.2310.

Example 37

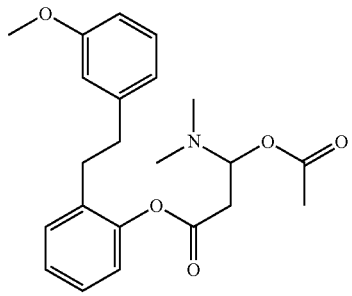

2-(3-methoxyphenethyl)phenyl 3-acetoxy-3-(dimethylamino)propanoate 1-(Dimethylamino)-3-(2-(3-methoxyphenethyl)phenoxy)propan-2-ylacetate (compound 164)

Colorless oil; $R_f$=0.19 (silica gel, hexanes:EtOAc 1:2); $^1$H-NMR (500 MHz, CDCl$_3$): δ=7.21 (t, J=7.8 Hz, 1H), 7.16 (ddd, J$_1$=1.7 Hz, J$_2$=7.8 Hz, J$_3$=7.8 Hz, 1H), 7.11 (dd, J$_1$=1.7 Hz, J$_2$=7.4 Hz, 1H), 6.87 (ddd, J$_1$=1.0 Hz, J$_2$=7.4 Hz, J$_3$=7.4 Hz, 1H), 6.84 (t, J=8.9 Hz, 2H), 6.78 (t, J=1.9 Hz, 1H), 6.76-6.73 (m, 1H), 5.39-5.34 (m, 1H), 4.19-4.09 (m, 2H), 3.80 (s, 3H), 2.91-2.84 (m, 4H), 2.69-2.61 (m, 2H), 2.30 (s, 6H), 2.05 (s, 3H) ppm; $^{13}$C-NMR (125 MHz, CDCl$_3$): δ=170.8, 159.7, 156.5, 144.2, 130.5, 130.3, 129.4, 127.4, 121.0, 120.9, 114.3, 111.3, 111.2, 70.4, 67.7, 59.7, 55.3, 46.4, 36.6, 33.2, 21.4 ppm; HRMS (EI): calcd for C$_{22}$H$_{29}$NO$_4$ [M$^+$]: 371.2097, found 371.2095.

Example 38

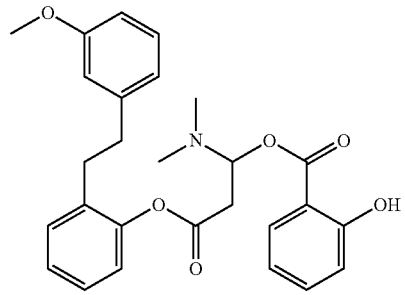

1-(dimethylamino)-3-(2-(3-methoxyphenethyl)phenoxy)-3-oxopropyl 2-hydroxybenzoate 1-(Dimethylamino)-3-(2-(3-methoxyphenethyl)phenoxy)propan-2-yl-2-hydroxy benzoate (Compound 165)

Colorless oil; $R_f$=0.23 (silica gel, hexanes:EtOAc 2:1); $^1$H-NMR (500 MHz, CDCl$_3$): δ=10.69 (s, 1H), 7.83 (dd, J$_1$=1.7 Hz, J$_2$=8.0 Hz, 1H), 7.44-7.41 (m, 1H), 7.20-7.16 (m, 2H), 7.11 (dd, J$_1$=1.6 Hz, J$_2$=7.4 Hz, 1H), 6.96 (dd, J$_1$=0.9 Hz, J$_2$=8.4 Hz, 1H), 6.91-6.88 (m, 2H), 6.81-6.77 (m, 1H), 6.76-6.72 (m, 3H), 5.70-5.66 (m, 1H), 4.30-4.29 (m, 2H), 3.76 (s, 3H), 2.91-2.82 (m, 6H), 2.40 (s, 6H) ppm; $^{13}$C-NMR (125 MHz, CDCl$_3$): δ=169.6, 161.8, 159.7, 156.3, 144.0, 136.0, 130.5, 130.4, 130.1, 129.4, 127.4, 121.2, 120.9, 119.4, 117.8, 114.3, 112.5, 111.3, 111.2, 71.2, 67.6, 59.4, 55.2, 46.1, 36.5, 32.8 ppm; HRMS (EI): calcd for C$_{27}$H$_{31}$NO$_5$ [M$^+$]: 449.2202, found 449.2200.

Example 39

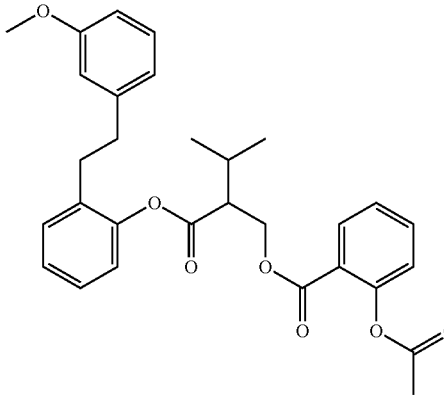

1-(dimethylamino)-3-(2-(3-methoxyphenethyl)phenoxy)-3-oxopropyl 2-acetoxybenzoate 2-(Dimethylamino)-3-(2-(3-methoxyphenethyl)phenoxy)propyl2-acetoxybenzoate (Compound 166)

Colorless oil; $R_f$=0.20 (silica gel, hexanes:EtOAc 1:1); $^1$H-NMR (500 MHz, CDCl$_3$): δ=7.98 (dd, $J_1$=1.6 Hz, $J_2$=7.8 Hz, 1H), 7.55 (ddd, $J_1$=1.7 Hz, $J_2$=7.8 Hz, $J_3$=7.8 Hz, 1H), 7.28 (ddd, $J_1$=1.1 Hz, $J_2$=7.7 Hz, $J_3$=7.7 Hz, 1H), 7.21-7.17 (m, 2H), 7.13 (dd, $J_1$=1.5 Hz, $J_2$=7.4 Hz, 1H), 7.11 (dd, $J_1$=1.0 Hz, $J_2$=8.1 Hz, 1H), 6.92-6.88 (m, 2H), 6.81 (d, J=7.7 Hz, 1H), 6.75-6.73 (m, 2H), 4.62-4.53 (m, 2H), 4.20-4.12 (m, 2H), 3.77 (s, 3H), 3.29-3.24 (m, 1H), 2.95-2.85 (m, 4H), 2.51 (s, 6H), 2.31 (s, 3H) ppm; $^{13}$C-NMR (125 MHz, CDCl$_3$): δ=169.9, 164.3, 159.7, 156.5, 150.9, 144.0, 134.1, 131.7, 130.4, 130.3, 129.4, 127.4, 126.1, 124.0, 123.2, 121.0, 120.9, 114.2, 111.4, 111.1, 65.7, 62.8, 62.0, 55.2, 42.6, 36.6, 32.6, 21.1 ppm; HRMS (EI): calcd for $C_{29}H_{33}NO_6$ [M$^+$]: 491.2308, found 491.2309.

Example 40

General Method for Deuteration of H-Compound to Form D-Compound

The H-compound (a compound of the invention, about 1.25 mmol) is dissolved in 3 mL of 100 mM pH=7 deuterated phosphate-buffered saline (D-PBS) diluted with 9.00 mL D$_2$O to a final concentration of 25 mM. 100 mM D-PBS pH=7 (pH paper) buffer is prepared by dissolving 259.5 mg of K$_3$PQ$_4$ in D$_2$O (12.00 mL) and adding 264 µL 20% DCl in D$_2$O. The reaction mixture is shaken at room temperature for 11 days while monitoring for completion of hydrogen/deuterium (H/D) exchange by LC/MS.

A small scale workup is performed to prepare the hydrochloride salt of the deuterated compound. Thus a 1.2 mL aliquot of the reaction mixture (10% of total volume) is diluted with 5 mL saturated NaHCO$_3$ and extracted with EtOAc (3×5 mL). The organic layer is dried over Na$_2$SO$_4$ and filtered. Evaporation of the solvent gave 20 mg of a colorless oil which is converted to the HCl salt by addition of a few drops of 4M HCl in dioxane. The salt is triturated with ether and the solvents were evaporated to give deuterated compound HCl salt. A 9.6 mL aliquot (80% of total volume) is diluted with 40 mL saturated NaHCO$_3$ and extracted once with EtOAc (200 mL). The organic layer is quickly dried over Na$_2$SO$_4$. Evaporation of the solvent gives the compound which is stored in a freezer.

Example 41

Preparation of Crude Sarpogrelate Hydrochloride 1-dimethylamino-3-[2-[2-(3-methoxyphenyl)ethyl]phenoxy]-2-propanol hydrochloride A 250 ml 13.7 g and water 25 ml were taken in a single-neck flask and stirred to dissolve. The solution is treated with 20% aqueous sodium hydroxide to a pH about 9 to about 14, and was extracted with 30 ml of toluene, and the organic layer was concentrated at 50° C. under reduced pressure to give a brown oil, which was dissolved in 30 mL of tetrahydrofuran. Then, butyryl anhydride 4.5 g was added and heated to reflux with stirring for about 1 to about 4 hours, and concentrated to dryness under reduced pressure at 40° C. Ethyl acetate (25 mL) is added to dissolve the residue and saturated hydrogen chloride in ethyl acetate solution is added dropwise to adjust PH 1 or lower while stirring for about 50-60 min to obtain sarpogrelate hydrochloride crude wet product, and dried under reduced pressure (−0.08~−0.1 MPa) at 45 to 55° C. to yield crude sarpogrelate hydrochloride 14.7 g, yield 86%, HPLC purity 98.6%.

Example 42

Purification of the Crude Hydrochloride Sarpogrelate

The crude sarpogrelate hydrochloride 5 g was dissolved in butanone (20 mL), heated while stirring until dissolved, refluxed for 20~30 min, cooled to 25-35° C., continued stirring 40~60 min, filtered, and the filter cake was rinsed with a small amount of methyl ethyl ketone to give a white loose solid, 55~65° C. and dried under reduced pressure to 24 h, to give sarpogrelate hydrochloride 4.6 g, yield 92%, HPLC purity of 99.9%.

Example 43

Purification of the Crude Hydrochloride Sarpogrelate

The crude sarpogrelate hydrochloride 5 g in butanone 30 ml was heated with stirring until dissolved and refluxed 20~30 min, cooling to 25~35° C., incubated with stirring 40~60 min, filtered, and the filter cake was rinsed with a small amount of methyl ethyl ketone to give a white loose solid, 55~65° C. and dried under reduced pressure to 24 h, to give 4.55 sarpogrelate hydrochloride, yield 91%, HPLC purity 99.7%.

Example 44

Purification of the Crude Hydrochloride Sarpogrelate

The crude sarpogrelate hydrochloride 5 g in butanone 40 ml is heated with stirring until dissolved and refluxed 20~30 min, cooling to 25~35° C., incubated with stirring 40~60 min, filtered, and the filter cake was rinsed with a small amount of methyl ethyl ketone to give a white solid, 55~65° C. and dried under reduced pressure to 24 h, to give sarpogrelate hydrochloride 4.5 g, yield 90%, HPLC purity 99.8%.

Example 45

Purification of the Crude Hydrochloride Sarpogrelate

The crude product was sarpogrelate hydrochloride 5 g, join butanone 20 ml, heated with stirring until dissolved and refluxed 20~30 min, cooled slowly with stirring to room temperature, at −10° C. stand for crystallization, filtration, The filter cake was rinsed with a small amount of methyl ethyl ketone to give a white fluffy solid, 55~65° C. and dried under reduced pressure to 24 h, to give the hydrochloride sarpogrelate 4.62 g, yield 92.4%, HPLC purity 99.2%, largest single matter content of 0.09%.

Example 46

1,3,4,9,10,10A-HEXAHYDRO-6-METHOXY-2H-10,4A-(IMINOETHANO) PHENANTRENE-11-CARBOXYLIC ACID 2,2,2-TRICHLOROETHYL ESTER

Dextromethorphan hydrobromide monohydrate (5.56 g, 15 mmoles) was dissolved in 60 ml of chloroform and a solution of 1.2 g sodium hydroxide in 60 mL of water. After stirring for 1 hour the organic layer was separated, dried (sodium sulfate), and evaporated in vacuum. The obtained oil was refluxed in 50 ml of toluene with 2.4 ml of 2,2,2-trichloroethyl chloroformate for 4 hours. The reaction was checked by TLC (Kieselgel 60, chloroform-methanol=95:5, Rf=0.7). After completion of the reaction the solvent was evaporated in vacuum. The residual oil was purified on a Kieselgel 60 (0.063-0.200) column (eluent: chloroform-methanol=95:5), giving 6.0 g oil (13.86 mmoles, yield: 92.42%). 1H-NMR (300 MHz, CDCl3, 30° C.): δ 0.94-1.12 (m, 1H, CH); 1.16-1.72 (m, 9H, CH); 2.26-2.37 (m, 1H, CH); 2.54-2.76 (m, 2H, CH); 3.06 (dd, 1H, J=17.7 and 6.0 Hz, CH); 3.72 (s, 3H, OCH3); 3.79-3.92 (m, 1H, CH), 4.32 (dd, 1H, J=4.6 and 4.4 Hz, CH); amide rotamers: [4.65 and 4.71 (d, 1H, J=12.3 Hz, CH2) and 4.66 and 4.79 (d, 1H, J=12.0 Hz, CH2)]; 6.66 (dd, 1H, J=8.4 and 3.0 Hz, Ar); 6.77 (d, 1H, J=3.0 Hz, Ar); amide rotamers: [6.95 and 6.96 (d, 1H, J=8.4 Hz, Ar)]; GC-MS: 98.0%; MS: EI m/e 431 (M+, 6.7%), 213 (100.0%).

Example 47

3-METHOXYMORPHINAN TETRAACETATOZINCATE

The above prepared trichloroethyl ester derivative 7 (6.0 g, 13.86 mmoles) was dissolved in 57.5 ml of acetic acid and 5.89 ml of distilled water, to which 2.9 g of powered zinc was added. After 50 minutes stirring the completeness of the reaction was checked by TLC. Further 2.9 g of zinc was added to the reaction mixture. After 1 hour stirring the reaction mixture was filtered. The obtained white powder was washed three times with ether. Yield: 10.7 g crude product; mp 161-164° C.; 1H-NMR (300 MHz, CDCl3, 30° C.): δ 0.80-1.00 (m, 1H, CH); 1.08-1.42 (m, 5H, CH); 1.43-1.53 (m, 1H, CH); 1.54-1.76 (m, 2H, CH); 1.82 (s, 6H, CH3COO—), 1.80-1.89 (m, 1H, CH); 2.32-2.48 (m, 2H, CH); 2.74-3.07 (m, 3H, CH); 3.39-3.46 (m, br, 1H, CH); 3.72 (s, 3H, OCH3); 3.00-5.00 (s, vbr, 3H, NH+ and H2O), 6.75-6.82 (m, 2H, Ar); 7.07 (d, 1H, J=8.4 Hz, Ar); FABMS: C+1=258.

Example 48

N-DESMETHYL-DEXTROMETHORPHAN

The above prepared 10.7 g of 3-methoxymorphinan tetraacetatozincate 8 was partitioned between 300 ml of chloroform and 100 ml of 1N sodium hydroxide solution in water. The organic layer was separated, dried (sodium sulfate), evaporated in vacuum to yield: 3.1 g (12.04 mmoles, yield: 86.9%); GC-MS: 99.45%; 1H-NMR (300 MHz, CDCl3, 30° C.): δ 1.00-1.12 (m, 1H, CH); 1.24-1.45 (m, 5H, CH); 1.46-1.69 (m, 3H, CH); 1.70-1.80 (m, 1H, CH); 2.14 (s, br, 1H, NH); 2.26-2.35 (m, 1H, CH); 2.55-2.76 (m, 3H, CH); 3.02-3.16 (m, 3H, CH); 3.79 (s, 3H, OCH3); 6.70 (dd, 1H, J=8.4 and 2.7 Hz, Ar); 6.81 (d, 1H, J=2.7 Hz, Ar); 7.03 (d, 1H, J=8.4 Hz, Ar); MS EI m/e 257 (M+, 100.0%), 228 (M−29), 214 (M−43), 212 (M−45), 171 (M−(2×43)).

Example 49

N-CD3-DEXTROMETHORPHAN

To the solution of the above prepared N-desmethyl-dextromethorphan 4 (3.1 g, 12.04 mmoles) in 265 ml of tetrahydrofuran 10.1 g of sodium hydride (60% dispersion in mineral oil) was added. After 20 minutes stirring 1 ml (2.329 g=16.067 mmoles) of iodomethane-d3 was dropped into the reaction mixture. The reaction was controlled by TLC. After 1 hour stirring at rt. the reaction mixture was poured into 180 ml of distilled water, which was extracted three times with 100 ml of diethyl ether. The organic layer was separated, dried (sodium sulfate), and evaporated in vacuum. The residue was crystallized in n-hexane. (Yield: 1.7 g, 6.195 mmoles, 51.5%; mp 98-103° C.). 1H-NMR (300 MHz, DMSO, 30° C.): δ 0.93-1.07 (m, 1H, CH); 1.11-1.40 (m, 5H, CH); 1.42-1.52 (m, 1H, CH); 1.53-1.66 (m, 2H, CH); 1.66-1.75 (m, 1H, CH); 1.93 (ddd, 1H, J=12.3, 12.2 and 3.3 Hz, CH); 2.25-2.38 (m, 2H, CH); 2.48 (dd, 1H, J=17.7 and 5.7 Hz, CH); 2.68 (dd, 1H, J=5.7 and 3.3 Hz, CH); 2.90 (d, 1H, J=17.7 Hz, CH); 3.70 (s, 3H, OCH3); 6.65 (dd, 1H, J=8.4 and 2.7 Hz, Ar); 6.72 (d, 1H, J=2.7 Hz, Ar); 7.00 (d, 1H, J=8.4 Hz, Ar); 8.85 (s, br, 1H, —OH); FAB-MS m/z 275 (M1H+); MS EI m/z 274 (M1+, 100.0%), 271 (M2+, ~2-3%).

Example 50

N-CD3-DEXTROMETHORPHAN (5) HYDROCHLORIDE SALT

N-CD3-dextromethorphan 5 (1.7 g) was dissolved in ethyl acetate-methanol mixture and was acidified with HCl in ethyl acetate to pH=2, n-hexane was added to the solution. The obtained crystals were filtered. Yield: 1.1 g (3.54 mmoles, 57.1%); mp 121-123° C. 1H-NMR (see FIG. 4) (300 MHz, DMSO, 30° C.): sum of protonated epimers: δ 0.87-1.03 (m, 1H, CH); 1.04-1.67 (m, 7H, CH); 1.88-2.05 (m, 1H, CH); 2.12-2.27 (m, 1H, CH); 2.33-2.49 (m, 2H, CH); 2.90-3.19 (m, 3H, CH); 3.50-3.56 (m, 1H, CH); 3.73 (s, 3H, OCH3); 6.79-6.85 (m, 2H, Ar); 7.09-7.16 (m, 1H, Ar); 11.18 and 11.22 (s, 1H, NH+); MS FAB m/z 275 (M1H+, 100.0%), 272 (M2H+, 2%); GC-MS: 98.8%; HPLC: 99.4% (220 nm); isotopic enrichment 97 atom % D.

Example 51

N-CD3-DEXTRORPHAN (6) HYDROCHLORIDE SALT

N-CD3-dextromethorphan 5 (1.25 g, 4.555 mmoles) was heated in 50 ml of hydrobromic acid (48%) at 110° C. for two hours. After cooling 125 ml of chloroform and 40 ml of ammonium hydroxide solution (25%) were added dropwise to the reaction mixture (pH=9). The organic layer was separated, dried (sodium sulfate), and evaporated in vacuum. The residue was dissolved in ethanol-ethyl acetate mixture. Acidifying the solution with HCl in ethyl acetate to pH=2, the obtained HCl salt was crystallized.

Yield: 1.0 g (3.369 mmoles, 74.0%); mp 122-127° C.; $^1$H-NMR (300 MHz, DMSO, 30° C.): sum of protonated epimers: δ 0.88-1.13 (m, 1H, CH); 1.10-1.67 (m, 7H, CH); 1.82-1.95 (m, 1H, CH); 2.09-2.19 (m, 1H, CH); 2.28-2.37 (m, 1H, CH); 2.40-2.49 (m, 1H, CH); 2.84-3.19 (m, 3H, CH); 3.50-3.56 (m, 1H, CH); 6.64 (dd, 1H, J=8.4 and 2.4 Hz, Ar); 6.71 (d, 1H, J=2.4 Hz, Ar); 7.00 (d, 1H, J=8.4 Hz, Ar); 9.22 (s, br, 1H, —OH); 10.69 and 10.71 (s, 1H, NH+); MS: EI m/e 260 (M1+, 100.0%), 257 (M2+, −2-3%); GC-MS: 97.3%; HPLC: 99.5% (220 nm); isotopic enrichment 97 atom % D.

Example 52

General Synthesis of Halogenated Compounds of Formulae I and II

To a suspension of zirconium(IV) chloride (0.05 mmol) in dichloromethane (2 mL), is added a solution of a compound of Formula I or II (0.5 mmol) and 1,3-dibromo-5,5-dimethylhydantoin (DBDMH; 0.25 mmol) in dichloromethane (2 mL) at room temperature. The mixture is stirred for 2 h at room temperature under room light. The reaction is quenched with saturated aqueous NaHCO₃ solution and extracted by diethyl ether, evaporation of which under reduced pressure yields the bromo compound. The organic layer is subjected to GC analysis using 1,2-dichlorobenzene as an internal standard.

Example 53

General Synthesis of N-Oxides of Compounds of Formulae I and II

A suspension of 5.00 mmol of a compound of Formula I or II in 30 ml absolute ethanol is heated until a clear solution is obtained. To the hot solution is then added 0.41 ml 30% H2O2 in one portion after which the mixture is heated to reflux on an oil bath. After 5 hours reflux another portion of 0.41 ml 30% H2O2 is added and refluxing is continued for 16 hours. A small amount of 10% Pd/C is then added and after 45 minutes refluxing the reaction mixture is allowed to cool down to room temperature to give a brown suspension. The suspension is concentrating using a rotary evaporator to a brown solid which is purified by flash chromatography on silica gel (230-400 mesh, eluent DCM:MeOH:NH3 68:30:2) to obtain the corresponding N-oxide.

Biological Studies

Example 54

Dex Metabolism and Central Effects of 5Ht2A Receptor Blockade

Antipsychotic drugs attenuate locomotor hyperactivity induced by psychostimulant and psychotomimetic drugs in laboratory rodents. While hyperactivity induced by dopaminergic agents such as d-amphetamine is reversed by both typical and atypical antipsychotics that are currently in the clinic use, 5HT2A receptor antagonists are more effective against hyperactivity induced by NMDA receptor antagonists such as phencyclidine-like channel blockers (Carlsson et al., The 5-HT2A receptor antagonist M100907 is more effective in counteracting NMDA antagonist-than dopamine agonist-induced hyperactivity in mice, *J. Neural. Transm.* 106(2):123-9 (1999)). Pimavanserin (ACP-103) is an example of a 5HT2A receptor antagonist that was administered in mice in combination with 0.3 mg/kg MK-801 (i.p.) 15 min before the test session (Vanover et al., Pharmacological and behavioral profile of N-(4-fluorophenylmethyl)-N-(1-methylpiperidin-4-yl)-N'-(4-(2-methylpropyloxy) phenylmethyl) carbamide (2R,3R)-dihydroxybutanedioate (2:1) (ACP-103), a novel 5-hydroxytryptamine (2A) receptor inverse agonist, *J Pharmacol Exp Ther.* 317(2):910-8 (2006 May); incorporated by reference). Motor activity data were collected during a 15-min session in a lit room. Mice had no prior exposure to the motor cages. Immediately before placing the mice in the locomotor chambers, effects on myorelaxation/ataxia were determined by placing each of the mouse's forepaws in contact with a horizontal wire while holding the mouse by the base of the tail. Mice were required to bring at least one hindpaw in contact with the wire within 10 s to be scored as a "pass" and failure to do so was considered ataxic. Each dose or dose combination was tested in a separate group of mice. ACP-103 significantly attenuated MK-801-induced hyperactivity in mice at doses of 0.1 and 0.3 mg/kg s.c. [F(7,63)=6.010; p<0.0001], consistent with an antipsychotic-like effect.

When given in combination with quinidine in patients with neurological diseases (Schoedel et al., Evaluating the safety and efficacy of dextromethorphan/quinidine in the treatment of pseudobulbar affect. Neuropsychiatric Disease and Treatment 2014:10 1161-1174; incorporated by reference in its entirety), dextromethorphan is used at the dose of 10 mg that may be administered twice a day. Currently known clinical dose of Sarpogrelate is 100 mg that is typically given three times a day (Doggrell (2004) sarpogrelate: cardiovascular and renal clinical potential, Expert Opinion on *Investigational Drugs*, 13:7, 865-874; incorporated by reference in its entirety). Thus, current clinical dose of Sarpogrelate significantly exceeds that of dextromethorphan. Given that the molecular weight of sarpogrelate is about 429 and molecular weight of dextromethorphan is about 271, combined use of dextromethorphan and sarpogrelate at the current clinical doses does not result in a molar ratio of 1:1. However, such molar ratio of 1:1 is a pre-requisite for preparing and using sarpogrelate salts of dextromethorphan. As the current clinical use of sarpogrelate is for peripheral (non-CNS) indications (Doggrell (2004) sarpogrelate: cardiovascular and renal clinical potential, Expert Opinion on *Investigational Drugs*, 13:7, 865-874; incorporated by reference in its entirety), use of sarpogrelate for CNS indications may require lower doses and therefore enable co-administration with dextromethorphan as sarpogrelate salt of dextromethorphan or as a mixture in a molar ratio of 1:1. In laboratory animals, sarpogrelate is typically given at doses of 25 mg/kg and above to induce peripheral effects (Ma et al., Effective treatment with combination of peripheral 5-hydroxytryptamine synthetic inhibitor and 5-hydroxytryptamine 2 receptor antagonist on glucocorticoid-induced whole-body insulin resistance with hyperglycemia. *J Diabetes Investig* 7(6):833-844 (2016); incorporated by reference in its entirety). An example of higher CNS activity of sarpogrelate is provided by an example where sarpogrelate is given to Sprague-Dawley rats at the doses of 0.3, 1 and 3 mg/kg 30 min prior to a centrally acting 5-HT2A agonist DOI (3 mg/kg; (1(2,5-dimethoxy-4-iodophenyl)-2-aminopropane)hydrochloride) and frequency of DOI-induced head shakes is reduced by co-administration of a compound of formula I or sarpogrelate.

A compound of formula I or SARPO, as well as both enantiomers of its primary metabolite M1 are 5HT2A receptor antagonists (Pertz et al., In-vitro pharmacology of a compound of formula I or SARPO, and the enantiomers of its major metabolite: 5-HT2A receptor specificity, stereoselectivity and modulation of ritanserin-induced depression of 5-HT contractions in rat tail artery, J Pharm Pharmacol. 47(4):310-6 (1995 April); incorporated by reference in its entirety). To confirm the ability of M1 S- and R-enantiomers to reach 5HT2A receptors in the CNS, rats are pretreated with 0.1 mg/kg of MK801 and attenuation of MK801-stimulated locomotor hyperactivity is monitored across a range of doses of both a compound of formula I or SARPO, and M1 enantiomers during 120-min test session conducted using conventional motor activity monitors.

DEX acts at a number of receptors and one of its targets is the NMDA receptor (Taylor et al., Pharmacology of dextromethorphan: Relevance to dextromethorphan/quinidine (Nuedexta®) clinical use. Pharmacol Ther. 164:170-82 (2016 August); incorporated by reference in its entirety). However, DEX is a less potent NMDA receptor antagonist than its metabolite, DO. Accordingly, DEX is less likely to induce phencyclidine-like motor activity than DO. The behavioral effects of DEX, DO and phencyclidine (PCP) were compared in rats. DO (15-120 mg/kg) was similar to PCP (1.25-20 mg/kg) in inducing dose-dependent locomotor hyperactivity, stereotypy and ataxia. DEX (15-120 mg/kg) induced moderate hyperactivity only at the higher doses about 45 min after treatment. DEX and DO modified the locomotor facilitation induced by 10 mg/kg PCP in opposite directions. Pretreatment with DO facilitated, whereas DEX dose-dependently inhibited PCP-elicited hyperactivity (Székely et al., Induction of phencyclidine-like behavior in rats by DO but not DEX, Pharmacol Biochem Behav, 40(2):381-6 (1991 October); incorporated by reference in its entirety).

Example 55

A compound of formula I or SARPO, as well as both enantiomers of its primary metabolite M1 are CYP2D6 inhibitors. DEX is a commonly used substrate in in vitro metabolism studies to reveal 2D6 inhibitory activity of biologically active substances and drugs. In a dedicated set of studies, a compound of formula I or SARPO, and M1 enantiomers are administered prior to DEX and rats' locomotor activity is monitored for 120 min in order to demonstrate that a compound of formula I or SARPO, and M1 enantiomers prevent emergence of hyperactivity in DEX-treated subjects. These studies are paralleled by measurements plasma DEX levels. The combination of pharmacokinetic (plasma DEX concentration) and pharmacodynamic (MK-801- and DEX-induced hyperactivity) studies are used to identify the M1 enantiomer and the dose level(s) producing the most optimal ratio of anti-hyperactivity and DEX metabolism-suppressing effects.

Example 57

Blood Glucose and Insulin Sensitivity

In contrast to the sulfonylurea drugs, which result in significantly higher basal insulin secretion compared to vehicle treatment, DO and its prodrug DEX did not significantly alter basal insulin secretion from mouse or human islets or in vivo (Marquard et al., Characterization of pancreatic NMDA receptors as possible drug targets for diabetes treatment. Nat Med 21(4):363-72 (2015); incorporated by reference in its entirety). More specifically, application of DEX via drinking water (4 mg/ml) overnight changed neither basal plasma insulin nor fasting blood glucose concentrations in mice, but led to significantly higher glucose-induced plasma insulin concentrations and glucose tolerance than were seen in non-DEX-treated controls (glucose administered intraperitoneally at 1.5 mg/kg body weight).

Marguard et al. (2015) suggested that effects of DEX are mediated via NMDA receptor channel blocker and specifically pointed at the rapid metabolism of DEX into DO, a potent inhibitor of the NMDA receptors. To prove NMDA receptor involvement, Marguard et al. demonstrated that glucose-stimulated insulin secretion and glucose tolerance are not observed in mice genetically engineered to lack NMDA receptor function.

To test whether DEX could lead to higher serum insulin concentrations and lower blood glucose concentrations in people with type 2 diabetes mellitus (T2DM), a Phase 2a, Double-blinded, placebo-controlled, randomized, crossover, single-dose proof-of-concept study was performed (Marquard et al., Characterization of pancreatic NMDA receptors as possible drug targets for diabetes treatment. Nat Med 21(4):363-72 (2015); incorporated by reference in its entirety). Twenty males with T2DM on metformin monotherapy (age 59 (46-66) years (mean (range)); mean body mass index (BMI) 29.2 (25.2-34.1) kg m−2; glycated hemoglobin (HbAlc) 6.9 (6.5-7.4)%) were recruited. Each received a single oral dose of 60 mg DEX, 270 mg DEX, 100 mg amantadine or placebo, followed by an oral glucose tolerance test (OGTT) 1 h after drug intake on four treatment days, separated by a washout period of 7-14 days. Consistent with the results in mice, DEX led to neither higher fasting serum insulin concentrations nor lower fasting blood glucose concentrations compared to placebo and did not provoke any severe hypoglycemic events up to a dose of 270 mg. In contrast, following oral glucose intake, both 60 and 270 mg DEX dosages resulted in significantly ($P<0.05$) higher maximal serum insulin concentrations compared to those seen with placebo.

In addition, the primary endpoint was reached for 270 mg DEX; that is, the area under the curve of blood glucose concentrations within the first 2 h of the OGTT (glucose AUC1-3 h) was significantly ($P<0.05$) smaller in individuals who received 270 mg doses of DEX than in the same individuals receiving placebo on a different treatment day.

Blood glucose level is also under control of peripheral 5HT2A receptors (Yamada et al., Hyperglycemia induced by the 5-HT receptor agonist, 5-methoxytryptamine, in rats: involvement of the peripheral 5-HT2A receptor. *Eur J Pharmacol.* 323(2-3):235-40 (1997); incorporated by reference in its entirety). More specifically, administration of non-selective 5HT receptor agonist such as 5-methoxytryptamine induced hyperglycemia that is prevented by pretreatment with 5-HT2A receptor antagonist or inverse agonist ketanserin as well as peripherally acting 5-HT2 receptor antagonist, xylamidine. These results suggested that 5-methoxytryptamine-induced hyperglycemia is mediated by the peripheral 5-HT2A receptors.

Second-generation antipsychotics with dual dopamine and serotonin receptor antagonism have been associated with an increased risk for impaired glucose tolerance and diabetes mellitus. Though this has been largely attributed to weight gain, there is also a direct, receptor-mediated effect of antipsychotics on glucose tolerance. Certain 5HT2A receptor antagonists such as ketanserin impair insulin sensitivity (Gilles et al., Antagonism of the serotonin (5-HT)-2 receptor and insulin sensitivity: implications for atypical antipsychotics. *Psychosom Med.* 67(5):748-51 (2005)); incorporated by reference in its entirety). In the study by Gilles et al., ten healthy male volunteers were included in a double-blind, placebo-controlled crossover study of a single dose of 40 mg of the 5-HT2 antagonist ketanserin versus placebo. Insulin sensitivity was measured by means of the euglycemic-hyperinsulinemic clamp technique. Subjects were treated with the alpha-1 adrenergic antagonist phenoxybenzamine in both parts of the study to control for ketanserin's effects at the level of this receptor. Compared with the placebo condition, subjects showed a significantly decreased insulin sensitivity after ketanserin (placebo: 9.4+/−3.6 mg/kg/min; ketanserin: 7.7+/−2.1 mg/kg/min; p=0.047).

Thus, combining DEX and 5-HT2A receptor antagonist or inverse agonists may lead to synergistic effects on blood glucose and insulin sensitivity that may be undesired in case of a long-term treatment as it may have unwanted metabolic side-effects qualitatively similar to those observed in patients treated with antipsychotic drugs. These effects may limit the doses of DEX and 5-HT2A receptor antagonist or inverse agonists that can be safely administered as a combination.

There are two approaches that are part of this invention and that enable therapeutic use of combinations of DEX and 5HT2A receptor antagonists while reducing the risks of peripheral metabolic adverse effects.

One approach is based on the use of 5HT2A receptor antagonist that inhibits CYP2D6 and thereby reduces the conversion of DEX into DO. Both DEX and DO are NMDA receptor channel blockers, and NMDA receptor inhibition in pancreatic islets was suggested to be responsible for glucose-stimulated insulin secretion, and glucose intolerance enhanced by DEX and DO (Marquard et al., Characterization of pancreatic NMDA receptors as possible drug targets for diabetes treatment. Nat Med 21(4):363-72 (2015); incorporated by reference in its entirety). Since DO is more potent NMDA receptor channel blocker than DEX (Pechnick et al., Comparison of the Effects of DEX, DO, and Levorphanol on the Hypothalamo-Pituitary-Adrenal Axis, The Journal Of Pharmacology and Experimental Therapeutics, 309:515-522 (2004); incorporated by reference in its entirety), inhibition of DEX metabolism via CYP2D6 may reduce the expression of effects of DEX on glucose-stimulated insulin secretion and glucose tolerance and, therefore, risks of metabolic side-effects.

The second approach is the selection of a 5HT2A receptor antagonist that has the best ratio of central vs. peripheral 5HT2A receptor occupancy. Accordingly, a 5HT2A receptor antagonist is chosen to produce therapeutically relevant central 5HT2A receptor occupancy at the doses that are at lowest risk of producing unwanted metabolic effects such as, but not limited to, glucose intolerance.

The compound of formula I is a 5HT2A receptor antagonist that has 2D6 inhibitory properties. Acute and chronic effects of a compound of formula I or SARPO, on glucose tolerance and insulin resistance have been examined (Takishita et al., Effect of sarpogrelate hydrochloride, a 5-HT2 blocker, on insulin resistance in Otsuka Long-Evans Tokushima fatty rats (OLETF rats), a type 2 diabetic rat model. J Cardiovasc Pharmacol 43(2):266-70 (2004); incorporated by reference in its entirety). In these studies, Otsuka Long-Evans Tokushima Fatty rats, a model of type 2 diabetes, were randomly assigned to 2 groups; those with 30 mg/kg BW/d a compound of formula I or SARPO, treatment of 4 weeks (HTB group) and without (control group). The glucose infusion rate was significantly increased in the HTB group compared with the control group. The blood glucose levels after oral glucose tolerance test and levels of plasma insulin and lipids were significantly lower in the HTB group than in the control group. a compound of formula I or SARPO, was shown to reverse insulin resistance induced by various means including glucocorticoid drug treatment (Ma et al., Effective treatment with a combination of peripheral 5-hydroxytryptamine synthetic inhibitor and 5-hydroxytryptamine-2 receptor antagonist on glucocorticoid-induced whole-body insulin resistance with hyperglycemia. J Diabetes Investig 7: 833-844 (2016); incorporated by reference in its entirety).

Synergistic effects of a compound of formula I or SARPO, on blood glucose and insulin sensitivity have been shown for several drugs including carbidopa (Ma et al., Effective treatment with a combination of peripheral 5-hydroxytryptamine synthetic inhibitor and 5-hydroxytryptamine-2 receptor antagonist on glucocorticoid-induced whole-body insulin resistance with hyperglycemia. J Diabetes Investig 7: 833-844 (2016); incorporated by reference in its entirety) and pioglitazone (Iizuka et al., Beneficial effects of a compound of sarpogrelate hydrochloride, a 5-HT2A receptor antagonist or inverse agonist, supplemented with pioglitazone on diabetic model mice. Endocr Res. 34(1-2):18-30 (2009); incorporated by reference in its entirety).

Insulin-sensitizing effects of a compound of formula I or SARPO, have also been confirmed in humans (Kokubu et al., Persistent insulin-sensitizing effects of sarpogrelate hydrochloride, a serotonin 2A receptor antagonist, in patients with peripheral arterial disease. Circ J 70(11): 1451-6 (2006); incorporated by reference in its entirety). Indices of insulin resistance (fasting immunoreactive insulin) were measured before and after 2 weeks of a compound of formula I or SARPO, administration (300 mg/day) in 24 patients (19 men, 76+/−9 years) with peripheral arterial disease. Sixteen of the 24 patients were also examined after 3 months of treatment. After 2 weeks of treatment, significant decreases in fasting immunoreactive insulin (p=0.03) were observed. After 3 months of treatment, significant decreases in fasting immunoreactive insulin (16.0+/−10.3 vs 9.2+/−2.0 microU/ml, p=0.03) were maintained.

A compound of formula I or SARPO, is rapidly metabolized into M1 that also has both 5HT2A receptor antagonist and 2D6 inhibitory properties. Both enantiomers of M1 are biologically active and share the ability to block 5HT2A receptors and 2D6. To establish which of the enantiomers has the most optimal properties for being combined with DEX, effects of these substances alone and in combination with DEX on oral glucose tolerance are assessed (Taniguchi et al., Diabetes, 55, 2371-2378 (2006); incorporated by reference in its entirety). This method is based on the measurement of whole blood glucose and plasma insulin. Test substances are administered to male Sprague-Dawley rats (group size: 8 per group). Animals are tested after an overnight food deprivation and individually housed. Test substance is administered 60 minutes before glucose challenge, i.e. after baseline blood glucose measurement. Animals are challenged with glucose at 2 g/kg as an oral gavage at TO, after blood glucose measurement. Blood glucose is measured from a drop of blood collected from the cut tip of the tail, using a commercially available glucose-meter at 8 time-points: baseline (before treatment), TO (before glucose) and then 15, 30, 60, 90, 120 and 180 minutes post-glucose challenge.

Example 58

Effects of Sarpo/M1 Alone on Ad Pathophysiology

Links between a chronic diabetic metabolic situation and the risk and emergence of AD pathophysiology have long been suspected and substantiated in the recent years (Goldwasser et al., Breakdown of the Cerebrovasculature and Blood-Brain Barrier: A Mechanistic Link between Diabetes Mellitus and Alzheimer's Disease. J Alzheimers Dis 54(2): 445-56 (2016 August 1); incorporated by reference in its entirety). In several large post-mortem series, more than a third of all subjects clinically diagnosed with typical AD showed evidence of cerebrovascular disease and had to be re-classified as mixed dementia (Grandal Leiros et al., Prevalence and concordance between the clinical and the post-mortem diagnosis of dementia in a psychogeriatric clinic, Neurologia S0213-4853(16) 30070-6 (2016); incorporated by reference in its entirety). From a clinical perspective, it is desirable to extend AD therapy beyond currently approved drugs and mechanisms, and also address the cognitive impairment by optimizing a latent diabetic metabolic situation or the fairly frequent Type 2 diabetes in the elderly subjects. Indeed, glycaemic control is thought to have an impact o the severity of cognitive impairment (Zilliox et al., Diabetes and Cognitive Impairment. Curr Diab Rep, 16 (9):87 (2016); incorporated by reference in its entirety).

Due to the specific anti-diabetic actions of a compound of formula I or SARPO, described above, it is, therefore, conceivable to attempt an added benefit on both, symptoms and disease progression in AD, and in cognitive impairment of mainly vascular origin (multi-infarct dementia, vascular dementia, vascular cognitive impairment, etc.).

Based on the Japanese regulatory label, the incidence of adverse events with a compound of formula I or SARPO, therapy in internal medicine is quite low as compared to placebo and the nature of AEs reported not unsettling; therefore, the benefit-risk ratio of added a compound of formula I or SARPO therapy seems defendable, also in an elderly, multimorbid population.

Example 59

Stereoselective Reversal of Psychostimulant-Induced Hyperactivity In Vivo by Compound M1

Motor activity data were collected during a 15-min session in a lit room. Mice had no prior exposure to the motor cages. Immediately before placing the mice in the locomotor chambers, effects on myorelaxation/ataxia were determined by placing each of the mouse's forepaws in contact with a horizontal wire while holding the mouse by the base of the tail. Mice were required to bring at least one hindpaw in contact with the wire within 10 s to be scored as a "pass" and failure to do so was considered ataxic. Each dose or dose combination was tested in a separate group of mice. ACP-103 significantly attenuated MK-801-induced hyperactivity in mice at doses of 0.1 and 0.3 mg/kg s.c. [$F(7,63)=6.010$; $p<0.0001$], consistent with an antipsychotic-like effect.

HEK-293 cells expressing human recombinant 5HT2A receptor were used in the antagonist radioligand binding studies. A compound of Formula I such as SARPO racemate and both enantiomers were applied at concentrations ranging from 3.0E–11 M to 1.0E–07 M. M1 enantiomers were applied at concentrations ranging from 1.0E–11 M to 3.0E–08 M. The IC50 values (concentration causing a half-maximal inhibition of control specific binding) and Hill coefficients (nH) were determined by non-linear regression analysis of the competition curves generated with mean replicate values using Hill equation curve fitting. The inhibition constants (Ki) were calculated using the Cheng Prusoff equation. Both sarpogrelate enantiomers were potent inhibitors of [3H] ketanserin binding (Table 1). M1 enantiomers also potently bind to 5HT2A receptors with the Ki values that are approximately one order of magnitude higher than those of sarpogrelate enantiomers (Table 1). There are no meaningful differences between enantiomers in terms of 5-HT2A receptor binding for sarpogrelate or its main metabolite.

TABLE 3

Inhibitory effects of sarpogrelate (racemate and enantiomers) and M-1 enantiomers on 5-HT2A receptor binding

| Compound | IC50, nM | pKi |
| --- | --- | --- |
| Sarpogrelate racemate | 9.6 | 8.3 |
| (+) Sarpogrelate | 7.5 | 8.4 |
| (−) Sarpogrelate | 11 | 8.2 |
| (+) M1 | 1.2 | 9.1 |
| (−) M1 | 1.3 | 9.2 |

To confirm the ability of M1 enantiomers to induce effects that are relevant to CNS diseases and that are known for 5-HT2A receptor agonists and inverse agonists, separate groups of female Wistar rats (n=6-9), housed 4-5 per cage under standard colony room conditions with free access to food and water, were pretreated intraperitoneally with varying doses of one of the two M1 enantiomers (0, 3 or 10 mg/kg) followed 15 minutes later by 0.1 mg/kg of MK801 or its vehicle and immediately thereafter placed into computer-controlled motor activity recording chambers (25× 35.5×34 cm, L×W×H; transparent Plexiglas walls and a non-transparent plastic floor; enclosed within sound-attenuating ventilated cubicles) for 60 minutes, during which infrared photocell interruptions (5 cm and 14 cm off the floor) were recorded as a measure of motor activity. MK-801 is a phencyclidine-like NMDA receptor channel blocked commonly used in psychopharmacology research on novel therapies including novel antipsychotics. Analysis of variance (ANOVA) has revealed main effects of the M1 dose and the interaction between M1 dose and MK-801 treatment factors for the (−) M1 enantiomer [$F(2,39)=6.154$; $p=0.0048$, $F(2,39)=4.613$; $p=0.0159$, respectively] and not for the (+) M1 enantiomer [$F(2,42)=0.5211$; $p=0.5977$, $F(2,42)=0.5229$; $p=0.5966$, respectively]. As shown in FIG. 7, both doses of the (−)M1 enantiomer as well as 3 mg/kg of a prototypical 5-HT2A receptor antagonist M-100,907 reduced hyperactivity induced by MK-801 (Dunnett's multiple comparisons test). Thus, despite no significant differences between M1 enantiomers in terms of binding to 5-HT2A receptors, surprisingly, only one of the enantiomers exerts efficacy in a preclinical model of psychomotor activation that is known to be sensitive to 5-HT2A receptor blockade.

Example 60

Sarpogrelate-Induced Reversal of Motor Hyperactivity Induced by Olfactory Bulbectomy in Rats In a dedicated set of studies, adult male Sprague-Dawley rats (Charles River, Germany) were subjected to bilateral olfactory bulbectomy performed under ketamine/xylasine anesthesia. The animals were allowed to recover for 14 days following surgery while being handled daily to eliminate any aggressiveness that would otherwise arise. Sham-operated animals were treated in the same way but the olfactory bulbs were left intact. Drugs administration and locomotor activity testing were performed 4 times for each rat with 72 hours break between consecutive test sessions. Prior to each test session, animals were first treated with dextromethorphan (0, 15, 30 or 60 mg/kg. per os) followed 15 min later by sarpogrelate (1, 3 and 10 mg/kg, intraperitoneal) and another 15 min later were placed into Opto-Varimex cages for locomotor activity recording over 30 min. Hyperactivity in rats after olfactory bulbectomy is observed mostly during the early portion of the test sessions. FIG. 8 presents average activity counted over the first 15 min of the test when activity of the bulbectomized animals was significantly higher than that of the sham controls. ANOVA revealed a significant main effects of both surgery and sarpogrelate dose factors [$F(1,88)=5.04$, $p=0.0273$; $F(3,88)=5.02$, $p=0.0029$, respectively]. Post hoc pairwise comparisons (Sidak's multiple comparisons test) confirmed that significant differences between bulbectomized and sham-operated were observed only in rats that were pretreated prior to the test with vehicle instead of sarpogrelate. Bulbectomized rats pretreated with 3 or 10 mg/kg of sarpogrelate spent less time in ambulations compared with the respective controls that received vehicle instead of sarpogrelate. These anti-hyperactivity effects of sarpogrelate are observed at the doses that do not affect activity of sham-operated rats and therefore do not reflect a generalized non-specific impairment of motor capabilities. Thus, surprisingly, despite being previously referred to as a peripherally restricted 5-HT2A receptor antagonist with only minimal penetration across the blood-brain barrier (Obata H et al. Antinociception in rat by sarpogrelate, a selective 5-HT(2A) receptor antagonist, is peripheral. Eur J Pharmacol 404(1-2):95-102 (2000)), sarpogrelate is observed to exert behaviorally specific antihyperactivity effects in rats after olfactory bulbectomy, a model commonly used to study CNS drugs such as antidepressants.

Example 61

Sarpogrelate-Induced Inhibition of Dextromethorphan Metabolism In Vitro and In Vivo Dextromethorphan O-demethylase activity was determined in human liver microsomes. Sarpogrelate (1.0E−8 M to 3.0E−5 M) or M−1 (concentration: 3.0E−9 M to 1.0E−5 M) and dextromethorphan were dissolved in acetonitrile and serially diluted with acetonitrile to the required concentrations to give a final organic solvent concentration of 1.0% in the incubation mixture. The incubation mixtures contained pooled human liver microsomes (final concentrations: 0.25 mg/ml), dextromethorphan, and a NADPH-generating system (1.3 mM NADP+, 3.3 mM glucose 6-phosphate, 3.3 mM MgCl2, and 0.4 U/ml glucose-6-phosphate dehydrogenase). After incubation and centrifugation, the supernatant was diluted 100-fold with acetonitrile and then injected into the LC-MS/MS system. All incubations were performed in triplicate, and mean values were used for analysis. The IC50 values (concentration causing a half-maximal inhibition of control specific binding) and Hill coefficients (nH) were determined by non-linear regression analysis of the competition curves generated with mean replicate values using Hill equation curve fitting. Both sarpogrelate enantiomers inhibited CYP2D6-mediated dextromethorphan O-demethylation (Table 4).

TABLE 4

Inhibitory effects of sarpogrelate (racemate and enantiomers) and M-1 enantiomers on CYP 2D6 activity

| Compound | IC50, µM |
|---|---|
| Sarpogrelate racemate | 1.2 |
| (+) Sarpogrelate | 0.58 |
| (−) Sarpogrelate | 1.3 |
| (+) M1 | 0.038 |
| (−) M1 | 0.096 |

While both enantiomers of M1 markedly inhibited 2D6 activity with the IC50 values of 0.038-0.096 µM, sarpogrelate enantiomers were approximately 10-15 times less potent (Table 4). Based on previous in vivo studies, sarpogrelate was classified as a weak 2D6 inhibitor. This classification was based on a less than 2-fold increase in the substrate AUC (i.e. per guidance provided by the US Food and Drug Administration, Draft guidance for industry: drug interaction studies—study design, data analysis, implication for dosing and labeling recommendations. Center for Drug Evaluation and Research, US FDA (2012), http://www.fda.gov/downloads/Drugs/GuidanceComplianceRegulatoryInformation/Guidance s/ucm292362.pdf).

Pharmacokinetic study was performed in male Wistar rats equipped with the jugular vein cannulas. Sarpogrelate hydrochloride was formulated in Pharmasolv: PBS buffer (5:95) mixture and administered at the dose of 2 mg/kg intravenously. Blood samples were collected from the jugular vein using heparin as anticoagulant at the scheduled time-points: 5 min, 15 min, 30 min, 1 h, 1.5 h, 2 h, 4 h, and 6 h. An LC-MS/MS bioanalytical method was used for the simultaneous quantification of sarpogrelate and M1 in plasma samples. Following 2 mg/kg intravenous bolus administration the plasma level curves showed small inter-individual variability (FIG. 9). Apparent terminal elimination half-life was estimated at 1.21±0.159 h. Formation of M1 metabolite of sarpogrelate was rapid as the highest M1 concentrations were measured at the first sampling time points. In spite of the rapid formation, concentrations of the free M1 metabolite were orders of magnitude lower in the circulation than those of the parent compound (M1/sarpogrelate ratio of 2.98±0.597%). Thus, although M1 enantiomers are significantly more potent 2D6 inhibitors than the parent compound, potential impact of M1 is mitigated by low relative exposure to M1 suggested by the ratio of plasma AUC for M1 and sarpogrelate.

Example 62

In a separate set of studies, ability of sarpogrelate to inhibit dextromethorphan metabolism in vivo was studied in rats. Adult male Sprague Dawley rats (RjHan:SD) purchased from Janvier Labs (France) were housed in a climate-controlled room under a 12 h light/12 h dark cycle with ad libitum access to food and water. Two-three days prior to blood sampling, rats were provided with a catheter in the jugular vein and, thereafter, rats treated once with Carprofen (5 mg/kg) directly after surgery and catheters were rinsed daily with Heparin (500 IE/ml) (20 l/rat/day). On the day of the experiment, dextromethorphan (50 mg/kg) was administered by oral gavage, immediately followed by intravenous bolus injection of sarpogrelate (1, 3 or 10 mg/kg; racemate or one of the enantiomers) or vehicle via vascular access port at t=0 h. Blood samples were collected at four time points until 6 hours post dextromethorphan administration. Sample size was 80 µl Li-heparin whole blood/time point, i.e. 40 µl Li-heparin plasma/time point. Whole blood samples were stored on ice until centrifugation (10 min at 3000 g, 4° C.). Plasma was prepared within 45 min after collection, frozen at −20° C. and stored at this temperature until processed for LC-MS analysis.

As shown in FIG. 10, in rats treated with sarpogrelate (racemate or enantiomers) plasma levels of dextromethorphan continued to be high even at the later time points while, in vehicle-treated rats, dextromethorphan levels declined towards the 6-h time point.

Surprisingly, quantification of the AUC for dextromethorphan indicated that, at the highest tested dose of 10 mg/kg, sarpogrelate increased the dextromethorhan AUC 5.3-6.9 fold. Even at the lower dose of 3 mg/kg, dextromethorphan AUC was increased 2.7 (for the (−) enantiomer) to 3.3 fold (for the (+) enantiomer).

TABLE 5

Area under the curve (0-6 h) analysis of dextromethorphan plasma concentration in rats treated with sarpogrelate (racemate and enantiomers)

| Treatment | Sarpogrelate dose (mg/kg) | Dextromethorphan AUC (ng * hr/ml) | Fold increase (relative to vehicle) |
|---|---|---|---|
| Vehicle | — | 605.8 | — |
| Sarpogrelate racemate | 1 | 2329.5 | 3.8 |
| | 3 | 3356.1 | 5.5 |
| | 10 | 3211.9 | 5.3 |

TABLE 5-continued

Area under the curve (0-6 h) analysis of dextromethorphan plasma concentration in rats treated with sarpogrelate (racemate and enantiomers)

| Treatment | Sarpogrelate dose (mg/kg) | Dextromethorphan AUC (ng * hr/ml) | Fold increase (relative to vehicle) |
|---|---|---|---|
| (+) Sarpogrelate | 1 | 827.0 | 1.4 |
| | 3 | 2021.5 | 3.3 |
| | 10 | 4154.3 | 6.9 |
| (−) Sarpogrelate | 1 | 921.4 | 1.5 |
| | 3 | 1649.5 | 2.7 |
| | 10 | 3195.9 | 5.3 |

Example 63

Inhibition of Phencyclidine-Induced Hyperactivity in Rats Treated by a Combination of Sarpogrelate and Dextromethorphan The behavioral effects of DEX, DO and phencyclidine (PCP) were compared in rats. DO (15-120 mg/kg) was similar to PCP (1.25-20 mg/kg) in inducing dose-dependent locomotor hyperactivity, stereotypy and ataxia. DEX (15-120 mg/kg) induced moderate hyperactivity only at the higher doses about 45 min after treatment. DEX and DO modified the locomotor facilitation induced by 10 mg/kg PCP in opposite directions.

In a dedicated set of studies, SARPO racemate and enantiomers were co-administered with DEX to demonstrate the ability of such drug combination(s) to counteract psychomotor activation and hyperactivity. Male Sprague-Dawley rats were administered intraperitoneally sarpogrelate racemate, (−) sarpogrelate, (+) sarpogrelate or vehicle as well as subcutaneous (racemate experiment) or oral (enantiomer experiments) dextromethorphan or vehicle (water) and were placed individually into the Opto-Varimex-4 autotracks. Fifteen minutes later rats were removed from the boxes, injected with phencyclidine (PCP; 5 mg/kg, subcutaneous) and returned to the auto-tracks for additional 105 min (i.e. until a total recording time of 120 min). Data analysis focused on the second half of the test (60-120 min). ANOVA has revealed significant interaction between the dose of sarpogrelate and the dose of dextromethorphan (FIG. 11, upper panel; $F(9,120)=2.38$, $P=0.015$).

Similar statistically significant interaction with the dose of dextromethorphan was observed for (−) sarpogrelate (FIG. 11, middle panel; $F(9,141)=3.07$, $P=0.002$) but not for (+) sarpogrelate (FIG. 11, lower panel; $F(9,120)=1.65$, $P=0.1$). The post-hoc analysis indicated that, in the presence of dextromethorphan, 3 mg/kg of sarpogrelate racemate as well as 1 mg/kg or 3 mg/kg of (−) sarpogrelate inhibited motor hyperactivity in PCP-treated rats (Dunnett's multiple comparisons test). This pattern of the results is surprising given that the (−) enantiomer of sarpogrelate is less potent than the (+) enantiomer in terms of inhibiting dextromethorphan metabolism both in vitro (Table 4) and in vivo (Table 5).

When given in the absence of dextromethorphan, neither sarpogrelate racemate nor sarpogrelate enantiomers reduced activity in PCP-treated rats. When given in combination with dextromethorphan, inhibitory effects of sarpogrelate were observed irrespective of whether dextromethorphan by itself reduced (subcutaneous administration, experiment with sarpogrelate racemate) or enhanced (oral administration, experiments with sarpogrelate enantiomers) motor activity in PCP-treated rats. Thus, presence of dextromethorphan may be required for sarpogrelate exert inhibitory effects in subjects with psychomotor activation such as rats with hyperactivity after exposure to a psychotomimetic drug PCP. Such pattern of supra-additive interactions between dextromethorphan and sarpogrelate is surprising.

Example 64

Effects of a Combination of Dextromethorphan and Sarpogrelate on Blood Glucose

To test whether a compound of Formula II such as DEX could lead to higher serum insulin concentrations and lower blood glucose concentrations in people with type 2 diabetes mellitus (T2DM), a Phase 2a, Double-blinded, placebo-controlled, randomized, crossover, single-dose proof-of-concept study was performed (Marquard et al., Characterization of pancreatic NMDA receptors as possible drug targets for diabetes treatment. Nat Med 21(4):363-72 (2015); incorporated by reference in its entirety). Twenty males with T2DM on metformin monotherapy (age 59 (46-66) years (mean (range)); mean body mass index (BMI) 29.2 (25.2-34.1) kg m−2; glycated hemoglobin (HbAlc) 6.9 (6.5-7.4%) were recruited. Each received a single oral dose of 60 mg DEX, 270 mg DEX, 100 mg amantadine or placebo, followed by an oral glucose tolerance test (OGTT) 1 h after drug intake on four treatment days, separated by a washout period of 7-14 days. Consistent with the results in mice, DEX led to neither higher fasting serum insulin concentrations nor lower fasting blood glucose concentrations compared to placebo and did not provoke any severe hypoglycemic events up to a dose of 270 mg. In contrast, following oral glucose intake, both 60 and 270 mg DEX dosages resulted in significantly ($P<0.05$) higher maximal serum insulin concentrations compared to those seen with placebo.

In addition, the primary endpoint was reached for 270 mg DEX; that is, the area under the curve of blood glucose concentrations within the first 2 h of the OGTT (glucose AUC1-3 h) was significantly ($P<0.05$) smaller in individuals who received 270 mg doses of DEX than in the same individuals receiving placebo on a different treatment day.

Indices of insulin resistance (fasting immunoreactive insulin) were measured before and after 2 weeks of a compound of formula I or SARPO, administration (300 mg/day) in 24 patients (19 men, 76+/−9 years) with peripheral arterial disease. Sixteen of the 24 patients were also examined after 3 months of treatment. After 2 weeks of treatment, significant decreases in fasting immunoreactive insulin (p=0.03) were observed. After 3 months of treatment, significant decreases in fasting immunoreactive insulin (16.0+/−10.3 vs 9.2+/−2.0 microU/ml, p=0.03) were maintained.

Example 65

Method of Assessment of Blood Glucose Levels and Oral Glucose Tolerance

Test substances were administered to male Wistar (Han) rats (180-280 g at the beginning of the experiments; Janvier Labs) housed in groups under free access to food and water. After overnight food deprivation, the tip of the tail was cut, each rat was weighed, housed individually and left without stress in a quiet room. Approximately 1 hour later, baseline blood glucose was measured from a drop of blood collected from the tail tip, using a commercially available glucose-meter (OneTouch®, Lifescan) and then rats received intraperitoneal injection of sarpogrelate and/or dextromethorphan and 30 min later blood glucose was measured again and rats immediately challenged with glucose at 2 g/kg by oral gavage. Then, blood glucose was measured at 6 time-points until 180 minutes post-glucose challenge. As shown in FIG. 12, there was a main effect of drug treatment ($F(4,59)=12.0$, $p<0.0001$). Post hoc pairwise group comparisons indicated that, when given alone, dextromethorphan has significantly reduced blood glucose level and this effect of dextromethorphan was reversed when it was administered in combination with sarpogrelate racemate or either of the enantiomers.

Example 66

52 Weeks of Chronic Toxicity Test and 5 Weeks of Recovery Test Using Beagle Dogs (Suzuki et al., Pharmacology & Therapeutics Vol 19 Supplement '91)

Compound 50 hydrochloride was given orally to beagle dogs at dose levels of 5, 20, 80, and 320 mg/kg/day for 52 consecutive weeks. No animal died or was sacrificed in extremis regardless of sex. As for general conditions, emesis was noted in males and females receiving 320 mg/kg/day and males receiving 80 mg/kg/day and salivation in females receiving 320 mg/kg/day. The body weight gain was inhibited in males and females receiving 320 mg/kg/day. Food consumption was inhibited in females receiving 80 mg/kg/day and over. Females receiving 320 mg/kg/day also showed an inhibition of water consumption. In the recovery period, the general conditions observed showed no difference between the control and treated groups. There was no treatment related change at electrocardiographic or ophthalmoscopic examination. In the urinalysis, an increase in protein was revealed in females receiving 320 mg/kg/day, in the hematological examination, an increase in a platelet count in males receiving 320 mg/kg/day, and in the biochemical examination, an increase in potassium in males receiving 80 mg/kg/day and over, and females receiving 320 mg/kg/day. These changes recovered after drug withdrawal. The relative weight of the thyroid and liver was increased in males receiving 80 mg/kg/day and over, but no treatment related change was seen in the histopathological examination. In the histopathological examination, fatty degeneration was revealed in the cortico-medullary border zone of the kidney in males receiving 320 mg/kg/day. In the recovery period, however, this change was not found. There was no effect dose level of compound 50 hydrochloride in a 52-week study was estimated at 20 mg/kg.

While contain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention. It will be understood by those skilled in the art that various changes in form and details may be made therein without departing from the spirit and scope of the invention as set forth in the appended claims. Those skilled in the art will recognize, or be able to ascertain using no more than routine experimentation, many equivalents to the specific embodiments of the invention described herein. Such equivalents are intended to be encompassed in the scope of the claims. Reasonable variations are not to be regarded as a departure from the scope of the invention. It will be obvious that the thus described invention may be varied and that various modifications, additions, substitutions, and variations to the illustrative examples set forth herein can be made without departing from the spirit of the invention and are, therefore, considered within the scope of the invention. All documents referenced above, including, but are not limited to, printed publications, and provisional and regular patent applications, are incorporated herein by reference in their entirety.

What is claimed is:

1. A composition for the treatment of brain injury and neuropsychiatric and neurodegenerative diseases or disorders comprising:
   a) a therapeutically and/or prophylactically effective amount of at least one compound of Formula I:

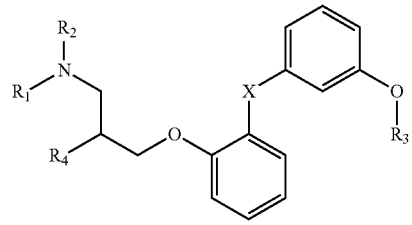

FORMULA I wherein,
$R_1$, $R_2$, and $R_3$ are $C_{1-10}$ alkyl, $C_{3-10}$ cycloalkyl, $C_{5-10}$ aryl, or $C_{5-10}$ heteroaryl;
X is a bond, or $C_{1-10}$ alkyl, or —CO— $C_{1-10}$ alkyl;
$R_4$ is NH—$R_5$, S—$R_5$, O—$R_5$, —CO—$R_5$, or —CO—O— $R_5$ wherein $R_5$ is an acyl radical; or
an enantiomer thereof, metabolite thereof, deuterated derivative thereof, halogenated derivative thereof, prodrug thereof, pharmaceutically acceptable salt thereof, N-oxide thereof, or a combination thereof; and
   b) a therapeutically effective amount of at least one compound of Formula II:

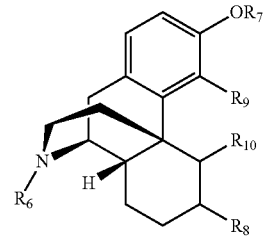

FORMULA IIa

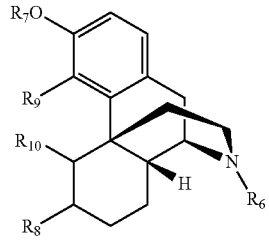

FORMULA IIb wherein,
$R_6$, $R_7$, and $R_8$ are independently H, D, substituted or unsubstituted $C_{1-10}$-alkyl, (halo)$_n$$C_{1-10}$-alkyl, wherein halogen is F, Cl, or Br, and n is an integer from 1 to 12;
$R_9$ and $R_{10}$ are independently H; $C_{1-10}$-alkyl; (halo)$_n$-$C_{1-10}$-alkyl wherein halogen is F, Cl, or Br, and n is an integer from 1 to 12; OH; or $R_9$ and $R_{10}$ together form a five-membered heterocycle wherein the hetero atom is O, S, or N; or an enantiomer thereof, metabolite thereof, deuterated derivative thereof, halogenated derivative thereof, prodrug thereof, pharmaceutically acceptable salt thereof, N-oxide thereof, or a combination thereof;

wherein:

a) the compound having Formula I is a compound selected from the group consisting of:

Compound 10

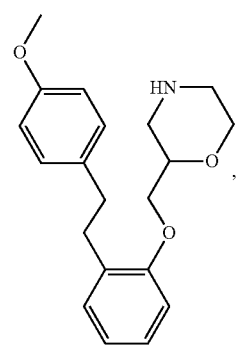

,

Compound 11

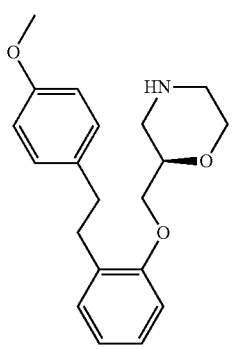

,

Compound 12

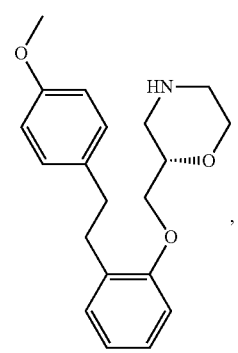

,

Compound 13

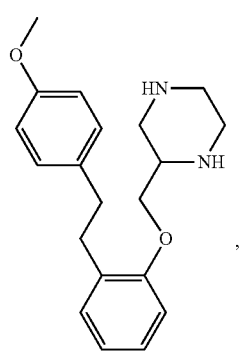

,

Compound 14

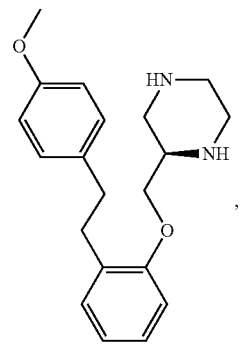

,

Compound 15

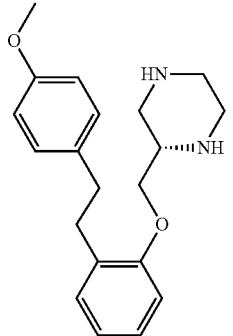

,

Compound 16

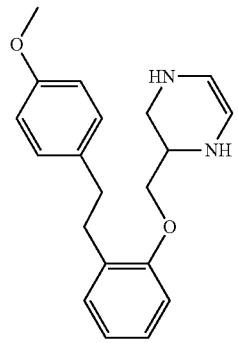

,

Compound 17

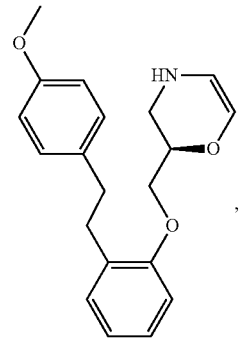

,

Compound 18
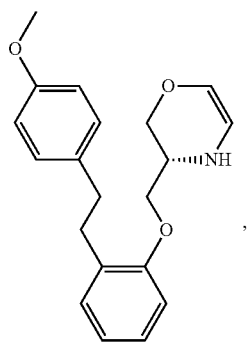
Compound 19
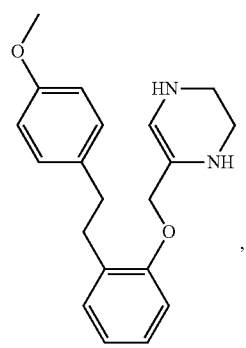
Compound 20
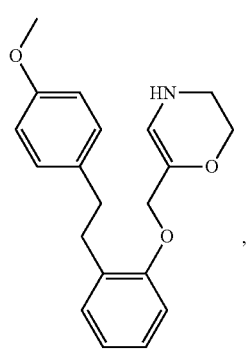
Compound 21
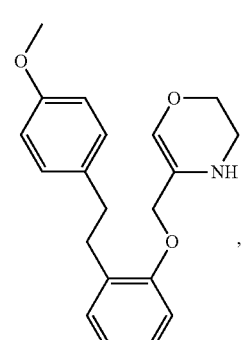
Compound 22
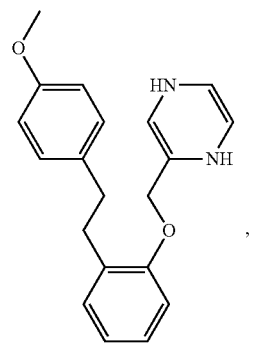
Compound 23
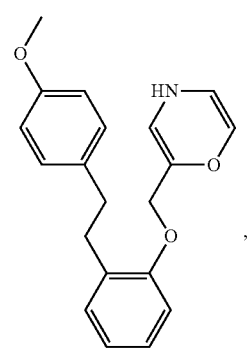
Compound 24
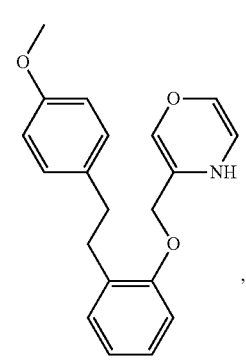
Compound 25
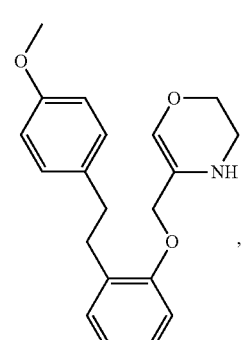

Compound 26
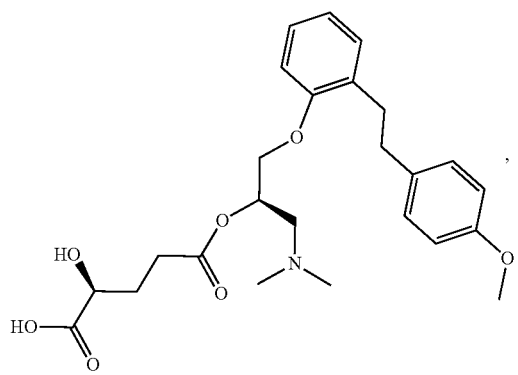
Compound 27
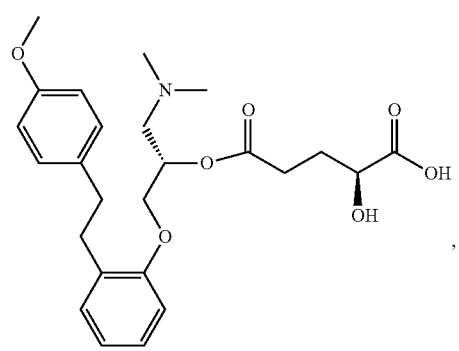
Compound 28
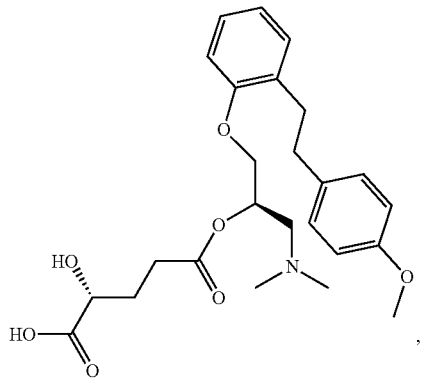
Compound 29
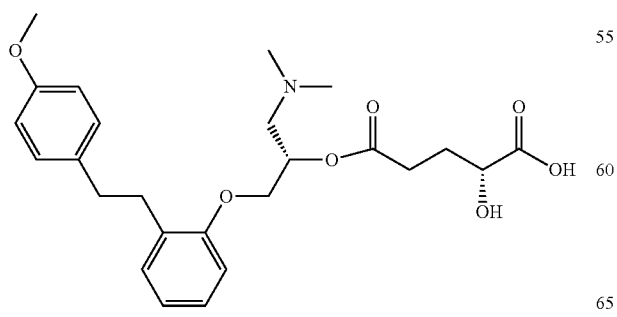
Compound 29
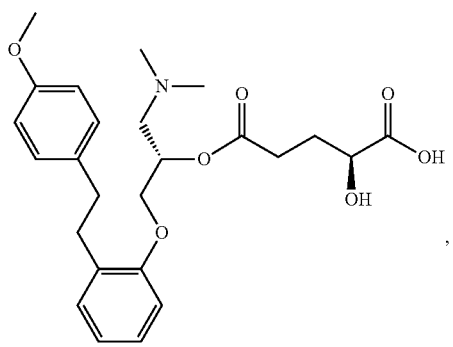
Compound 30
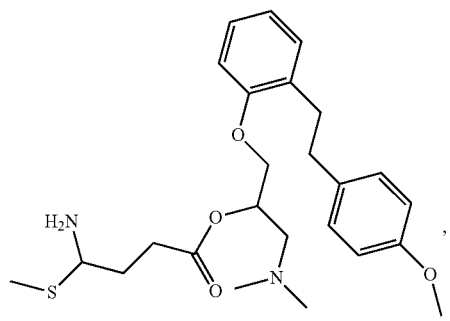
Compound 31
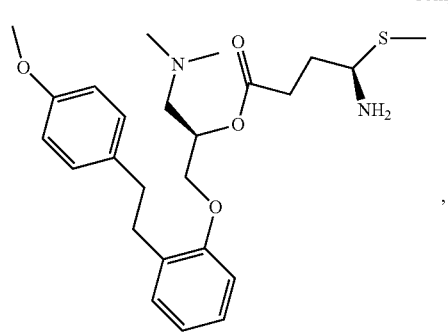
Compound 32
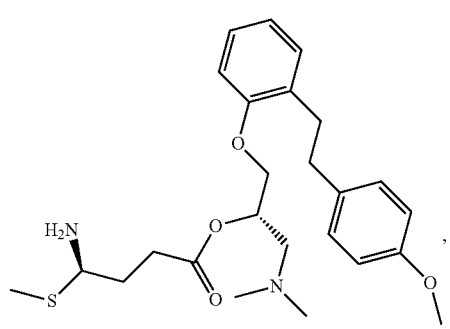

Compound 33
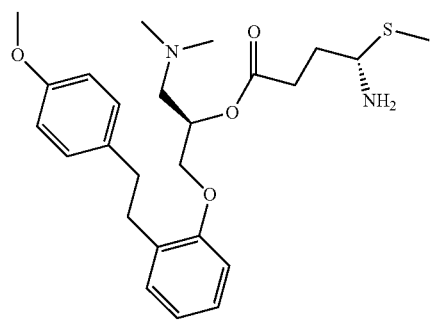
Compound 34
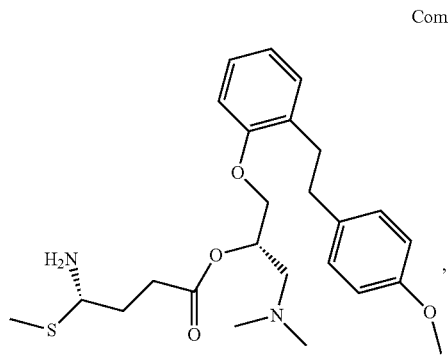
Compound 35
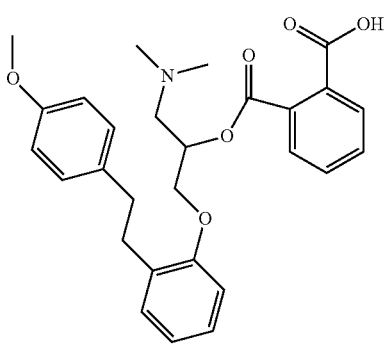
Compound 36
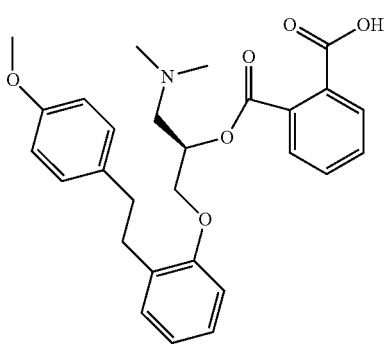
Compound 37
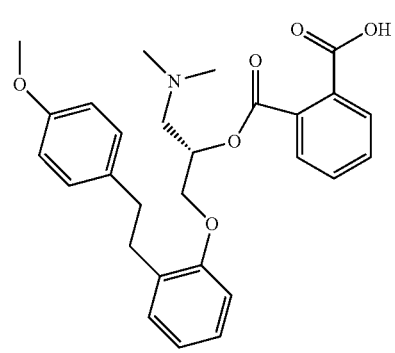
Compound 38
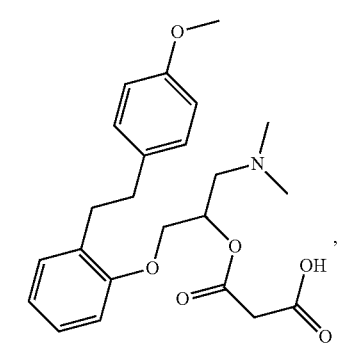
Compound 39
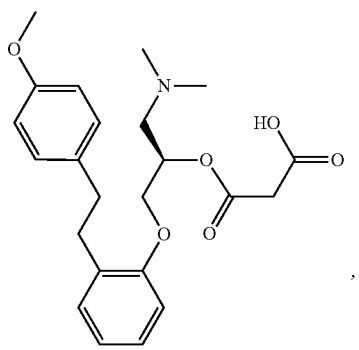
Compound 40
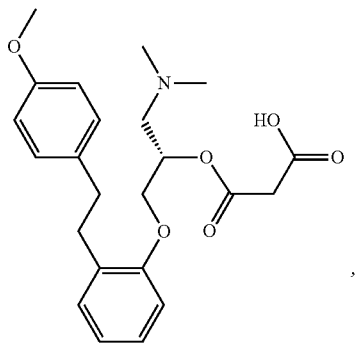

-continued
Compound 41
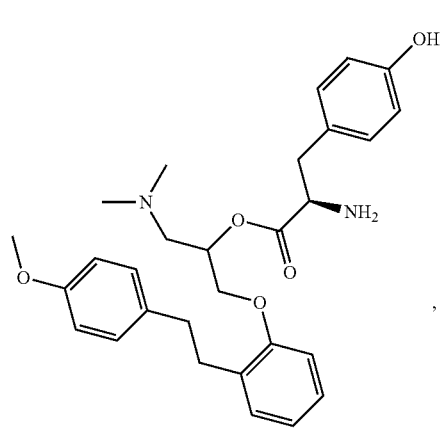,
Compound 42
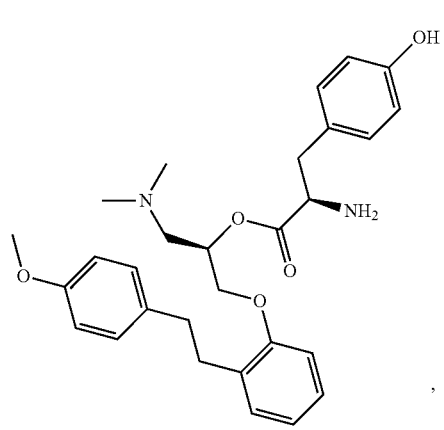,
Compound 43
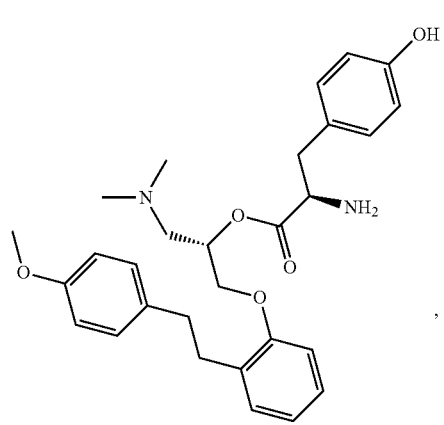,
Compound 44
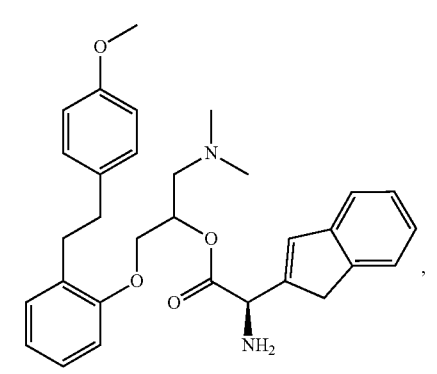,
-continued
Compound 45
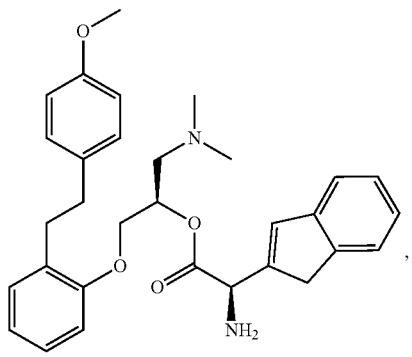,
Compound 46
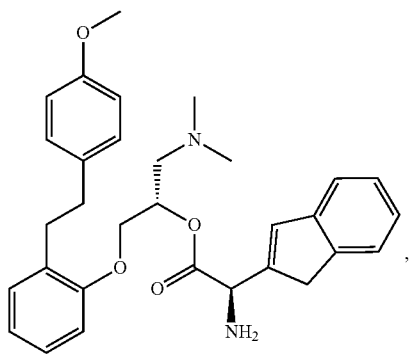,
Compound 47
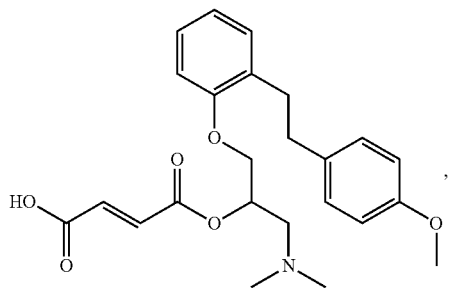,
Compound 48
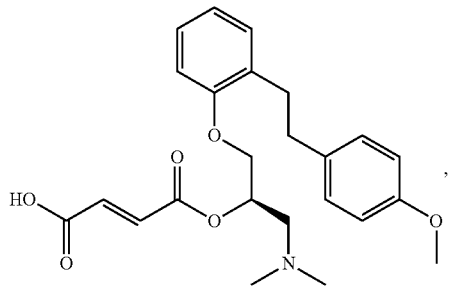,
Compound 49
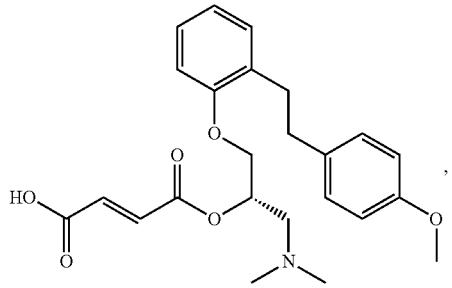, Compound 50
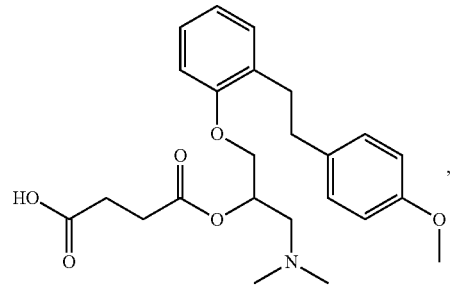
Compound 51
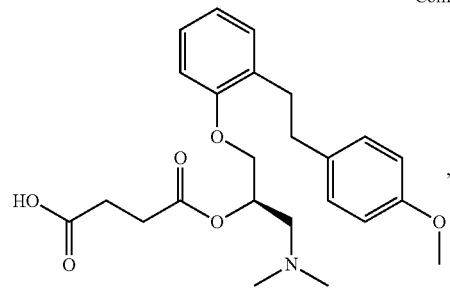
Compound 52
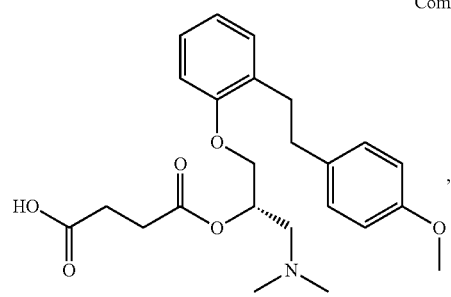
Compound 53
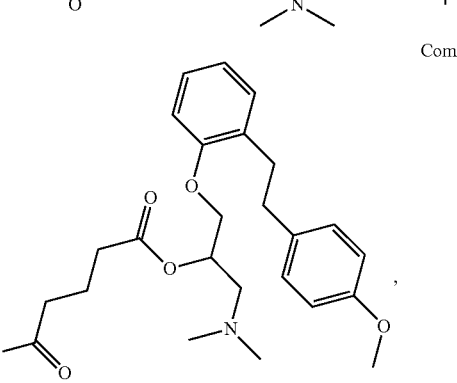
Compound 54
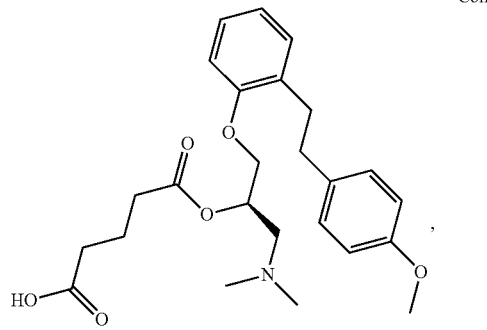
Compound 55
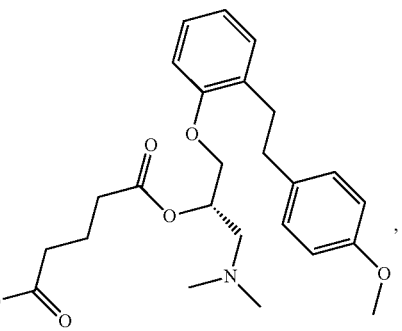
Compound 56
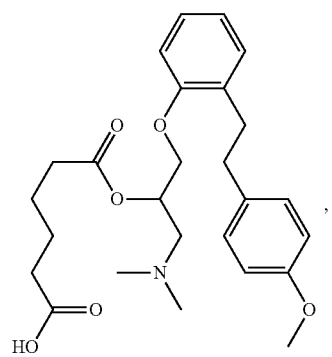
Compound 57
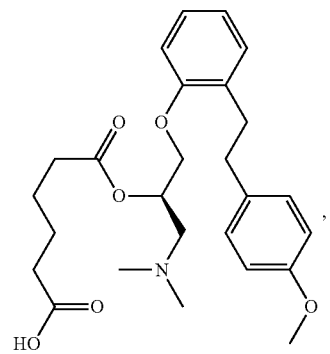
Compound 58
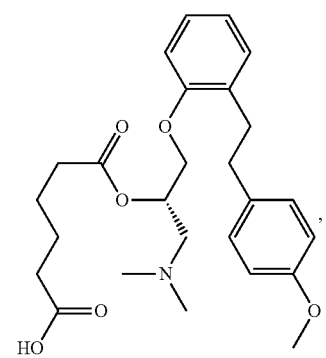

Compound 59
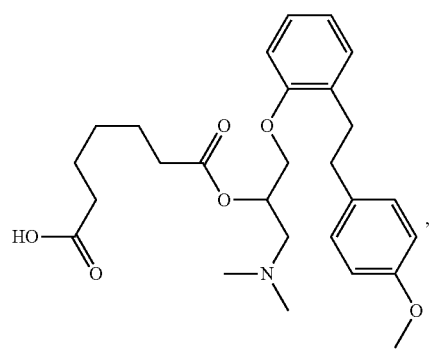
Compound 60
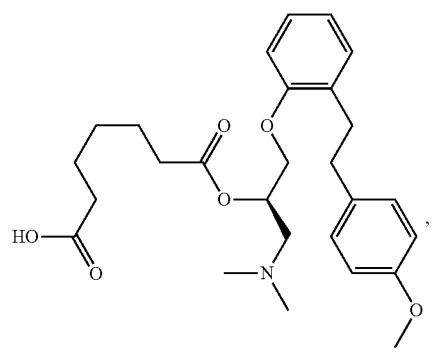
Compound 61
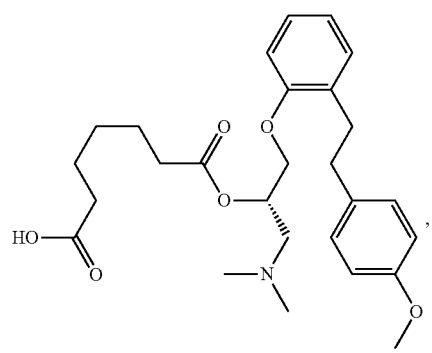
Compound 62
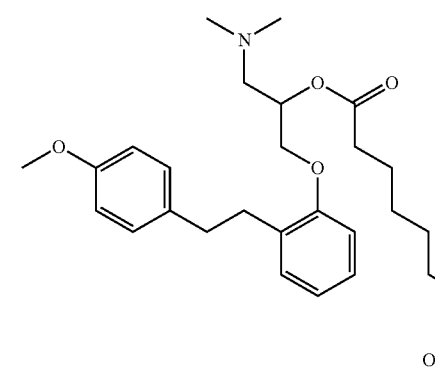
Compound 63
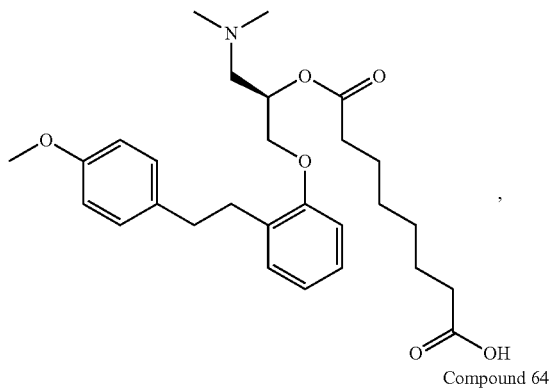
Compound 64
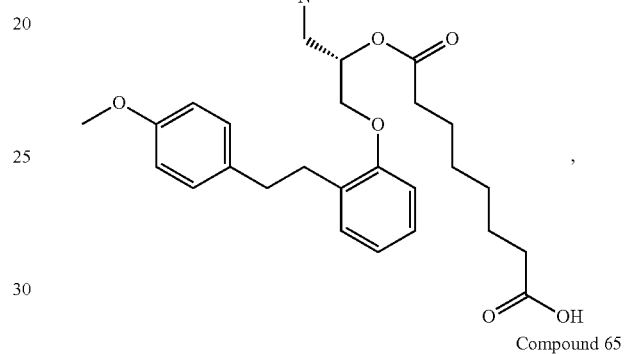
Compound 65
Compound 66
Compound 67

Compound 68
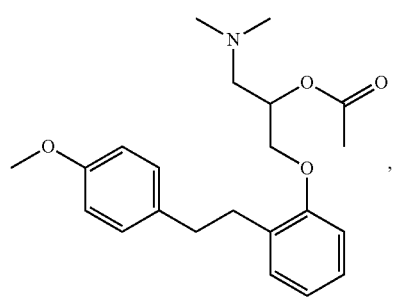
Compound 69
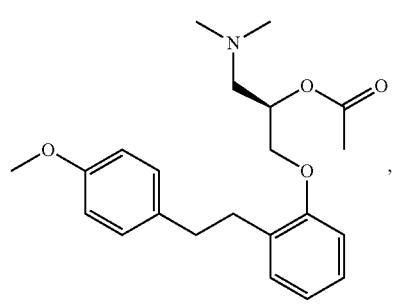
Compound 70
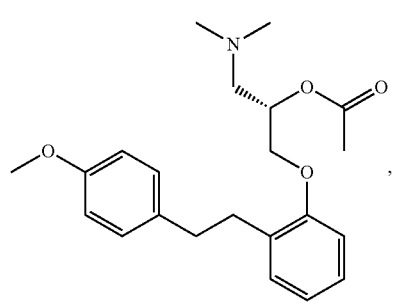
Compound 71
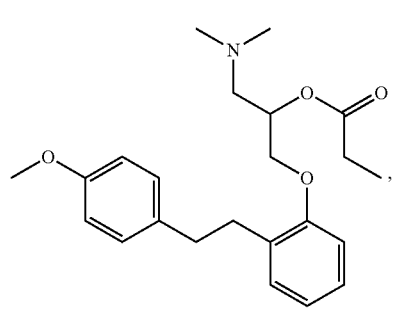
Compound 72
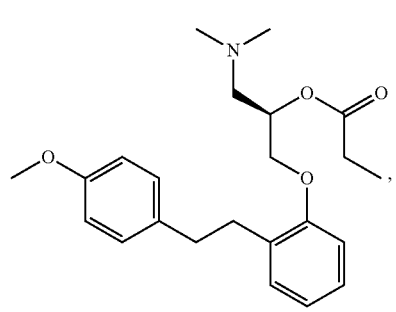
Compound 73
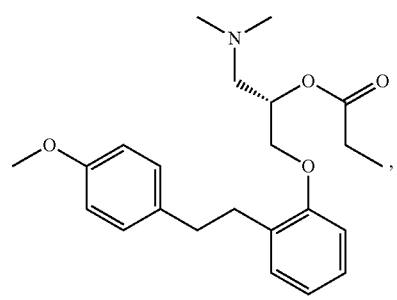
Compound 74
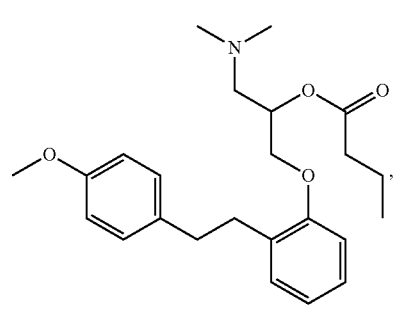
Compound 75
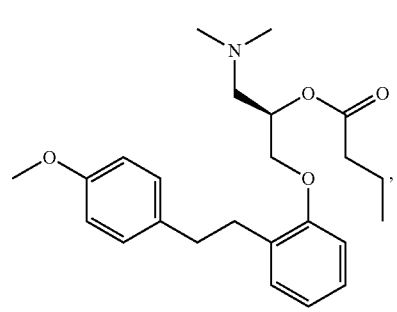
Compound 76
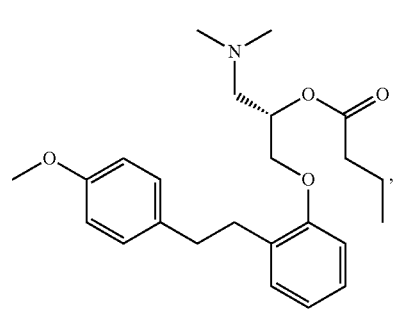
Compound 77
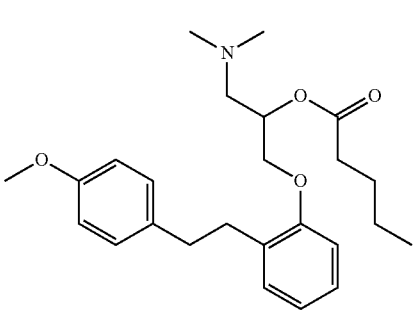

Compound 78
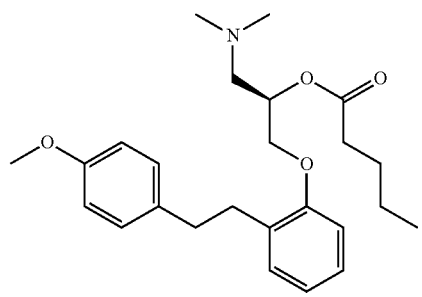
Compound 79
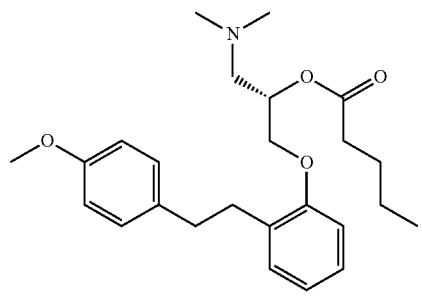
Compound 80
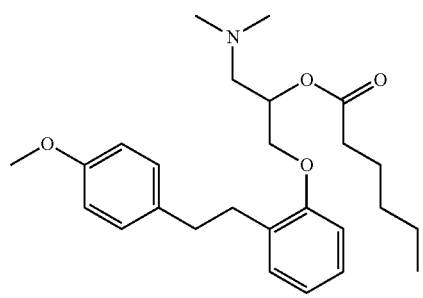
Compound 81
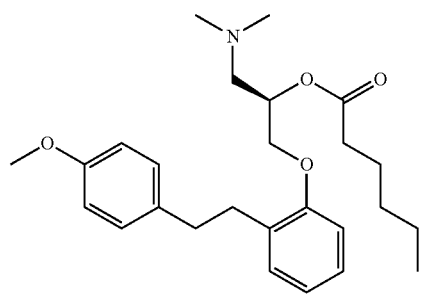
Compound 82
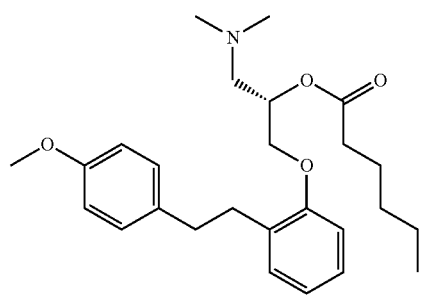
Compound 83
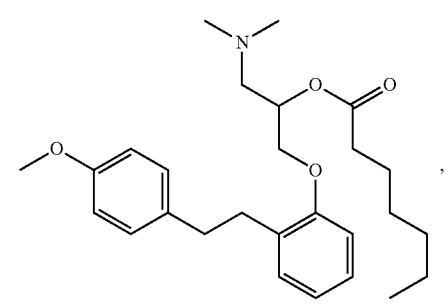
Compound 84
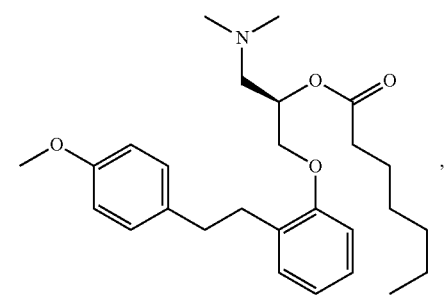
Compound 85
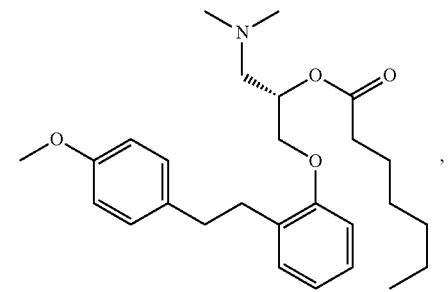
Compound 86
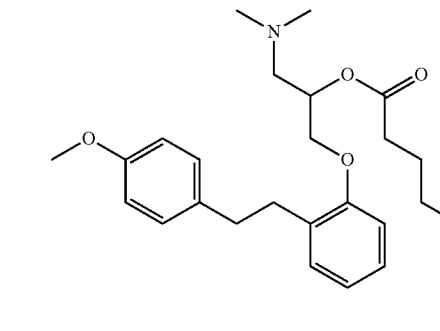

Compound 87
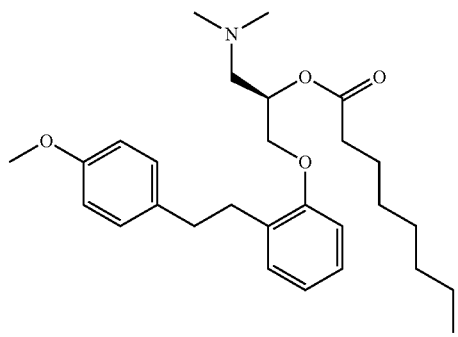
Compound 88
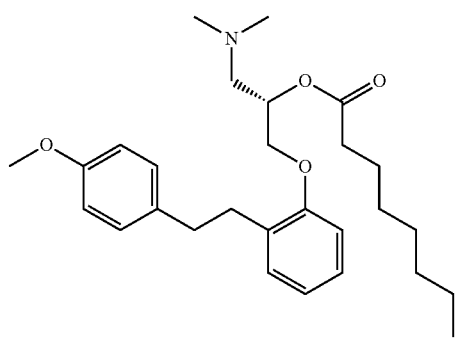
Compound 89
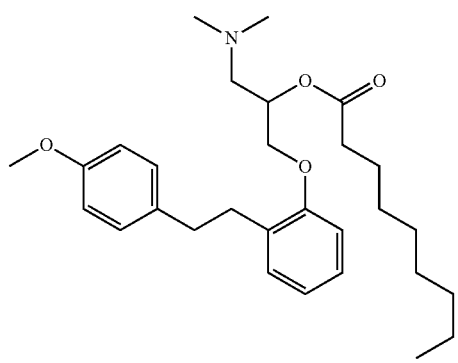
Compound 90
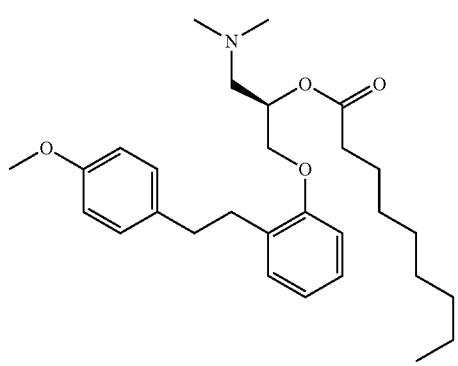
Compound 91
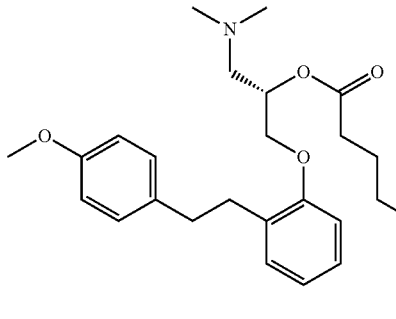
Compound 92
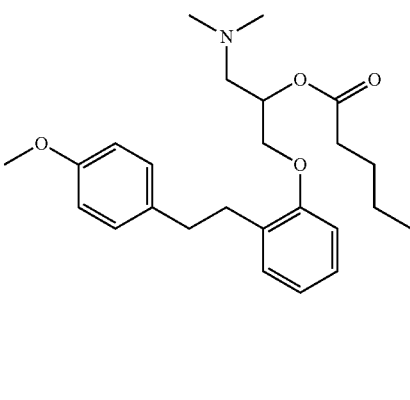
Compound 93
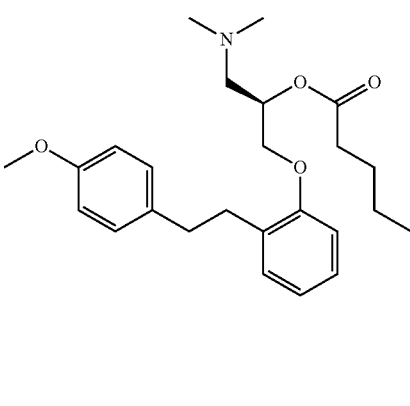
Compound 94
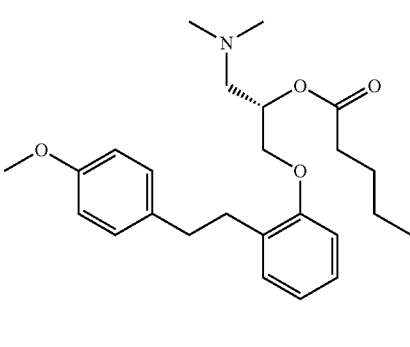

Compound 95
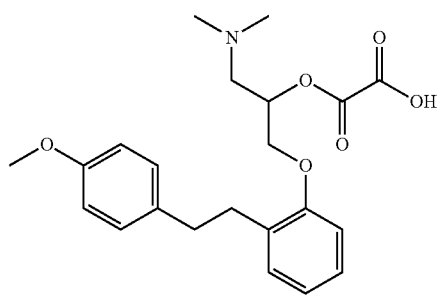
Compound 96
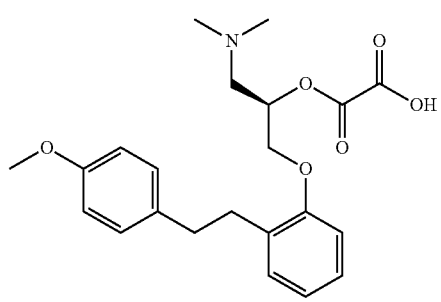
Compound 97
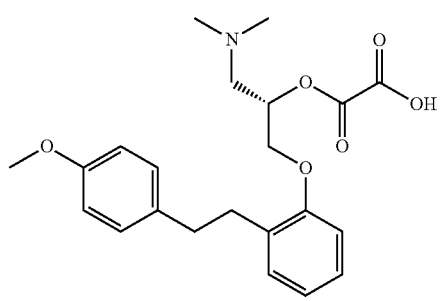
Compound 98
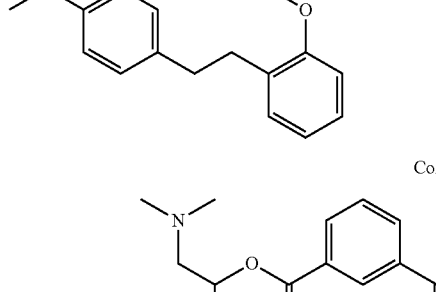
Compound 99
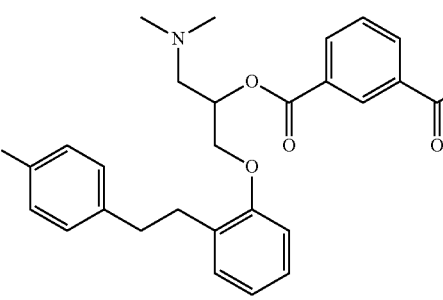
Compound 100
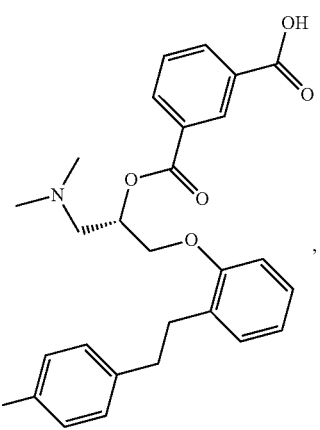
Compound 101
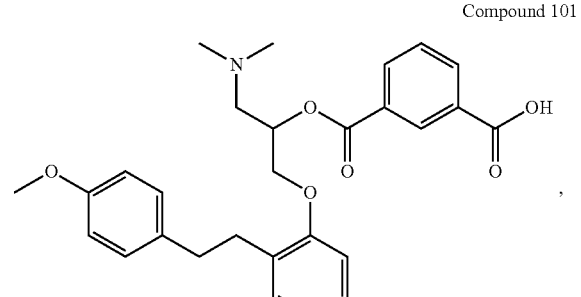
Compound 102
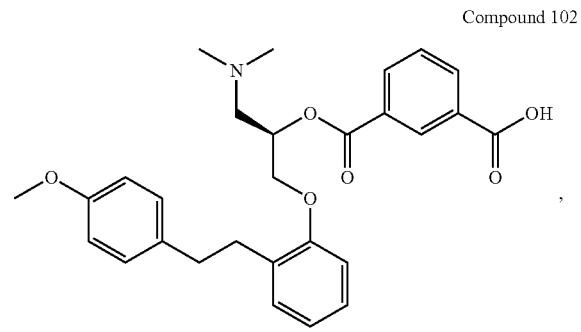
Compound 103
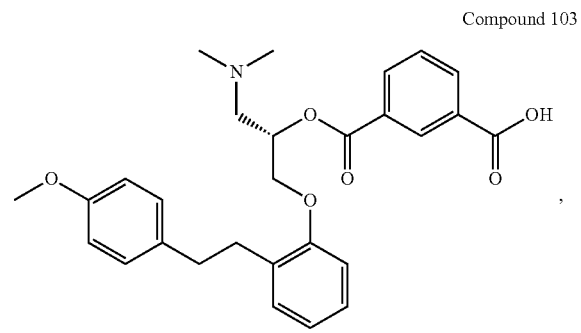

Compound 104
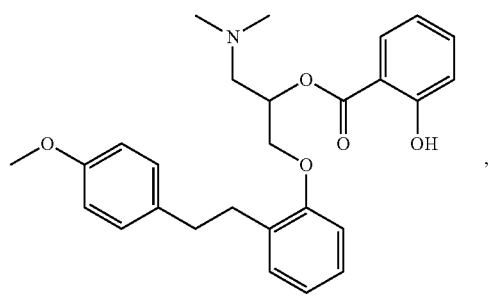
Compound 105
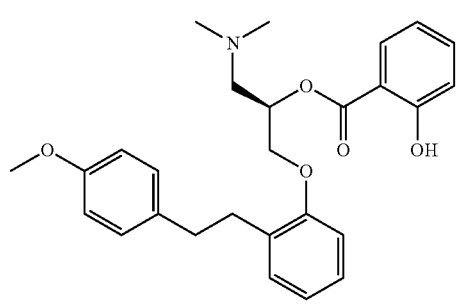
Compound 106
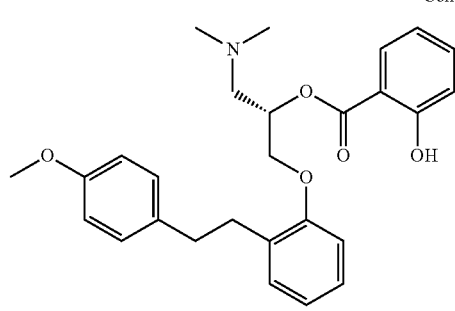
Compound 107
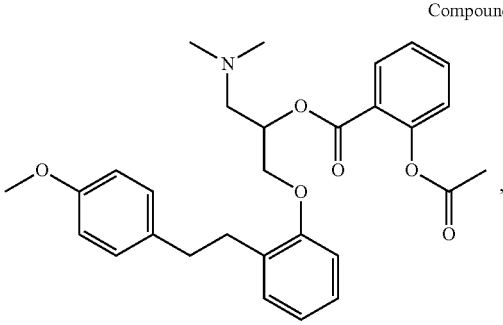
Compound 108
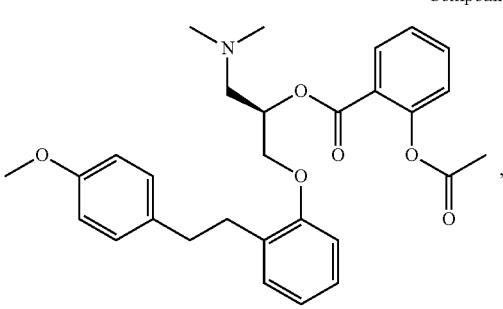
Compound 109
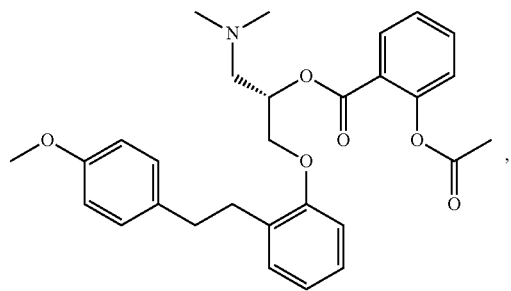
Compound 110
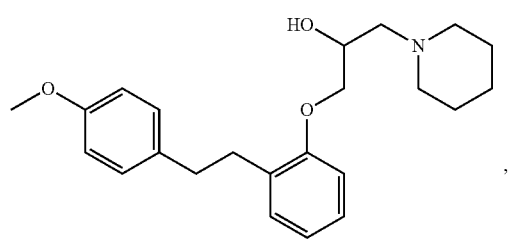
Compound 111
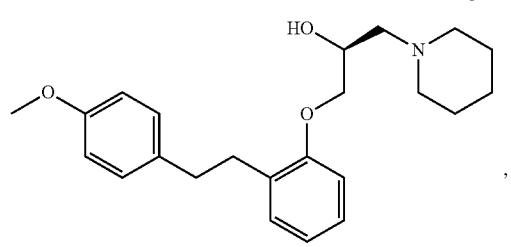
Compound 112
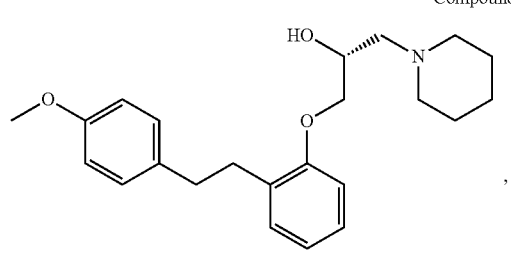
Compound 113
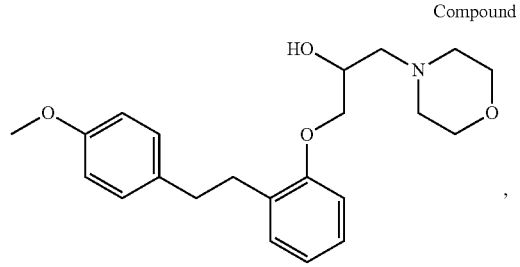
Compound 114
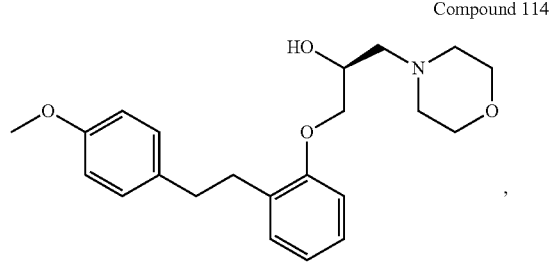

Compound 115
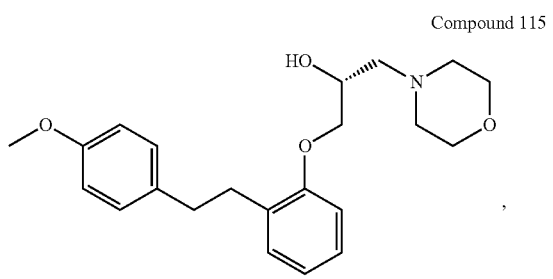
Compound 116
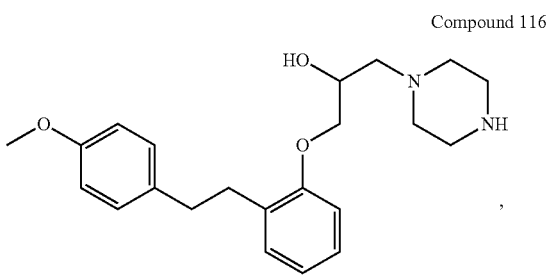
Compound 117
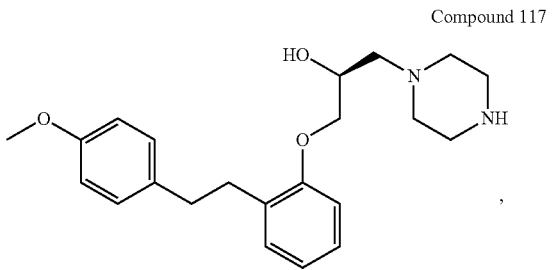
Compound 118
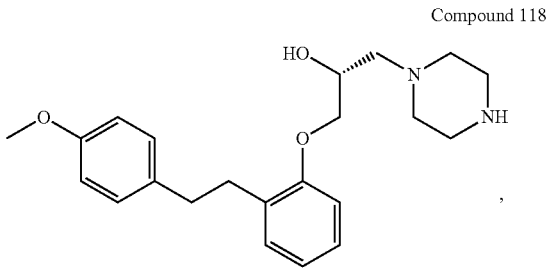
Compound 119
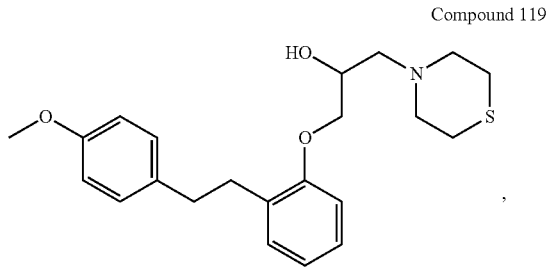
Compound 120
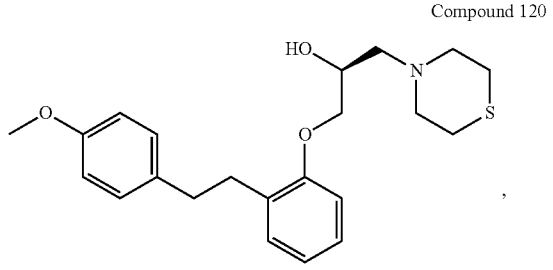
Compound 121
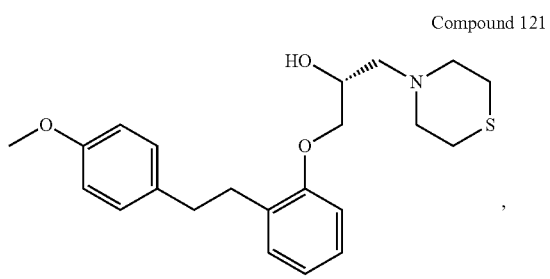
Compound 122
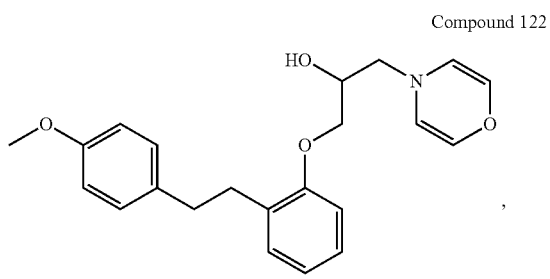
Compound 123
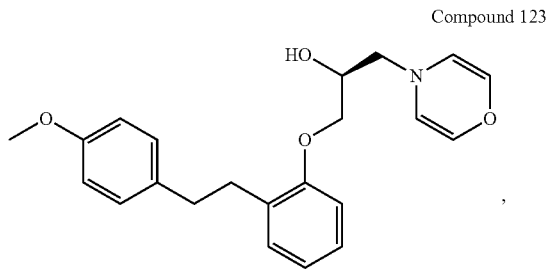
Compound 124
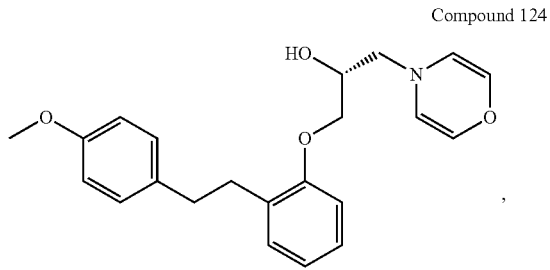
Compound 125
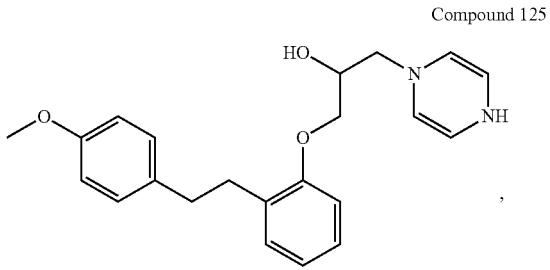
Compound 126
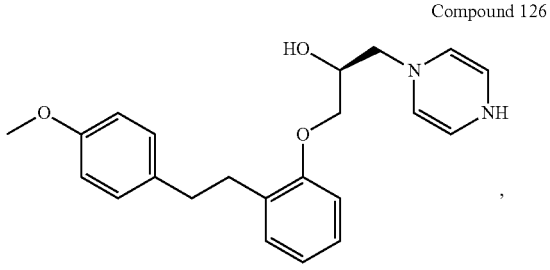

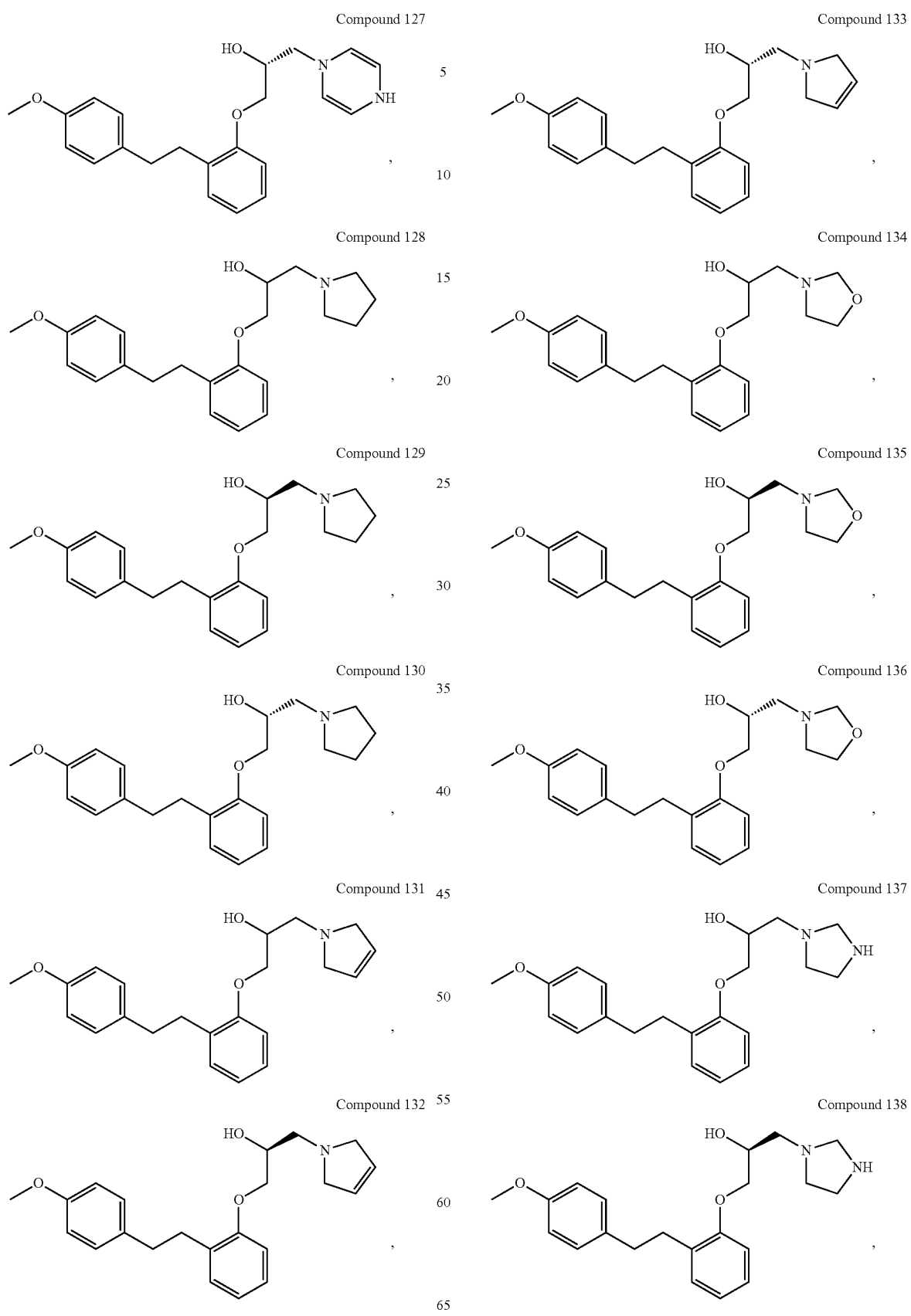

Compound 139
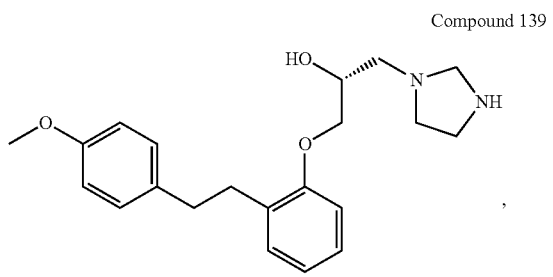
Compound 140
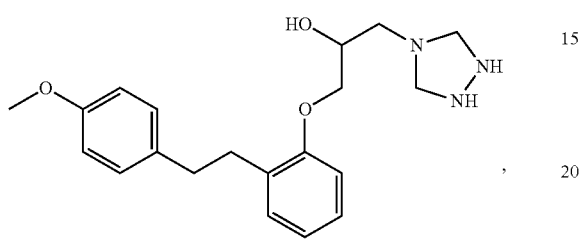
Compound 141
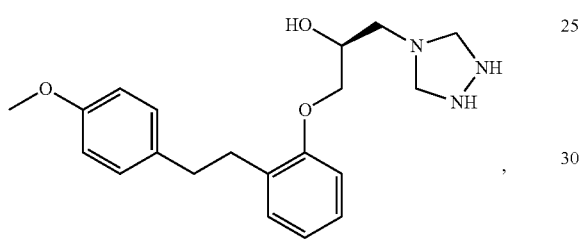
Compound 142
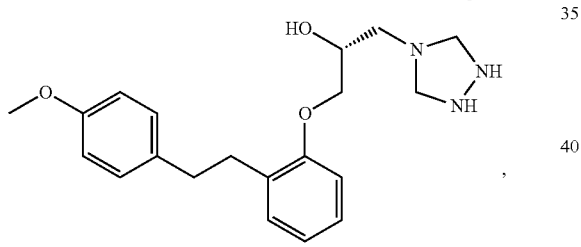
Compound 143
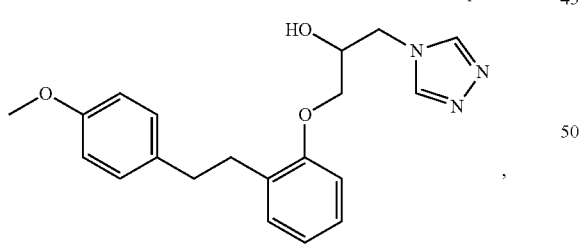
Compound 144
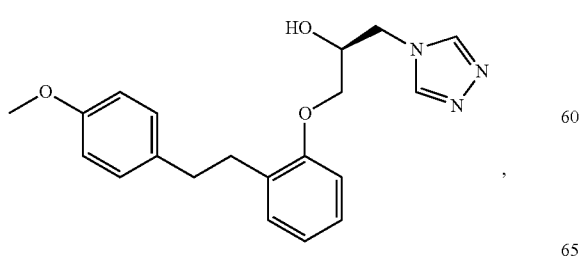
Compound 145
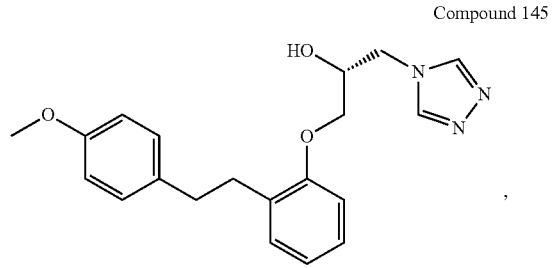
Compound 146
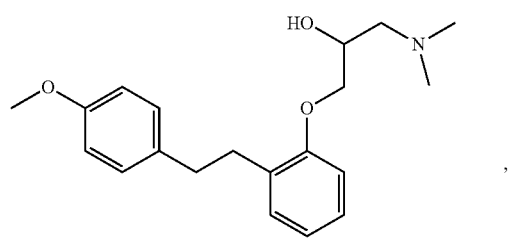
Compound 147
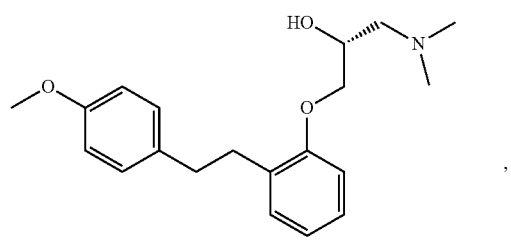
Compound 148
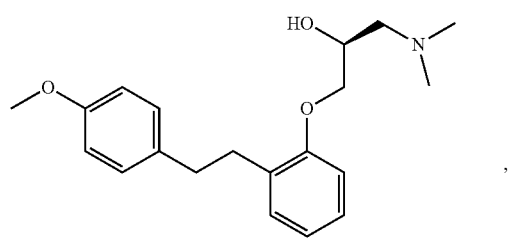
Compound 158
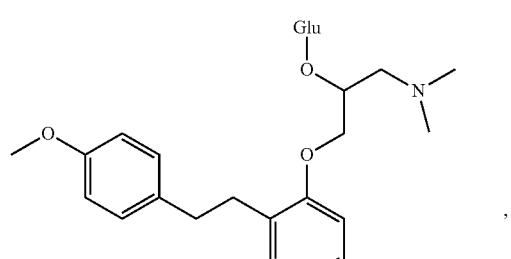
Compound 159
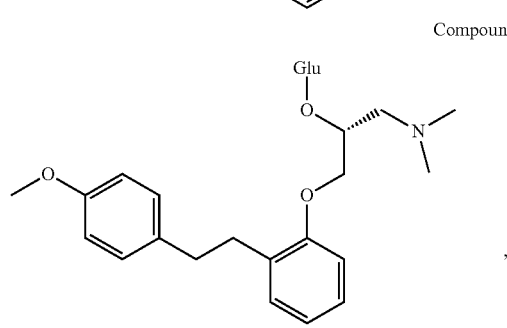

Compound 160
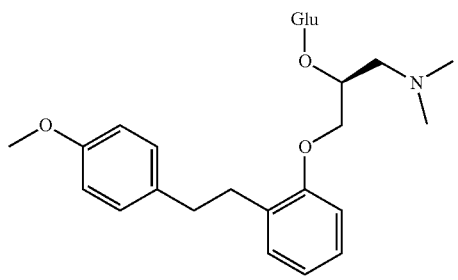
Compound 161
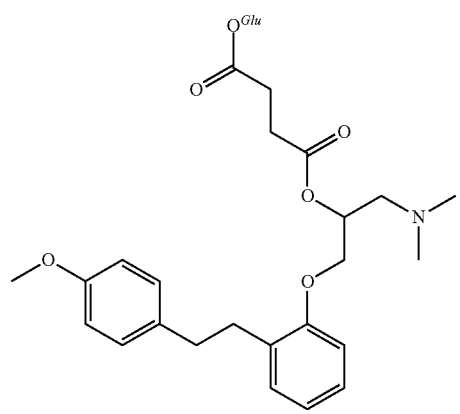
Compound 162
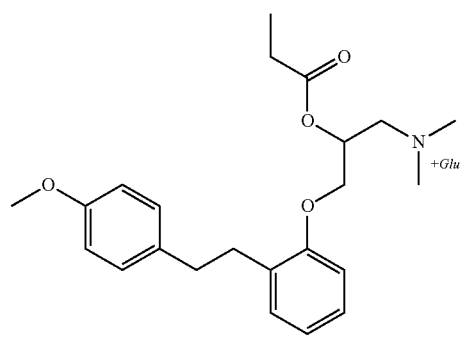
Compound 171
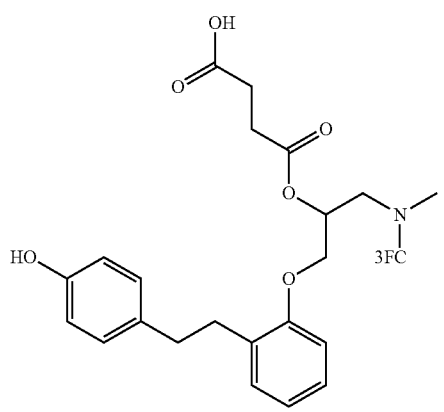
Compound 172
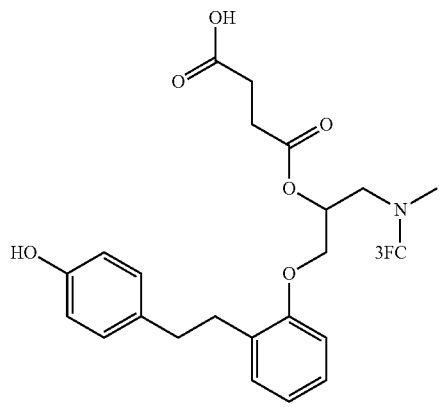
Compound 173
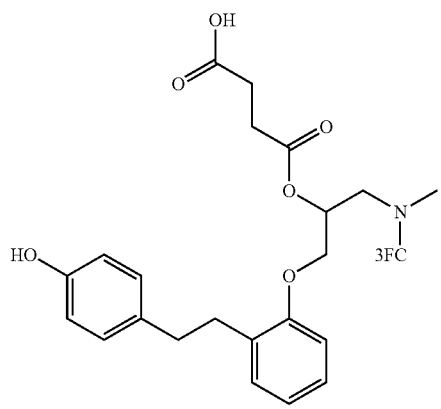
Compound 174
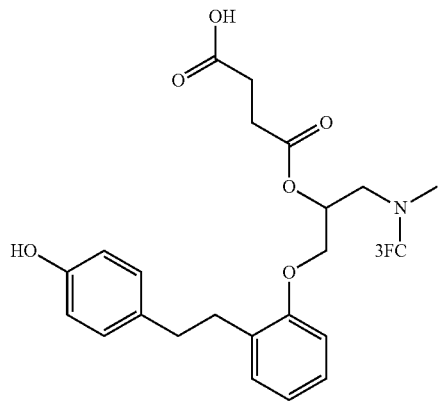

Compound 175
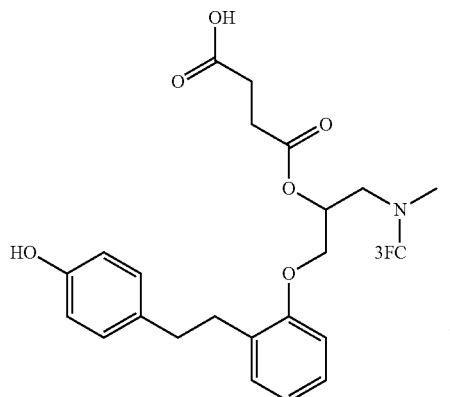
Compound 176
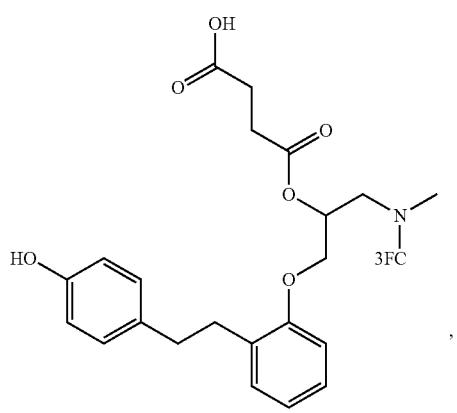
Compound 177
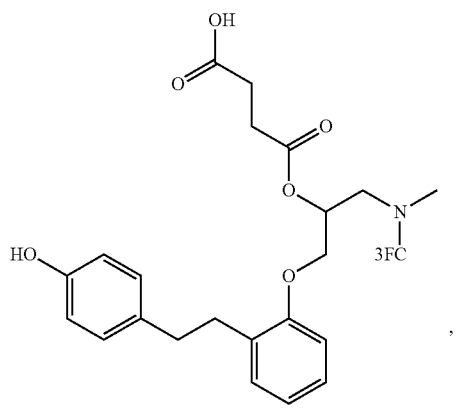
Compound 178
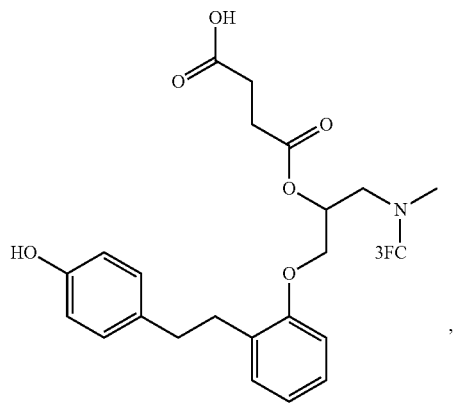
Compound 183
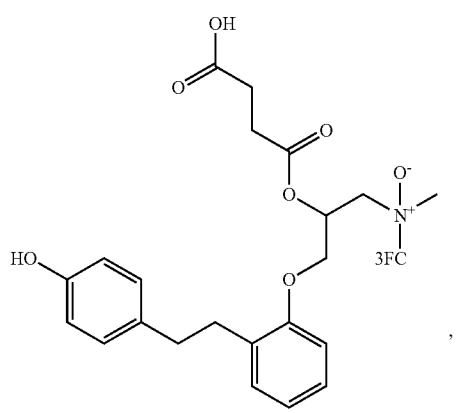
Compound 184
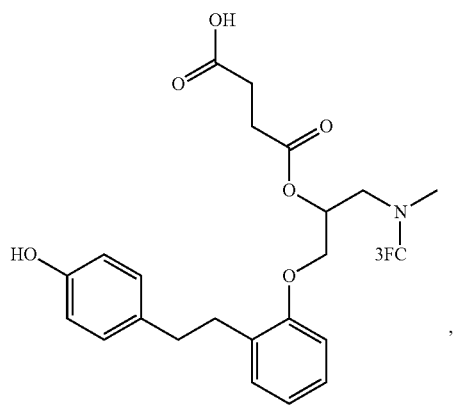

Compound 185
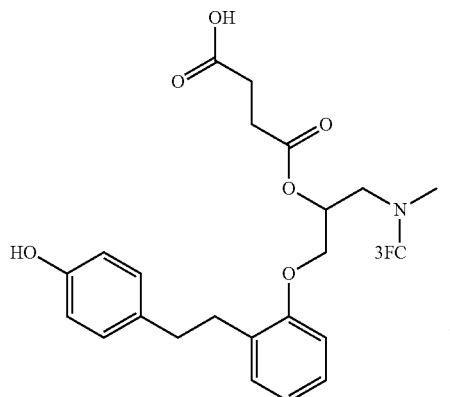
Compound 186
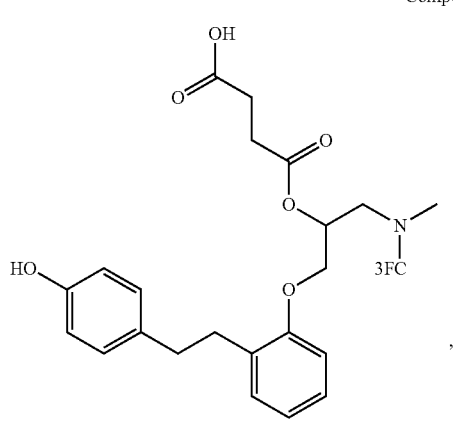
Compound 187
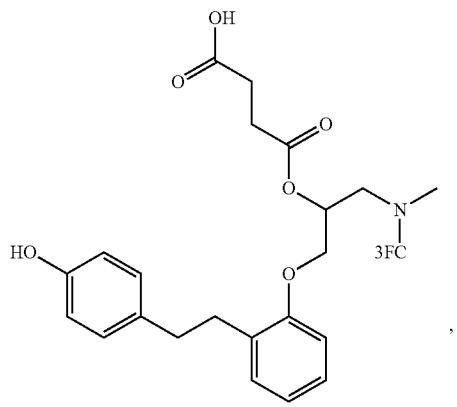
Compound 188
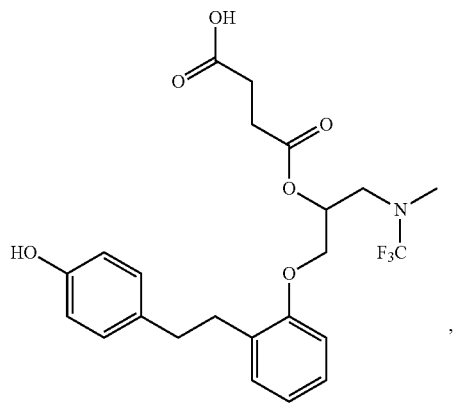
Compound 189
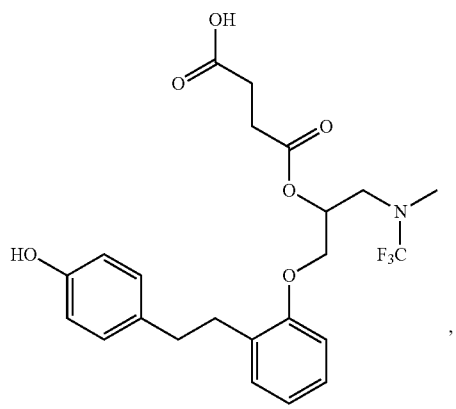
Compound 190
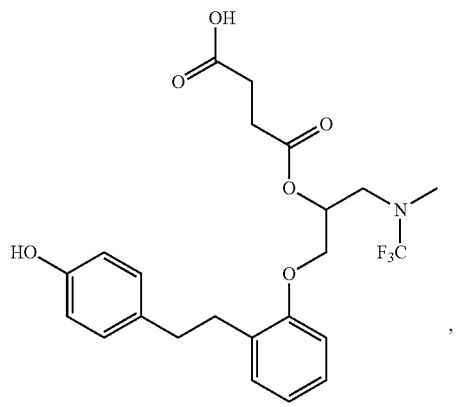

Compound 191
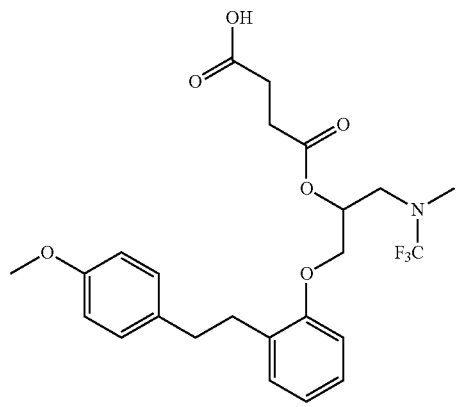
Compound 194
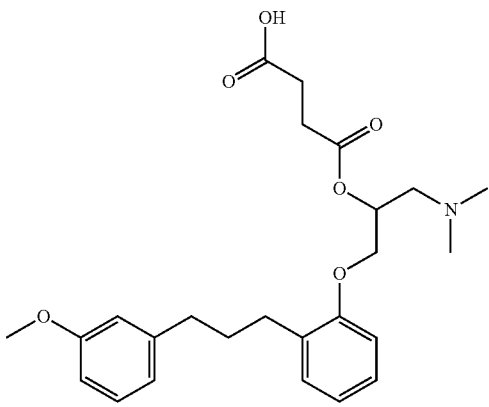
Compound 192
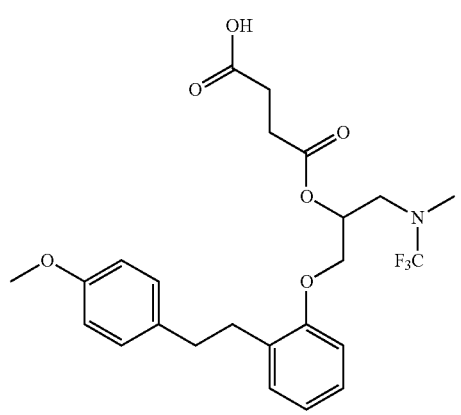
Compound 195
Compound 193
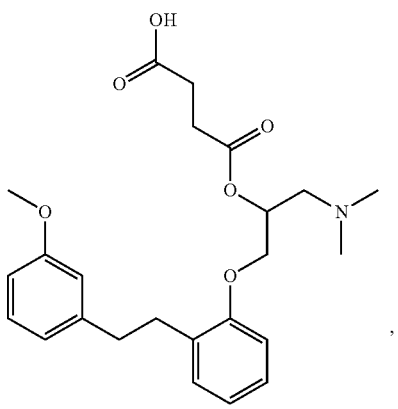
Compound 196
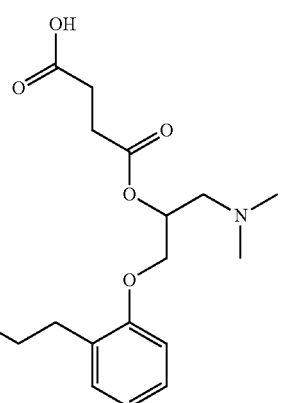

247
-continued
Compound 197
Compound 198
Compound 199
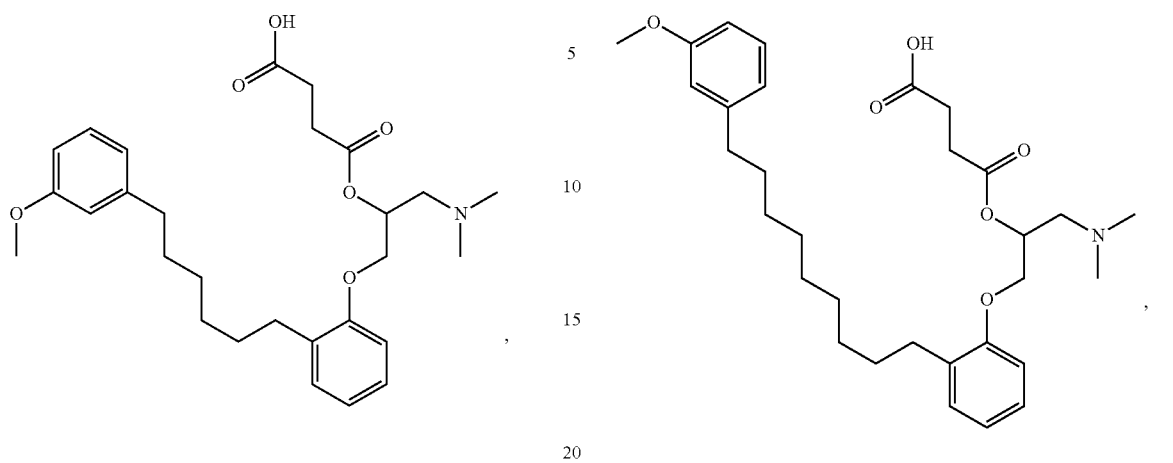
248
-continued
Compound 200
Compound 201
Compound 202
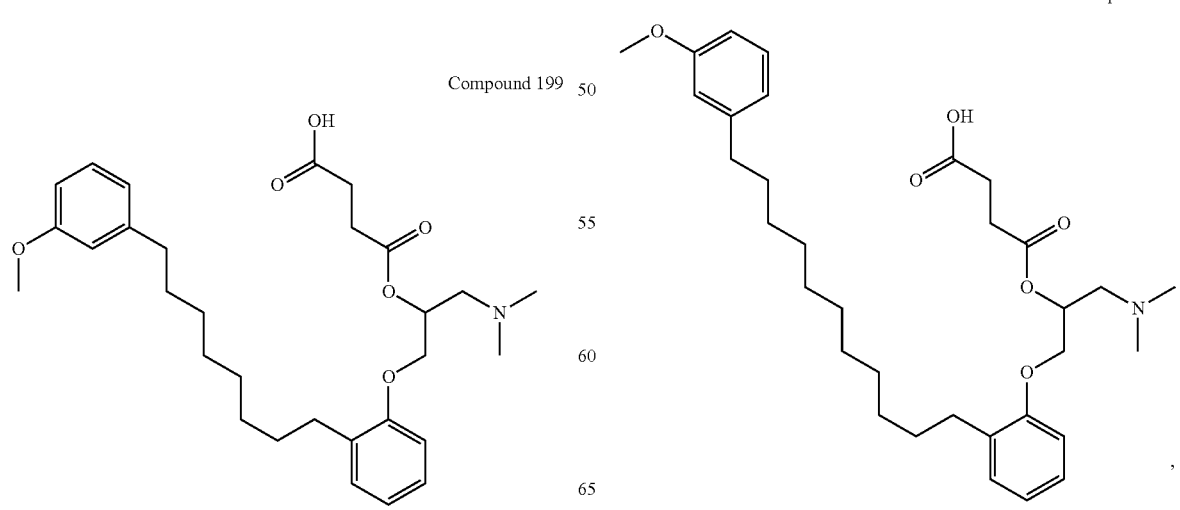

Compound 203
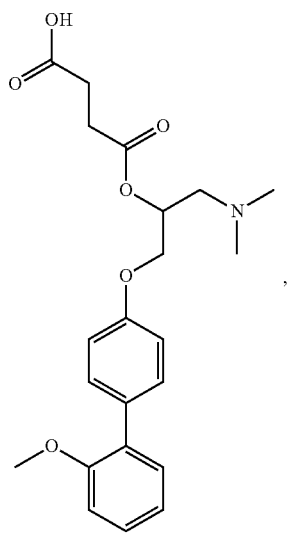
Compound 204
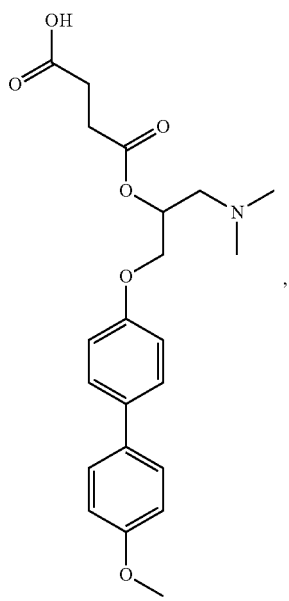
Compound 205
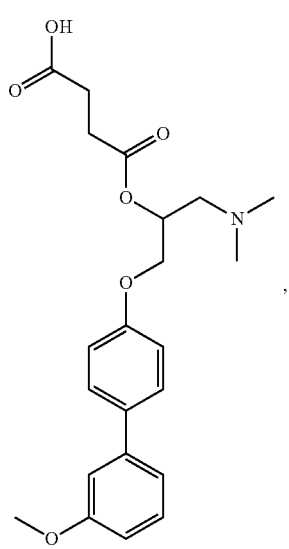
Compound 206
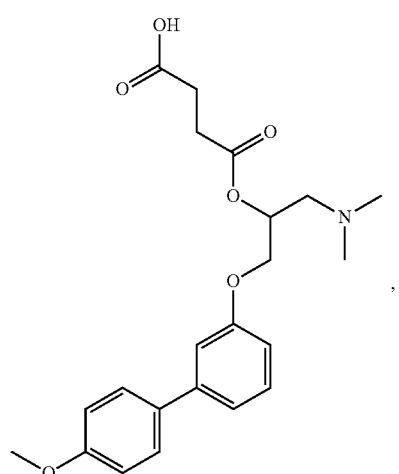
Compound 207
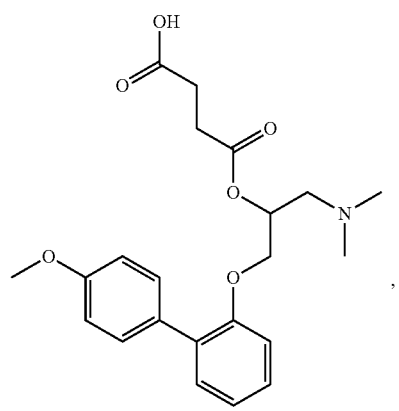
Compound 208
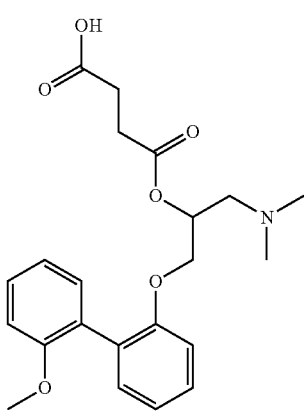

Compound 209
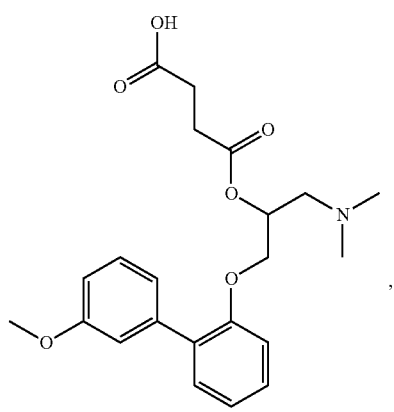
Compound 210
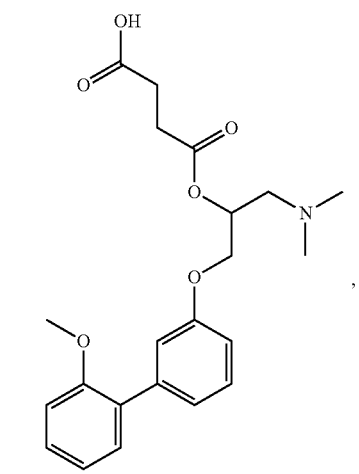
Compound 211
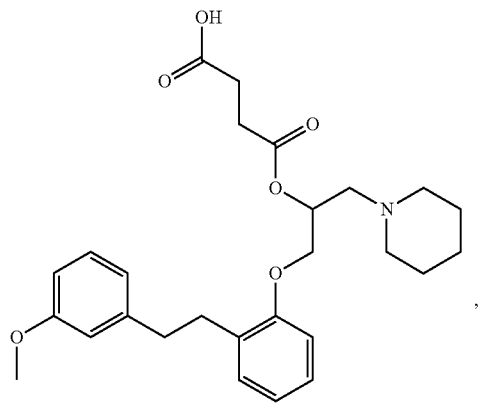
Compound 212
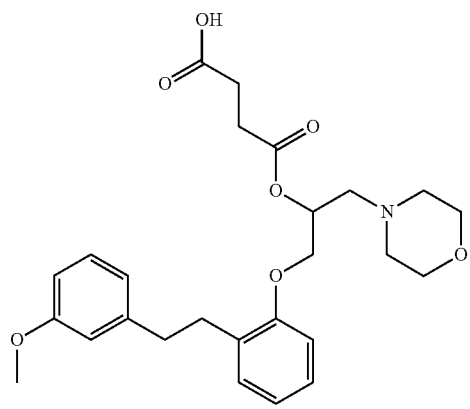
Compound 213
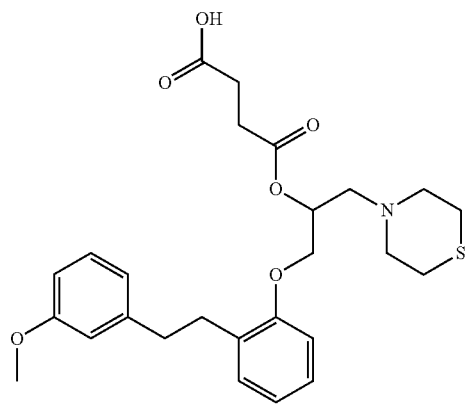
Compound 214

Compound 215
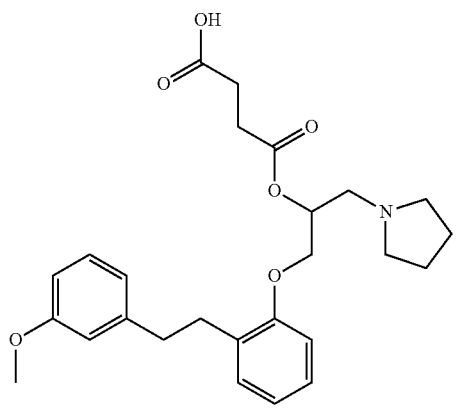
Compound 216
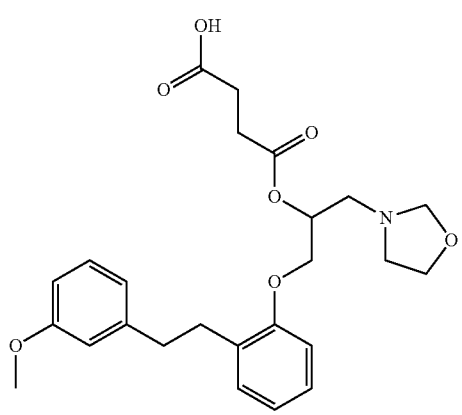
Compound 217
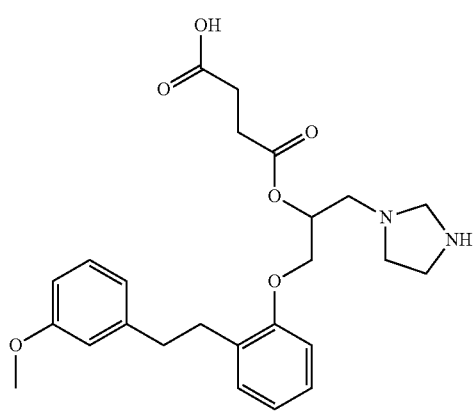
Compound 218
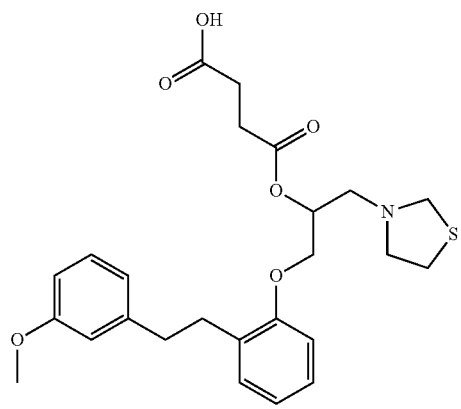
Compound 219
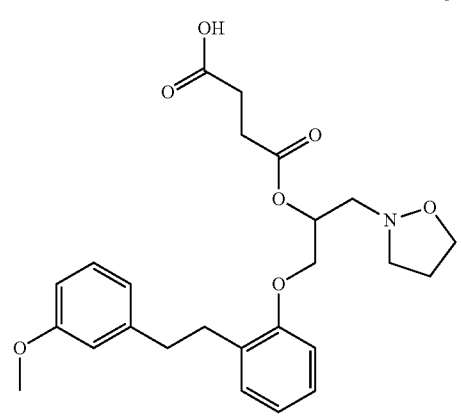
Compound 220
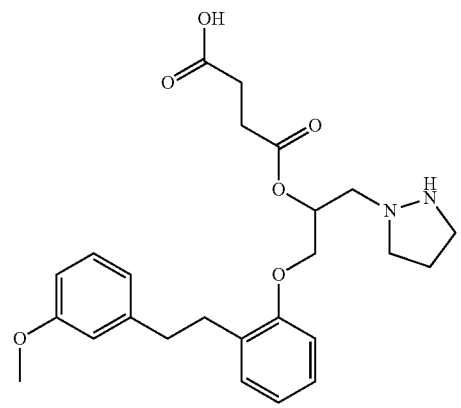

Compound 221

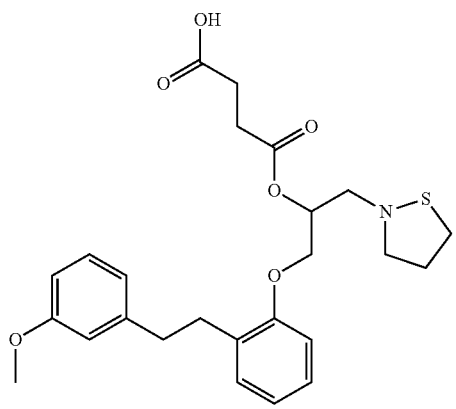

Compound 222

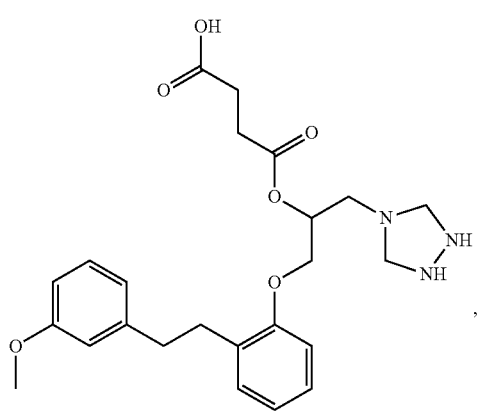

Compound 223

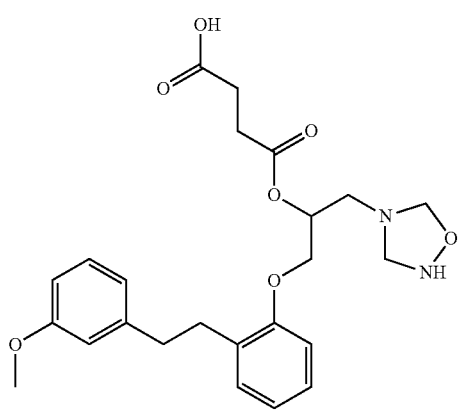

Compound 224

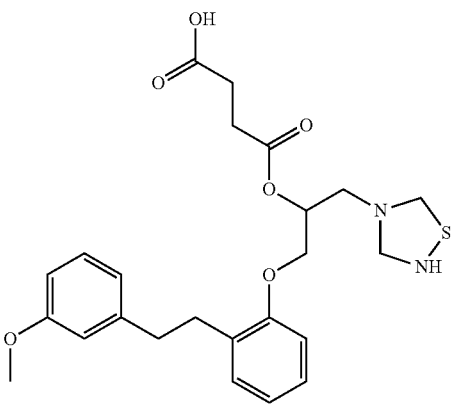

or an enantiomer thereof, metabolite thereof, deuterated derivative thereof, halogenated derivative thereof, prodrug thereof, pharmaceutically acceptable salt thereof, N-oxide thereof, or a combination thereof; and b) the compound of Formula II is at least one compound selected from the group consisting of:

Compound 149

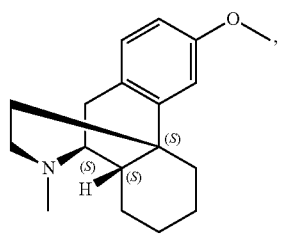

Compound 150

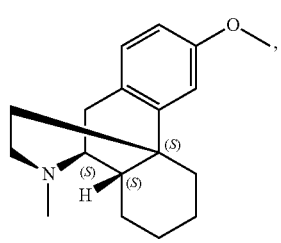

Compound 151

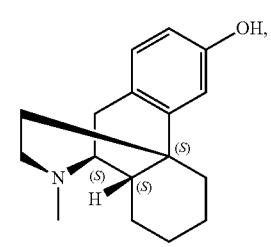

Compound 153

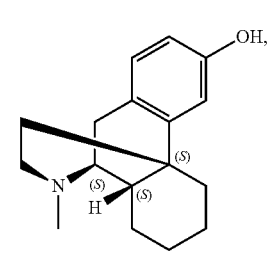

Compound 154

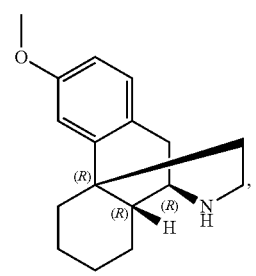

Compound 155

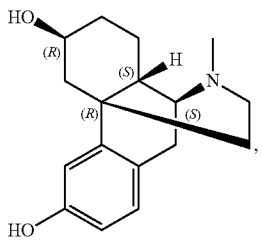

Compound 156

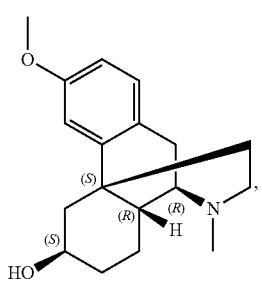

Compound 157

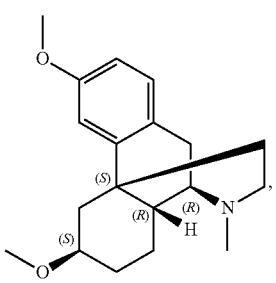

Compound 179

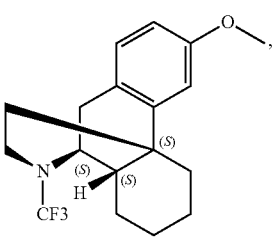

Compound 180

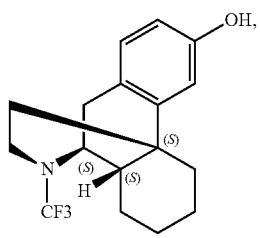

Compound 181

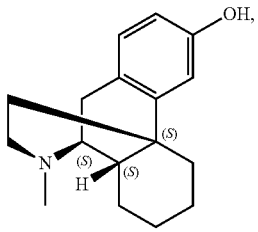

Compound 182

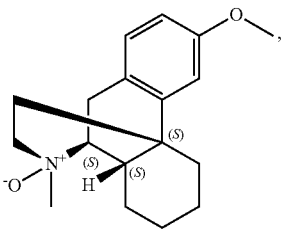

or an enantiomer thereof, metabolite thereof, deuterated derivative thereof, halogenated derivative thereof, prodrug thereof, pharmaceutically acceptable salt thereof, N-oxide thereof, or a combination thereof.

2. The composition of claim 1, wherein the compound of Formula I is:
sarpomethionate, wherein $R_1$, $R_2$, and $R_3$ are methyl, X is ethyl, and $R_4$ is methionate, wherein sarpomethionate is racemate, (S), or (R) enantiomer;
sarpophthallate, wherein $R_1$, $R_2$, and $R_3$ are methyl, X is ethyl, and $R_4$ is phthalate, wherein sarpophthallate is racemate, (S), or (R) enantiomer;
sarpomalonate, wherein $R_1$, $R_2$, and $R_3$ are methyl, X is ethyl, and $R_4$ is malonate, wherein sarpomalonate is racemate, (S), or (R) enantiomer;
sarpotyrosinate, wherein $R_1$, $R_2$, and $R_3$ are methyl, X is ethyl, and $R_4$ is tyrosinate, wherein sarpotyrosinate is racemate, (S), or (R) enantiomer; or
sarpotryptophanate, wherein $R_1$, $R_2$, and $R_3$ are methyl, X is ethyl, and $R_4$ is tryptophanate, wherein sarpotryptophanate is racemate, (S), or (R) enantiomer.

3. The composition of claim 2, wherein the compound of Formula II is

Compound 149

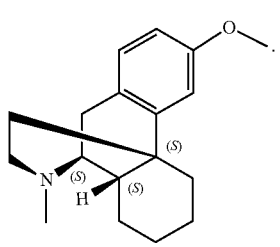

4. The composition of claim 3, wherein the composition is a salt comprising diastereomeric mixture, or a pure diastereomer thereof.

5. A pharmaceutical composition for the treatment of brain injury and neuropsychiatric and neurodegenerative diseases or disorders comprising a therapeutically and/or prophylactically effective amount of a dual acting agent capable of inhibiting CYP 2D6 and acting as a 5-HT2A receptor antagonist selected from the group consisting of

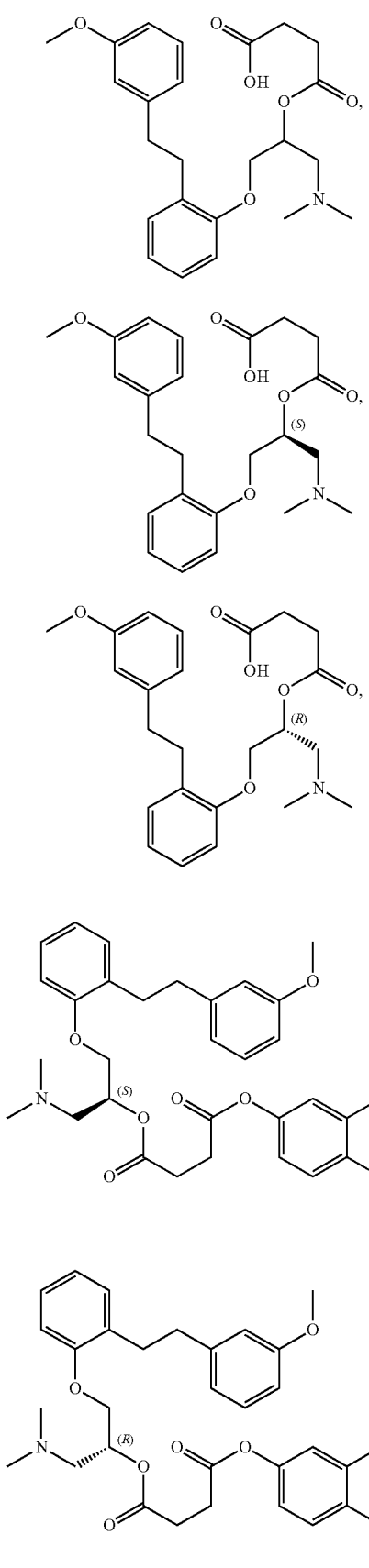
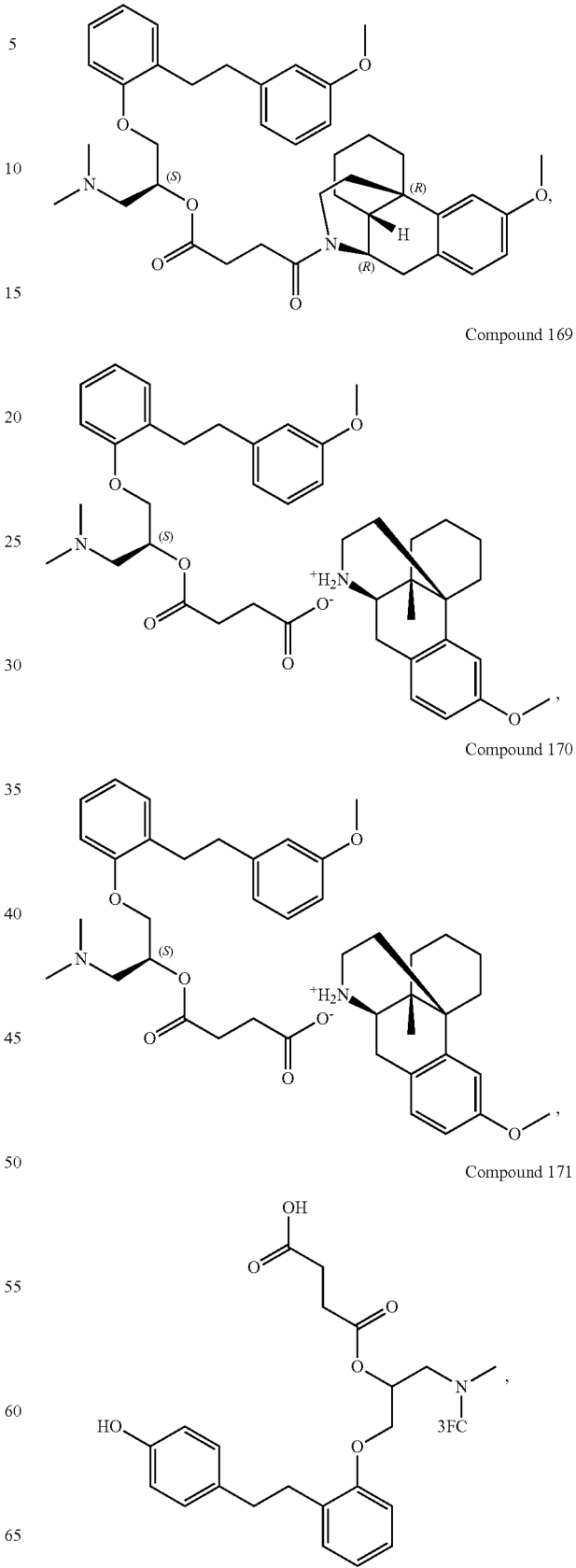

Compound 172
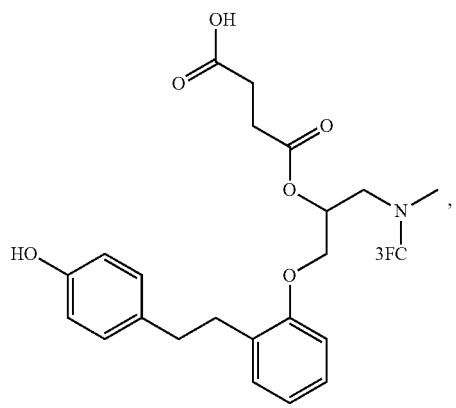
Compound 175
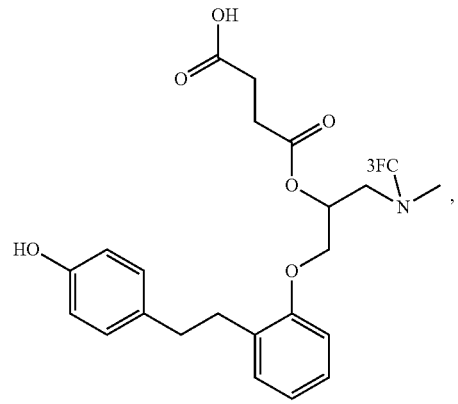
Compound 173
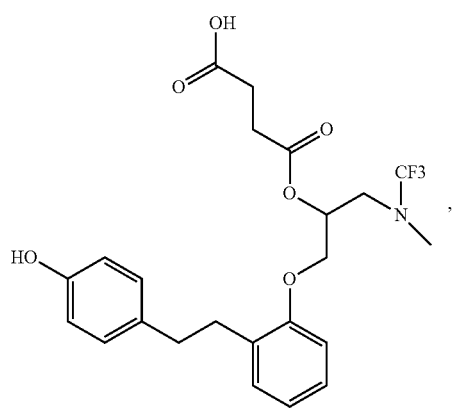
Compound 176
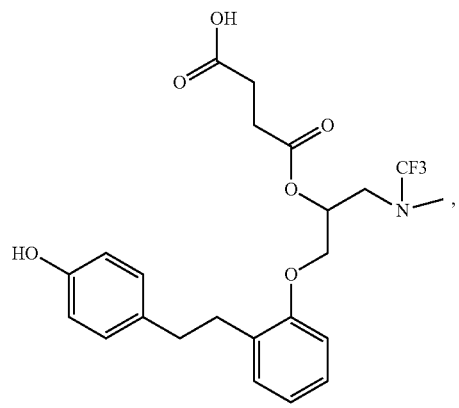
Compound 174
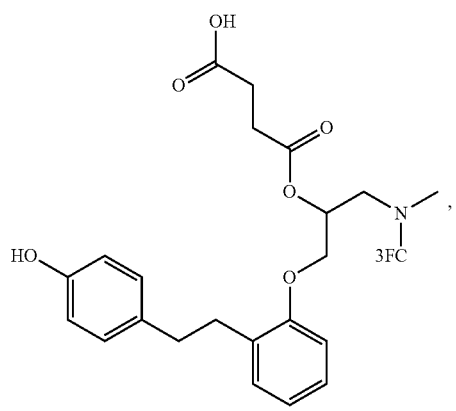
Compound 177
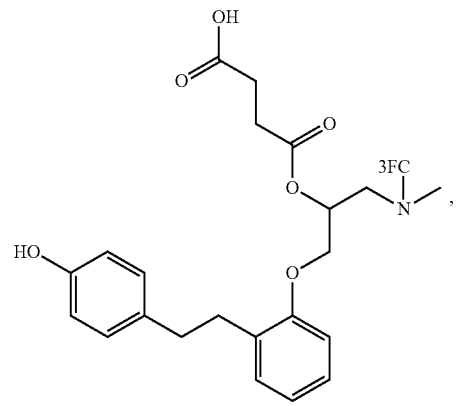

Compound 178

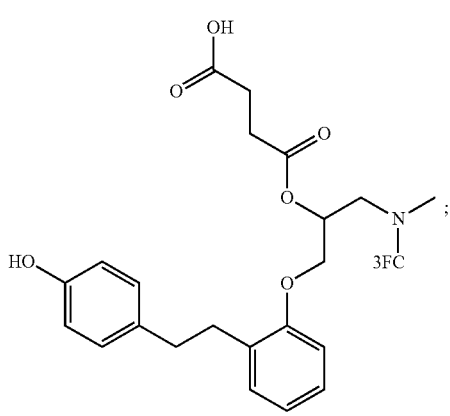

or metabolites thereof, deuterated derivatives thereof, fluorinated derivatives thereof, prodrugs thereof, pharmaceutically acceptable salts, N-oxides thereof, or a combination thereof; and a therapeutically and/or prophylactically effective amount of an NMDA receptor antagonist Compound 149

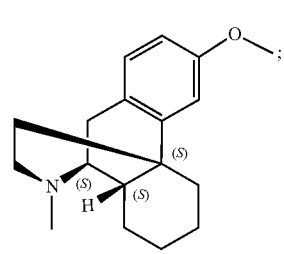

or metabolites thereof, deuterated derivatives thereof, fluorinated derivatives thereof, prodrugs thereof, pharmaceutically acceptable salts, N-oxides thereof, or a combination thereof.

6. The composition of claim 5, further comprising one or more compounds selected from the group consisting of thioridazine, perphenazine, fluphenazine, haloperidol, zuclopenthixol, risperidone, sertindole, nortriptyline, amitriptyline, imipramine, fluoxetine, ajmaline, amiodarone, amitriptyline, aprindine, azelastine, celecoxib, chlorpheniramine, chlorpromazine, diphenhydramine, doxorubicin, fluphenazine, fluvastatin, haloperidol, imipramine, indinavir, lasoprazole, levomepromazine, lopinavir, loratadine, mequitazine, methadone, metoclopramide, mibefradil, moclobemide, nelfinavir, nevirapine, nicardipine, norfluoxetine, perphenazine, pimozide, terfenadine, thioridazine, cimetidine, quinidine, cisapride, citalopram, clomipramine, clozapine, cocaine, anitidine, risperidone, ritonavir, saquinavir, sertraline, terbinafine, ticlopidine, trifluperidol, yohimbine, doxepin, mianserin, imipramine, 2-chloroimipramine, amitriptyline, amoxapine, desipramine, protriptyline, trimipramine, nortriptyline, maprotiline, phenelzine, isocarboxazid, tranylcypromine, trazodone, citalopram, sertraline, aryloxy indanamine, benactyzine, escitalopram, fluvoxamine, venlafaxine, desvenlafaxine, duloxetine, mirtazapine, nefazodone, selegiline, sibutramine, milnacipran, tesofensine, brasofensine, moclobemide, rasagiline, nialamide, iproniazid, iproclozide, toloxatone, butriptyline, dosulepin, dibenzepin, iprindole, lofepramine, opipramol, dapoxetine, thioridazine, perphenazine, fluphenazine, haloperidol, zuclopenthixol, risperidone, sertindole, nortriptyline, amitriptyline, imipramine, fluoxetine, paroxetine, amitriptyline, aprindine, azelastine, celecoxib, chlorpheniramine, diphenhydramine, doxorubicin, fluphenazine, fluvastatin, haloperidol, imipramine, indinavir, lasoprazole, levomepromazine, lopinavir, loratadine, mequitazine, methadone, metoclopramide, mibefradil, moclobemide, nelfinavir, nevirapine, nicardipine, norfluoxetine, perphenazine, pimozide, terfenadine, thioridazine, cimetidine, quinidine, cisapride, citalopram, clomipramine, clozapine, cocaine, desipramine, ranitidine, risperidone, ritonavir, saquifine, ticlopidine, trifluperidol, yohimbine, doxepin, mianserin, imipramine, 2-chloroimipramine, amitriptyline, amoxapine, protriptyline, trimipramine, nortriptyline, maprotiline, phenelzine, isocarboxazid, tranylcypromine, trazodone, citalopram, sertraline, aryloxy indanamine, benactyzine, escitalopram, fluvoxamine, venlafaxine, desvenlafaxine, duloxetine, mirtazapine, nefazodone, selegiline, sibutramine, milnacipran, tesofensine, brasofensine, moclobemide, rasagiline, nialamide, iproniazid, iproclozide, toloxatone, butriptyline, dosulepin, dibenzepin, iprindole, lofepramine, and dapoxetine.

7. The pharmaceutical composition of claim 5, wherein the composition is a fumarate salt, hydrobromide salt, or a combination thereof.

8. A method of increasing an NMDA receptor antagonist plasma levels in a subject in need thereof of, the method comprising administering a therapeutically effective composition comprising the composition of claim 1 to the subject.

9. The method of claim 8, wherein the NMDA receptor antagonist is selected from the group consisting of:

Compound 149

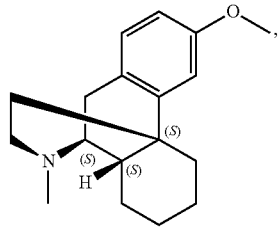

Compound 150

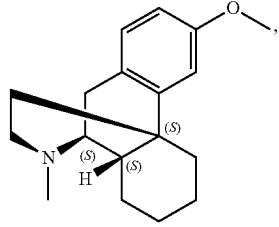

Compound 151

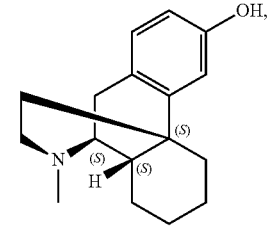

265
-continued

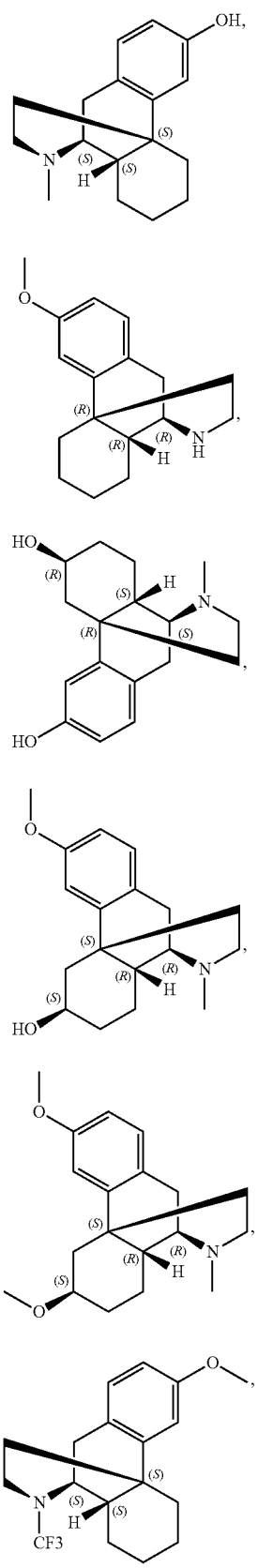

Compound 153

266
-continued

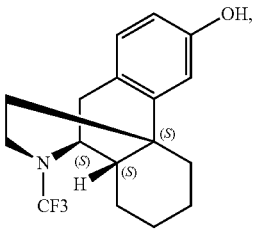
Compound 180

Compound 154

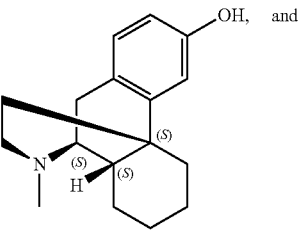
Compound 181

Compound 155

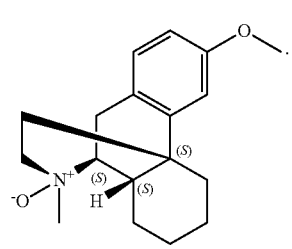
Compound 182

Compound 156

10. The method of claim 8, wherein the NMDA receptor antagonist is Compound 149, and the composition is administered once or twice a day, wherein the daily dose of compound 149 is about 0.1 mg to about 1000 mg, resulting in an $AUC_{o-12}$ of Compound 149 that is greater than the $AUC_{o-12}$ of the NMDA receptor antagonist Compound 149 that would be achieved by administering the same amount of the NMDA receptor antagonist Compound 149 without the dual agent.

11. The method of claim 10, wherein the composition further comprises a polymer, an emulsifier, a binder, a disintegrating agent, and/or a lubricant, and wherein the method further comprises administering the composition to the subject once or twice a day for at least 1 day, 2 consecutive days, 3 consecutive days, 4 consecutive days, 5 consecutive days, 6 consecutive days, 7 consecutive days, 8 consecutive days, 9 consecutive days, 10 consecutive days, 11 consecutive days, 12 consecutive days, 13 consecutive days, 14 consecutive days, 15 consecutive days, 16 consecutive days, 17 consecutive days, 18 consecutive days, 19 consecutive days, 20 consecutive days, 21 consecutive days, 22 consecutive days, 24 consecutive days, 25 consecutive days, 26 consecutive days, 27 consecutive days, 28 consecutive days, 29 consecutive days, 30 consecutive days, 31 consecutive days, 32 consecutive days, 33 consecutive days, 34 consecutive days, 35 consecutive days, 36 consecutive days, 37 consecutive days, 38 consecutive days, 39 consecutive days, 40 consecutive days, 41 consecutive days, 42 consecutive days, 43 consecutive days, 44 consecutive days, 45 consecutive days, 46 consecutive days, 47 consecutive days, 48 consecutive days, 49 consecutive days, 50 consecutive days, 51 consecutive days, 52 consecutive days, 53 consecutive days, 54 consecutive days, 55 consecutive days, 56 consecutive days, 57 consecutive days, 58 consecutive days, 59 consecutive days, 60 consecutive days, 70 consecutive days, 80 consecutive days, 90 consecutive days, Compound 157

Compound 179

100 consecutive days, 110 consecutive days, 120 consecutive days, 130 consecutive days, 140 consecutive days, 150 consecutive days, 160 consecutive days, 170 consecutive days, 180 consecutive days, 190 consecutive days, or 200 consecutive days.

12. The method of claim 8, wherein the $AUC_{o-12}$ of the dual agent, is at least about 10 ng/hr/mL, about 100 ng/hr/mL, 200 ng/hr/mL, about 300 ng/hr/mL, or about 400 ng/hr/mL.

13. The method of claim 8, wherein the method comprises an oral dosage form comprising tablets, capsules, liquids, or solutions and the administration is cutaneous, oral, nasal, anal, rectal, vaginal, sublingual, buccal, sublabial, muscular, intramuscular, intravenous, peritoneal, epidural, intracerebral, intracerebral or topical, intraarticular, intracardiac, intracavernous, intradermal, intralesional, intramuscular, intraocular, intraosseous, intraperitoneal, intrathecal, intrauterine, intravaginal, intravesical, intravitreal, transdermal, or transmucosal.

14. The method of claim 8, wherein the subject is in need of a symptomatic and disease-modifying prophylactic, treatment, or prevention of behavioral and psychological symptoms of dementia (BPSD) comprising delusions, hallucinations, agitation, aggression, dysphoria, anxiety, euphoria, apathy, disinhibition, irritability/lability, aberrant motor activity, night-time behavioral disturbances, appetite and eating abnormalities, or a combination thereof.

15. A method of use of the composition of claim 1 for a therapeutic and/or prophylactic treatment for a disease or disorder in a patient in need thereof, comprising:
   a) administering a therapeutically effective amount of the composition;
   b) targeting CYP2D6 enzyme, and NMDA and 5-HT2A receptors;
   c) wherein the disease or disorder is behavioral and psychological symptoms of dementia (BPSD); and producing a symptomatic relief and/or disease modification.

16. A method of use of the composition of claim 3 for a therapeutic and/or prophylactic treatment for a disease or disorder in a patient in need thereof, comprising:
   a) administering a therapeutically effective amount of the composition;
   b) targeting CYP2D6 enzyme, and NMDA and 5-HT2A receptors;
   c) wherein the disease or disorder is behavioral and psychological symptoms of dementia (BPSD); and
   d) producing a symptomatic relief and/or disease modification.

17. A method of use of the composition of claim 5 for a therapeutic and/or prophylactic treatment for a disease or disorder in a patient in need thereof, comprising:
   a) administering a therapeutically effective amount of the composition;
   b) targeting CYP2D6 enzyme, and NMDA and 5-HT2A receptors;
   c) wherein the disorder is behavioral and psychological symptoms of dementia (BPSD); and
   d) producing a symptomatic relief and/or disease modification.

* * * * *